US009926293B2

(12) United States Patent
Stockwell et al.

(10) Patent No.: US 9,926,293 B2
(45) Date of Patent: Mar. 27, 2018

(54) MULTIVALENT RAS BINDING COMPOUNDS

(71) Applicant: THE TRUSTEES OF COLUMBIA UNIVERSITY IN THE CITY OF NEW YORK, New York, NY (US)

(72) Inventors: Brent R. Stockwell, New York, NY (US); Matthew Welsch, New York, NY (US)

(73) Assignee: The Trustees of Columbia University in the City of New York, New York, NY (US)

(*) Notice: Subject to any disclaimer, the term of this patent is extended or adjusted under 35 U.S.C. 154(b) by 0 days.

(21) Appl. No.: 15/077,865

(22) Filed: Mar. 22, 2016

(65) Prior Publication Data

US 2016/0229836 A1 Aug. 11, 2016

Related U.S. Application Data

(63) Continuation of application No. PCT/US2015/033318, filed on May 29, 2015.

(60) Provisional application No. 62/005,831, filed on May 30, 2014.

(51) Int. Cl.

| | |
|---|---|
| ***C07D 209/14*** | (2006.01) |
| ***A61K 31/496*** | (2006.01) |
| ***C07D 401/12*** | (2006.01) |
| ***C07D 403/12*** | (2006.01) |
| ***C07D 401/14*** | (2006.01) |
| ***C07D 295/108*** | (2006.01) |

(52) U.S. Cl.

CPC ......... *C07D 401/12* (2013.01); *C07D 209/14* (2013.01); *C07D 295/108* (2013.01); *C07D 401/14* (2013.01); *C07D 403/12* (2013.01)

(58) Field of Classification Search

None

See application file for complete search history.

(56) References Cited

U.S. PATENT DOCUMENTS

2017/0158702 A1* 6/2017 Vacca .................. C07D 209/14

FOREIGN PATENT DOCUMENTS

WO 03037252 A2 5/2003
WO 2015/074123 A1 * 5/2015

OTHER PUBLICATIONS

Supplementary European Search Report.

* cited by examiner

*Primary Examiner* — Emily A Bernhardt

(74) *Attorney, Agent, or Firm* — Bryan Cave, LLP

(57) ABSTRACT

The present invention provides, inter alia, compounds having the structure:

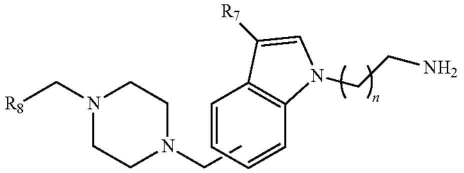

wherein $R_7$, $R_8$ and n are as disclosed herein, that selectively bind a RAS protein at two or more sites and methods for their synthesis. Compositions and kits containing the compounds, as well as methods of using the compounds and compositions for ameliorating or treating the effects of a disease associated with altered RAS signaling, such as a cancer, in a subject and methods for effecting cancer cell death are also provided herein. Methods of identifying a multivalent compound which binds selectively to a target protein also are provided herein.

10 Claims, 58 Drawing Sheets
(37 of 58 Drawing Sheet(s) Filed in Color)

Selected effector residues interacting with key RAS residues

Top pharmacophore compounds tanimoto: 0.91
31MEW78 tanimoto: 0.88
31MEW79

Switch I and II

3 Sites Targeted

Top-scoring commercial fragments in D38 and A59 sites

D38 fragment
docking score: - 8.33

A59 fragment
docking score: -8.50

Top-scoring designed D38 fragments docking score: -8.39 docking score: -8.38

Different indole substitutions designed for A59 site 1 2

3 4

Two of the top designed A59-D38 binding compounds

31MEW44
docking score: -9.33

34MEW43
docking score: -9.60

3-site compound based on 34MEW43

34MEW95
docking score: -10.0

Schematic of the 3-site compound design

| **Single full compound library** | vs. | **fragment growth approach** |
|---|---|---|
| | | 28 + |
| | | 82 x 4 x 97 x 2 x 2 = 127,264 + |
| 82 x 4 x 97 x 2 x 28 x 82 x 25 | | active A59-D38 compounds x 82 x 25 = 2,050 |
| 3,652,476,800 | | 129,342 |

MULTIVALENT RAS BINDING COMPOUNDS

CROSS REFERENCE TO RELATED APPLICATIONS

This application is a continuation of International Application No. PCT/US2015/033318, filed May 29, 2015, which claims benefit of U.S. Patent Application Ser. No. 62/005,831, filed on May 30, 2014 which applications are incorporated by reference herein in their entireties.

GOVERNMENT FUNDING

This invention was made with government support under grants 5R01CA097061, 5R01GM085081, R01CA161061, and 1S10RR025431-01A1 awarded by the National Institutes of Health and grant CHE 0840451 awarded by the National Science Foundation. The government has certain rights in the invention.

FIELD OF INVENTION

The present invention provides, inter alia, compounds that selectively bind a RAS protein at two or more sites. Compositions and kits containing the compounds, as well as methods of using the compounds and compositions for ameliorating or treating the effects of a disease associated with altered RAS signaling in a subject and methods for effecting cancer cell death are also provided herein.

INCORPORATION BY REFERENCE OF SEQUENCE LISTING

This application contains references to amino acids and/or nucleic acid sequences that have been filed concurrently herewith as sequence listing text file 0365302_sequences.txt, file size of 132 KB, created on May 29, 2015. The aforementioned sequence listing is hereby incorporated by reference in its entirety pursuant to 37 C.F.R. §1.52(e)(5).

BACKGROUND OF THE INVENTION

At least 85% of human proteins are considered to be challenging targets for small molecule drugs using conventional discovery approaches, such as high-throughput screening of existing chemical libraries (Hopkins et al., 2002). A particularly important, but historically intractable, subset of these proteins are those that elicit their biological effects through protein-protein interactions (Nero et al., 2014); while some protein-protein interactions consisting of short alpha helical domains inserted into a deep hydrophobic pocket in an interacting protein have been amenable to disruption with small molecules (e.g., the p53-Mdm2 interaction (Vassilev et al., 2004)), many protein-protein interactions have been largely resistant to small molecule inhibition using high-throughput screening of standard chemical libraries. Within this category are the RAS GTPases, which are proposed to be among the most tantalizing and thoroughly validated targets in cancer biology due to their high prevalence and frequent essentiality in lethal malignancies (Downward et al., 2003). RAS gene mutations are found at high rates in three of the top four lethal malignancies in the United States—pancreatic (90%), colon (45%), and lung cancers (35%) (Id.). Many tumors have been shown to be dependent on continued expression of oncogenic RAS proteins in cell and animal models (Weinstein et al., 2008). However, RAS proteins have been viewed as challenging targets, primarily due to the lack of a sufficiently large and deep hydrophobic site for small molecule binding, aside from the GTP-binding site. The picomolar affinity of GTP (John et al., 1990) makes competitive inhibition impractical, in contrast to the ATP-binding site on kinases. For these reasons, traditional high-throughput screening has been unable to provide high affinity small molecule RAS ligands.

The RAS proteins play a central role in a number of signal transduction pathways controlling cell growth and differentiation. They function as a binary switch, transitioning from an inactive GDP-bound state to an active GTP-bound state (Downward et al., 2003). GTP binding enables several residues, primarily in the switch I region (residues 30-40) and the switch II region (residues 60-70) to adopt a conformation that permits RAS effector proteins to bind; this transition is reciprocally regulated by GTPase activating proteins (GAPs) and guanine nucleotide exchange factors (GEFs). A mutation resulting in the impairment of the intrinsic GTPase activity of RAS proteins, or preventing GAP binding, constitutively activates downstream signaling pathways and contributes to the malignant phenotype. Thus, there exists an unmet need for compounds that selectively bind a RAS protein, particularly an oncogenic mutant of a RAS protein.

SUMMARY OF THE INVENTION

One embodiment of the present invention is a compound that selectively binds a RAS protein at two or more sites.

Another embodiment of the present invention is a compound selected from the group consisting of

31MEW78

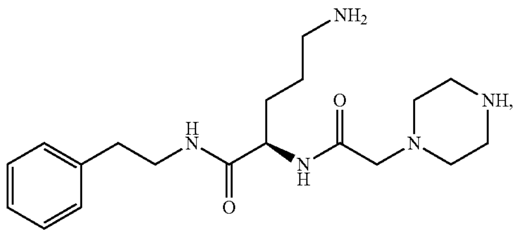

31MEW79

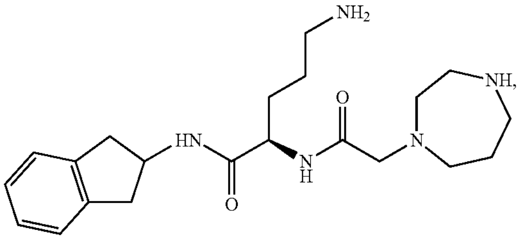

and crystalline forms, hydrates, or pharmaceutically acceptable salts thereof.

A further embodiment of the present invention is a compound having the structure of formula (V):

(V)

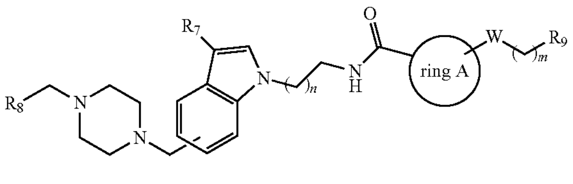

wherein:

$R_7$ is selected from the group consisting of H, halide, $C_{1-4}$ aliphatic, and aryl, wherein the aryl is optionally substituted with one or more groups consisting of halide, ether, $C_{1-4}$alkyl, —O—$C_{1-4}$alkyl and a combination thereof, wherein the alkyl is optionally substituted with one or more groups consisting of halide, ether, and a combination thereof;

$R_8$ is selected from the group consisting of no atom, H, alkyl, aryl, and $C_{1-4}$alkyl-O-aryl wherein the alkyl is optionally substituted with the group consisting of halide, ether, and a combination thereof, and the aryl is optionally substituted with one or more groups consisting of halide, ether, $C_{1-4}$alkyl, and a combination thereof;

$R_9$ is selected from the group consisting of no atom, H, $C_{1-4}$alkyl, and aryl optionally substituted with the group consisting of ether, halide, and a combination thereof;

W is selected from the group consisting of no atom and NH;

m and n are independently selected from the group consisting of an integer between 0-5; and ring A is a heterocycle with at least 1 ring nitrogen and optionally substituted with $C_{1-4}$alkyl or a halide, or a crystalline form, hydrate, or pharmaceutically acceptable salt thereof.

An additional embodiment of the present invention is a compound having the structure of formula (VI):

(VI)

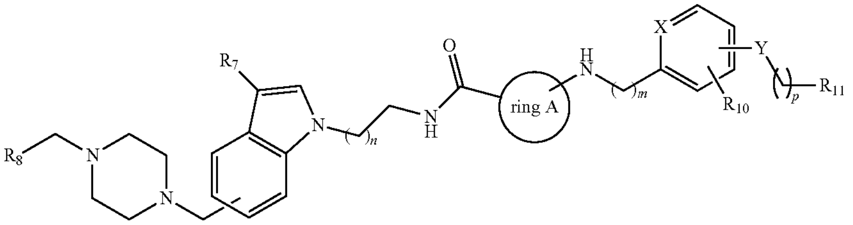

wherein:

$R_7$ is selected from the group consisting of H, halide, $C_{1-4}$ aliphatic, and aryl, wherein the aryl is optionally substituted with one or more groups consisting of halide, ether, $C_{1-4}$alkyl, —O—$C_{1-4}$alkyl, and a combination thereof, wherein the alkyl is optionally substituted with one or more groups consisting of halide, ether, and a combination thereof;

$R_8$ and $R_{11}$ are independently selected from the group consisting of no atom, H, alkyl, aryl and $C_{1-4}$alkyl-O-aryl, wherein the alkyl is optionally substituted with the group consisting of halide, ether, and a combination thereof, and the aryl is optionally substituted with one or more groups consisting of halide, ether, $C_{1-4}$alkyl, —O—$C_{1-4}$alkyl, and a combination thereof, wherein the alkyl is optionally substituted with the group consisting of halide, ether, and a combination thereof;

$R_{10}$ is selected from the group consisting of no atom, H, halide, $C_{1-4}$ aliphatic, and —O—$C_{1-4}$alkyl;

X is selected from the group consisting of CH and N;

Y is selected from the group consisting of no atom and O;

m, n, and p are independently selected from the group consisting of an integer between 0-5; and ring A is a heterocycle with at least 1 ring nitrogen and optionally substituted with $C_{1-4}$alkyl or a halide, or a crystalline form, hydrate, or pharmaceutically acceptable salt thereof.

Another embodiment of the present invention is a compound selected from the group consisting of

31MEW44

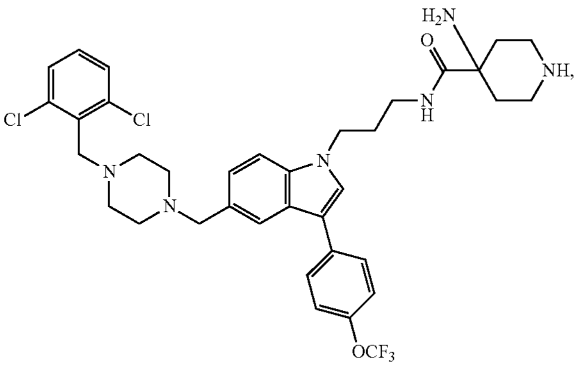

-continued

34MEW43

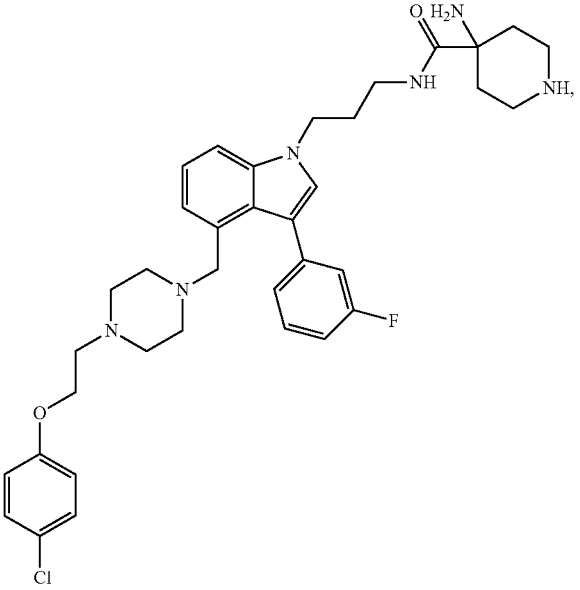

-continued
34MEW95
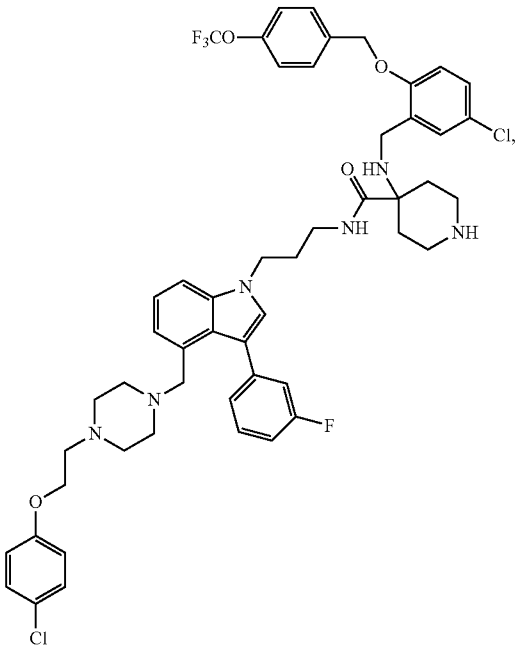
36MEW3
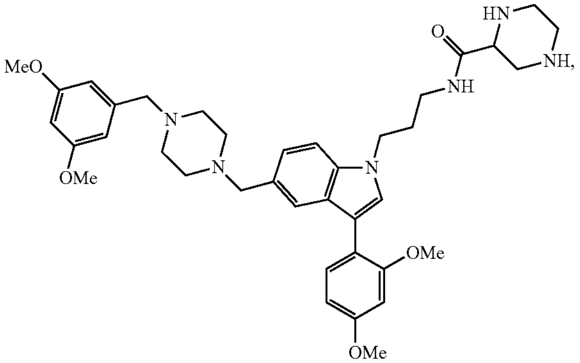
32MEW56
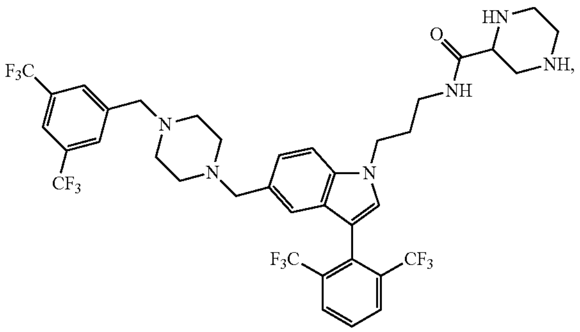
-continued
34MEW45
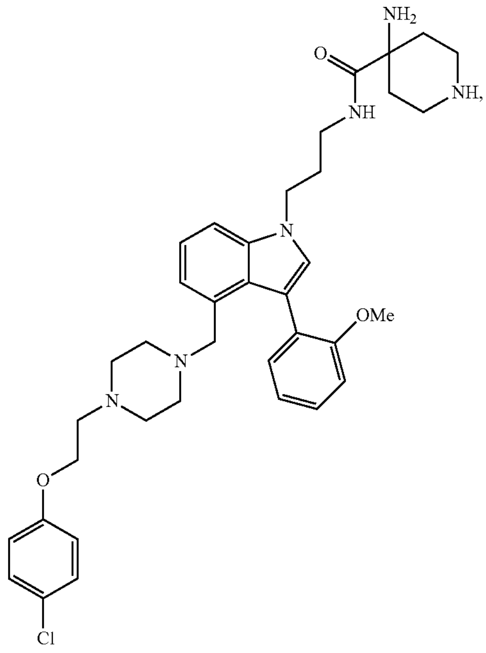
43MEW65
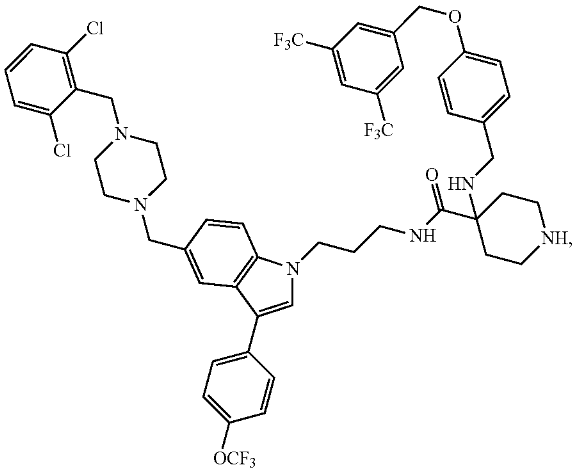

-continued

43MEW73

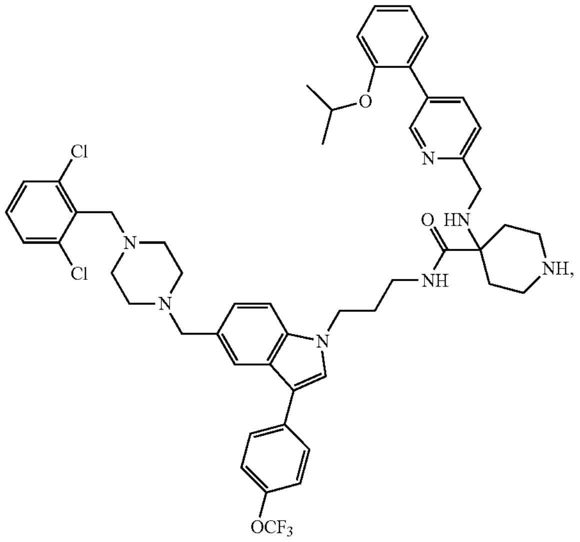

-continued

35MEW12

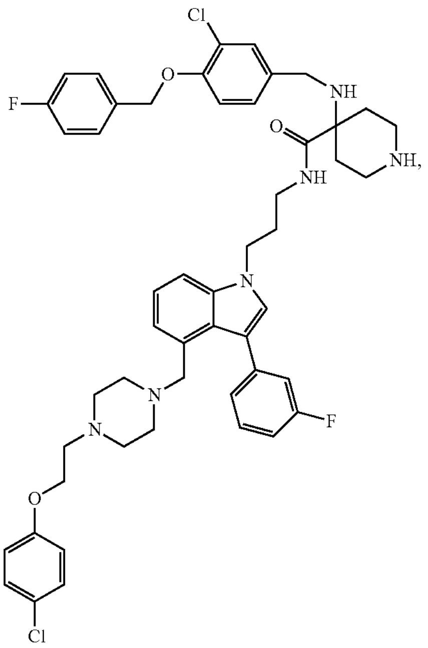

and crystalline forms, hydrates, or pharmaceutically acceptable salts thereof.

A further embodiment of the present invention is a compound having the structure:

43MEW63

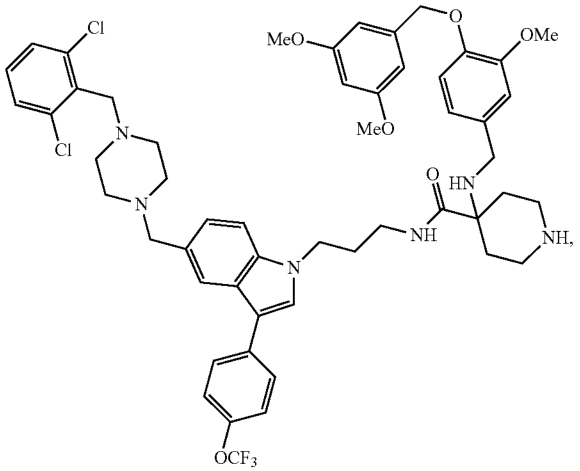

31MEW44

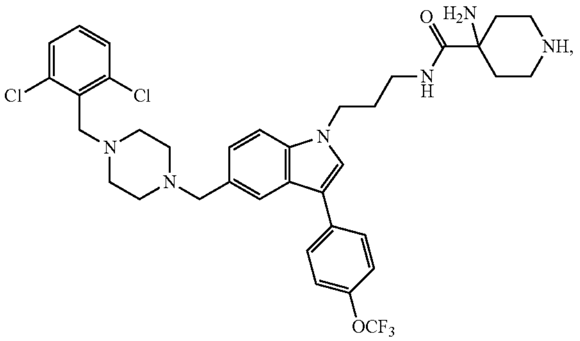

or a crystalline form, hydrate, or pharmaceutically acceptable salt thereof.

An additional embodiment of the present invention is a compound having the structure:

34MEW43

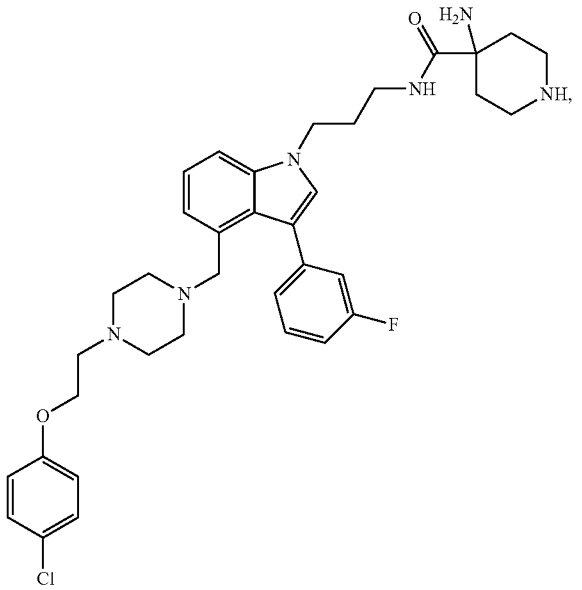

or a crystalline form, hydrate, or pharmaceutically acceptable salt thereof.

Another embodiment of the present invention is a compound having the structure:

34MEW95

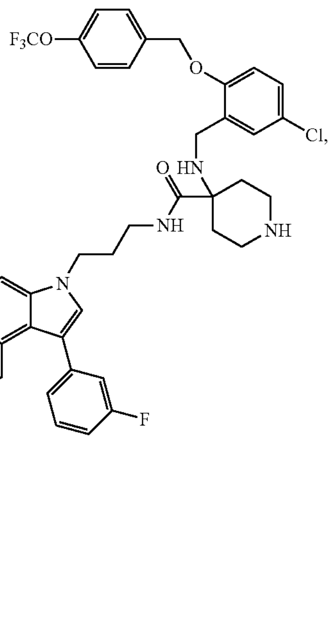

or a crystalline form, hydrate, or pharmaceutically acceptable salt thereof.

A further embodiment of the present invention is a pharmaceutical composition that comprises a pharmaceutically acceptable carrier and any compound disclosed herein.

An additional embodiment of the present invention is a method for ameliorating or treating the effects of a disease associated with altered RAS signaling in a subject. The method comprises administering to the subject an effective amount of any compound disclosed herein.

Another embodiment of the present invention is a method for ameliorating or treating the effects of a disease associated with altered RAS signaling in a subject. The method comprises administering to the subject an effective amount of any pharmaceutical composition disclosed herein.

A further embodiment of the present invention is a method for effecting cancer cell death. The method comprises contacting a cancer cell with an effective amount of any compound disclosed herein.

Another embodiment of the present invention is a kit for treating or ameliorating the effects of a disease related to altered RAS signaling in a subject in need thereof. The kit comprises an effective amount of any compound or pharmaceutical composition disclosed herein, packaged together with instructions for its use.

A further embodiment of the present invention is a kit for treating or ameliorating the effects of a cancer in a subject in need thereof. The kit comprises an effective amount of any compound or pharmaceutical composition disclosed herein, packaged together with instructions for its use.

An additional embodiment of the present invention is a composition that comprises any compound disclosed herein.

An additional embodiment of the present invention is a method of preparing a compound having the structure of formula (VII):

(VII)

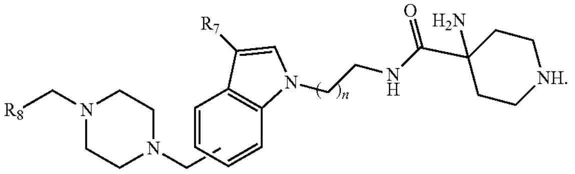

The method comprises the steps of i) reacting a compound having the structure:

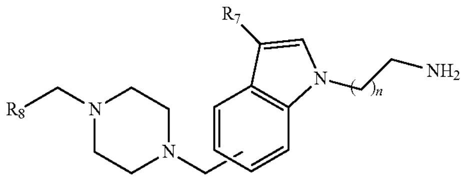

with a compound having the structure:

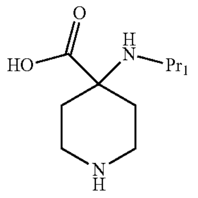

under conditions sufficient to form a compound having the structure:

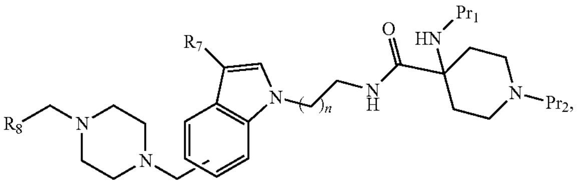

wherein:

$R_7$ is selected from the group consisting of H, halide, $C_{1-4}$ aliphatic, and aryl, wherein the aryl is optionally substituted with one or more groups consisting of halide, ether, $C_{1-4}$alkyl, —O—$C_{1-4}$alkyl, and a combination thereof, wherein the alkyl is optionally substituted with one or more groups consisting of halide, ether, and a combination thereof;

$R_8$ is selected from the group consisting of no atom, H, alkyl, aryl and $C_{1-4}$alkyl-O-aryl, wherein the alkyl is optionally substituted with the group consisting of halide, ether, and a combination thereof, and the aryl is optionally substituted with one or more groups consisting of halide, ether, $C_{1-4}$alkyl, and a combination thereof;

n is selected from the group consisting of an integer between 0-5; and $Pr_1$ and $Pr_2$ are independently selected from the group consisting of nitrogen protecting groups;

ii) removing the $Pr_1$ protecting group; and iii) removing the $Pr_2$ protecting group.

An additional embodiment of the present invention is a method of preparing a compound having the structure of formula (VIII):

(VIII)

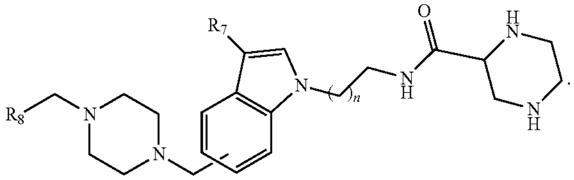

The method comprises the steps of i) reacting a compound having the structure:

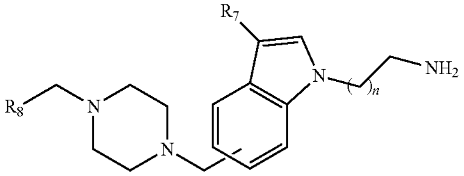

with a compound having the structure:

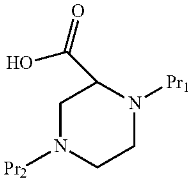

under conditions sufficient to form a compound having the structure:

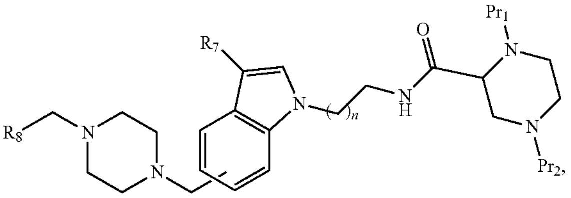

wherein:

$R_7$ is selected from the group consisting of H, halide, $C_{1-4}$ aliphatic, and aryl, wherein the aryl is optionally substituted with one or more groups consisting of halide, ether, $C_{1-4}$alkyl, —O—$C_{1-4}$alkyl, and a combination thereof, wherein the alkyl is optionally substituted with one or more groups consisting of halide, ether, and a combination thereof;

$R_8$ is selected from the group consisting of no atom, H, alkyl, aryl and $C_{1-4}$alkyl-O-aryl, wherein the alkyl is optionally substituted with the group consisting of halide, ether, and a combination thereof, and the aryl is optionally substituted with one or more groups consisting of halide, ether, $C_{1-4}$alkyl, and a combination thereof;

n is selected from the group consisting of an integer between 0-5; and $Pr_1$ and $Pr_2$ are independently selected from the group consisting of nitrogen protecting groups;

ii) removing the $Pr_1$ protecting group; and iii) removing the $Pr_2$ protecting group.

An additional embodiment of the present invention is a method of preparing a compound having the structure of formula (IX):

(IX)

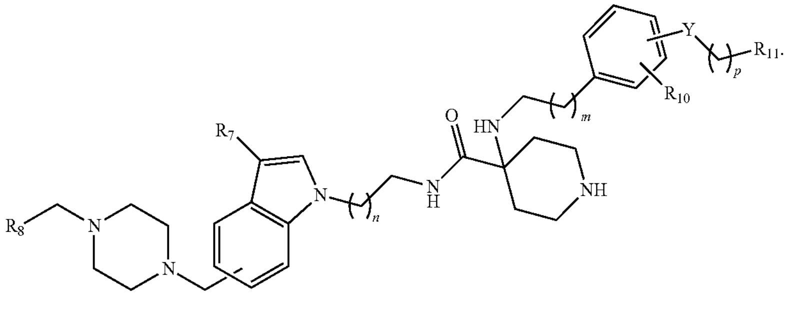

The method comprises the steps of i) reacting a compound having the structure:

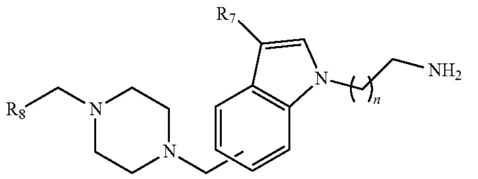

with a compound having the structure:

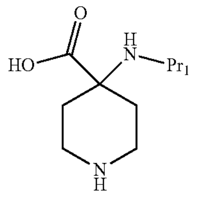

under conditions sufficient to form a compound having the structure:

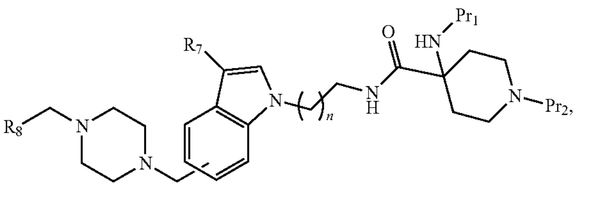

wherein:

$R_7$ is selected from the group consisting of H, halide, $C_{1-4}$ aliphatic, and aryl, wherein the aryl is optionally substituted with one or more groups consisting of halide, ether, $C_{1-4}$alkyl, —O—$C_{1-4}$alkyl, and a combination thereof, wherein the alkyl is optionally substituted with one or more groups consisting of halide, ether, and a combination thereof;

$R_8$ and $R_{11}$ are independently selected from the group consisting of no atom, H, alkyl, aryl and $C_{1-4}$alkyl-O-aryl, wherein the alkyl is optionally substituted with the group consisting of halide, ether, and a combination thereof, and the aryl is optionally substituted with the group consisting of halide, ether, $C_{1-4}$alkyl, —O—$C_{1-4}$alkyl, and a combination thereof, wherein the alkyl is optionally substituted with the group consisting of halide, ether, and a combination thereof;

$R_{10}$ is selected from the group consisting of no atom, H, halide, $C_{1-4}$ aliphatic and —O—$C_{1-4}$alkyl;

Y is selected from the group consisting of no atom and O;

m, n, and p are independently selected from the group consisting of an integer between 0-5; and;

$Pr_1$ and $Pr_2$ are independently selected from the group consisting of nitrogen protecting groups;

ii) removing the $Pr_1$ protecting group iii) reacting the product of step ii) with a compound having the structure:

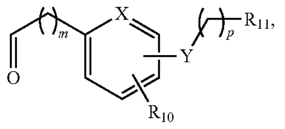

wherein X is selected from the group consisting of CH and N; and iv) removing the $Pr_2$ protecting group.

An additional embodiment of the present invention is a method of identifying a multivalent compound which binds selectively to a target protein. The method comprises the steps of i) identifying a first and second target site on the target protein, wherein the first and second target sites are adjacent to each other;

ii) identifying a first compound fragment that selectively binds to the target protein at the first target site and a second compound fragment that selectively binds to the target protein at the second site; and iii) creating a structure of the multivalent compound comprising the first compound fragment linked to the second compound fragment, thereby identifying the multivalent compound.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A shows co-crystal structures of HRAS with PI3Kγ (grey, PDB: 1HE8), the RAS-binding domain of CRAF (yellow, PDB: 3KUD), and RALGDS (red, PDB: 1LFD) aligned. FIG. 1B shows an example of the conserved interactions across the D38 site with the effectors. Each effector has either an arginine or lysine capable of making an electrostatic interaction with E37 on HRAS. FIG. 1C shows the selected effector residues that interact with residues 36-39 on HRAS. FIG. 1D shows co-crystal structures of HRAS with PI3Kγ (grey, PDB: 1HE8), the RAS binding domain of CRAF (yellow, PDB: 3KUD), RALGDS (red, PDB: 1LFD) aligned. FIG. 1E shows the same view as FIG. 1D, with the individual residues shown. FIG. 1F shows the residues on the effector proteins interacting with I36. Each effector has a complementary hydrophobic residue. FIG. 1G shows the conformational change undergone by I36 going from the GDP to GTP form. $HRAS^{A59G}$ bound to GDP in yellow (PDB: 1LF5) and $HRAS^{A59G}$ bound to GTP in blue (PDB: 1LF0). FIG. 1H shows a view of I36 transition, with a surface representation for the GDP form. In the GTP-bound form, I36 adopts a solvent exposed state. FIG. 1I shows basic residues of the effector proteins in close proximity to D38. FIG. 1J shows effector residues with hydrogen bonding properties close to S39. FIG. 1K shows that each effector has either a arginine or lysine capable of making an electrostatic interaction with E37. FIG. 1L shows the selected effector residues interacting with residues 36-39 on HRAS.

FIG. 9A shows $^1H$-$^{15}N$ HSQC spectrum of KRAS G12D bound to GppNHp. FIG. 9B shows 3D-1H-15N-1H-NOESY-HSQC and 3D-1H-15N-1H-TOCSY-HSQC experiments were performed to confirm assignments. FIG. 9B shows representative strips for residues T35-E37 in $KRAS^{G12D}$ bound to GppNHp from $^{15}N$ NOESY-HSQC spectrum (blue) and $^{15}N$ TOCSY-HSQC spectrum (purple). $^{15}N$ TOCSY-HSQC spectrum helped identify the spin system and $^{15}N$ NOESY-HSQC spectrum was then used for sequential assignments. The path in red shows the sequential NOEs of $H_N$-$H_N$ or $H_N$-$H_{alpha}$.

FIG. 11A shows $KRAS^{G12D}$ (PDB: 4DSN) with the switch I region shown in green and the switch 2 region in purple. FIG. 11B shows the location of three sites on KRAS targeted: D38 site in yellow, A59 site in blue, Y32 site in red. FIG. 11C shows flip of Y32 from the GDP-bound to GTP-bound forms. $HRAS^{A59G}$ bound to GDP in yellow (PDB: 1LF5) and $HRAS^{A59G}$ bound to GTP in blue (PDB: 1LF0). FIG. 11D shows surface representation of the GDP bound form. FIG. 11E shows surface representation of the GTP-bound form, revealing a larger pocket that is otherwise blocked by Y32 in the GDP bound form.

FIG. 12A shows two of the top-scoring existing fragments docked into the D38 and A59 sites. FIG. 12B shows two top-scoring designed D38 fragments, docked as methylamine amides to represent the type of linkage that would occur to the adjacent A59 fragment. FIG. 12C shows examples of the indole scaffolds and substituent arrangements attempted. The highest-scoring set was the substitution pattern in panel 4. FIG. 12D shows the structures and predicted docking poses of two of the two-site, D38-A59-binding compounds.

FIG. 13A shows a view of the D38-binding moiety of 34MEW43, which shows the interaction of the amine groups with the side chains of D38 and D33. The amine indicated was optimally positioned to extend into the adjacent Y32 site. FIG. 13B shows the structure and predicted docking pose of the three-site inhibitor 34MEW95, based on the two-site compound 34MEW43. FIG. 13C shows a schematic of the scaffold for the three-site compounds with the points of diversity indicated and the library size of a single three-site compound vs. the sequential fragment docking approach implemented.

FIG. 14A shows (left panel) the docking pose of 31MEW44 in $KRAS^{G12D}$ (PDB: 4DSN) with residues shifting upon compound treatment colored in red, and (right panel) $^1H$-$^{15}N$ HSQC spectrum of 50 μM $KRAS^{G12D}$ bound-to GppNHp in the absence (blue) and presence (red) of 250 μM inhibitor 31MEW44. FIG. 14B-FIG. 14C show biochemical evaluation of 34MEW43. FIG. 14B shows 1H-15N HSQC spectrum of 50 μM $KRAS^{G12D}$ bound to GppNHp in the absence (blue) and presence (red) of 250 μM inhibitor 34MEW43. Zoom in on the residues of D38 pocket are shown in the top left corner. These residues are growing (I36), shrinking (E37), or shifting (S39) upon compound treatment. FIG. 14C shows differential scanning fluorimetry of 5 μM $KRAS^{G12D}$ bound to GTP in the presence of increasing concentration of compound. The ΔTm was calculated by subtracting the Tm of liganded $KRAS^{G12D}$ protein from unliganded $KRAS^{G12D}$ and are expressed as absolute value of the mean±sem. FIG. 14D shows in vitro RAS pulldown in the presence of 31MEW44 and 34MEW43 with GTP-loaded $KRAS^{G12D}$ using CRAF-RBD agarose beads. FIG. 14E shows in vitro RAS pulldown in the presence of 31MEW44 and 34MEW43 using GTP-loaded $KRAS^{G12D}$ and GST-tagged RALGDS using glutathione beads. FIG. 14F shows MST of the three-site compound 34MEW95 and the compound from which it was derived, 34MEW43, using $KRAS^{G12D}$-GppNHp. FIG. 14G shows MST of the two-site compound 31MEW44 and its differential selectivity towards the active (GppNHp bound) form vs. inactive (GDP bound) form of $KRAS^{G12D}$. FIG. 14H shows the effect of mutating residues within the docking site on $KRAS^{G12D}$ on the affinity of 31MEW44 by MST. FIG. 14I shows isothermal calorimetery titration (top left panel) of $KRAS^{G12D}$-GppNHp into 31MEW44 and the thermodynamic parameters (right panel) of 31MEW44 binding. FIG. 14J shows normalized thermophoretic traces of a dilution series of 31MEW44 with GppNHp bound $KRAS^{G12D}$, RHEB, RHOA, and RALA. FIG. 14K-FIG. 14L shows the effect of 31MEW44 binding to $KRAS^{G12D}$. FIG. 14K (left panel) shows 31MEW44 bound to $KRAS^{G12D}$ with shifted residues highlighted. FIG. 14K (right panel) shows the reverse view of $KRAS^{G12D}$ with shifted residues highlighted. FIG. 14L shows chemical shift perturbations for each residue in $KRAS^{G12D}$ upon 31MEW44 binding.

FIG. 16A shows (top panel) images of MDA-MB-231 cells after 72 hours in low adherence plates forming three dimensional multicellular spheroids when untreated, and killed by 31MEW44 at 20 μM, and (bottom panel) dose-response curves of the effect of 31MEW44 on viability in MDA-MB-231 and SW480 cells grown in low adherence plates, expressed as growth inhibition. FIG. 16B shows dose-response curves with 31MEW44, 34MEW43 and 34MEW95.

FIG. 22A shows relative quantity of uPA RNA, FIG. 22B shows relative quantity of MMP9 RNA, FIG. 22C shows relative quantity of cMYC RNA, and FIG. 22D shows relative quantity of lactate dehydrogenase RNA.

FIG. 29A shows 31MEW44-treated and vehicle-treated tumors from the tumor xenograft mice of FIG. 26 after dissection. FIG. 29B shows a quantitative graph of average tumor size. Eight week old nude female mice were injected with 7 million MDA-MB-231 cells. After tumors reached an average size of 58 cubic millimeters they were treated with vehicle orally (10 doses), 31MEW44 orally (180 mg/kg, 10 doses), or by a combination of intravenous and intraperitoneal injections (30 mg/kg, 4 IV doses, 6 IP doses) over two weeks.

FIG. 31A shows the effect of 31MEW44 on the viability of a panel of cancer cell lines. Cell lines were treated in 6-well format for 24 hours with 5 μM 31MEW44. FIG. 31B shows the correlation of cell line sensitivity of mutant RAS knockdown to 2.5 μM 31MEW44 treatment. The viability was measured 72 hours after reverse transfection with siRNA when cell death control siRNA resulted in complete loss of viability. Knockdown was confirmed by qPCR of the mutated isoform.

FIG. 32A shows the measured viability 72 hours post-transfection of cell lines that were reverse transfected with siRNA against the mutated RAS isoform. FIG. 32B shows the percent viability after 24 hours of treatment with the inhibitor at 5 μM plotted against the percent viability measured 72 hours after reverse transfection.

FIG. 35A shows qPCR of KRAS, PI3K, and BRAF. Each transfected population was analyzed for expression of each targeted gene. FIG. 35B shows a western blot of downstream phosphorylated ERK1/2 and AKT (S473) compared to total ERK1/2 and AKT in transfected cell lines. Immediately preceeding the evaluation of 31MEW44, a sample of cells from each transfection condition were taken, lysed and analyzed.

In FIG. 36A, BJeLR cells were seeded in 2% FBS in DMEM 18 hours prior to treatment with 31MEW44 and U0126 in 2% FBS in DMEM for 3 hours. Cells were then lysed and the lysate was incubated with RalBP1 agarose beads for 2 hours before being washed twice with PBS, denatured and subsequently detected by western blotting. FIG. 36B shows cRAF, PI3Kγ, and pan-RAS pulldowns from BJeLR cells seeded in 10% FBS in DMEM 18 hours prior to treatment with 31MEW44 in 10% FBS in DMEM for 3 hours.

FIG. 38A shows the effect of 31MEW44 on a patient-derived T-ALL sample PDTALL22 as a luciferase expressing primograft. Mice were randomized into two treatment groups of 5 mice with equal loads of luciferase. Mice were treated with 31MEW44 (30 mg/kg) or vehicle by intraperitoneal injection once daily on days: 0, 1, 4, 5, and 7. FIG. 38B shows representative images of mice from each treatment group at days 0, 4, and 8 (final day) of the study. FIG. 38C is a bar graph representing spleen weight in grams. FIG. 38D shows the percentage of human CD45+ cells in the spleen of vehicle and 31MEW44-treated mice.

FIG. 39A is a survival curve of $KP^{f/f}C$ and wild-type mice that received 30 mg/kg 31MEW44 once daily for five days. FIG. 39B is a graph showing the measurement of wild-type mouse weight each day of the five day study. FIG. 39C shows an analysis of tissue samples taken from $KP^{f/f}C$ mice by western blotting for phosphorylated ERK1/2, total ERK1/2, phosphorylated AKT (S473), and total AKT. Samples were taken prior to treatment (biopsy, bx) and post-treatment (necropsy, nx) from each of three mice receiving either 31MEW44 (30 mg/kg) or vehicle dosed once daily by intraperitoneal injection. FIG. 39D shows images from representative sections of the biopsy and necropsy samples from 31MEW44 and vehicle treated mice. Hematoxylin and eosin, phosphorylated ERK1/2, total ERK1/2, and cleaved caspase-3 were detected by immunohistochemistry. FIG. 39E-FIG. 39F show an analysis of cleaved caspase-3 in $KP^{f/f}C$ mice tumor sections. FIG. 39E shows immunohistochemistry of tumor sections taken before and after treatment using an anti-cleaved caspase-3 antibody. FIG. 39F is a graph showing the quantification of the levels of cleaved caspase-3. Levels are expressed as number of cleaved caspase-3 positive cells per 40× field. Shown is an average of 3 sections taken from 3 separate mice +/− the standard deviation.

DETAILED DESCRIPTION OF THE INVENTION

Figure 1A:
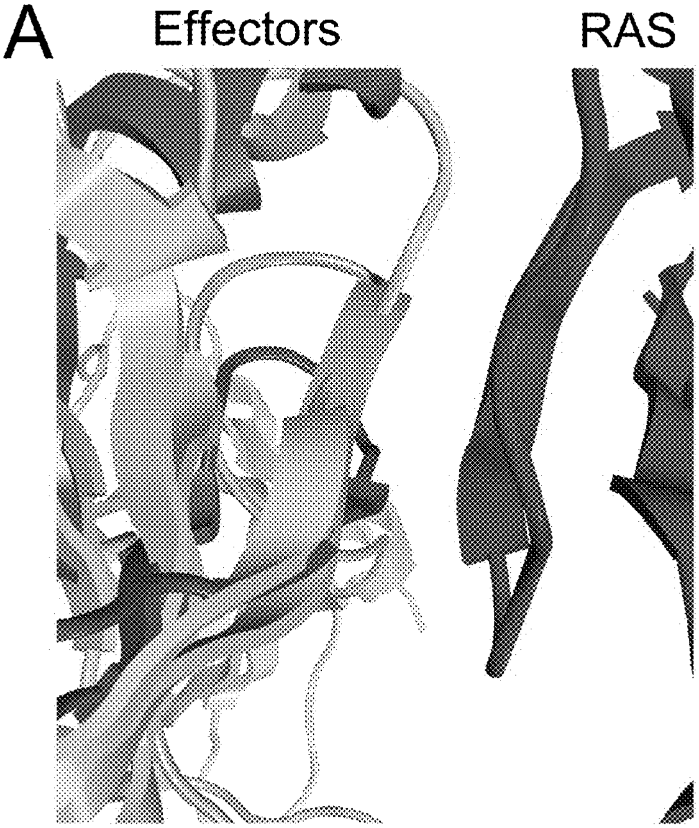
FIG. 1A-FIG. 1C show design and biochemical evaluation of inhibitors derived from a RAS-effector-inspired pharmacophore model.
Figure 1B:
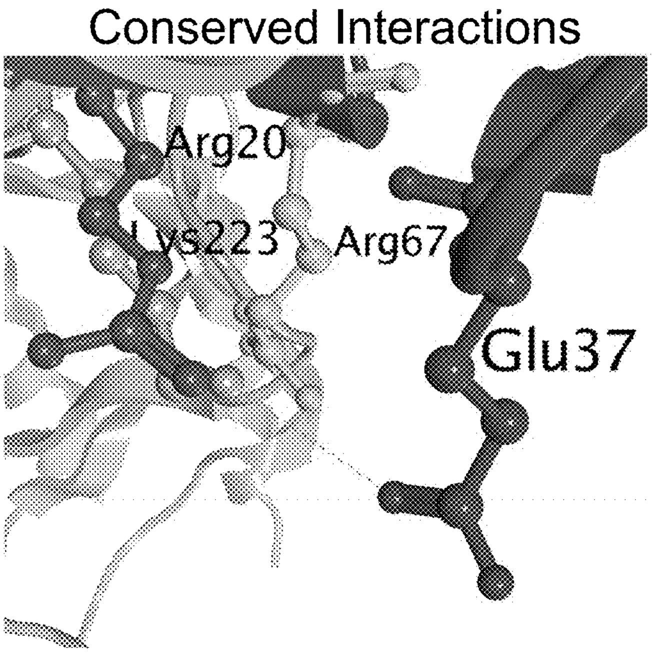
Figure 1C:
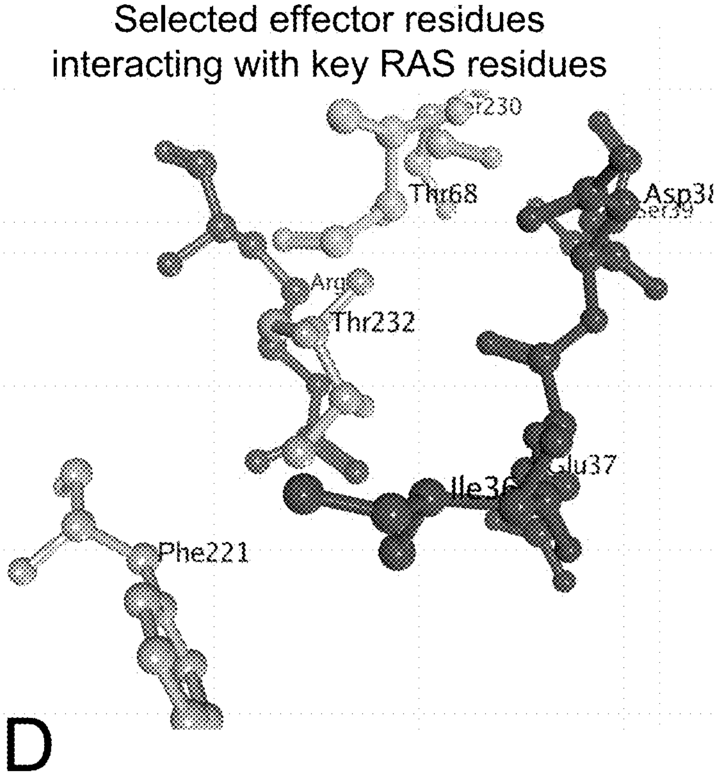
Figure 1D:
FIG. 1D-FIG. 1L show analysis of the interaction between HRAS with three effector proteins and creation of a RAS-effector-derived pharmacophore model.
Figure 1E:
Figure 1F:
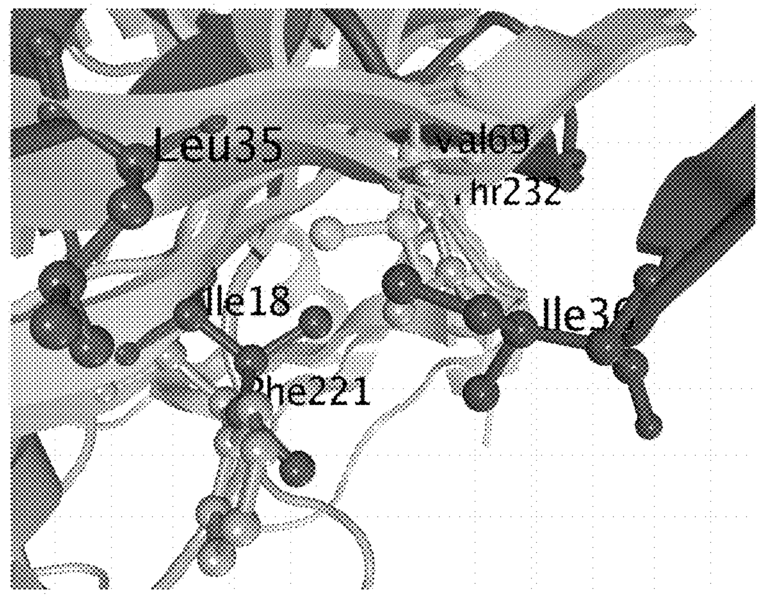
Figure 1G:
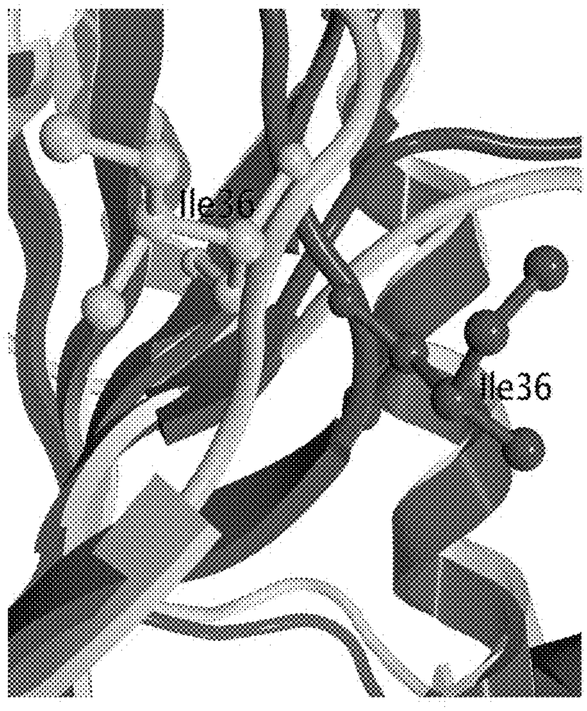
Figure 1H:
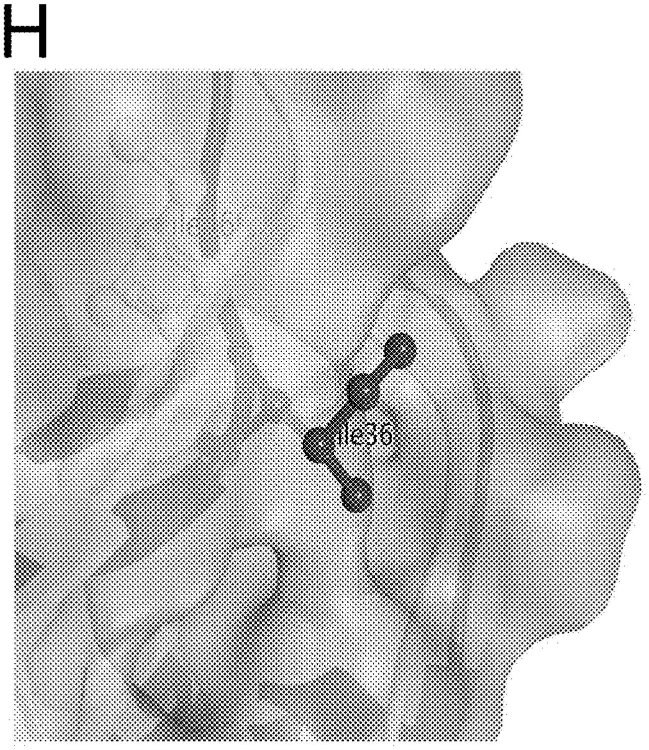
Figure 1I:
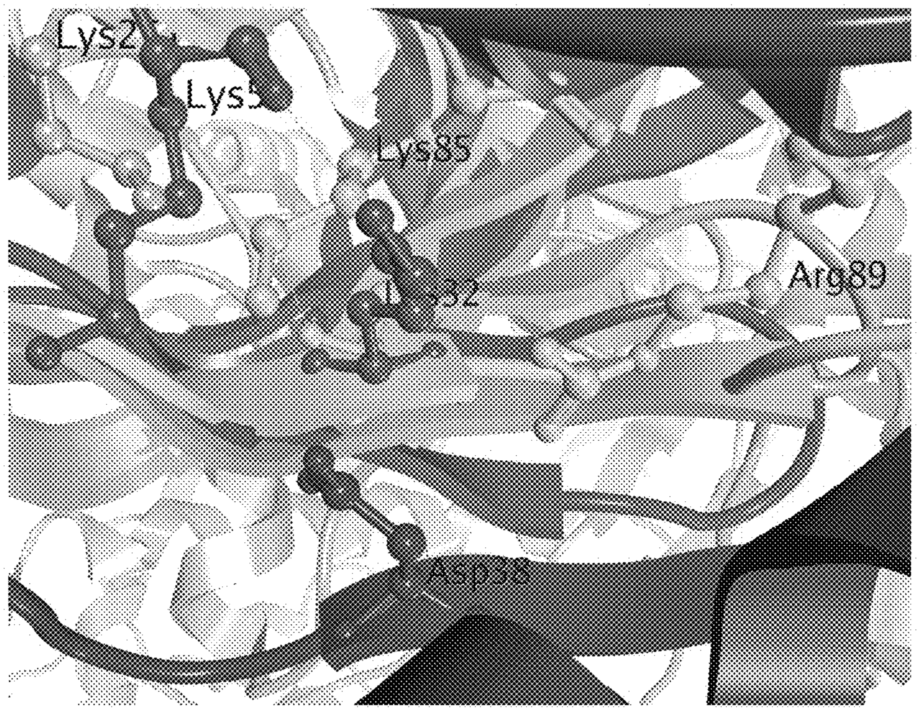
Figure 1J:
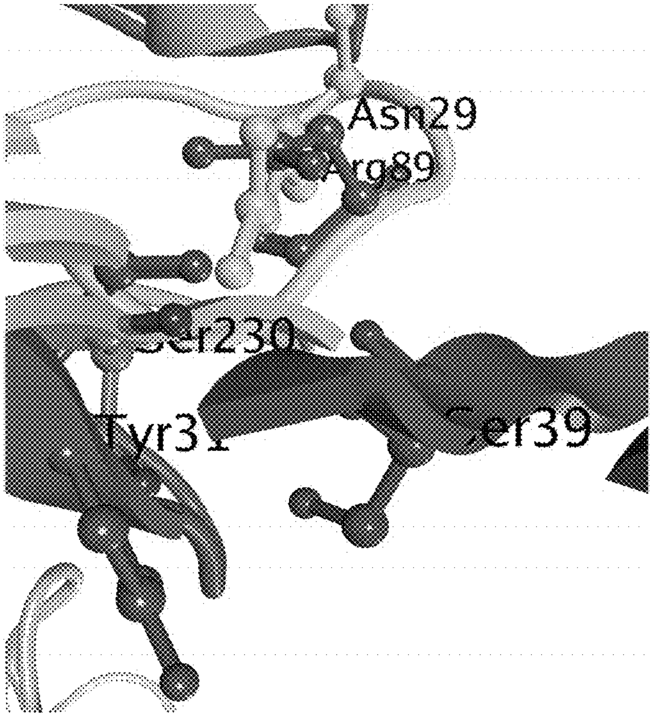
Figure 1K:
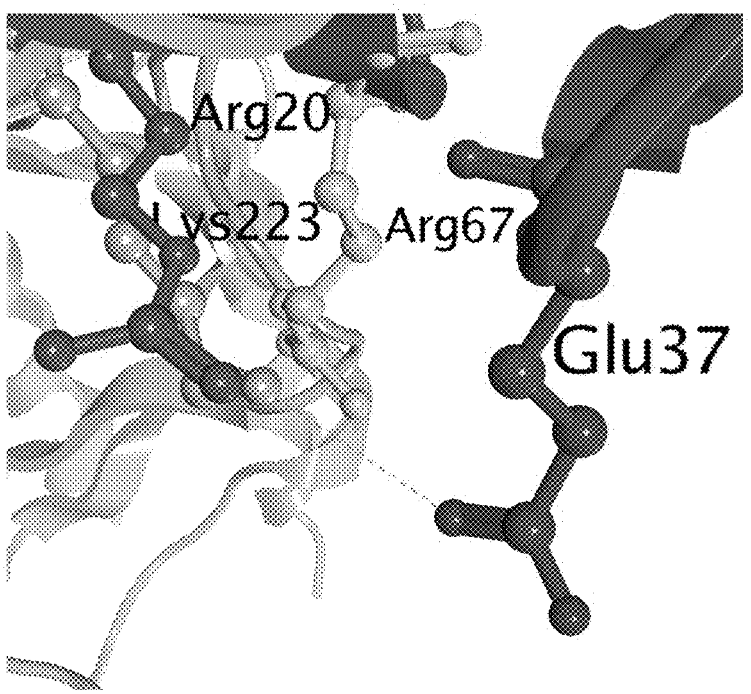
Figure 1L:
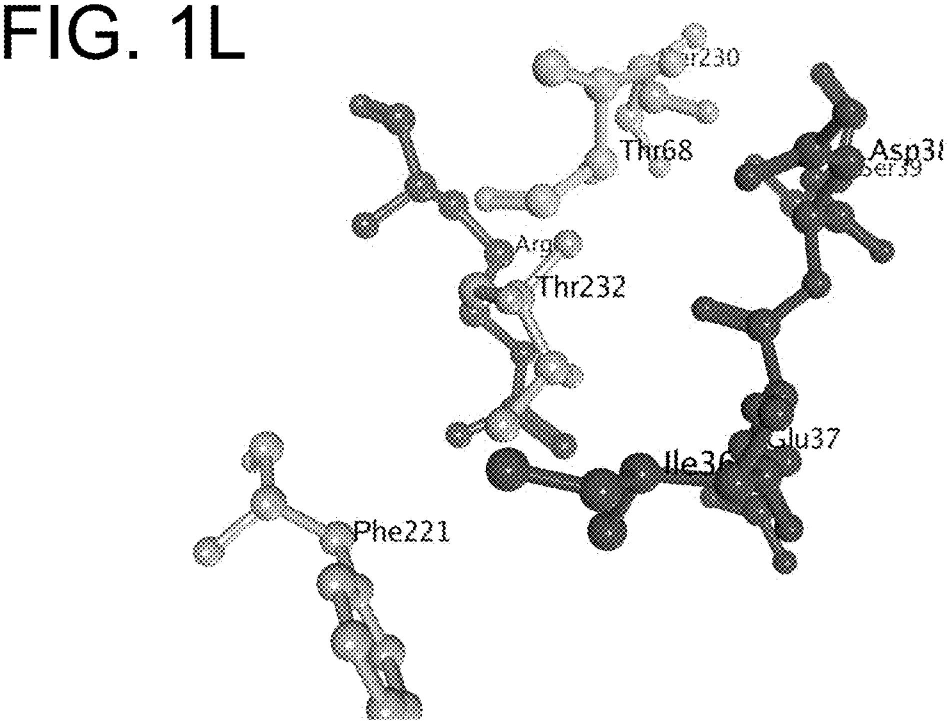
Figure 2:
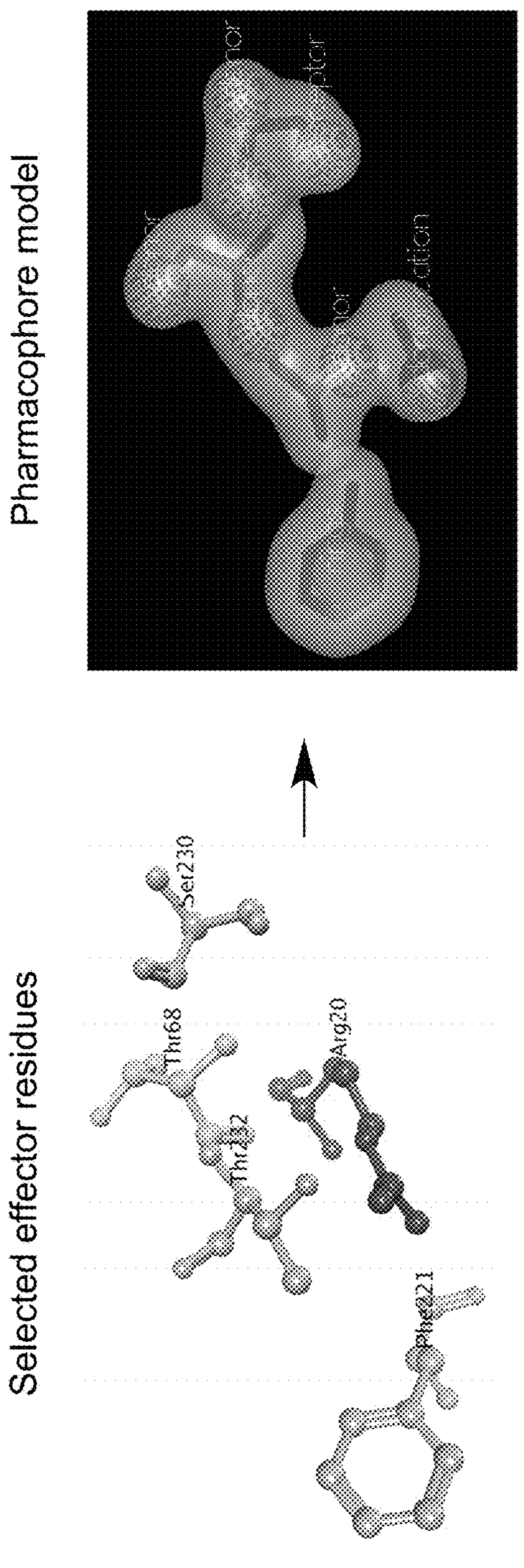
FIG. 2 shows conversion of the selected effector residues into a searchable pharmacophore model.

One embodiment of the present invention is a compound that selectively binds a RAS protein at two or more sites.

As used herein, "selectively binds", and grammatical variations thereof, means a binding reaction between two molecules that is at least two times the background and more typically more than 10 to 100 times background molecular associations under physiological conditions. Likewise, compounds "selective" for a given form of a RAS protein may exhibit molecular associations under physiological conditions at least two times the background and more typically more than 10 to 100 times background.

As used herein, RAS proteins include all RAS isoforms, which are members of a family of GTPase proteins frequently mutated in numerous cancers. The terms, "isoform" and grammatical variations thereof, refer to functionally similar proteins that have a similar, but not identical amino acid sequence, and may also be differentially post-translationally modified. RAS isoforms include, but are not limited to HRAS, KRAS, and NRAS. The HRAS, KRAS, and NRAS proteins are highly homologous to one another and have similar mechanisms of action. However, these proteins are distinct in their post-translational modifications, resulting in disparate cell trafficking routes and subcellular localization. Hence, HRAS, KRAS, and NRAS affect cellular processes in distinct ways. For example, HRAS is the most effective RAS protein at transforming fibroblasts. Furthermore, NRAS transforms hematopoietic cells most efficiently. Likewise, KRAS-deficient mice are embryonic lethal whereas NRAS or HRAS knock outs are essentially phenotypically normal (Parikh, et al., 2007). Representative HRAS, KRAS, and NRAS nucleic acid and polypeptide sequences are shown in Tables 1, 2, and 3, respectively, below.

TABLE 1

HRAS Sequences

| SEQ ID NO. | Nucleotide/Polypeptide | Organism | Gene Name | Additional Information |
|---|---|---|---|---|
| 1 | Nucleotide | *Homo sapiens* | HRAS | Variant 1 |
| 2 | Nucleotide | *Homo sapiens* | HRAS | Variant 2 |
| 3 | Nucleotide | *Homo sapiens* | HRAS | Variant 3 |

TABLE 1-continued

HRAS Sequences

| SEQ ID NO. | Nucleotide/Polypeptide | Organism | Gene Name | Additional Information |
|---|---|---|---|---|
| 4 | Polypeptide | *Homo sapiens* | HRAS | Isoform 1 |
| 5 | Polypeptide | *Homo sapiens* | HRAS | Isoform 2 |
| 6 | Nucleotide | *Mus musculus* | HRAS | Variant 1 |
| 7 | Nucleotide | *Mus musculus* | HRAS | Variant 2 |
| 8 | Nucleotide | *Mus musculus* | HRAS | Variant 3 |
| 9 | Polypeptide | *Mus musculus* | HRAS | Isoform 1 |
| 10 | Polypeptide | *Mus musculus* | HRAS | Isoform 2 |
| 11 | Nucleotide | *Rattus norvegicus* | HRAS | Variant 1 |
| 12 | Nucleotide | *Rattus norvegicus* | HRAS | Variant 2 |
| 13 | Polypeptide | *Rattus norvegicus* | HRAS | |
| 14 | Nucleotide | *Canis lupus familiaris* | HRAS | Variant 1 |
| 15 | Nucleotide | *Canis lupus familiaris* | HRAS | Variant 2 |
| 16 | Polypeptide | *Canis lupus familiaris* | HRAS | Isoform 1 |
| 17 | Polypeptide | *Canis lupus familiaris* | HRAS | Isoform 2 |
| 18 | Nucleotide | *Gallus gallus* | HRAS | |
| 19 | Polypeptide | *Gallus gallus* | HRAS | |
| 20 | Nucleotide | *Bos taurus* | HRAS | Variant 1 |
| 21 | Nucleotide | *Bos taurus* | HRAS | Variant 2 |
| 22 | Polypeptide | *Bos taurus* | HRAS | Isoform 1 |
| 23 | Polypeptide | *Bos taurus* | HRAS | Isoform 2 |

TABLE 2

KRAS Sequences

| SEQ ID NO. | Nucleotide/ Polypeptide | Organism | Gene Name | Additional Information |
|---|---|---|---|---|
| 24 | Nucleotide | *Homo sapiens* | KRAS | Variant a |
| 25 | Nucleotide | *Homo sapiens* | KRAS | Variant b |
| 26 | Polypeptide | *Homo sapiens* | KRAS | Isoform a |
| 27 | Polypeptide | *Homo sapiens* | KRAS | Isoform b |
| 28 | Nucleotide | *Mus musculus* | KRAS | |
| 29 | Polypeptide | *Mus musculus* | KRAS | |
| 30 | Nucleotide | *Rattus norvegicus* | KRAS | |
| 31 | Polypeptide | *Rattus norvegicus* | KRAS | |
| 32 | Nucleotide | *Canis lupus familiaris* | KRAS | Predicted variant 1 |
| 33 | Nucleotide | *Canis lupus familiaris* | KRAS | Predicted variant 2 |
| 34 | Polypeptide | *Canis lupus familiaris* | KRAS | Predicted isoform 1 |
| 35 | Polypeptide | *Canis lupus familiaris* | KRAS | Predicted isoform 2 |
| 36 | Nucleotide | *Gallus gallus* | KRAS | |
| 37 | Polypeptide | *Gallus gallus* | KRAS | |
| 38 | Nucleotide | *Bos taurus* | KRAS | |
| 39 | Polypeptide | *Bos taurus* | KRAS | |

TABLE 3

NRAS Sequences

| SEQ ID NO. | Nucleotide/Polypeptide | Organism | Gene Name |
|---|---|---|---|
| 40 | Nucleotide | Homo sapiens | NRAS |
| 41 | Polypeptide | *Homo sapiens* | NRAS |
| 42 | Nucleotide | *Mus musculus* | NRAS |
| 43 | Polypeptide | *Mus musculus* | NRAS |

TABLE 3-continued

NRAS Sequences

| SEQ ID NO. | Nucleotide/Polypeptide | Organism | Gene Name |
|---|---|---|---|
| 44 | Nucleotide | *Rattus norvegicus* | NRAS |
| 45 | Polypeptide | *Rattus norvegicus* | NRAS |
| 46 | Nucleotide | *Canis lupus familiaris* | NRAS |
| 47 | Polypeptide | *Canis lupus familiaris* | NRAS |
| 48 | Nucleotide | *Gallus gallus* | NRAS |
| 49 | Polypeptide | *Gallus gallus* | NRAS |
| 50 | Nucleotide | *Bos taurus* | NRAS |
| 51 | Polypeptide | *Bos taurus* | NRAS |

The term "sites", and grammatical variations thereof, means any region of a protein, including those regions comprising the exterior, solvent-exposed portion of a protein. Such a site may be a pocket where other protein species or compounds interact with the RAS protein. Sites also may become available for binding upon conformation change. For example, RAS has a pocket present only in the active form, when Y32 undergoes a conformational change in which it flips over to the other end of the nucleotide-binding site and forms a hydrogen bond with the gamma phosphate of GTP. This change unveils a pocket (termed the Y32 site) that is not present in the GDP-bound form. Compounds of the present invention may bind a RAS protein at two or more sites, including 2, 3, 4, 5, 6, 7, 8, 9, 10, or more sites on the RAS protein.

In one aspect of this embodiment, the compound selectively binds to a first site on the RAS protein that comprises at least one amino acid from the switch 1 region (near D38). As used herein, "near", as it relates to distances from certain residues, such as D38, A59, or I21, means within about 9 angstroms of the residue, including, but not limited to, within 1, 2, 3, 4, 5, 6, 7, or 8 angstroms of the residue on the RAS protein that corresponds to the amino acid number (such as 38, 59, or 21) of the human HRAS protein (SEQ ID NO. 4 or 5). The corresponding regions of HRAS from other animal, as well as NRAS, KRAS, or other RAS proteins from human and other animals, are also within the scope of the present invention and are readily determined by one skilled in the art. See, e.g., Valencia et al., 1991. "Corresponds," with reference to amino acid numbers on RAS, means consistent with, as done by sequence alignment. Multiple sequence alignment methods including pair-wise sequence alignment methods, may be used to determine the position in a RAS protein that corresponds to the positions listed above. Methods of sequence alignment are well-known. Many sequence alignment softwares are available. These programs include, e.g., BLAST, ClustalW, SEQALN, DNA Baser, MEME/MAST, BLOCKS, and eMOTIF. Preferably, the sequence alignment software is BLAST.

Preferably, the compound selectively binds to a second site on the RAS protein that comprises at least one amino acid located between the switch 1 and switch 2 regions (near A59). In another preferred aspect, the compound also selectively binds to at least one amino acid near I21 (Y32 site) of the RAS protein.

In the present invention, the switch 1 region, located near the D38 site, includes residues 30-40 corresponding to the human RAS protein (e.g., SEQ ID NOs: 4, 5, 26, 27, or 41). The D38 site is one region of conserved interaction between RAS proteins and RAF, RALGDS, and PI3K. The switch 2 region is near A59 and comprises residues 60-70 corresponding to the human RAS protein (e.g., SEQ ID NOs: 4, 5, 26, 27, or 41). The A59 site is located between the switch 1 and switch 2 regions and is adjacent to the D38 site.

As used herein, "at least one amino acid" from any of the regions or locations of a RAS protein disclosed herein include 1, 2, 3, 4, 5, 6, 7, 8, 9, 10, or more amino acids, up to, and including, the number of amino acids comprising the entire designated region or location of RAS.

In another aspect of this embodiment, the compound is selective for a GTP-bound RAS protein. As disclosed further in the Examples, the GTP-bound, active form of a RAS protein contains a pocket, termed the "Y32 site", that is not present in the GDP-bound, inactive form of RAS protein. The Y32 site is located near residue I21 of the human RAS protein (e.g., SEQ ID NOs: 4, 5, 26, 27, or 41). Residue Y32 undergoes a conformation change in the active, GTP-bound form of RAS protein, revealing the aforementioned pocket. Therefore, oncogenic RAS isoforms, and the cancer cells that express them, may be targeted by compounds selective for GTP-bound RAS at, for example, the Y32 site. Preferably, compounds of the present invention may also be selective for a non-GDP-bound form of the RAS protein. A non-GDP-bound form of a RAS protein may be, for example, a GTP-bound form of a RAS protein or a RAS protein not bound to any nucleotides.

In a further aspect of this embodiment, the RAS protein is an isoform selected from the group consisting of HRAS, KRAS, NRAS, and combinations thereof.

In an additional aspect of this embodiment, the RAS protein is an oncogenic mutant. As used herein, an "oncogenic mutant" is a RAS variant that contains an alteration in the amino acid sequence and has the potential to cause a cell to become cancerous. In the context of RAS protein, an oncogenic mutant may be a constitutively active, continually GTP-bound isoform of RAS protein. Preferably, the RAS protein is an oncogenic mutant selected from the group consisting of $HRAS^{G12D}$, $KRAS^{G12D}$, $NRAS^{Q61K}$, $NRAS^{G13V}$, and $NRAS^{G13D}$, the mutations based on the human isoform for the respective protein, e.g., SEQ ID NO: 4, 5, 26, 27, or 41. In terms of oncogenicity, mutations at residues 12-13 of a RAS protein render RAS's GTPase portion insensitive to activation by GAPs, while mutations at residue 61 affect the enzymatic active site of a RAS protein directly, thereby essentially inactivating the GTPase activity of a RAS protein.

In another aspect of this embodiment, the compound selectively binds to at least one amino acid near D38, A59, and optionally I21 (Y32 site) in a RAS protein. Preferably, the compound comprises a region A that binds to at least one amino acid near D38 on a RAS protein and comprises a heterocycle with at least one ring nitrogen.

As used herein, the term "heterocycle" means substituted or unsubstituted non aromatic ring structures. Preferably the heterocycle comprises 3 to 8 membered rings, and at least one heteroatom, preferably one to four heteroatoms, more preferably one or two heteroatoms. Such heterocycles may include at least one ring nitrogen. The term "heterocycle" also includes polycyclic ring systems having two or more cyclic rings in which two or more carbons are common to two adjoining rings wherein at least one of the rings is heterocyclic, e.g., the other cyclic ring(s) can be cycloalkyls, cycloalkenyls, cycloalkynyls, aryls, heteroaryls, and/or heterocyclyls. Heterocycle groups of the present invention include, for example, piperidine, piperazine, pyrrolidine, morpholine, lactones, lactams, and the like.

The term "heteroatom" as used herein means an atom of any element other than carbon or hydrogen. Preferred heteroatoms are nitrogen, oxygen, and sulfur; more preferably, nitrogen and oxygen.

In one preferred embodiment, the A region of the compound comprises a fragment having formula (I):

(I)

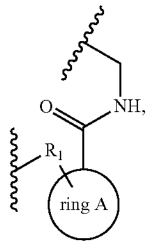

wherein ring A is a heterocycle with at least one ring nitrogen, and $R_1$ is selected from the group consisting of no atom, amine, and $C_{1-4}$ aliphatic. More preferably, the A region of the compound is selected from the group consisting of:

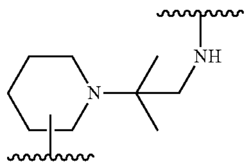

,

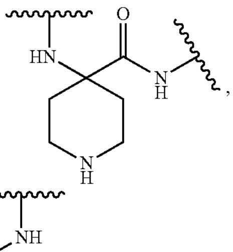

, and

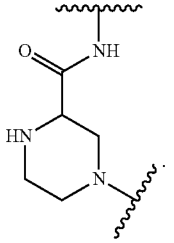

The terms "amine" and "amino" are art-recognized and refer to both unsubstituted and substituted amines and salts thereof, e.g., a moiety that can be represented by

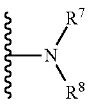

or

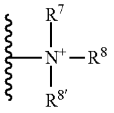

wherein $R^7$, $R^8$, and $R^{8'}$ each independently represent a hydrogen or a hydrocarbyl group, or $R^7$ and $R^8$ taken together with the N atom to which they are attached complete a heterocycle having from 4 to 8 atoms in the ring structure. The term "primary" amine means only one of $R^7$ and $R^8$ or one of $R^7$, $R^8$, and $R^{8'}$ is a hydrocarbyl group. Secondary amines have two hydrocarbyl groups bound to N. In tertiary amines, all three groups, $R^7$, $R^8$, and $R^{8'}$, are replaced by hydrocarbyl groups.

The term "$C_{x-y}$" when used in conjunction with a chemical moiety, such as, alkyl, alkenyl, or alkoxy is meant to include groups that contain from x to y carbons in the chain.

For example, the term "$C_{x-y}$alkyl" means substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "aliphatic", as used herein, means a group composed of carbon and hydrogen atoms that does not contain aromatic rings. Accordingly, aliphatic groups include alkyl, alkenyl, alkynyl, and carbocyclyl groups. A preferred $C_{1-4}$ aliphatic is a vinyl moiety.

The term "alkyl" means the radical of saturated aliphatic groups that does not have a ring structure, including straight-chain alkyl groups, and branched-chain alkyl groups. In certain embodiments, a straight chain or branched chain alkyl has 4 or fewer carbon atoms in its backbone (e.g., $C_1$-$C_4$ for straight chains, $C_3$-$C_4$ for branched chains).

The term "alkenyl", as used herein, means an aliphatic group containing at least one double bond.

The term "alkynyl", as used herein, means an aliphatic group containing at least one triple bond.

In another preferred embodiment, the compound comprises a region B that binds to at least one amino acid near A59 on the RAS protein and comprises an indole. The term "indole" is art-recognized and means any compound containing a benzene ring fused to a pyrrole ring.

More preferably, the B region of the compound comprises a structure of formula (III):

(III)

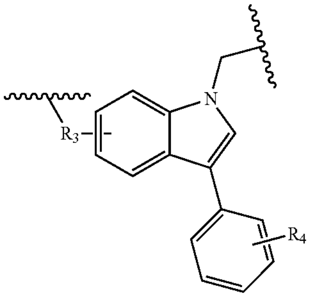

wherein $R_3$ is selected from the group consisting of heterocycle, aryl, and amine, which heterocycle, aryl, and amine may be optionally substituted with the group selected from halide, $C_{1-4}$ aliphatic, and combinations thereof; and $R_4$ is selected from the group consisting of no atom, H, aryl, halide, $C_{1-4}$ aliphatic —O—$C_{1-4}$alkyl wherein the alkyl is optionally substituted with the group consisting of halide, ether, and a combination thereof.

The term "aryl" as used herein includes substituted or unsubstituted single-ring aromatic groups in which each atom of the ring is carbon. Preferably the ring is a 3- to 8-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "substituted" means moieties having substituents replacing a hydrogen on one or more carbons of the backbone. It will be understood that "substitution" or "substituted with" includes the implicit proviso that such substitution is in accordance with the permitted valence of the substituted atom and the substituent, and that the substitution results in a stable compound, e.g., which does not spontaneously undergo transformation such as by rearrangement, cyclization, elimination, etc. The permissible substituents can be one or more and the same or different for appropriate organic compounds.

As used herein, a "halide" means a halogen atom such as fluorine, chlorine, bromine, iodine, or astatine.

In another preferred embodiment, the B region of the compound is selected from the group consisting of

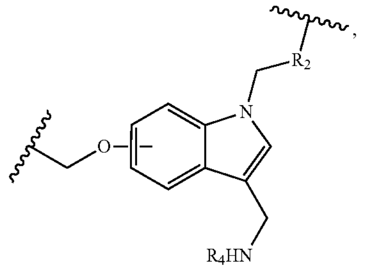

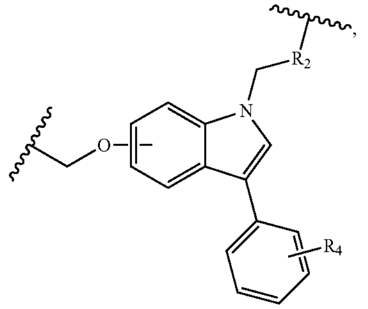

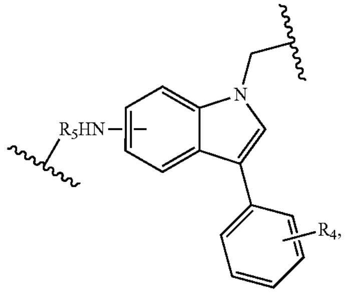

and

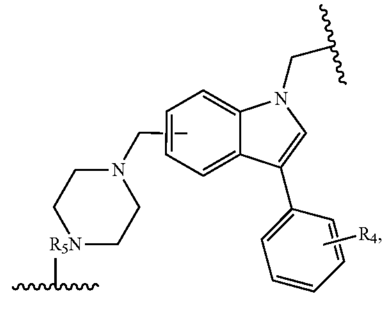

wherein $R_2$ and $R_5$ are independently selected from the group consisting of no atom, aryl, and $C_{1-4}$ aliphatic; and $R_4$ is selected from the group consisting of no atom, H, aryl, halide, $C_{1-4}$ aliphatic, —O—$C_{1-4}$alkyl wherein the alkyl is optionally substituted with the group consisting of halide, ether, and a combination thereof.

In another preferred embodiment, the compound comprises a region C that binds to at least one amino acid near I21 (Y32 site) of the RAS protein and comprises an aromatic ring. More preferably, the C region of the compound comprises a structure of formula (IV):

(IV)

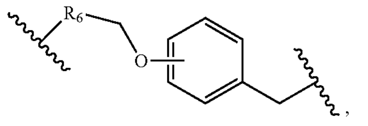

wherein $R_6$ is selected from the group consisting of no atom, H, alkyl, and aryl, wherein the alkyl is optionally substituted with the group consisting of halide, ether, and a combination thereof, and the aryl is optionally substituted with the group consisting of halide, ether, $C_{1-4}$alkyl, and a combination thereof.

As used herein, an "aromatic ring" is an aryl or a heteroaryl. The term "heteroaryl" includes substituted or unsubstituted aromatic single ring structures, preferably 3- to 8-membered rings, more preferably 5- to 7-membered rings, even more preferably 5- to 6-membered rings, whose ring structures include at least one heteroatom, preferably one to four heteroatoms, more preferably one or two heteroatoms. The term "heteroaryl" also includes polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "ether", as used herein, means a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

In a further aspect of this embodiment, the compound has a structure of formula (V):

(V)

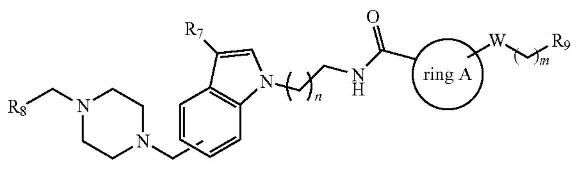

wherein:

$R_7$ is selected from the group consisting of H, halide, $C_{1-4}$ aliphatic, and aryl, wherein the aryl is optionally substituted with one or more groups consisting of halide, ether, $C_{1-4}$alkyl, —O—$C_{1-4}$alkyl and a combination thereof, wherein the alkyl is optionally substituted with one or more groups consisting of halide, ether, and a combination thereof;

$R_8$ is selected from the group consisting of no atom, H, alkyl, aryl, and $C_{1-4}$alkyl-O-aryl wherein the alkyl is optionally substituted with the group consisting of halide, ether, and a combination thereof, and the aryl is optionally substituted with one or more groups consisting of halide, ether, $C_{1-4}$alkyl, and a combination thereof;

$R_9$ is selected from the group consisting of no atom, H, $C_{1-4}$alkyl, and aryl optionally substituted with the group consisting of ether, halide, and a combination thereof;

W is selected from the group consisting of no atom and NH;

m and n are independently selected from the group consisting of an integer between 0-5; and ring A is a heterocycle with at least 1 ring nitrogen and optionally substituted with $C_{1-4}$alkyl or a halide, or a crystalline form, hydrate, or pharmaceutically acceptable salt thereof.

As used herein, an "integer between 0-5" means 0, 1, 2, 3, 4, or 5.

In an additional aspect of this embodiment, the compound has a structure of formula (VI):

(VI)

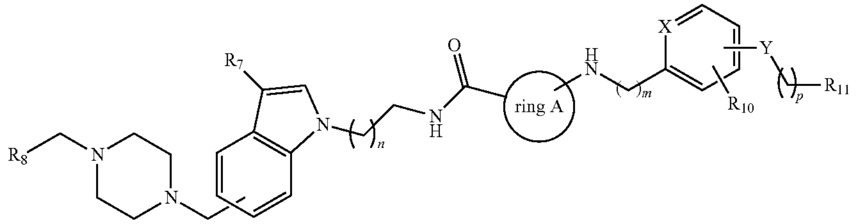

wherein:

$R_7$ is selected from the group consisting of H, halide, $C_{1-4}$ aliphatic, and aryl, wherein the aryl is optionally substituted with one or more groups consisting of halide, ether, $C_{1-4}$alkyl, —O—$C_{1-4}$alkyl, and a combination thereof, wherein the alkyl is optionally substituted with one or more groups consisting of halide, ether, and a combination thereof;

$R_8$ and $R_{11}$ are independently selected from the group consisting of no atom, H, alkyl, aryl and $C_{1-4}$alkyl-O-aryl, wherein the alkyl is optionally substituted with the group consisting of halide, ether, and a combination thereof, and the aryl is optionally substituted with one or more groups consisting of halide, ether, $C_{1-4}$alkyl, —O—$C_{1-4}$alkyl, and a combination thereof, wherein the alkyl is optionally substituted with the group consisting of halide, ether, and a combination thereof;

$R_{10}$ is selected from the group consisting of no atom, H, halide, $C_{1-4}$ aliphatic, and —O—$C_{1-4}$alkyl;

X is selected from the group consisting of CH and N;

Y is selected from the group consisting of no atom and O;

m, n, and p are independently selected from the group consisting of an integer between 0-5; and ring A is a heterocycle with at least 1 ring nitrogen and optionally substituted with $C_{1-4}$alkyl or a halide, or a crystalline form, hydrate, or pharmaceutically acceptable salt thereof.

In another aspect of this embodiment, the compound is selected from the group consisting of

31MEW44

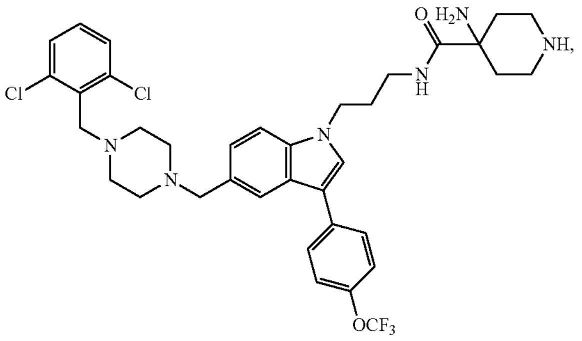

34MEW43

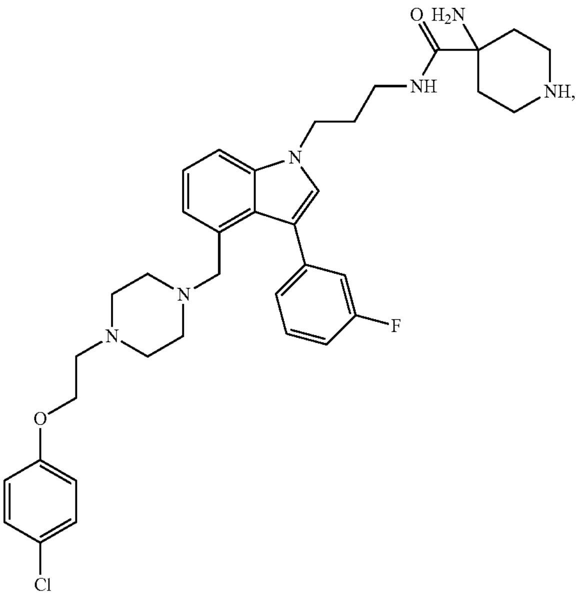

-continued

34MEW95

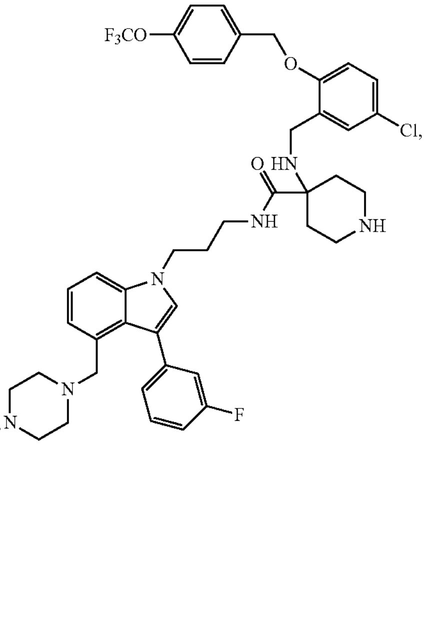

36MEW3

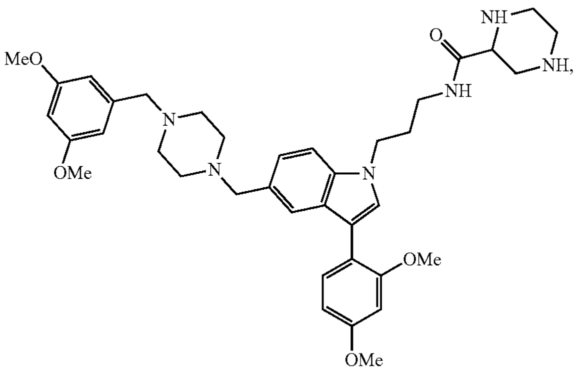

32MEW56

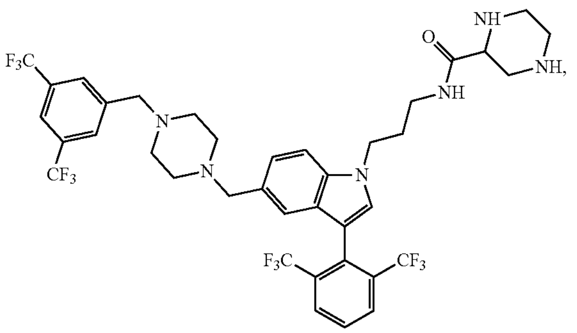

-continued
34MEW45
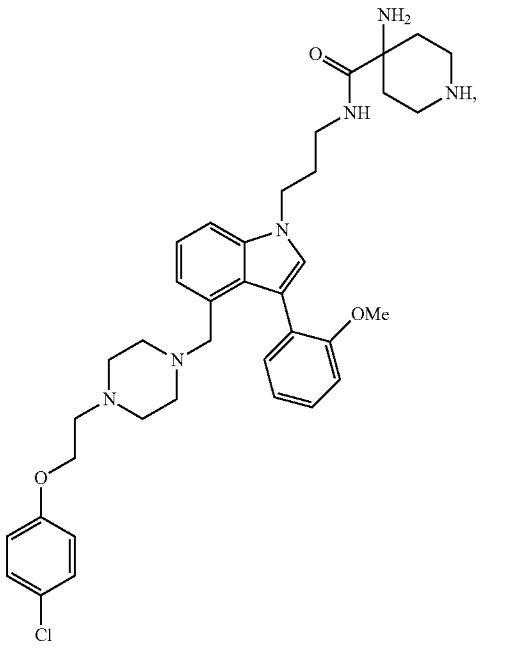
-continued
43MEW73
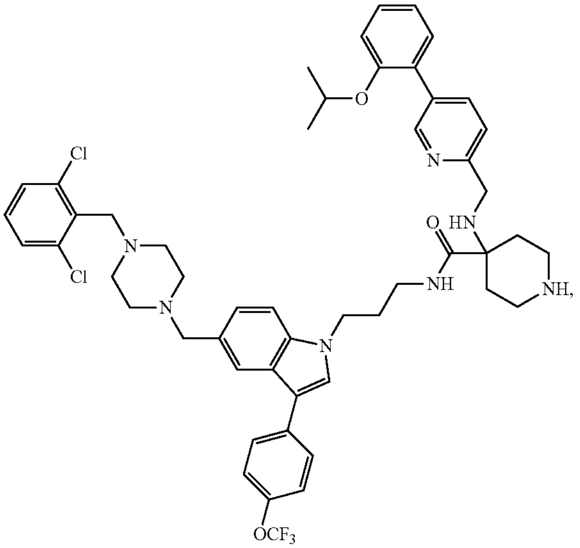
43MEW65
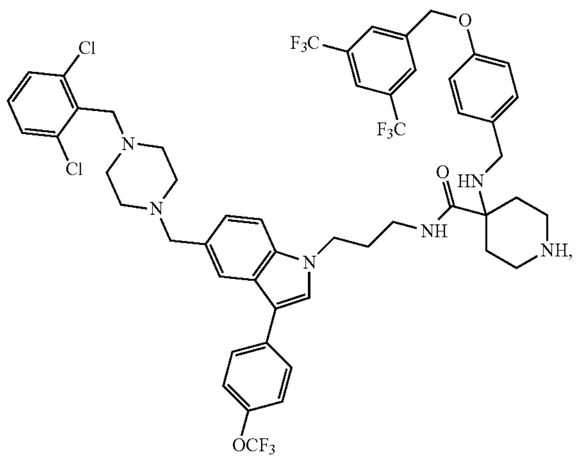
43MEW63
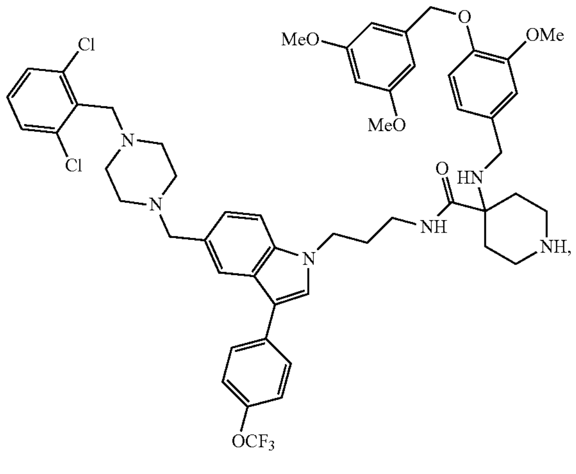

-continued

35MEW12

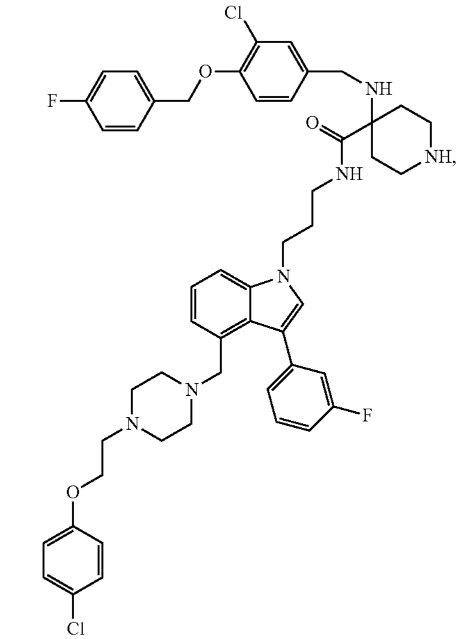

and crystalline forms, hydrates, or pharmaceutically acceptable salts thereof.

In one preferred embodiment, the compound is

31MEW44

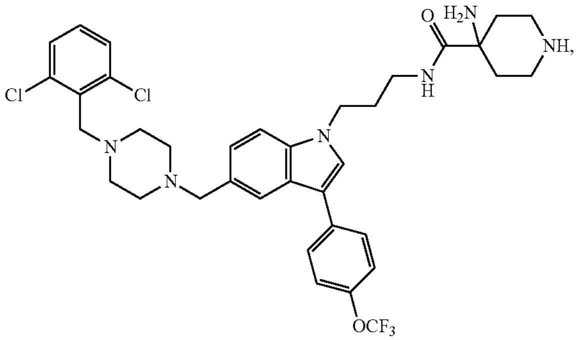

or a crystalline form, hydrate, or pharmaceutically acceptable salt thereof.

In another preferred embodiment, the compound is

34MEW43

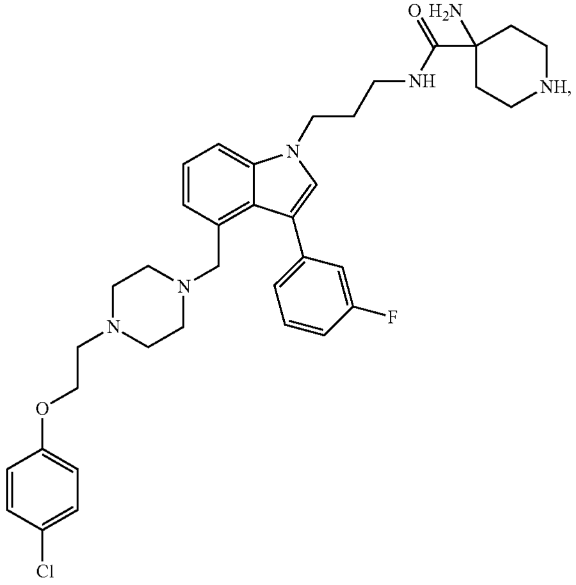

or a crystalline form, hydrate, or pharmaceutically acceptable salt thereof.

In a further preferred embodiment, the compound is

34MEW95

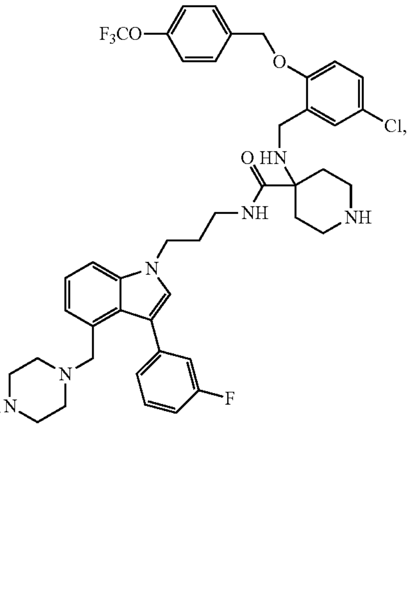

or a crystalline form, hydrate, or pharmaceutically acceptable salt thereof.

Another embodiment of the present invention is a compound selected from the group consisting of

31MEW78

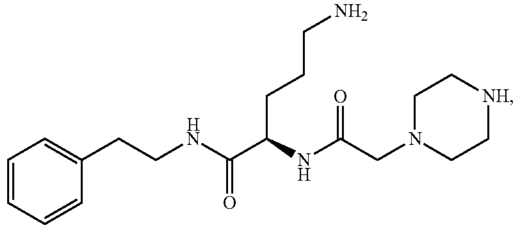

31MEW79

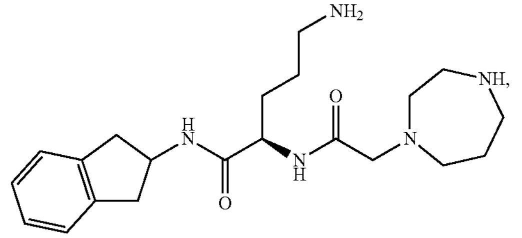

and crystalline forms, hydrates, or pharmaceutically acceptable salts thereof.

A further embodiment of the present invention is a compound having the structure of formula (V):

(V)

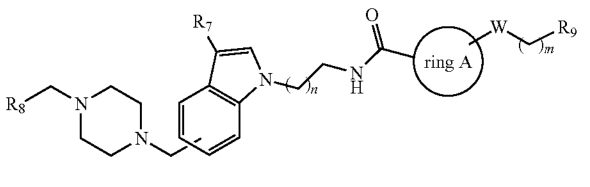

wherein:

$R_7$ is selected from the group consisting of H, halide, $C_{1-4}$ aliphatic, and aryl, wherein the aryl is optionally substituted with one or more groups consisting of halide, ether, $C_{1-4}$alkyl, —O—$C_{1-4}$alkyl and a combination thereof, wherein the alkyl is optionally substituted with one or more groups consisting of halide, ether, and a combination thereof;

$R_8$ is selected from the group consisting of no atom, H, alkyl, aryl, and $C_{1-4}$alkyl-O-aryl wherein the alkyl is optionally substituted with the group consisting of halide, ether, and a combination thereof, and the aryl is optionally substituted with one or more groups consisting of halide, ether, $C_{1-4}$alkyl, and a combination thereof;

$R_9$ is selected from the group consisting of no atom, H, $C_{1-4}$alkyl, and aryl optionally substituted with the group consisting of ether, halide, and a combination thereof;

W is selected from the group consisting of no atom and NH;m and n are independently selected from the group consisting of an integer between 0-5; and ring A is a heterocycle with at least 1 ring nitrogen and optionally substituted with $C_{1-4}$alkyl or a halide, or a crystalline form, hydrate, or pharmaceutically acceptable salt thereof.

An additional embodiment of the present invention is a compound having the structure of formula (VI):

(VI)

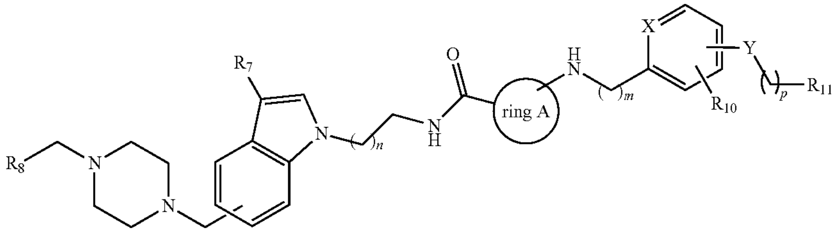

wherein:

$R_7$ is selected from the group consisting of H, halide, $C_{1-4}$ aliphatic, and aryl, wherein the aryl is optionally substituted with one or more groups consisting of halide, ether, $C_{1-4}$alkyl, —O—$C_{1-4}$alkyl, and a combination thereof, wherein the alkyl is optionally substituted with one or more groups consisting of halide, ether, and a combination thereof;

$R_8$ and $R_{11}$ are independently selected from the group consisting of no atom, H, alkyl, aryl and $C_{1-4}$alkyl-O-aryl, wherein the alkyl is optionally substituted with the group consisting of halide, ether, and a combination thereof, and the aryl is optionally substituted with one or more groups consisting of halide, ether, $C_{1-4}$alkyl, —O—$C_{1-4}$alkyl, and a combination thereof, wherein the alkyl is optionally substituted with the group consisting of halide, ether, and a combination thereof;

$R_{10}$ is selected from the group consisting of no atom, H, halide, $C_{1-4}$ aliphatic, and —O—$C_{1-4}$alkyl;

X is selected from the group consisting of CH and N;

Y is selected from the group consisting of no atom and 0;

m, n, and p are independently selected from the group consisting of an integer between 0-5; and ring A is a heterocycle with at least 1 ring nitrogen and optionally substituted with $C_{1-4}$alkyl or a halide, or a crystalline form, hydrate, or pharmaceutically acceptable salt thereof.

Another embodiment of the present invention is a compound selected from the group consisting of

31MEW44

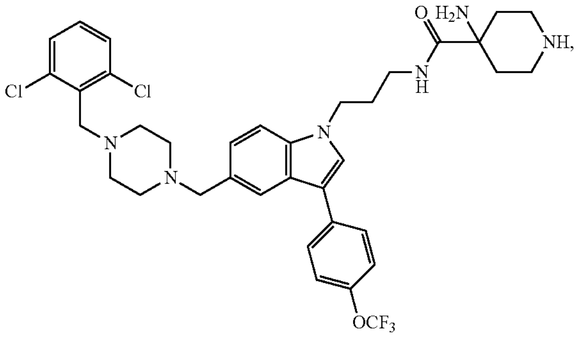

34MEW43

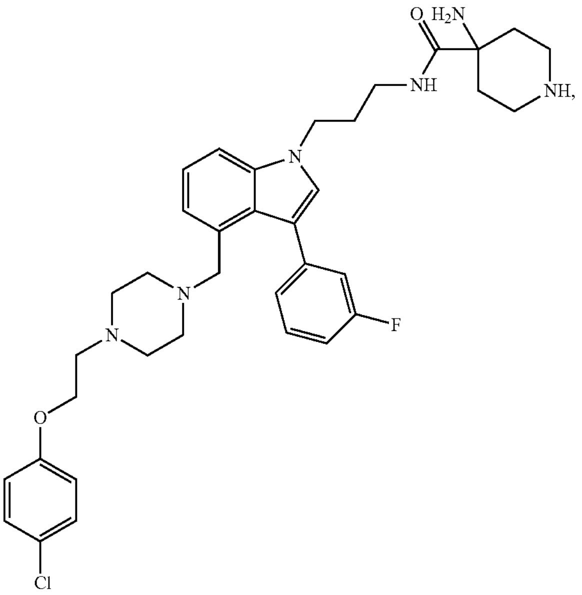

34MEW95

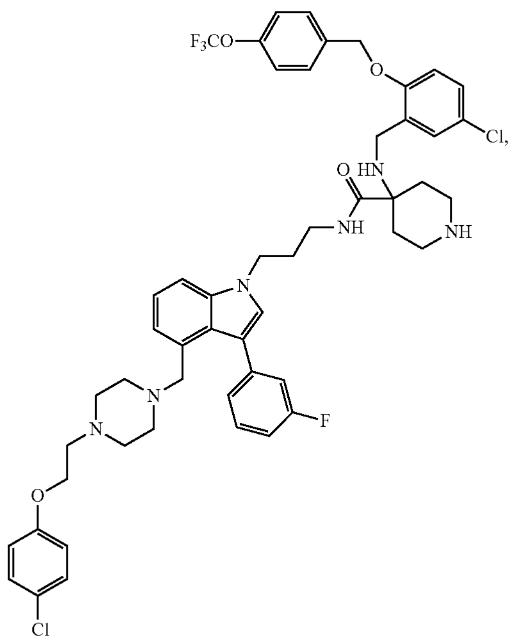

and crystalline forms, hydrates, or pharmaceutically acceptable salts thereof.

A further embodiment of the present invention is a compound having the structure:

31MEW44

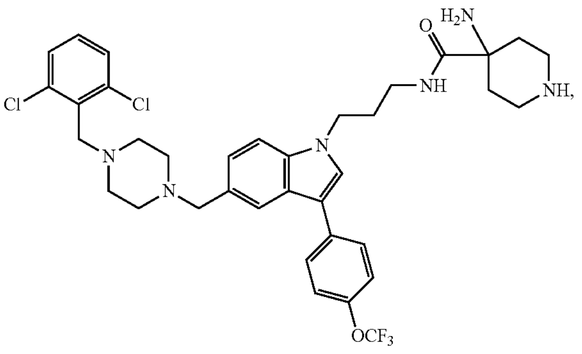

or a crystalline form, hydrate, or pharmaceutically acceptable salt thereof.

An additional embodiment of the present invention is a compound having the structure:

34MEW43

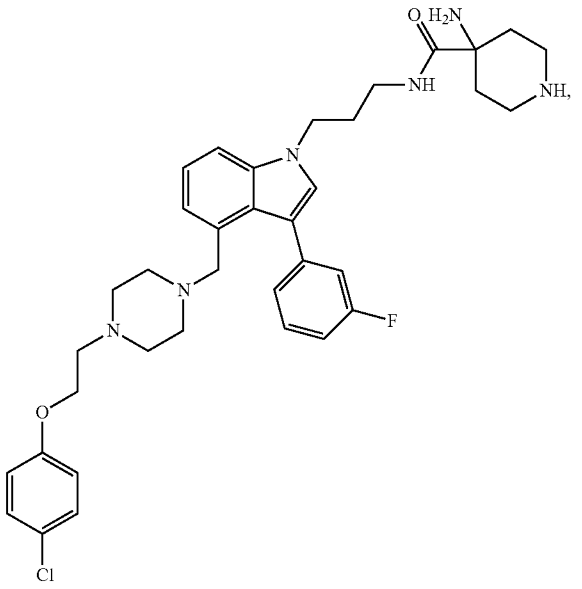

or a crystalline form, hydrate, or pharmaceutically acceptable salt thereof.

Another embodiment of the present invention is a compound having the structure:

34MEW95

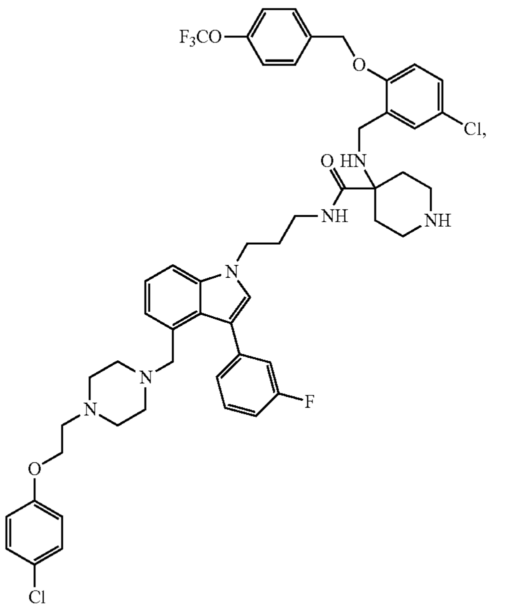

or a crystalline form, hydrate, or pharmaceutically acceptable salt thereof.

A further embodiment of the present invention is a pharmaceutical composition. The pharmaceutical composition comprises a pharmaceutically acceptable carrier and any compound disclosed herein. Preferably, the compound has the structure of formula (V), formula (VI), or a crystalline form, hydrate, or pharmaceutically acceptable salt thereof. More preferably, the compound is 34MEW43, 31MEW44, 34MEW95, or a crystalline form, hydrate, or pharmaceutically acceptable salt thereof.

An additional embodiment of the present invention is a method for ameliorating or treating the effects of a disease associated with altered RAS signaling in a subject. The method comprises administering to the subject an effective amount of any compound disclosed herein.

As used herein, the terms "ameliorate", "ameliorating" and grammatical variations thereof mean to decrease the severity of the symptoms of a disease in a subject.

As used herein, the terms "treat," "treating," "treatment" and grammatical variations thereof mean subjecting an individual subject to a protocol, regimen, process or remedy, in which it is desired to obtain a physiologic response or outcome in that subject, e.g., a patient. In particular, the methods and compositions of the present invention may be used to slow the development of disease symptoms or delay the onset of the disease or condition, or halt the progression of disease development. However, because every treated subject may not respond to a particular treatment protocol, regimen, process or remedy, treating does not require that the desired physiologic response or outcome be achieved in each and every subject or subject population, e.g., patient population. Accordingly, a given subject or subject population, e.g., patient population, may fail to respond or respond inadequately to treatment.

As used herein, a "subject" is a mammal, preferably, a human. In addition to humans, categories of mammals within the scope of the present invention include, for example, primates, farm animals, domestic animals, laboratory animals, etc. Some examples of agricultural animals include cows, pigs, horses, goats, etc. Some examples of domestic animals include dogs, cats, etc. Some examples of laboratory animals include primates, rats, mice, rabbits, guinea pigs, etc.

As used herein, the phrase "altered RAS signaling" means any deviation in the activity of a RAS protein from that typically observed from wild-type RAS protein in a given tissue. Altered RAS signaling may include, for example, increased RAS signaling or decreased RAS signaling. Altered RAS signaling may be caused by one or more mutations in the RAS protein, such as the oncogenic mutations disclosed above. For example, certain RAS protein mutations may enable RAS protein to constitutively exist in its GTP-bound conformation, either by discouraging interaction of RAS protein with various GAP proteins or by disabling the GTPase activity of RAS protein.

In the present invention, the disease associated with altered RAS signaling may be a cancer, a neurological disorder, a metabolic disorder, an immunological disorder, an inflammatory disorder, and a developmental disorder. Preferably, the disease is selected from the group consisting of autism, rasopathies, neurofibromatosis type 1, Noonan syndrome, Costello syndrome, cardiofaciocutaneous syndrome, hereditary gingival fibromatosis type 1, Legius syndrome, Leopard syndrome, diabetic retinopathy, diabetes, hyperinsulinemia, chronic idiopathic urticarial, autoimmune lymphoproliferative syndrome, and capillary malformation-arteriovenous malformation.

In the present invention, cancers include both solid and hemotologic cancers. Non-limiting examples of solid cancers include adrenocortical carcinoma, anal cancer, bladder cancer, bone cancer (such as osteosarcoma), brain cancer, breast cancer, carcinoid cancer, carcinoma, cervical cancer, colon cancer, endometrial cancer, esophageal cancer, extrahepatic bile duct cancer, Ewing family of cancers, extracranial germ cell cancer, eye cancer, gallbladder cancer, gastric cancer, germ cell tumor, gestational trophoblastic tumor, head and neck cancer, hypopharyngeal cancer, islet cell carcinoma, kidney cancer, large intestine cancer, laryngeal cancer, leukemia, lip and oral cavity cancer, liver cancer, lung cancer, lymphoma, malignant mesothelioma, Merkel cell carcinoma, mycosis fungoides, myelodysplastic syndrome, myeloproliferative disorders, nasopharyngeal cancer, neuroblastoma, oral cancer, oropharyngeal cancer, osteosarcoma, ovarian epithelial cancer, ovarian germ cell cancer, pancreatic cancer, paranasal sinus and nasal cavity cancer, parathyroid cancer, penile cancer, pituitary cancer, plasma cell neoplasm, prostate cancer, rhabdomyosarcoma, rectal cancer, renal cell cancer, transitional cell cancer of the renal pelvis and ureter, salivary gland cancer, Sezary syndrome, skin cancers (such as cutaneous t-cell lymphoma, Kaposi's sarcoma, mast cell tumor, and melanoma), small intestine cancer, soft tissue sarcoma, stomach cancer, testicular cancer, thymoma, thyroid cancer, urethral cancer, uterine cancer, vaginal cancer, vulvar cancer, and Wilms' tumor.

Examples of hematologic cancers include, but are not limited to, leukemias, such as adult/childhood acute lymphoblastic leukemia, adult/childhood acute myeloid leukemia, chronic lymphocytic leukemia, chronic myelogenous leukemia, and hairy cell leukemia, lymphomas, such as AIDS-related lymphoma, cutaneous T-cell lymphoma, adult/childhood Hodgkin lymphoma, mycosis fungoides, adult/childhood non-Hodgkin lymphoma, primary central nervous system lymphoma, Sezary syndrome, cutaneous T-cell lymphoma, and Waldenstrom macroglobulinemia, as well as other proliferative disorders such as chronic myeloproliferative disorders, Langerhans cell histiocytosis, multiple myeloma/plasma cell neoplasm, myelodysplastic syndromes, and myelodysplastic/myeloproliferative neoplasms.

Preferably, the cancer is selected from the group consisting of pancreatic cancer, colorectal cancer, lung cancer, skin cancer, urinary bladder cancer, thyroid cancer, hematopoietic cancer, prostate cancer, breast cancer, liver cancer, soft tissue cancer, leukemia and bone cancer.

In a preferred aspect of this embodiment, the cancer is selected from the group consisting of pancreatic cancer, colorectal cancer, fibrosarcoma, breast cancer, lung cancer, skin cancer, leukemia and bone cancer.

Another embodiment of the present invention is a method for ameliorating or treating the effects of a disease associated with altered RAS signaling in a subject. The method comprises administering to the subject an effective amount of any pharmaceutical composition disclosed herein.

Suitable and preferred subjects, diseases, and pharmaceutical composition are as disclosed herein.

A further embodiment of the present invention is a method for effecting cancer cell death. The method comprises contacting a cancer cell with an effective amount of any compound disclosed herein. In this embodiment, "contacting" means bringing the compound into close proximity to the cancer cell. This may be accomplished using conventional techniques of drug delivery to mammals or in the in vitro situation by, e.g., providing the compound to a culture media in which the cancer cell is located.

Suitable and preferred compounds are as disclosed herein. In this embodiment, effecting cancer cell death may be accomplished in cancer cells having various mutational backgrounds as disclosed above.

The methods of this embodiment, which may be carried out in vitro or in vivo, may be used to effect cancer cell death by, e.g., killing cancer cells, in cells of the types of cancer disclosed herein.

In one aspect of this embodiment, the cancer cell is a mammalian cancer cell. Preferably, the mammalian cancer cell is obtained from a mammal selected from the group consisting of humans, primates, farm animals, and domestic animals and laboratory animals. More preferably, the mammalian cancer cell is a human cancer cell.

Another embodiment of the present invention is a kit for treating or ameliorating the effects of a disease related to altered RAS signaling in a subject in need thereof. The kit comprises an effective amount of any compound or pharmaceutical composition disclosed herein, packaged together with instructions for its use.

Suitable and preferred subjects, diseases, compounds, and pharmaceutical compositions are as disclosed herein.

An additional embodiment of the present invention is a kit for treating or ameliorating the effects of a cancer in a subject in need thereof. The kit comprises an effective amount of any compound or pharmaceutical composition disclosed herein, packaged together with instructions for its use.

Suitable and preferred subjects, diseases, compounds, and pharmaceutical compositions are as disclosed herein.

The kits of the present invention may also include suitable storage containers, e.g., ampules, vials, tubes, etc., for the compounds and compositions of the present invention and other reagents, e.g., buffers, balanced salt solutions, etc., for use in administering the compounds and compositions to subjects. The compounds and compositions of the present invention may be present in the kits in any convenient form, such as, e.g., in a solution or in a powder form. The kits may further include a packaging container, optionally having one or more partitions for housing the compounds and pharmaceutical compositions and other optional reagents.

Another embodiment of the present invention is a composition comprising any compound disclosed herein.

In one aspect of this embodiment, the composition is a research reagent. As used herein, a "research reagent" is any compound or composition used in the execution of investigational activities.

An additional embodiment of the present invention is a method of preparing a compound having the structure of formula (VII):

(VII)

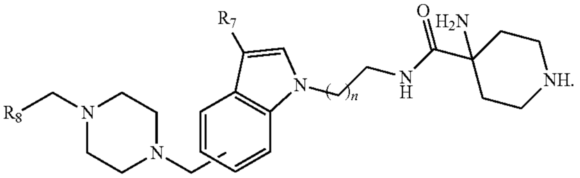

The method comprises the steps of i) reacting a compound having the structure:

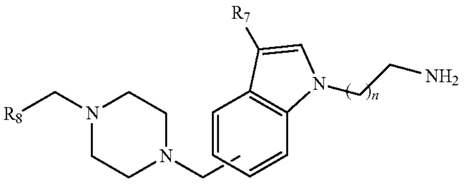

with a compound having the structure:

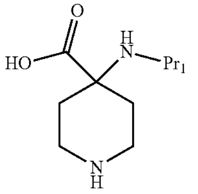

under conditions sufficient to form a compound having the structure:

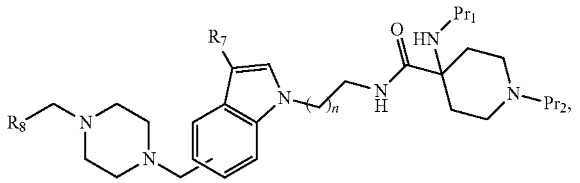

wherein:

$R_7$ is selected from the group consisting of H, halide, $C_{1-4}$ aliphatic, and aryl, wherein the aryl is optionally substituted with one or more groups consisting of halide, ether, $C_{1-4}$alkyl, —O—$C_{1-4}$alkyl, and a combination thereof, wherein the alkyl is optionally substituted with one or more groups consisting of halide, ether, and a combination thereof;

$R_8$ is selected from the group consisting of no atom, H, alkyl, aryl and $C_{1-4}$alkyl-O-aryl, wherein the alkyl is optionally substituted with the group consisting of halide, ether, and a combination thereof, and the aryl is optionally substituted with one or more groups consisting of halide, ether, $C_{1-4}$alkyl, and a combination thereof;

n is selected from the group consisting of an integer between 0-5; and $Pr_1$ and $Pr_2$ are independently selected from the group consisting of nitrogen protecting groups;

ii) removing the $Pr_1$ protecting group; and iii) removing the $Pr_2$ protecting group.

In one aspect of this embodiment the reaction of step i) is carried out in the presence of dimethylformamide. In another aspect of this embodiment $Pr_1$ and $Pr_2$ are $F_{moc}$ or Boc.

In one aspect of this embodiment, the compound has the structure

31MEW44

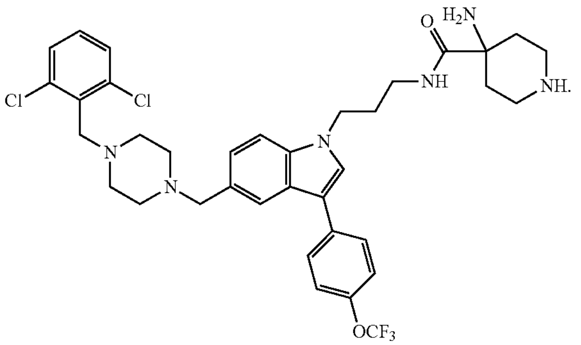

In another aspect of this embodiment, the compound has the structure

34MEW43

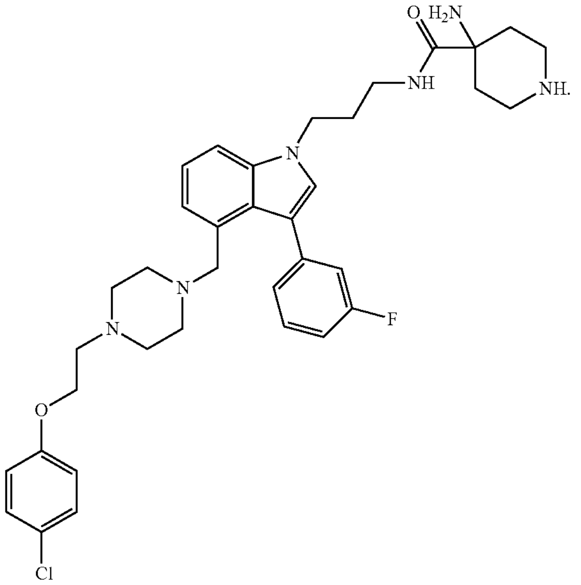

In another aspect of this embodiment, the compound has the structure

34MEW45

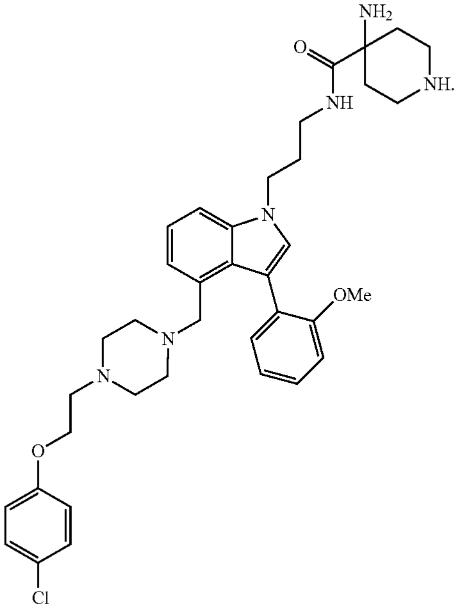

An additional embodiment of the present invention is a method of preparing a compound having the structure of formula (VIII):

(VIII)

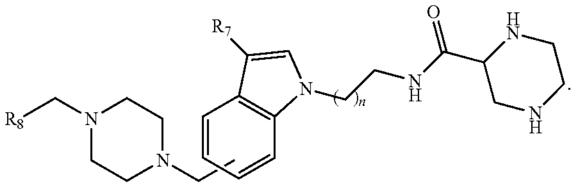

The method comprises the steps of i) reacting a compound having the structure:

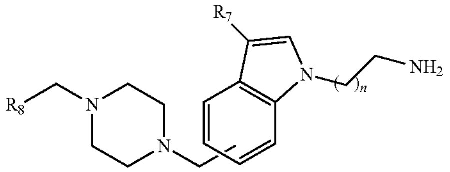

with a compound having the structure:

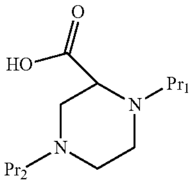

under conditions sufficient to form a compound having the structure:

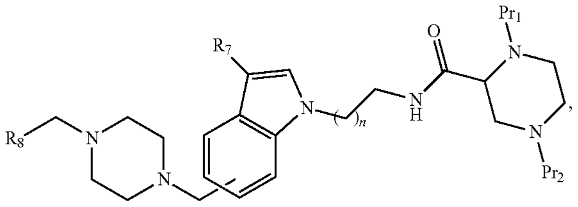

wherein:

$R_7$ is selected from the group consisting of H, halide, $C_{1-4}$ aliphatic, and aryl, wherein the aryl is optionally substituted with one or more groups consisting of halide, ether, $C_{1-4}$alkyl, —O—$C_{1-4}$alkyl, and a combination thereof, wherein the alkyl is optionally substituted with one or more groups consisting of halide, ether, and a combination thereof;

$R_8$ is selected from the group consisting of no atom, H, alkyl, aryl and $C_{1-4}$alkyl-O-aryl, wherein the alkyl is optionally substituted with the group consisting of halide, ether, and a combination thereof, and the aryl is optionally substituted with one or more groups consisting of halide, ether, $C_{1-4}$alkyl, and a combination thereof;

n is selected from the group consisting of an integer between 0-5; and $Pr_1$ and $Pr_2$ are independently selected from the group consisting of nitrogen protecting groups;

ii) removing the $Pr_1$ protecting group; and iii) removing the $Pr_2$ protecting group.

In one aspect of this embodiment the reaction of step i) is carried out in the presence of dimethylformamide. In another aspect of this embodiment $Pr_1$ and $Pr_2$ are $F_{moc}$ or Boc.

In one aspect of this embodiment, the compound has the structure

36MEW3

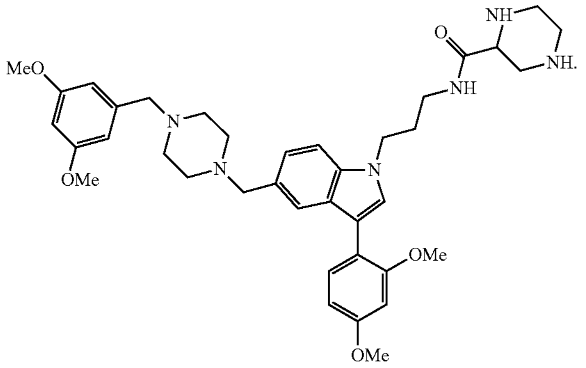

In another aspect of this embodiment, the compound has the structure

32MEW56

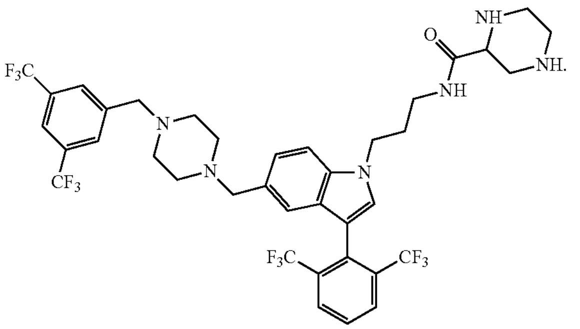

An additional embodiment of the present invention is a method of preparing a compound having the structure of formula (IX):

(IX)

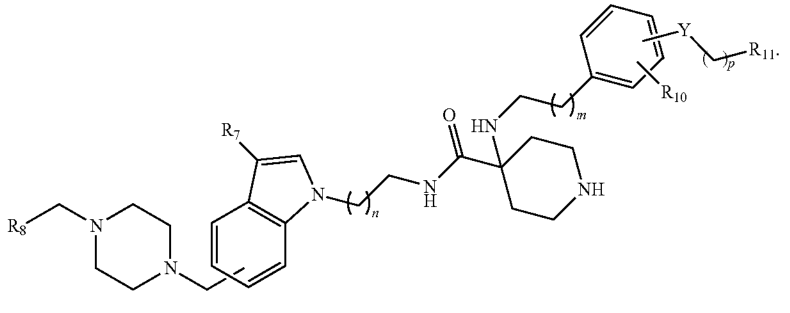

The method comprises the steps of i) reacting a compound having the structure:

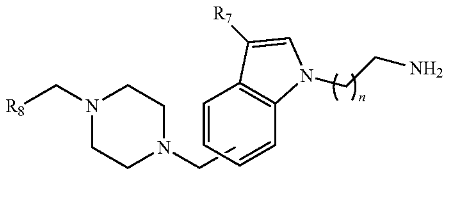

with a compound having the structure:

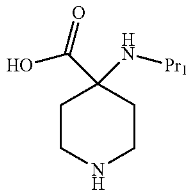

under conditions sufficient to form a compound having the structure:

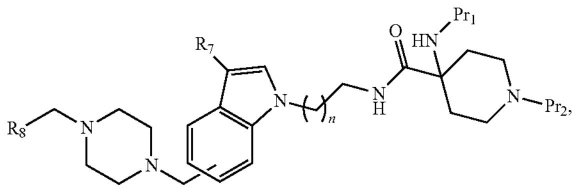

wherein:

$R_7$ is selected from the group consisting of H, halide, $C_{1-4}$ aliphatic, and aryl, wherein the aryl is optionally substituted with one or more groups consisting of halide, ether, $C_{1-4}$alkyl, —O—$C_{1-4}$alkyl, and a combination thereof, wherein the alkyl is optionally substituted with one or more groups consisting of halide, ether, and a combination thereof;

$R_8$ and $R_{11}$ are independently selected from the group consisting of no atom, H, alkyl, aryl and $C_{1-4}$alkyl-O-aryl, wherein the alkyl is optionally substituted with the group consisting of halide, ether, and a combination thereof, and the aryl is optionally substituted with the group consisting of halide, ether, $C_{1-4}$alkyl, —O—$C_{1-4}$alkyl, and a combination thereof, wherein the alkyl is optionally substituted with the group consisting of halide, ether, and a combination thereof;

$R_{10}$ is selected from the group consisting of no atom, H, halide, $C_{1-4}$ aliphatic and —O—$C_{1-4}$alkyl;

Y is selected from the group consisting of no atom and O;

m, n, and p are independently selected from the group consisting of an integer between 0-5; and; $Pr_1$ and $Pr_2$ are independently selected from the group consisting of nitrogen protecting groups;

ii) removing the $Pr_1$ protecting group iii) reacting the product of step ii) with a compound having the structure:

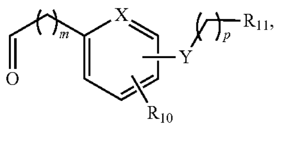

wherein X is selected from the group consisting of CH and N; and iv) removing the $Pr_2$ protecting group.

In one aspect of this embodiment the reaction of step i) is carried out in the presence of dimethylformamide. In one aspect of this embodiment the reaction of step iii) is carried out in the presence of dichloroethane. In another aspect of this embodiment $Pr_1$ and $Pr_2$ are $F_{moc}$ or Boc.

In one aspect of this embodiment, the compound has the structure

34MEW95

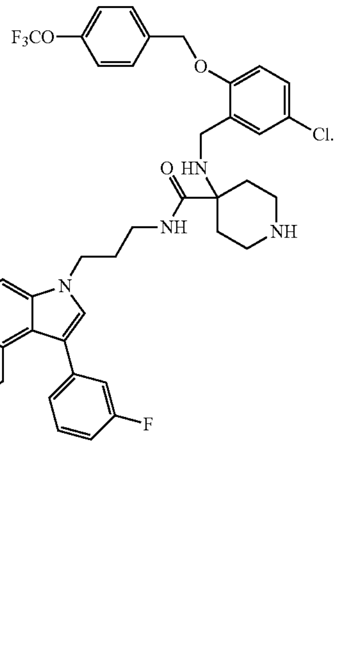

In another aspect of this embodiment, the compound has the structure

43MEW65

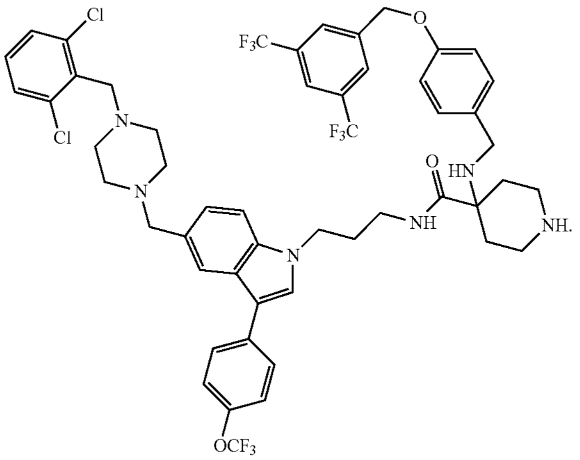

In another aspect of this embodiment, the compound has the structure

43MEW73

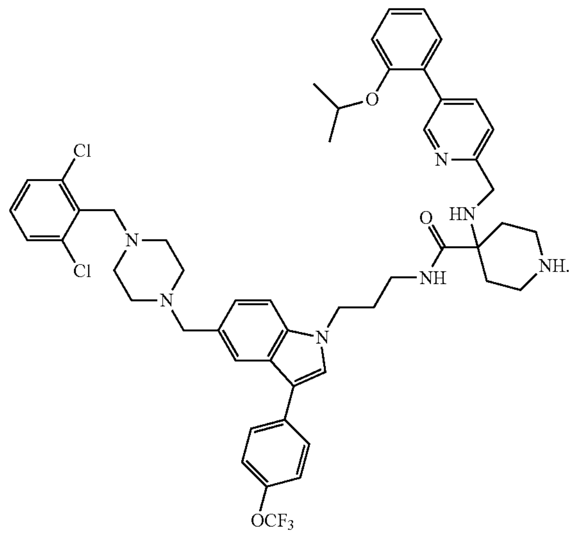

In another aspect of this embodiment, the compound has the structure

43MEW63

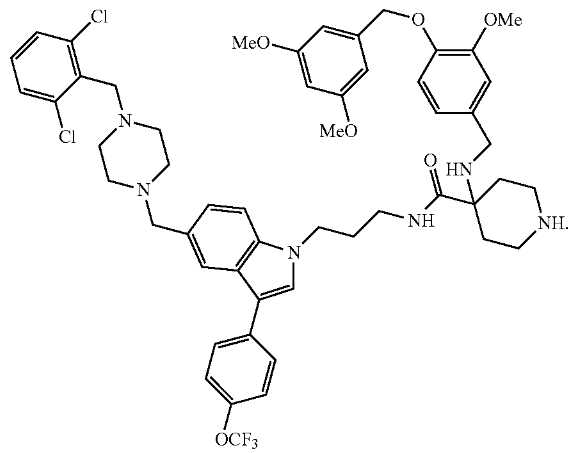

In another aspect of this embodiment, the compound has the structure

35MEW12

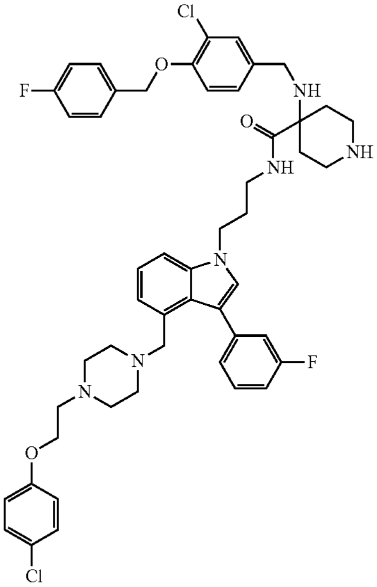

An additional embodiment of the present invention is a method of identifying a multivalent compound which binds selectively to a target protein.

The method comprises the steps of i) identifying a first and second target site on the target protein, wherein the first and second target sites are adjacent to each other;

ii) identifying a first compound fragment that selectively binds to the target protein at the first target site and a second compound fragment that selectively binds to the target protein at the second site; and iii) creating a structure of the multivalent compound comprising the first compound fragment linked to the second compound fragment, thereby identifying the multivalent compound.

In one aspect of this embodiment, step i) further comprises identifying a third target site on the target protein adjacent to the first and or second target site(s);

step ii) further comprises identifying a third compound fragment that selectively binds to the target protein at the third target site; and step iii) further comprises creating a structure of the compound comprising the third compound fragment linked to the first and/or the second compound fragment(s).

In one aspect of this embodiment, step ii) comprises the steps of a) identifying compounds that bind to the target sites from a chemical library; and b) creating an in silico library based on a set of structural and functional criteria for the compounds identified in step a) to identify compound fragments that are likely to selectively bind to the target sites. In another aspect of this embodiment the criteria comprise fragment size, hydrophobicity, electrophilicity/nucleophilicity and ability to form hydrogen bonds. In yet another aspect of this embodiment each in silico library consists essentially of synthetically feasible fragments. In yet another aspect of this embodiment compound fragments are identified based on high docking scores.

In one aspect of this embodiment, the target sites are shallow sites. In another aspect of this embodiment the target sites are present at a position where the target protein binds to a second protein. In another aspect of this embodiment the multivalent compound reduces binding of the target protein to the second protein.

In one aspect of this embodiment, the target protein is a GTPase. In another aspect of this embodiment, wherein the target protein is a RAS protein, preferably KRAS, more preferrably $KRAS^{G12D}$.

In one preferred aspect of this embodiment, the first target site is D38. In another preferred aspect of this embodiment the second target site is A59. In yet another preferred aspect of this embodiment the third target site is Y32.

In the present invention, the term "crystalline form" means the crystal structure of a compound. A compound may exist in one or more crystalline forms, which may have different structural, physical, pharmacological, or chemical characteristics. Different crystalline forms may be obtained using variations in nucleation, growth kinetics, agglomeration, and breakage. Nucleation results when the phase-transition energy barrier is overcome, thereby allowing a particle to form from a supersaturated solution. Crystal growth is the enlargement of crystal particles caused by deposition of the chemical compound on an existing surface of the crystal. The relative rate of nucleation and growth determine the size distribution of the crystals that are formed. The thermodynamic driving force for both nucleation and growth is supersaturation, which is defined as the deviation from thermodynamic equilibrium. Agglomeration is the formation of larger particles through two or more particles (e.g., crystals) sticking together and forming a larger crystalline structure.

The term "hydrates", as used herein, means a solid or a semi-solid form of a chemical compound containing water in a molecular complex. The water is generally in a stoichiometric amount with respect to the chemical compound.

As used herein, "pharmaceutically acceptable salts" refer to derivatives of the compounds disclosed herein wherein the compounds are modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include salts from ammonia, L-arginine, betaine, benethamine, benzathine, calcium hydroxide, choline, deanol, diethanolamine (2,2'-iminobis(ethanol)), diethylamine, 2-(diethylamino)-ethanol, 2-aminoethanol, ethylenediamine, N-ethyl-glucamine, hydrabamine, 1H-imidazole, lysine, magnesium hydroxide, 4-(2-hydroxyethyl)-morpholine, piperazine, potassium hydroxide, 1-(2-hydroxy-ethyl)-pyrrolidine, sodium hydroxide, triethanolamine (2,2',2"-nitrilotris(ethanol)), trometh-amine, zinc hydroxide, acetic acid, 2,2-dichloro-acetic acid, adipic acid, alginic acid, ascorbic acid, L-aspartic acid, benzenesulfonic acid, benzoic acid, 2,5-dihydroxybenzoic acid, 4-acetamido-benzoic acid, (+)-camphoric acid, (+)-camphor-10-sulfonic acid, carbonic acid, cinnamic acid, citric acid, cyclamic acid, decanoic acid, dodecylsulfuric acid, ethane-1,2-disulfonic acid, ethanesulfonic acid, 2-hydroxy-ethanesulfonic acid, ethylenediamonotetraacetic acid, formic acid, fumaric acid, galacaric acid, gentisic acid, D-glucoheptonic acid, D-gluconic acid, D-glucuronic acid, glutamic acid, glutantic acid, glutaric acid, 2-oxo-glutaric acid, glycero-phosphoric acid, glycine, glycolic acid, hexanoic acid, hippuric acid, hydrobromic acid, hydrochloric acid isobutyric acid, DL-lactic acid, lactobionic acid, lauric acid, lysine, maleic acid, (−)-L-malic acid, malonic acid, DL-mandelic acid, methanesulfonic acid, galactaric acid, naphthalene-1,5-disulfonic acid, naphthalene-2-sulfonic acid, 1-hydroxy-2-naphthoic acid, nicotinic acid, nitric acid, octanoic acid, oleic acid, orotic acid, oxalic acid, palmitic acid, pamoic acid (embonic acid), phosphoric acid, propionic acid, (−)-L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid. Further pharmaceutically acceptable salts can be formed with cations from metals like aluminum, calcium, lithium, magnesium, potassium, sodium, zinc and the like. (also see Pharmaceutical salts, Berge, S. M. et al., J. Pharm. Sci., (1977), 66, 1-19).

The pharmaceutically acceptable salts of the present invention can be synthesized from a compound disclosed herein which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

In the present invention, an "effective amount" or a "therapeutically effective amount" of a compound or composition disclosed herein is an amount of such compound or composition that is sufficient to effect beneficial or desired results as described herein when administered to a subject. Effective dosage forms, modes of administration, and dosage amounts may be determined empirically, and making such determinations is within the skill of the art. It is understood by those skilled in the art that the dosage amount will vary with the route of administration, the rate of excretion, the duration of the treatment, the identity of any other drugs being administered, the age, size, and species of mammal, e.g., human patient, and like factors well known in the arts of medicine and veterinary medicine. In general, a suitable dose of a compound or composition according to the invention will be that amount of the compound or composition which is the lowest dose effective to produce the desired effect. The effective dose of a compound or composition of the present invention may be administered as two, three, four, five, six or more sub-doses, administered separately at appropriate intervals throughout the day.

A suitable, non-limiting example of a dosage of any of the compounds or compositions disclosed herein is from about 1 mg/kg to about 2400 mg/kg per day, such as from about 1 mg/kg to about 1200 mg/kg per day, 75 mg/kg per day to about 300 mg/kg per day, including from about 1 mg/kg to about 100 mg/kg per day. Other representative dosages of such agents include about 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 75 mg/kg, 80 mg/kg, 90 mg/kg, 100 mg/kg, 125 mg/kg, 150 mg/kg, 175 mg/kg, 200 mg/kg, 250 mg/kg, 300 mg/kg, 400 mg/kg, 500 mg/kg, 600 mg/kg, 700 mg/kg, 800 mg/kg, 900 mg/kg, 1000 mg/kg, 1100 mg/kg, 1200 mg/kg, 1300 mg/kg, 1400 mg/kg, 1500 mg/kg, 1600 mg/kg, 1700 mg/kg, 1800 mg/kg, 1900 mg/kg, 2000 mg/kg, 2100 mg/kg, 2200 mg/kg, and 2300 mg/kg per day. The effective dose of compounds or compositions disclosed herein, may be administered as two, three, four, five, six or more sub-doses, administered separately at appropriate intervals throughout the day.

The compounds or compositions of the present invention may be administered in any desired and effective manner: for oral ingestion, or as an ointment or drop for local administration to the eyes, or for parenteral or other administration in any appropriate manner such as intraperitoneal, subcutaneous, topical, intradermal, inhalation, intrapulmonary, rectal, vaginal, sublingual, intramuscular, intravenous, intraarterial, intrathecal, or intralymphatic. Further, compounds or compositions of the present invention may be administered in conjunction with other treatments. Compounds or compositions of the present invention may be encapsulated or otherwise protected against gastric or other secretions, if desired.

The compositions of the invention comprise one or more active ingredients in admixture with one or more pharmaceutically-acceptable diluents or carriers and, optionally, one or more other compounds, drugs, ingredients and/or materials. Regardless of the route of administration selected, the agents/compounds of the present invention are formulated into pharmaceutically-acceptable dosage forms by conventional methods known to those of skill in the art. See, e.g., Remington, The Science and Practice of Pharmacy ($21^{st}$ Edition, Lippincott Williams and Wilkins, Philadelphia, Pa.).

Pharmaceutically acceptable diluents or carriers are well known in the art (see, e.g., Remington, The Science and Practice of Pharmacy ($21^{st}$ Edition, Lippincott Williams and Wilkins, Philadelphia, Pa.) and The National Formulary (American Pharmaceutical Association, Washington, D.C.)) and include sugars (e.g., lactose, sucrose, mannitol, and sorbitol), starches, cellulose preparations, calcium phosphates (e.g., dicalcium phosphate, tricalcium phosphate and calcium hydrogen phosphate), sodium citrate, water, aqueous solutions (e.g., saline, sodium chloride injection, Ringer's injection, dextrose injection, dextrose and sodium chloride injection, lactated Ringer's injection), alcohols (e.g., ethyl alcohol, propyl alcohol, and benzyl alcohol), polyols (e.g., glycerol, propylene glycol, and polyethylene glycol), organic esters (e.g., ethyl oleate and tryglycerides), biodegradable polymers (e.g., polylactide-polyglycolide, poly(orthoesters), and poly(anhydrides)), elastomeric matrices, liposomes, microspheres, oils (e.g., corn, germ, olive, castor, sesame, cottonseed, and groundnut), cocoa butter, waxes (e.g., suppository waxes), paraffins, silicones, talc, silicylate, etc. Each pharmaceutically acceptable diluent or carrier used in a pharmaceutical composition of the invention must be "acceptable" in the sense of being compatible with the other ingredients of the formulation and not injurious to the subject. Diluents or carriers suitable for a selected dosage form and intended route of administration are well known in the art, and acceptable diluents or carriers for a chosen dosage form and method of administration can be determined using ordinary skill in the art.

The compositions of the invention may, optionally, contain additional ingredients and/or materials commonly used in pharmaceutical compositions. These ingredients and materials are well known in the art and include (1) fillers or extenders, such as starches, lactose, sucrose, glucose, mannitol, and silicic acid; (2) binders, such as carboxymethylcellulose, alginates, gelatin, polyvinyl pyrrolidone, hydroxypropylmethyl cellulose, sucrose and acacia; (3) humectants, such as glycerol; (4) disintegrating agents, such as agar-agar, calcium carbonate, potato or tapioca starch, alginic acid, certain silicates, sodium starch glycolate, cross-linked sodium carboxymethyl cellulose and sodium carbonate; (5) solution retarding agents, such as paraffin; (6) absorption accelerators, such as quaternary ammonium compounds; (7) wetting agents, such as cetyl alcohol and glycerol monostearate; (8) absorbents, such as kaolin and bentonite clay; (9) lubricants, such as talc, calcium stearate, magnesium stearate, solid polyethylene glycols, and sodium lauryl sulfate; (10) suspending agents, such as ethoxylated isostearyl alcohols, polyoxyethylene sorbitol and sorbitan esters, microcrystalline cellulose, aluminum metahydroxide, bentonite, agar-agar and tragacanth; (11) buffering agents; (12) excipients, such as lactose, milk sugars, polyethylene glycols, animal and vegetable fats, oils, waxes, paraffins, cocoa butter, starches, tragacanth, cellulose derivatives, polyethylene glycol, silicones, bentonites, silicic acid, talc, salicylate, zinc oxide, aluminum hydroxide, calcium silicates, and polyamide powder; (13) inert diluents, such as water or other solvents; (14) preservatives; (15) surface-active agents; (16) dispersing agents; (17) control-release or absorption-delaying agents, such as hydroxypropylmethyl cellulose, other polymer matrices, biodegradable polymers, liposomes, microspheres, aluminum monostearate, gelatin, and waxes; (18) opacifying agents; (19) adjuvants; (20) wetting agents; (21) emulsifying and suspending agents; (22), solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan; (23) propellants, such as chlorofluorohydrocarbons and volatile unsubstituted hydrocarbons, such as butane and propane; (24) antioxidants; (25) agents which render the formulation isotonic with the blood of the intended recipient, such as sugars and sodium chloride; (26) thickening agents; (27) coating materials, such as lecithin; and (28) sweetening, flavoring, coloring, perfuming and preservative agents. Each such ingredient or material must be "acceptable" in the sense of being compatible with the other ingredients of the formulation and not injurious to the subject. Ingredients and materials suitable for a selected dosage form and intended route of administration are well known in the art, and acceptable ingredients and materials for a chosen dosage form and method of administration may be determined using ordinary skill in the art.

The compositions of the present invention suitable for oral administration may be in the form of capsules, cachets, pills, tablets, powders, granules, a solution or a suspension in an aqueous or non-aqueous liquid, an oil-in-water or water-in-oil liquid emulsion, an elixir or syrup, a pastille, a bolus, an electuary or a paste. These formulations may be prepared by methods known in the art, e.g., by means of conventional pan-coating, mixing, granulation or lyophilization processes.

Solid dosage forms for oral administration (capsules, tablets, pills, dragees, powders, granules and the like) may be prepared, e.g., by mixing the active ingredient(s) with one or more pharmaceutically-acceptable diluents or carriers and, optionally, one or more fillers, extenders, binders, humectants, disintegrating agents, solution retarding agents, absorption accelerators, wetting agents, absorbents, lubricants, and/or coloring agents. Solid compositions of a similar type may be employed as fillers in soft and hard-filled gelatin capsules using a suitable excipient. A tablet may be made by compression or molding, optionally with one or more accessory ingredients. Compressed tablets may be prepared using a suitable binder, lubricant, inert diluent, preservative, disintegrant, surface-active or dispersing agent. Molded tablets may be made by molding in a suitable machine. The tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein. They may be sterilized by, for example, filtration through a bacteria-retaining filter. These compositions may also optionally contain opacifying agents and may be of a composition such that they release the active ingredient only, or preferentially, in a certain portion of the gastrointestinal tract, optionally, in a delayed manner. The active ingredient can also be in microencapsulated form.

Liquid dosage forms for oral administration include pharmaceutically-acceptable emulsions, microemulsions, solutions, suspensions, syrups and elixirs. The liquid dosage forms may contain suitable inert diluents commonly used in the art. Besides inert diluents, the oral compositions may also include adjuvants, such as wetting agents, emulsifying and suspending agents, sweetening, flavoring, coloring, perfuming and preservative agents. Suspensions may contain suspending agents.

The compositions of the present invention for rectal or vaginal administration may be presented as a suppository, which may be prepared by mixing one or more active ingredient(s) with one or more suitable nonirritating diluents or carriers which are solid at room temperature, but liquid at body temperature and, therefore, will melt in the rectum or vaginal cavity and release the active compound. The pharmaceutical compositions of the present invention which are suitable for vaginal administration also include pessaries, tampons, creams, gels, pastes, foams or spray formulations containing such pharmaceutically-acceptable diluents or carriers as are known in the art to be appropriate.

Dosage forms for the topical or transdermal administration include powders, sprays, ointments, pastes, creams, lotions, gels, solutions, patches, drops and inhalants. The active agent(s)/compound(s) may be mixed under sterile conditions with a suitable pharmaceutically-acceptable diluent or carrier. The ointments, pastes, creams and gels may contain excipients. Powders and sprays may contain excipients and propellants.

The compositions of the present invention suitable for parenteral administrations may comprise one or more agent (s)/compound(s) in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain suitable antioxidants, buffers, solutes which render the formulation isotonic with the blood of the intended recipient, or suspending or thickening agents. Proper fluidity can be maintained, for example, by the use of coating materials, by the maintenance of the required particle size in the case of dispersions, and by the use of surfactants. These pharmaceutical compositions may also contain suitable adjuvants, such as wetting agents, emulsifying agents and dispersing agents. It may also be desirable to include isotonic agents. In addition, prolonged absorption of the injectable pharmaceutical form may be brought about by the inclusion of agents which delay absorption.

In some cases, in order to prolong the effect of a drug (e.g., pharmaceutical formulation), it is desirable to slow its absorption from subcutaneous or intramuscular injection. This may be accomplished by the use of a liquid suspension of crystalline or amorphous material having poor water solubility.

The rate of absorption of the active agent/drug then depends upon its rate of dissolution which, in turn, may depend upon crystal size and crystalline form. Alternatively, delayed absorption of a parenterally-administered agent/drug may be accomplished by dissolving or suspending the active agent/drug in an oil vehicle. Injectable depot forms may be made by forming microencapsule matrices of the active ingredient in biodegradable polymers. Depending on the ratio of the active ingredient to polymer, and the nature of the particular polymer employed, the rate of active ingredient release can be controlled. Depot injectable formulations are also prepared by entrapping the drug in liposomes or microemulsions which are compatible with body tissue. The injectable materials can be sterilized for example, by filtration through a bacterial-retaining filter.

Any formulation of the invention may be presented in unit-dose or multi-dose sealed containers, for example, ampules and vials, and may be stored in a lyophilized condition requiring only the addition of the sterile liquid diluent or carrier, for example water for injection, immediately prior to use. Extemporaneous injection solutions and suspensions may be prepared from sterile powders, granules and tablets of the type described above.

The terminology used herein is for the purpose of describing particular embodiments only and is not intended to be limiting. As used in the specification and the appended claims, the singular forms "a," "an," and "the" include plural referents unless the context clearly dictates otherwise.

For recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

The following examples are provided to further illustrate the methods of the present invention. These examples are illustrative only and are not intended to limit the scope of the invention in any way.

EXAMPLES

Example 1

Materials and Methods

Software

Molecular docking was performed using GLIDE (Schrodinger, Inc). Modeling of proteins and ligands were performed using Molecular Operating Environment [MOE] (Chemical Computing Group). All chemical structures were drawn using Chemdraw Ultra version 10.0. (Perkin Elmer). All statistical analyses, $EC_{50}$ determinations, and viability curves were produced using Prism 5.0c (GraphPad Software).

In Silico Libraries

Libraries of commercially available compounds were compiled from the inventories of Asinex, Enamine, Chembridge, ChemDiv, IBS, Life, Maybridge and TimTec.

The unfiltered commercially available compound library was converted to conformer libraries using OMEGA (Openeye scientific) and screened against the pharamcophore model using ROCS (Openeye scientific).

A fragment subset of about 60,000 compounds of the unfiltered library was selected using the following filter criteria: Log P<3, hydrogen bond acceptors ≤3, hydrogen bond donors 3, molecular weight<300, aqueous solubility>0.5 mM. Chemical descriptors were calculated using MOE (Chemical Computing Group)

Designed libraries of synthetically accessible compounds were compiled using selected commercially available reagents from the inventory of Sigma-Aldrich and Chem-Impex using the Combigen application in MOE (chemical computing group).

Cell Viability Assays

All cell culture assays were incubated at 37° C., 5% $CO_2$ in media containing Dulbecco's Modified Eagle Medium (DMEM) with 10% fetal bovine serum (FBS) and 1% penicillin-streptomycin (PS). 384-well format for $EC_{50}$ determination: cells were trypsinized, counted, and seeded into 384-well plates at 1,000 cells/well. After 12-16 hours, compounds (as 50 mM stocks in DMSO) were arrayed in an 8- or 16-point dilution series in 384-well polypropylene plates. Compound solutions were transferred at a 1:5 dilution into the assay plates. After 48 hours, a 50% Alamar blue solution was added to a final concentration of 10% Alamar blue. After 6 hours of incubation, fluorescence intensity was determined using a Victor3 plate reader (Perkin Elmer) with a 535 nm excitation filter and a 590 nm emission filter. All compound measurements were performed in triplicate. For experiments performed in 6-well format, cells were trypsinized, counted, and seeded into 6-well plates at 200,000 cells per well 16 h prior to use. Media was then aspirated and replaced with 2 mL of media containing compounds at the indicated concentrations (from 10 mM stocks in DMSO). After 24 hours, cells were trypsinized and viability was determined using Trypan Blue exclusion assay.

Western Blots

BJeLR cells were seeded in 60 mm dishes at 1 million cells/dish in media containing DMEM and 10% FBS with 1% penicillin and streptomycin (PS), 12-16 hours prior to use. The medium was then aspirated and compounds added as solutions in serum free medium (DMEM with 1% PS) to the dishes and treated for 24 hours or at the indicated time points. Following treatment, the medium was aspirated from each dish and cells were washed twice with PBS. Cells were lysed with 60 μl buffer (50 mM HEPES, 40 mM NaCl, 2 mM EDTA, 0.5% Triton-X, 1.5 mM sodium orthovanadate, 50 mM NaF, 10 mM sodium pyrophosphate, 10 mM sodium β-glycerophosphate and protease inhibitor tablet ((Roche), pH 7.4). Unlysed cells and debris were pelleted for 12 minutes at 12,000 rpm at 4° C. Samples were separated using SDS-polyacrylamide gel electrophoresis and transferred to a polyvinylidene difluoride membrane. Transfer was performed using the iBlot system (Invitrogen). Membranes were treated with Li-COR odyssey blocking buffer for 1 hour at 25° C., then incubated with primary antibody (1:1000) in a 1:1 solution of PBS-T and Li-COR odyssey blocking buffer overnight at 4° C. Following three 5 minute washes in PBS-T, the membrane was incubated with secondary antibodies (1:2000) in a 1:1 solution of PBS-T and Li-COR Odyssey blocking buffer for 45 minutes at 25° C. Following three 5 minute washes in PBS-T, the membrane was scanned using the Li-COR Odyssey Imaging System. Antibodies for pERK1/2, ERK1/2, pAKT ser473, AKT, pan-RAS, RALA, PI3Kgamma (Cell signaling), and RAF-1 (Santa Cruz) were detected using a goat anti-rabbit or goat anti-mouse IgG antibody conjugated to an IRdye at 800CW and 680CW conjugated, respectively (Li-COR biosciences).

Multicellular Tumor Spheroids

Multicellular tumor spheroids (MCTSs) were grown in 96-well Corningware Ultra Low Attachment (ULA) Plates (CLS 3474). 100 μL of cell suspension containing $2\times10^4$ cells/ml were added to each well of the ULA plate containing 100 μL of a 2× solution of the desired concentration of compounds. Cells were incubated at 37° C., 5% $CO_2$ for 72 hours to allow for MCTS formation. After 72 hours, 50 μL of a 50% solution of Alamar blue and medium was added and incubated for 12 hours prior to measurements on a Victor3 plate reader as previously described.

Culture Conditions and Viability Measurements in Patient Derived T-ALL Samples

Patient Samples

T-ALL samples were provided by Columbia Presbyterian Hospital, the Eastern Cooperative Oncology Group (ECOG), University of Padova, and Hospital Central de Asturias with informed consent and analyzed under the supervision of the Columbia University Medical Center Institutional Review Board committee.

Primary Cell Co-Culture and In Vitro Cell Viability Assays.

For the analysis of 31MEW44 on primary T-ALL patient samples, cells were cultured in MEM medium supplemented with 10% FBS, 10% human heat-inactivated serum, 1% penicillin/streptomycin, 1% GlutaMAX, human IL-7 (10 ng/mL), human SCF (50 ng/mL), human FLT3-ligand (20 ng/mL), and insulin (20 nmol/L) on a feeder layer of MS5 stromal cells overexpressing the NOTCH ligand Delta-like 1 as described by Amstrong et al. (Armstrong et al., 2009). In these experiments, T-ALL lymphoblasts were cultured in triplicate and treated with either vehicle, DMSO, or 31MEW44 (doses ranging from 1 to 5 μM). Cells were harvested 72 hours after treatment and analyzed cell viability using the BD cell viability kit with liquid counting beads (BD Bioscience) gating out stroma cells (GFP+), dead cells and particles (PI+). We acquired data using a FACSCanto II flowcytometer (BD Bioscience) and analyzed it using FlowJo software (Tree Star, Inc.). Viability data is represented as % relative to vehicle treatment.

Sequencing

A region of 124 bp from coding exon 1 of the human NRAS gene, including G12-G13 mutation hotspot, was amplified from the genomic DNA of six primary T-ALL samples by polymerase chain reaction and was analyzed by direct dideoxynucleotide sequencing using primers FW: 5'-GCTGGTGTGAAATGACT-3' (SEQ ID NO: 52) and RV: 5'-GCTACCACTGGGCCTCACCT-3' (SEQ ID NO: 53).

Cosmic

Primary T-ALL (PDTALL) 22 cells have a synonymous variant: GCA/GCT (A) and also a variant: GGT/GTT (G13) (G13V). PDTALL 26 cells have a missense variant GGT/GAT (G13) (G13D).

Patient-Derived Xenograft

Animals were maintained in the animal facility at the Irving Cancer Center at Columbia University Medical Campus and all animal procedures were approved by the Columbia University IACUC. To generate primary xenografts, cells from T-ALL sample PD22, harboring a mutated allele of NRAS, were transplanted via intravenous injection into lethally irradiated primary recipients as previously described (Chiang et al., 2008). Upon detection of human lymphoblasts (human CD45+ cells) in peripheral blood, mice were sacrificed; lymphoblasts isolated from the spleens were transduced with retroviral particles expressing a fusion protein between the red cherry fluorescent protein and luciferase (MigR1 CherryLUC), and cells were re-injected in sublethally irradiated mice (Piovan et al., 2013).

Mice transplanted with retrovirally transduced cells were imaged regularly until luciferase activity was detected. Tumor cells were harvested from the spleens of these mice, and injected into secondary recipients. Secondary recipients were randomized into two groups of 5 mice with equal loads of luciferase. Animals were treated I.P. with vehicle or 31MEW44 30 mg/kg in 5% DMSO in HBSS at pH 4, once daily on days 0; 1; 4; 5; 7 and 8, and imaged at day 0 (before treatment), at day 4 and at day 8. Mice were sacrificed at day 8; spleen weight and presence of human $CD45^+$ cells in the spleen (lymphoblasts) were documented together with changes in luciferase signal over treatment.

Caspase 3/7 Activation Assay

HT-1080 cells were seeded into 384-well plates at 1,000 cells/well. After 12-16 hours, compounds (as 50 mM stocks in DMSO) were arrayed in a dilution series in 384-well polypropylene plates. Compound solutions were transferred at a 1:5 dilution into the assay plates for a total volume of 40 μL. After 24 hours, 8 μL of a 1:100 solution of rhodamine 110 bis-(N-CBZ-1-aspartyl-1-glutamyl-1-valyl-aspartic acid amide) to lysis buffer (APO-1, Promega) was added and the plate was wrapped in aluminum foil and incubated at room temperature for 16 hours. Fluorescence intensity was then determined using a Victor3 plate reader (Perkin Elmer) with a 490 nm excitation filter and a 535 nm emission filter. A viability curve was performed in parallel with the same incubation time using the procedure described in the "cell viability assays" section.

Molecular Cloning, Protein Expression, and Purification

Human KRAS4B sequence containing the oncogenic Q61H mutation in pENTR221 vector was purchased from Invitrogen (Ultimate ORF Clone 10H9852). To generate the wild-type KRAS sequence, a H61Q back mutation was introduced using QuickChange II site-directed mutagenesis (Agilent Technologies) and confirmed by DNA sequencing (GeneWiz, Inc.). Wild-type KRAS4B sequence encoding the catalytic domain (amino acids 1-169 in KRAS) was amplified by PCR and cloned into Nde 1-BamH1 sites of pET-15b vector (Novagen) containing the N-terminal $His_6$ tag. A G12D point mutation was introduced using Quick-Change II site-directed mutagenesis (Agilent Technologies). DNA sequencing was performed to confirm the correct amino acid sequence of the construct (GeneWiz, Inc.).

Mutagenesis of the $KRAS^{G12D}$ plasmid was performed using a QuikChange XL site-directed mutagenesis kit from Agilent technologies, according to the manufacturer's protocol. Primers were designed using the Agilent QuikChange Primer Design application and purchased from Integrated DNA Technologies. $KRAS^{G12D\ D38A}$ forward primer 5' ATA TGA TCC AAC AAT AGA GGC TTC CTA CAG GAA GCA AGT AG 3' (SEQ ID NO: 66), $KRAS^{G12D\ D38A}$ reverse primer 5' CTA CTT GCT TCC TGT AGG AAG CCT CTA TTG TTG GAT CAT AT 3' (SEQ ID NO: 67), $KRAS^{G12D\ I36N}$ forward primer 5' CAT TTT GTG GAC GAA TAT GAT CCA ACA AAT GAG GAT TCC TAC AGG 3' (SEQ ID NO: 68), $KRAS^{G12D\ I36N}$ reverse primer 5' CCT GTA GGA ATC CTC ATT TGT TGG ATC ATA TTC GTC CAC AAA ATG 3' (SEQ ID NO: 69). DNA sequencing was performed to confirm the correct amino acid sequence of the construct (GeneWiz, Inc.).

NMR

For NMR studies, uniformly $^{15}$N-labeled $KRAS^{G12D}$ protein with N-terminal $His_6$ tag was prepared. The $KRAS^{G12D}$ construct was expressed in *Escherichia coli* BL21-Gold (DE3) cells (Stratagene) growing at 37° C. in M9 minimal medium supplemented with 100 μg/mL ampicillin, metals, 30 mg nicotinic acid, 3 mg p-aminobenzoic acid, 0.3 mg biotin, 0.5 mg thiamine hydrochloride, and 0.6 g $^{15}NH_4Cl$ as the sole nitrogen source. When the $OD_{600\ nm}$ reached 0.9, protein expression was induced with 1 mM isopropyl β-D-thiogalactoside at 15° C. overnight. Cells were pelleted and lysed by sonication in buffer containing 10 mM Tris-HCl, 500 mM NaCl, 5 mM imidazole, 5 mM $MgCl_2$, pH 7.5, 0.5% CHAPS (w/v), 1 mM PMSF, and 1 mM TCEP. Cell lysate was then centrifuged at 15,000×g for 45 minutes at 4° C. $KRAS^{G12D}$ was first purified from cell lysate using Ni Sepharose 6 Fast Flow beads (GE Life Sciences) and then using gel filtration Superdex 100 column. The fractions containing $KRAS^{G12D}$ were pooled together and verified by SDS-PAGE. Protein concentration was determined using absorbance at 280 nm with an extinction coefficient of 11,920 $M^{-1}$ $cm^{-1}$ (calculated using MOE). Thrombin was added at 5 U/mg protein to cleave the N-terminal $His_6$ tag. The reaction was allowed to proceed overnight at 4° C. The next day, the protein solution was passed over Ni-Sepharose 6 Fast Flow beads (GE Life Sciences) and flowthrough containing the $^{15}$N-labeled $KRAS^{G12D}$ protein without histidine tag was concentrated and flash frozen. Purity was checked by SDS-PAGE gel.

To load a specific nucleotide onto $^{15}$N-labeled $KRAS^{G12D}$, the protein was first incubated with 10 molar excess of EDTA for 1 hour at room temperature, then buffer exchanged into HEPES NMR buffer (50 mM HEPES pH 7.4, 50 mM NaCl), and lastly supplemented with 2 mM $MgCl_2$, 2 mM TCEP, and 10 molar excess of GDP or GppNHp nucleotide.

For biochemical studies, the $KRAS^{G12D}$ construct was expressed in *Escherichia coli* BL21-Gold (DE3) cells (Stratagene) growing at 37° C. in LB media with 100 μg/mL ampicillin and induced when the $OD_{600\ nm}$ reached 1.0, with 1 mM isopropyl β-D-thiogalactoside at 15° C. overnight. Protein purification was the same as for the $^{15}$N-labeled protein, except the N-terminal $His_6$ tag was not removed.

In Vitro RAS Pulldown

A 20 μM solution of $KRAS^{G12D}$ in 50 mM HEPES, 200 mM sodium chloride, 2 mM TCEP with 1 mM EDTA and 1 mM GTP was gently rotated at 25° C. to remove the endogenous nucleotide. Magnesium chloride was then added to 5 mM and the resulting solution was rotated at 4° C. for 4 hours. The GTP-loaded $KRAS^{G12D}$ was then diluted to 20 nM and incubated with the inhibitors and 5 μL of CRAF-RBD agarose beads (Millipore), 10 μL of RAF1-RBD agarose beads (EMD Millipore, CN: 14-278), or 100 nM RALGDS (Abcam, CN: ab132590) with 20 μL of glutathione beads for 2 hours. The beads were separated from the lysate via a 0.1 μm filter spin cup and centrifuging at 14,000-15,000 rpm. They were then washed twice with PBS before the addition of 1×SDS. The quantity of RAS in the samples was then analyzed using the previously described Western blotting procedure.

Cell-Based RAS Pulldown

BJeLR cells were seeded at one million cells/10 cm dish in 10% FBS and incubated at 37° C. overnight. The medium was then aspirated and replaced with serum free media containing the inhibitors (from 10 mM DMSO stocks). The cells were then incubated for 24 hours at 37° C. The medium was removed, washed with cold PBS, lysed and spun down at 13,000 rpm at 4° C. to remove unlysed cells and debris. The lysate was incubated with Raf-1 RBD agarose beads (EMD millipore) for 2 hours with rotation at 4° C. The solution was then spun down at 1500×g and the supernatant removed. The beads were washed twice with PBS, resuspended in 2.5×SDS, and then analyzed by western blotting procedure.

Determining RAS Dependency Using siRNAs Targeting RAS Isoforms

Small interfering RNAs (siRNAs) targeting each RAS isoform were purchased from Dharmacon Technologies. Reverse transfection was performed by preparing a solution of 1 mL of Opti-MEM (Invitrogen), 6 μL of lipo-RNAiMAX (Invitrogen) and 2-5 μL of RNAi solution (10 μM stock), and by incubating the mixture (1 mL/well) in a 6-well plate for 20-30 minutes at 37° C. While the siRNA complex was forming, 0.2 million cells were suspended in 1 mL of 2× serum-containing media. The cell solution (1 mL) was transferred to each well of the E-well plate containing siRNA complex (1 mL), and the 6-well plate was returned to the culture incubator. At 24, 48, 72, and 96 hours post-transfection, cells were trypsinized and the number of viable cells was determined using trypan blue exclusion assay.

Confirming RAS Knockdown Using RT-gPCR Experiment

Cells were detached from the 6-well plate, and 0.5 million cells were collected as a pellet by centrifuging at 1,000 rpm for 5 minutes. Total cellular RNA sample was prepared using RNAeasy extraction kits (QIAgen) according to manufacturer's instruction. The resulting RNA sample was reverse-transcribed using a High Capacity cDNA Reverse Transcription kit (Life Technologies). The cDNA samples were mixed with TaqMan® probes for each RAS isoform gene, and arrayed on 96-well plates in triplicate. Each plate was loaded onto a ViiA7 Real-Time PCR system (Life Technologies) for qPCR reaction. Comparative analysis (ΔΔCt analysis) was performed with ACTB (human actin b), an internal reference gene.

Immunoprecipitations

BJeLR cells were seeded 16 hours prior to use in 10% FBS in DMEM. Media was aspirated and replaced with media containing 31MEW44 (from a 10 mM DMSO stock). After 6 hours cells were washed twice with ice cold buffer (25 mM tris, 100 mM NaCl, 1 mM TCEP, 5 mM $MgCl_2$, 0.1% tween-20 and 1 protease inhibitor/25 mL). Cells were scrapped, pelleted at 13,000 rpm for 10 minutes at 4° C., then passed through a 26 gauge needle several times. The solution was spun down a second time at 13,000 rpm for 15 minutes at 4° C., to remove unlysed cells and debris. HRAS antibody (Santa cruz, SC-520) was then added to the lysate (1:100) and the solution was rocked at 4° C. for 16 hours. Protein A agrose beads were then added and the solution was rotated at 4° C. for an additional 6 hours. The solutions were spun down at 1500×g for 2 minutes and the supernatant was removed by syringe. The beads were washed twice by this process with buffer, then resuspended in 2.5×SDS.

RALA Activation Assay

BJeLR cells were seeded 16 hours prior to use in 2% FBS in DMEM. Media was aspirated and replaced with media containing 31MEW44 (from a 10 mM DMSO stock). After 6 hours cells were washed twice with ice cold buffer (25 mM tris, 100 mM NaCl, 1 mM TCEP, 5 mM $MgCl_2$, 0.1% tween-20 and 1 protease inhibitor/25 mL). Cells were scrapped, pelleted at 13,000 rpm for 10 minutes at 4° C., then passed through a 26 gauge needle several times. The solution was spun down a second time at 13,000 rpm for 15 minutes at 4° C., to remove unlysed cells and debris. RALBP1 agarose beads (EMD Millipore) were then added to the lysate and the solution was rotated at 4° C. for 2 hours. The solutions were spun down at 1500×g for 2 minutes and the supernatant was removed by syringe. The beads were washed twice by this process with buffer, then resuspended in 2.5×SDS.

Differential Scanning Fluorimetry

A fluorescent thermal shift assay was used to investigate the binding of synthesized ligands to K-Ras G12D protein. The assay was carried out in triplicate in 384-well optical plates containing 5 μM protein, varying concentration of ligand from 500 μM to 1 μM, and 5×SYPRO Orange dye (Invitrogen). Samples were heated at 3° C./minute from 25° C. to 95° C. and protein unfolding was observed by monitoring the fluorescence of SYPRO orange dye (Invitrogen) at an excitation of 470 nm and an emission of 623 nm using a ViiA7 real-time PCR machine (Applied Biosystems). K-Ras G12D protein preloaded with the specified nucleotide was incubated with ligand for 30 minutes at room temperature before the addition of SYPRO Orange dye. All experiments were performed in triplicate. Data were analyzed using Protein Thermal Shift™ Software (Applied Biosystems) to determine the unfolding transition temperature, Tm, of each well. The ΔTm was calculated by subtracting the Tm of liganded K-Ras G12D protein from unliganded K-Ras G12D and are expressed as absolute value of the mean±sem.

Protein NMR Spectroscopy

The $^{1}H$-$^{15}N$ HSQC experiments were performed on Bruker Avance III 500 (500 MHz) and Avance III 500 Ascend (500 MHz) spectrometers at 298K. The buffer consisted of 50 mM HEPES pH 7.4, 50 mM NaCl, 2 mM $MgCl_2$, 2 mM TCEP, and 10% $D_2O$. Assignments of wild-type KRAS loaded with GDP were previously published by Vo et al. (2013). The conditions reported in Vo et al., 2013 were used to efficiently transfer the assignments to the peaks of $^{1}H$-$^{15}N$ HSQC spectrum of the $KRAS^{G12D}$ GDP protein and then to $KRAS^{G12D}$ GppNHp loaded protein. To verify the assignments, 3D-$^{1}H$-$^{15}N$-$^{1}H$-NOESY-HSQC and 3D-$^{1}H$-$^{15}N$-$^{1}H$-TOCSY-HSQC experiments were performed on $KRAS^{G12D}$ protein loaded with either GDP or GppNHp nucleotide. The 3D NMR experiments were performed on Bruker Avance $US^2$ 800 (800 MHz) and Bruker Avance III 600 (600 MHz) spectrometers equipped with cryogenic probes. The $^{15}N$-NOESY-HSQC data set were recorded using a mixing time of 75 ms. The $^{15}N$-TOCSY-HSQC data were recorded using a mixing time of 60 ms. All data were processed and analyzed using TopSpin 3.1 (Bruker). The assignments were performed using Sparky (T. D. Goddard and D. G. Kneller, UCSF).

Nucleotide Displacement Assay

To investigate whether compounds were binding to the same site as GTP, a fluorescent polarization assay was implemented using fluorescently-labeled BODIPY-GTP as a probe. When BODIPY-GTP is free in solution, it has a low polarization. However, when BODIPY-GTP is bound to K-Ras protein, the polarization intensity is high. K-Ras G12D bound to BODIPY-GTP was incubated with different concentrations of ligand or unlabeled GTP or GDP in buffer containing 25 mM Tris-HCl, pH 8, 100 mM NaCl, 5 mM $MgCl_2$, 1 mM EDTA, and 1 mM TCEP. The final concentration of K-Ras G12D bound to BODIPY-GTP in each well was 2.5 μM. The samples were incubated at 25° C. for 12 hours with gentle shaking to allow for the slow intrinsic nucleotide release reaction to take place. The change in fluorescence was measured on a Victor3 plate reader (Perkin Elmer) in 384-well black low-volume plates (Corning, Inc.). The BODIPY-GTP fluorophore was excited at 485 nm and emission was monitored at 535 nm.

Gene Expression Analysis by RT-qPCR

Cells from six-well plates were trypsinized and centrifuged at 3,000 rpm for 3 minutes. The cell pellet was then lysed and the RNA was extracted using QIAshreader and RNAeasy extraction kits (QIAGEN) according to the manufacturer's protocol. 2 micrograms of RNA from each sample was then converted to cDNA using the TaqMan RT Kit (Applied Biosystems). Primers for Quantitative PCR (qPCR) were designed with Primer Express. qPCR was performed using Power SYBR Green Master Mix (Applied Biosystems) in a 96-well format, in triplicate, using an Applied Biosystems 7300 Cycler set to absolute quantification. Expression changes were computed using the ΔΔCt method with GAPDH as an internal reference gene. The primers used were as follows: urokinase-type plasminogen activator (uPA) Forward 5' GGATGTGCCCTGAAGGA- CAA 3' (SEQ ID NO: 54), reverse 5' TGCGGATCCAGGG-TAAGAAG 3' (SEQ ID NO: 55); matrix metalloprotease 9 (MMP9) forward 5' GAGTGGCAGGGGGAAGATGC 3' (SEQ ID NO: 56), reverse 5' CCTCAGGGCACTGCAG-GATG 3' (SEQ ID NO: 57); lactate dehydrogenase (LDH) forward 5' GCCCGACGTGCATTCCCGATTCCTT 3' (SEQ ID NO: 58), reverse 5' GACGGCTTTCTCCCTCTT-GCTGACG 3' (SEQ ID NO: 59); CMYC forward 5' TCAAGAGGTGCCACGTCTCC 3' (SEQ ID NO: 60), reverse 5' TCTTGGCAGCAGGATAGTCCTT 3' (SEQ ID NO: 61).

RAS, PI3K and BRAF Overexpression.

Phoenix-AMPHO (ATCC: CRL-3213) cells were seeded in a 6-well plate at 600,000 cells/well 24 hours prior to use in 10% FBS and 1% PS in DMEM. A solution of lipofectamine 2000 (6 μL) in 100 μL opti-mem media (reduced serum media) and the plasmid (2.5 μg) in 100 μL opti-mem media were combined and incubated 5 minutes at 25° C., then added to 1.8 mL of opti-mem in each well. After 12 hours, the media was replaced with 10% FBS and 1% PS in DMEM. The next day the supernatant was collected three times spaced 4 hours apart and polybrene was added (1/1000). The supernatant was filtered (0.45 μm) and added to HT1080 cells seeded at 100,000 cells per well (6-well dish) in 2 mL portions spaced 4 hours apart. After 48 hours, the cells were trypsinized and re-seeded in medium containing puromycin (2 μg/mL). After 6 days of selection the cells were analyzed for expression using the aforementioned qPCR procedure. 2 mL solutions of the inhibitors were added to a 6-well plate of the transfected HT-1080 cells (100,000 cells/well) and treated for 24 hours. The cells were then trypsinized, re-suspended in 1 mL of medium and viability was measured by VI-CELL (Beckman Coulter) through mixing with trypan blue.

Microscale Thermophoresis $KRAS^{G12D}$ (250 μM) in 25 mM HEPES, 100 mM sodium chloride, 2 mM TCEP with 20 mM EDTA and 1 mM GppNHp was shaken at 220 rpm at 30° C. to remove the endogenous nucleotide, The solution was placed on ice for 2 minutes prior to the addition of 65 mM $MgCl_2$. After an additional 10 minutes incubation on ice, 200 uL of a 10 uM solution of $KRAS^{G12D}$ was combined with 200 uL of a 20 uM solution of NT-647-NHS-ester dye (from a 652.4 μM stock). The protein/dye mixture was rotated at 4° C. for 30 minutes, before being separated from the excess dye and buffer exchanged into 25 mM Tris, 100 mM sodium chloride, 2 mM TCEP, and 5 mM $MgCl_2$ via a nap-5 column. The test compounds were arrayed across a 16-point dilution series consisting of 1.5% DMSO with 25 mM Tris, 100 mM NaCl, 2 mM TCEP, 5 mM $MgCl_2$ and 0.05% tween-20. Thermophoretic movement of the fluorescently labeled protein with the inhibitors was performed using a Monolith NT.115 (Nanotemper Technologies). RALA and RHOA were purchased commercially from Abcam (RALA CN:ab102555, RHOA CN:ab101594).

Isothermal Titration Calorimetry (ITC)

All ITC experiments were carried out at 25° C. on a MicoCal Auto-$ITC_{200}$ system (GE Healthcare). Due to low solubility of 31MEW44 in aqueous buffers, for all ITC experiments the compound was loaded into the cell and the $KRAS^{G12D}$•GppNHp protein was loaded into the syringe.

Working stocks of compound 31MEW44 were prepared in 100% DMSO at 20 mM. 450 μL of the compound solution was loaded into the cell at 250 μM in ITC buffer (25 mM Tris pH 7.4, 1 mM TCEP, 100 mM NaCl, 5 mM $MgCl_2$, 0.05% Tween-20) with a final DMSO concentration at 1.25% (v/v). $KRAS^{G12D}$•GppNHp was buffer exchanged into same ITC buffer using Amicon Ultra 10 kDa size exclusion filter spin columns (buffer replaced with ITC buffer four times). Prior to loading 130 μL of $KRAS^{G12D}$•GppNHp into the syringe at 2.5 mM, DMSO was added to match the amount DMSO present in the cell. ITC titration experiments were carried out at 25° C. with 19 injections, 2 μl per injection, and 180 seconds between each injection. Reference cell power was set to 5 μcal/sec. A control experiment was performed where ITC buffer was titrated into compound 31MEW44 alone to account for heat released due to dilution. This background was subtracted from test data before the final dissociation constant was obtained. Data were analyzed using the one-site binding model in Origin 7.1 software. The dissociation constant, $K_d$, was calculated according to equation $K_d=1/K_a$. Gibbs free energy, ΔG, was calculated from the equation $\Delta G=-RT\ln K_a$. $-T\Delta S$ was calculated from the equation $\Delta G=\Delta H-T\Delta S$. All other parameters, $K_a$, n, ΔH, were determined directly from the titration data.

Mutagenesis

Mutagenesis of the $KRAS^{G12D}$ plasmid was performed using a QuikChange XL site-directed mutagenesis kit from Agilent Technologies, according to the manufacturer's protocol. Primers were designed using the Agilent QuikChange Primer Design application and purchased from Integrated DNA Technologies: $KRAS^{G12D\ D38A}$ forward primer 5' ATA TGA TCC AAC AAT AGA GGC TTC CTA CAG GAA GCA AGT AG 3' (SEQ ID NO: 62), $KRAS^{G12D\ D38A}$ reverse primer 5' CTA CTT GCT TCC TGT AGG AAG CCT CTA TTG TTG GAT CAT AT 3' (SEQ ID NO: 63), $KRAS^{G12D\ I36N}$ forward primer 5' CAT TTT GTG GAC GAA TAT GAT CCA ACA AAT GAG GAT TCC TAC AGG 3' (SEQ ID NO: 64), $KRAS^{G12D\ I36N}$ reverse primer 5' CCT GTA GGA ATC CTC ATT TGT TGG ATC ATA TTC GTC CAC AAA ATG 3' (SEQ ID NO: 65).

Microsomal Stability

Test compounds (0.5 μM) were incubated at 37° C. for up to 45 minutes in 50 mM of potassium phosphate buffer (pH 7.4) containing microsomal protein (0.5 mg/mL) and an NADPH generating system (0.34 mg/mL β-nicotinamide adenine dinucleotide phosphate (NADP), 1.56 mg/mL glucose-6-phosphate, 1.2 units/mL glucose-6-phosphate dehydrogenase). At 0, 5, 15, 30 and 45 minute intervals an aliquot was taken and quenched with acetonitrile (ACN) containing an internal standard. No-cofactor controls at 45 minutes were prepared. Following completion of the experimentation, the samples were analyzed by LC-MS/MS using a Shimadzu HPLC and an Applied Biosystem AP 14000.

In Vivo Pharmacokinetic Analysis 27 mg of 31MEW44, was dissolved in 5.4 mL of 10% NMP/90% PEG-400 to yield a dosing solution with a final concentration of 5 mg/mL. The dose formulation was prepared freshly in the morning of dosing day. A total of 42 male C57 adult mice, each approximately 25 grams in body weight, were administered at 20 mg/kg dose via a single IV bolus injection or a single oral gavage. Blood samples (approximately 400 μL) were collected from three mice per time point via terminal brachial bleed at pre-dose and 30 minutes, 1 hour, 2 hours, 4 hours, 8 hours and 12 hours post-dose. Blood samples were placed into tubes containing K2 EDTA anti-coagulant, and centrifuged at about 2,100 g (rcf) for 10 minutes at 4° C. to separate plasma. Following centrifugation, the resulting plasma was transferred to clean tubes and stored frozen at −80° C. The mouse plasma samples (50 μL) were aliquoted, spiked with internal standard (250 ng/mL tolbutamide), and then extracted with protein precipitation. The supernatant of each sample was diluted and injected into a LC-MS/MS system. The data acquisition and processing were performed using a Sciex API 5500 mass spectrometer with Analyst 1.6.2 software. The standard curve range for the plasma samples was analyzed using a calibration curve of 0.5-5000 ng/mL. The pharmacokinetic (PK) analysis and interpretation of the results were conducted using Winnonlin Phoenix Software.

Mouse Xenograft

For the therapeutic study, athymic nude mice (eight weeks; Charles River Laboratories) were injected with 7 million MDA-MB-231 cells subcutaneously. After 3 days, mice were separated into treatment groups of roughly equal tumor size (58 mm$^3$) and dosed with 180 mg/kg 31MEW44 orally (12 mg/mL, 10% DMSO, pH 4), vehicle orally, or by a combination of intraperitoneal and intravenous injections at 30 mg/kg (4 mg/mL, 5% DMSO in HBSS at pH 4). Over 14 days mice received a total of 10 doses of 31MEW44 or vehicle orally, or six intraperitoneal injections and 4 intravenous injections. Tumor size was measured by electronic caliper every 2 days and calculated using the formula: 0.523×Length×width$^2$.

For the pharmacodynamic study, athymic nude mice (eight weeks; Charles River Laboratories) were injected with 8 million MDA-MB-231 cells subcutaneously. After four days, mice were separated into treatment groups of roughly equal tumor average size and population, and dosed with 30 mg/kg 31MEW44 in 5% DMSO HBSS at pH 4 intraperitoneal or vehicle (5% DMSO HBSS at pH 4) once per day for six days. Tumor size was measured by electronic caliper every two days and calculated using the formula: 0.523×Length×width$^2$.

Mice were euthanized using a $CO_2$ gas chamber before xenograft dissection. Tumors were then weighed, frozen and stored at −80° C. Segments of the tumor were taken (about 60 mg) and suspended in 120 µL lysis buffer. Xenografts were then lysed by sonication (40 amp for 10-15 seconds) and samples were centrifuged at 14,000 rpm at 4° C. for 30 minutes to remove unlysed cells and debris. The supernatant was then analyzed by Western blotting using the aforementioned protocol.

KP$^{f/f}$C Mouse Study

KRAS$^{LSLG12D}$; p53$^{fl/fl}$; Pdx1-Cre (KP$^{F/F}$C) mice have been previously described (Bardeesy et al., 2006). Animals were housed in a barrier facility and monitored daily prior to enrollment on studies. All experiments were carried out in compliance with established IACUC guidelines of Columbia University.

Animal Surgery

KP$^{F/F}$C were palpated twice weekly to assess for tumor formation. Upon discovery of a palpable mass deemed amenable to surgery, tumors were accessed by abdominal laparotomy as previously described for biopsy procedures (Sastra et al., 2014). In short, mice were anesthetized with isofluorane, prepared for aseptic surgery, and injected with buprenorphine intra-operatively to initiate post-operative analgesia. Following visual identification, tumors were held in place with a pair of biopsy forceps while a small-diameter biopsy punch (2-mm diameter, Zivic Instruments PUN2000) was used to cleanly remove a tissue sample. The resultant wound was filled with an absorbable, gelatin compressed sponge to staunch possible bleeding. Incisions were sutured closed and the mouse was allowed to recover from 24-48 hours prior to study initiation.

Sample Processing and Storage

Biopsy samples derived from small animal surgery were divided in two specimens. The first was stored in 10% buffered formalin phosphate overnight at 4° C. and then placed in 70% ethanol for extended storage prior to processing and embedding in paraffin wax blocks. The second was embedded in O.C.T. compound and subsequently frozen atop a bath of liquid nitrogen prior to long-term storage at −80° C. Tumor samples taken at necropsy were processed and stored identically to those described above.

Immunohistochemistry

Paraffin embedded samples were sectioned at 5 µM thickness and mounted on positively charged sample slides. These slides were heated at 60° C. for 15-30 minutes and subsequently rehydrated by standard protocols. Unmasking was performed in 10 mM citrate buffer, pH 6 for 5 minutes in a pressure cooker at high temperature, followed by a peroxidase quench in 3% hydrogen peroxide for 20 minutes. Blocking was carried out using 1.5% horse serum and 2% animal free blocker (Vector Labs) in TBS-T for 1 hour at room temperature. Slides were incubated with primary antibody (cleaved caspase-3, catalog no. 9664; ERK, catalog no. 4695; pERK, catalog no. 4376. All antibodies from Cell Signaling) overnight at 4° C. Slides were then allowed to equilibrate to room temperature prior to washing with TBS-T and incubation with secondary antibody (ImmPress polymer reagent, Vector Labs). Signal was developed with ImmPACT DAB Peroxidase Substrate (Vector Labs). Slides were counterstained with hematoxylin for 30 seconds. For quantification of cleaved-caspase 3 staining, all available 40× fields on three separate sections of biopsy samples and twenty total 40× fields from two separate sections of necropsy samples were analyzed for each study mouse.

Drug Studies

Mice were dosed once daily with 30 mg/kg of 31MEW44 by way of intraperitoneal injection. Mice were monitored closely for changes in health status and were sacrificed after 5 days on study or once they met endpoint criteria in keeping with IACUC standards.

Example 2

Synthesis of Chemical Materials

General Information

All reactions were carried out under a nitrogen atmosphere under anhydrous conditions unless indicated otherwise. Anhydrous methylene chloride (DCM), tetrahydrofuran (THF) and N,N-dimethylformamide (DMF) were purchased from Sigma-Aldrich. Reactions were magnetically stirred and monitored by thin layer chromatography carried out by Merck pre-coated 0.25 mm silica plates containing a 254 nm fluorescence indicator. Flash chromatography was performed on a Teledyne combiflash companion automatic flash chromatography system. Preparative thin layer chromatography was performed on 1 mm plates. Proton nuclear magnetic resonance spectra CH NMR, 300 MHz, 400 MHz, 500 MHz) and proton decoupled carbon nuclear magnetic resonance spectra ($^{13}$C NMR, 100 MHz, 125 MHz) were obtained on a Bruker DPX 300, 400, or 500 MHz instruments in deuterochloroform (CDCl$_3$) with residual chloroform as internal standard. Other deuterated solvents that were used include d$_4$-MeOD and d$_6$-DMSO.

Abbreviations

DIPEA=diisopropylethyl amine, EtOAc=ethyl acetate, MeOH=methanol, DCE=1,2-dichloroethane, Pd(PPh$_3$)$_4$=Tetrakis(triphenylphosphine)palladium(0), Na$_2$SO$_4$=sodium sulfate, MgSO$_4$=magnesium sulfate, NaHCO$_3$=sodium bicarbonate, NH$_4$Cl=ammonium chloride, TFA=trifluoroacetic acid, HBTU=O-(Benzotriazol-1-yl)-N,N,N',N'-tetramethyluronium hexafluorophosphate, HCl=hydrochloric acid, THF=tetrahydrofuran, rt=room temperature.

Synthesis of Two- and Three-Site Compounds
Scheme 1-synthesis of 31MEW44:
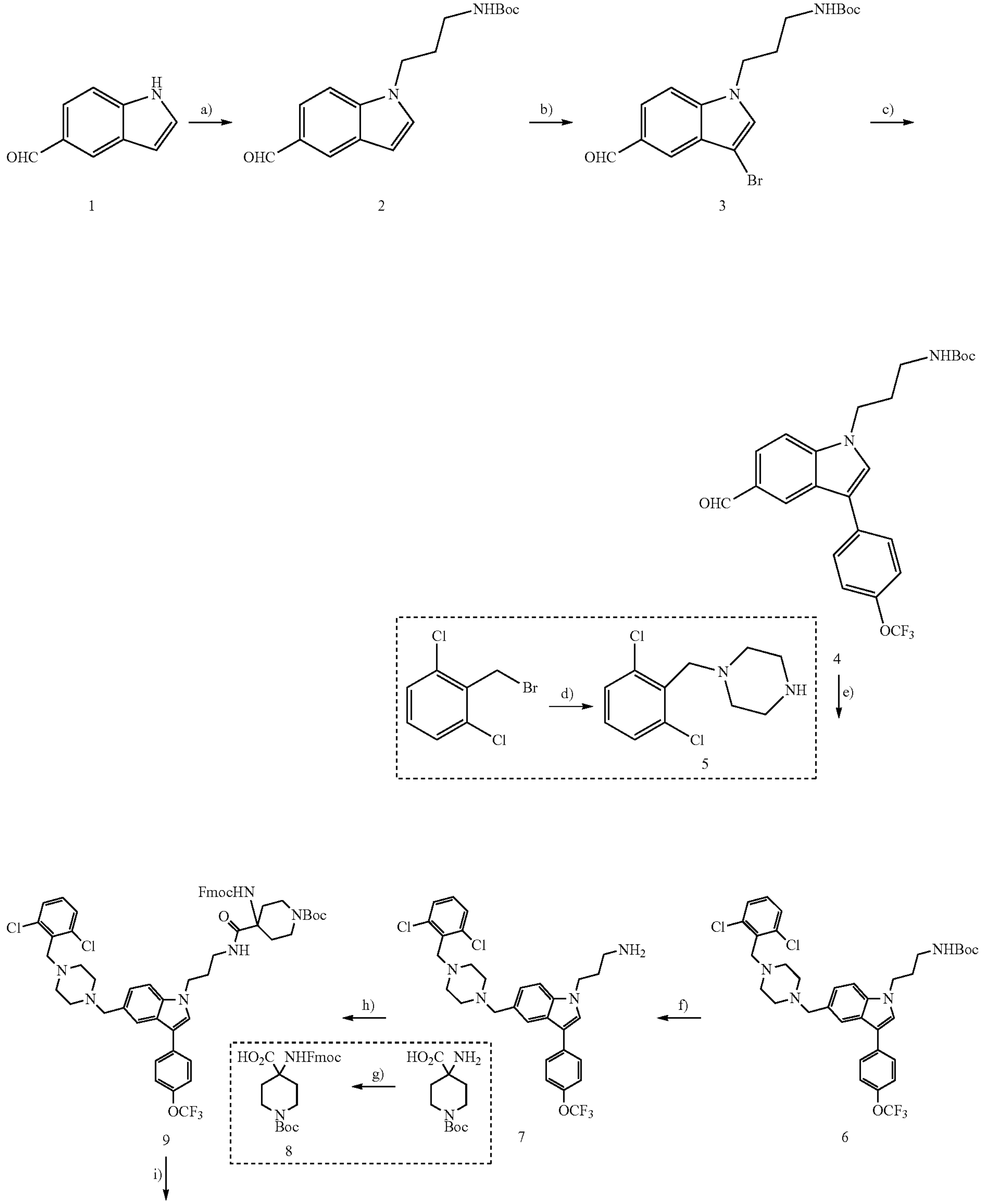

-continued

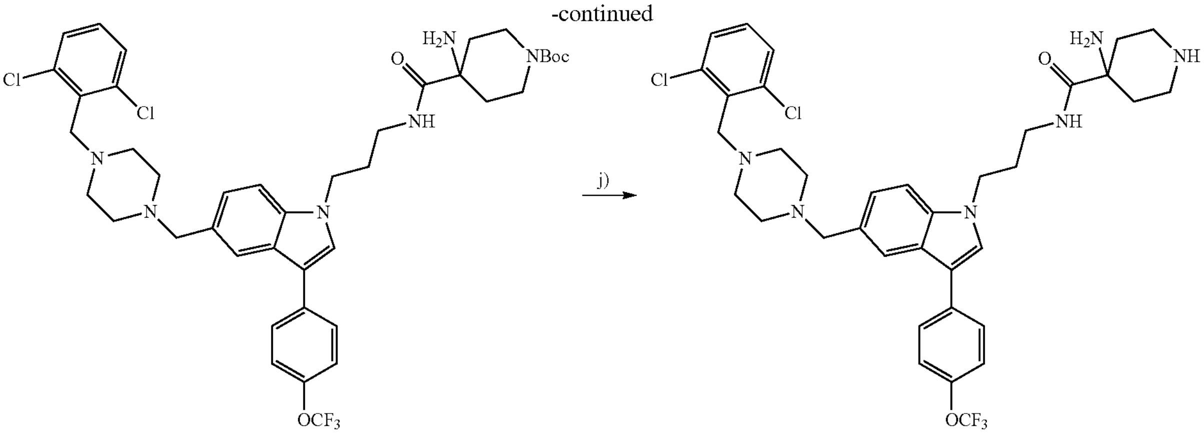

10 31MEW44 a) NaH (1.2 eq), NaI (1.0 eq), 0° C., then 3-(Boc-amino)propyl bromide (1.5 eq) 80° C., DMF, 12-36 hr; b) $Br_2$, -78° C., THF, 2 hr; c) boronic acid (1.5 eq), $Pd(PPh_3)_4$ (5%), $K_2CO_3$, 80° C., dioxane/water (5:1), 36 hr; d) piperazine (4.0 eq), 0° C. to 25° C., THF, 12 h; e) compound 5 (3.0 eq), $ZnCl_2$ (0.1 eq), 60° C., 1,2-DCE, 3 hr, then $NaBH_3CN$ (2.0 eq) in MeOH, 60° C., 3 hr; f) HCl in dioxane (xs), 25° C., 12 hr; g) Fmoc chloride (1.5 eq), $Na_2CO_3$ 10% in $H_2O$ (5 eq), THF, 0° C. to 25° C., 12 hr; h) compound 8 (1.2 eq), EDIPA (1.2 eq), HBTU (1.2 eq), 0° C., 20 min, then compound 7, DMF, 25° C., 4 hr; i) piperdine (6.0 eq) 25° C., DCM, j) HCl in dioxane (xs), 25° C. 12 hr.

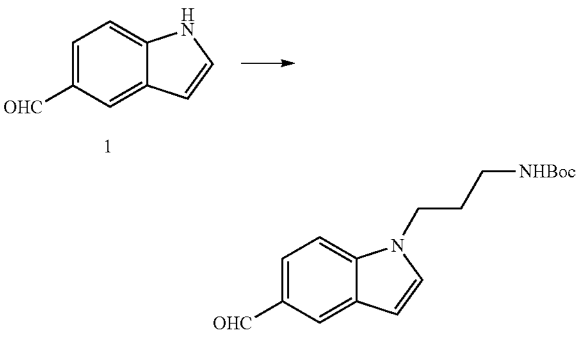

1

2 tert-butyl 3-(5-formyl-1H-indol-1-yl)propylcarbamate (Scheme 1, Compound 2)

To a solution of 1H-indole-5-carbaldehyde (Scheme 1, compound 1) (3.5 g, 24 mmol) in DMF (100 mL) at 0° C., sodium hydride (60% in mineral oil) (1.1 g, 28.8 mmol, 1.2 eq) was added in several portions over about 5 minutes. The mixture was stirred for 45 minutes at 0° C. before the sequential addition of 3-(Boc-amino)propyl bromide (8 g, 33.6 mmol, 1.4 eq) and sodium iodide (3.6 g, 24 mmol, 1.0 eq). The solution was warmed to 80° C. and stirred for 48 hours. Upon completion, the reaction was diluted with saturated aqueous $NaHCO_3$ and extracted 3 times with EtOAc. The combined organic layers were washed with brine, dried ($Na_2SO_4$), concentrated, and the crude material was purified by combi flash 0 to 50% EtOAc in hexanes (3.4 g, 47% yield). $^1H$ NMR (400 MHz, Chloroform-d) δ 10.05 (s, 1H), 8.18 (d, J=1.5 Hz, 1H), 7.81 (dd, J=8.7, 1.6 Hz, 1H), 7.26 (d, J=3.1 Hz, 1H), 6.75-6.60 (m, 1H), 4.54 (s, 1H), 4.25 (t, J=6.9 Hz, 2H), 3.17 (d, J=7.2 Hz, 2H), 2.08 (p, J=6.9 Hz, 2H), 1.47 (s, 8H). $^{13}C$ NMR (101 MHz, $CDCl_3$) 192.44, 156.08, 139.19, 129.79, 129.34, 128.41, 126.56, 121.80, 109.80, 103.60, 44.05, 38.04, 30.63, 28.38.

HRMS (m/z): [M+] cald for C17H22N2O3, 302.37. found 302.16.

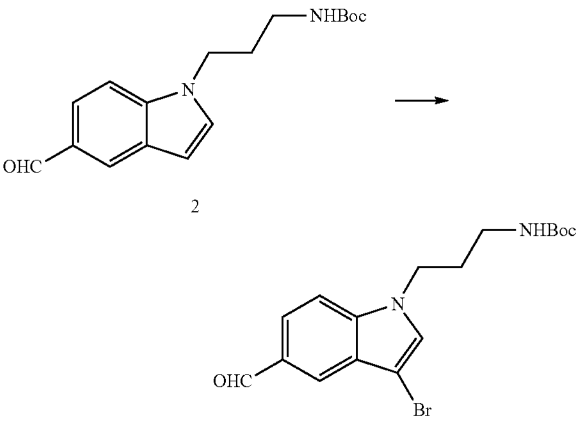

2

3 tert-butyl 3-(3-bromo-5-formyl-1H-indol-1-yl)propylcarbamate (Scheme 1, Compound 3)

To a solution of tert-butyl 3-(5-formyl-1H-indol-1-yl) propylcarbamate (Scheme 1, compound 2) (1.8 g, 5.95 mmol) in THF (120 mL) at −78° C., $Br_2$ (0.367 mL, 7.1 mmol, 1.2 eq) was added dropwise over about 5 minutes. The resulting mixture was stirred at −78° C. for 2 hours. Upon completion, the reaction contents were poured onto a solution of ice (about 300 g), water (200 mL), ammonium hydroxide (1 mL, 12 M), sodium thiosulfate pentahydrate (1 mL, saturated solution in water). The crude material was extracted 3 times with EtOAc, the combined organic layers were washed with brine, dried ($Na_2SO_4$), concentrated, and the crude material was purified by combiflash 0 to 50% EtOAc in hexanes to yield tert-butyl 3-(3-bromo-5-formyl-1H-indol-1-yl)propylcarbamate (Scheme 1, compound 3) (1.2 g, 53% yield). $^1H$ NMR (400 MHz, Chloroform-d) δ 10.09 (s, 1H), 8.12 (d, J=1.5 Hz, 1H), 7.86 (dd, J=8.7, 1.5 Hz, 1H), 7.43 (d, J=8.6 Hz, 1H), 7.30 (s, 1H), 4.57 (s, 1H), 4.23 (t, J=6.9 Hz, 2H), 3.18 (d, J=6.8 Hz, 2H), 2.08 (q, J=6.7 Hz, 2H), 1.47 (s, 9H). $^{13}C$ NMR (101 MHz, CDCl3) 191.19, 155.31, 137.89, 128.98, 127.87, 126.53, 124.05, 121.63, 109.40, 91.20, 78.67, 76.65, 76.33, 76.01, 43.54, 37.09, 29.82, 27.57, 27.54. HRMS (m/z): [M+] cald for C17H21BrN2O3, 381.26. found 380.07.

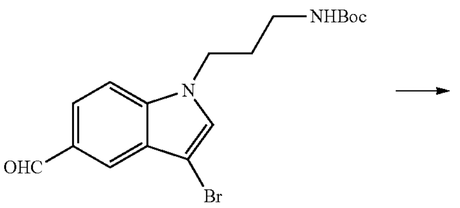

3

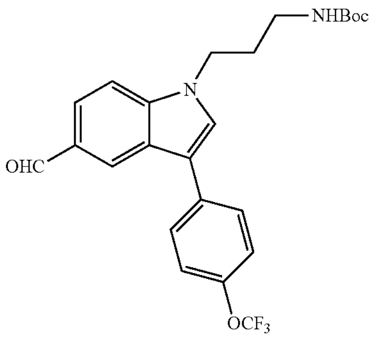

4 tert-butyl 3-(5-formyl-3-(4-(trifluoromethoxy)phenyl)-1H-indol-1-yl)propylcarbamate (Scheme 1, Compound 4)

To a solution of tert-butyl 3-(3-bromo-5-formyl-1H-indol-1-yl)propylcarbamate (Scheme 1, compound 3) (1.49 g, 3.91 mmol) in dioxane (30 mL), 4-(trifluoromethoxy)phenylboronic acid (1.20 g, 5.87 mmol, 1.5 eq), $Pd(PPh_3)_4$ (0.225 g, 0.195 mmol, 0.05 eq), and a solution of potassium carbonate (1.08 g, 7.82 mmol, 2.0 eq) were added sequentially. The resulting mixture was heated to 80° C. and stirred for 48 hours. Upon completion, the reaction was diluted with saturated aqueous $NaHCO_3$ and extracted 3 times with EtOAC. The combined organic layers were dried ($Na_2SO_4$), concentrated, and the crude material was purified by combiflash 0 to 40% EtOAc in hexanes to yield tert-butyl 3-(5-formyl-3-(4-(trifluoromethoxy)phenyl)-1H-indol-1-yl) propylcarbamate (Scheme 1, compound 4) (1.3 g, 72%). $^1$H NMR (400 MHz, Chloroform-d) δ10.00 (s, 1H), 8.33 (d, J=1.6 Hz, 1H), 7.78 (dd, J=8.7, 1.6 Hz, 1H), 7.66-7.59 (m, 2H), 7.41 (d, J=5.6 Hz, 2H), 7.29 (d, J=8.3 Hz, 2H), 5.01 (s, 1H), 4.24 (t, J=6.9 Hz, 2H), 3.30 ? 3.09 (m, 2H), 2.16-1.97 (m, 3H), 1.45 (s, 9H). $^{13}$C NMR (101 MHz, CDCl3) 191.45, 155.36, 139.01, 132.36, 128.96, 127.71, 126.66, 125.19, 124.10, 121.66, 120.61, 116.82, 109.40, 76.58, 76.26, 75.94, 43.21, 29.63, 27.43. HRMS (m/z): [M+] cald for C24H25F3N2O4, 462.46. found 462.18.

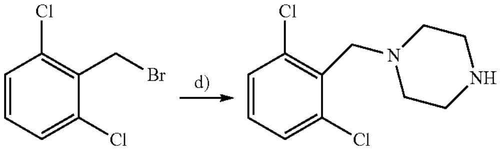

5

1-(2, 6-dichlorobenzyl)piperazine (5)

To a solution of piperazine (112 mmol, 6.0 eq) in THF (180 mL) at 0° C., a solution of 2,6-dichlorobenzyl bromide (4.5 g, 18.8 mmol) in THF (20 mL) was added dropwise over 10 minutes. The resulting mixture was slowly allowed to warm to room temperature and stirred for 24 hours. Upon completion, the THF was removed and the crude material was re-suspended in DCM and water, and extracted 2 additional times with DCM. The combined organic layers were dried ($Na_2SO_4$), concentrated, and the crude material was purified by combiflash 0 to 20% MeOH in DCM to provide 1-(2,6-dichlorobenzyl)piperazine (Scheme 1, compound 5) (2.3 g, 50% yield). $^1$H NMR (400 MHz, Methanol-$d_4$) δ 7.62-7.30 (m, 2H), 7.23 (dd, J=8.7, 7.4 Hz, 1H), 3.74 (s, 2H), 2.92-2.69 (m, 4H), 2.56 (t, J=4.9 Hz, 4H). $^{13}$C NMR (101 MHz, MeOD) 136.76, 133.67, 129.18, 128.24, 56.55, 53.41, 44.95. HRMS (m/z): [M+] cald for C11H14C12N2, 245.15. found 245.06.

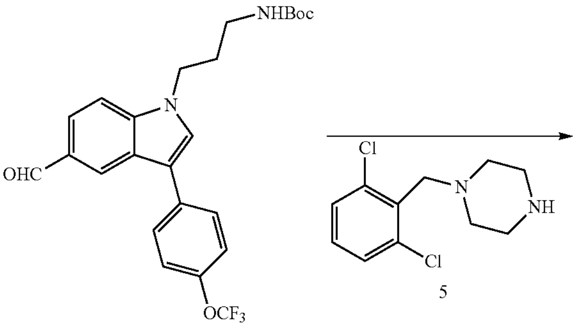

4 5

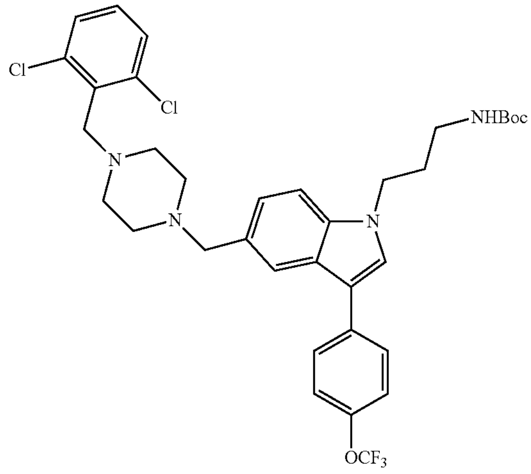

6 tert-butyl 3-(5-((4-(2,6-dichlorobenzyl)piperazin-1-yl)methyl)-3-(4-(trifluoromethoxy)phenyl)-1H-indol-1-yl)propylcarbamate (Scheme 1, Compound 6)

To a solution of tert-butyl 3-(5-formyl-3-(4-(trifluoromethoxy)phenyl)-1H-indol-1-yl)propylcarbamate (Scheme 1, compound 4) (1.1 g, 2.38 mmol) in DCE (15 mL), 1-(2,6-dichlorobenzyl)piperazine (Scheme 1, compound 5) (1.75 g, 7.14 mmol, 3.0 eq) and zinc chloride (65 mg, 0.476 mmol, 0.2 eq) were added. The resulting mixture was stirred at 60° C. for 2 hours before the addition of a solution of sodium cyanoborohydride (309 mg, 4.76 mmol, 2.0 eq) in methanol (3 mL). The mixture was stirred for an additional 6 hours at 60° C. Upon completion, the reaction was concentrated and purified directly by combiflash 0 to 5% MeOH in DCM to yield tert-butyl 3-(5-((4-(2,6-dichlorobenzyl)piperazin-1-yl)methyl)-3-(4-(trifluoromethoxy)phenyl)-1H-indol-1-yl)propylcarbamate (6) (0.7 g, 42% yield). $^{1}$H NMR (400 MHz, Methanol-$d_4$) δ 8.01 (d, J=1.6 Hz, 1H), 7.82-7.74 (m, 2H), 7.65 (s, 1H), 7.58 (d, J=8.5 Hz, 1H), 7.43-7.33 (m, 5H), 7.32-7.22 (m, 2H), 4.37-4.26 (m, 4H), 3.87 (s, 2H), 3.33 (p, J=1.6 Hz, 4H), 3.22-3.03 (m, 6H), 2.82 (s, 4H), 2.05 (t, J=6.8 Hz, 2H), 1.45 (s, 8H). $^{13}$C NMR (101 MHz, MeOD) 137.27, 136.67, 134.52, 132.90, 129.55, 128.34, 128.23, 127.60, 126.30, 124.15, 122.22, 121.12, 115.36, 110.27, 61.40, 55.10, 51.60, 49.79, 43.43, 29.96, 27.36. HRMS (m/z): [M+] cald for C35H39Cl2F3N4O3, 691.61. found 691.24.

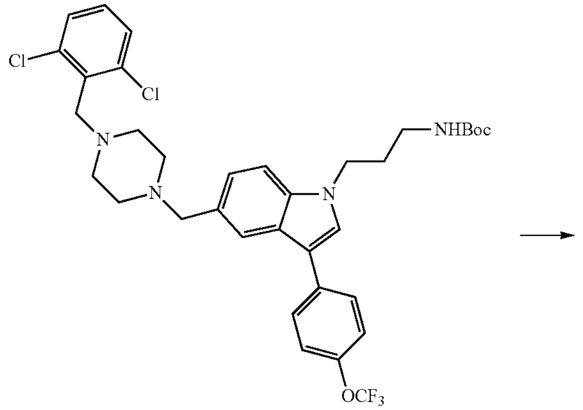

6

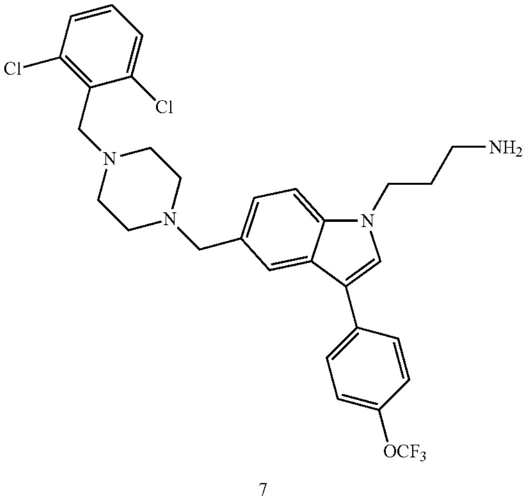

7

3-(5-((4-(2,6-dichlorobenzyl)piperazin-1-yl)methyl)-3-(4-(trifluoromethoxy)phenyl)-1H-indol-1-yl)propan-1-amine (Scheme 1, Compound 7)

To a solution of tert-butyl 3-(5-((4-(2,6-dichlorobenzyl)piperazin-1-yl)methyl)-3-(4-(trifluoromethoxy)phenyl)-1H-indol-1-yl)propylcarbamate (Scheme 1, compound 6) (2.8 g, 4.05 mmol) in dioxane (80 mL) a solution of HCl (4 M in dioxane) was added (30 mL, 7.50 mmol) and the resulting solution was stirred for 24 hours. Upon completion, the dioxane was removed, and the crude material was re-suspended in methanol and an excess of potassium carbonate was added (about 6 g). The slurry was stirred at room temperature for 1 hour to ensure basification. The potassium carbonate was filtered off, the solution was concentrated and purified by preparative TLC (20% MeOH in DCM) to provide 3-(5-((4-(2,6-dichlorobenzyl)piperazin-1-yl)methyl)-3-(4-(trifluoromethoxy)phenyl)-1H-indol-1-yl)propan-1-amine (Scheme 1, compound 7) (1.5 g, 63% yield).

$^{1}$H NMR (400 MHz, DMSO-$d_6$) δ 8.21-7.97 (m, 2H), 7.90 (s, 1H), 7.83 (d, J=8.3 Hz, 2H), 7.66 (d, J=8.5 Hz, 1H), 7.49-7.29 (m, 6H), 4.37 (t, J=6.9 Hz, 2H), 3.72 (s, 2H), 2.80 (t, J=7.5 Hz, 3H), 2.75-2.58 (m, 4H), 2.51 (p, J=1.9 Hz, 2H), 2.19-2.04 (m, 2H). $^{13}$C NMR (101 MHz, DMSO) 146.47, 136.74, 136.36, 134.79, 133.44, 130.38, 128.94, 128.42, 128.18, 125.46, 121.83, 121.76, 114.42, 110.76, 55.68, 51.36, 43.24, 40.40, 40.19, 40.12, 39.98, 39.77, 39.69, 39.56, 39.48, 39.35, 39.27, 39.15, 36.76, 28.12. HRMS (m/z): [M+] cald for C30H31Cl2F3N40, 591.49. found 591.18.

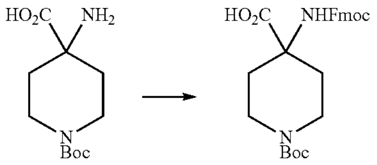

8

4-((9H-fluoren-9-yl)methoxy)carbonylamino)-1-(tert-butoxycarbonyl)piperidine-4-carboxylic acid (Scheme 1, Compound 8)

A solution of 4-amino-1-(tert-butoxycarbonyl)piperidine-4-carboxylic acid (5 g, 20.5 mmol) in THF (300 mL) and $Na_2CO_3$ (6.45 g, 61.5 mmol, 3.0 eq in 64.5 mL of water) was cooled to 0° C. before the dropwise addition of a solution of Fmoc chloride (5.3 g, 30.7 mmol, 1.5 eq) in THF (30 mL). The resulting mixture was slowly warmed to 25° C. and stirred for an additional 12 hours. Upon completion, the reaction contents were carefully acidified with HCl (1 M), and the crude material was extracted with EtOAc (three times). The combined organic layers were dried ($Na_2SO_4$), concentrated, and the crude material was purified by combiflash 0 to 10% A MeOH in DCM to provide 4-(((9H-fluoren-9-yl)methoxy)carbonylamino)-1-(tert-butoxycarbonyl)piperidine-4-carboxylic acid (Scheme 1, compound 8) (4.02 g, 42% yield).

$^{1}$H NMR (400 MHz, Chloroform-d) δ 7.75 (d, J=7.5 Hz, 2H), 7.57 (d, J=7.5 Hz, 2H), 7.45-7.34 (m, 2H), 7.30 (td, J=6.9, 6.3, 1.4 Hz, 2H), 4.68-4.26 (m, 2H), 4.19 (t, J=6.5 Hz, 1H), 3.96-3.65 (m, 3H), 3.08 (s, 2H), 1.91-1.77 (m, 2H), 1.48 (s, 9H). $^{13}$C NMR (101 MHz, $CDCl_3$) 177.19, 154.73, 143.67, 141.32, 127.72, 127.08, 124.95, 119.97, 80.06, 67.90, 66.86, 57.49, 47.19, 31.98, 28.42, 25.57. HRMS (m/z): [M+] cald for C26H30N2O6, 466.53. found 466.2.

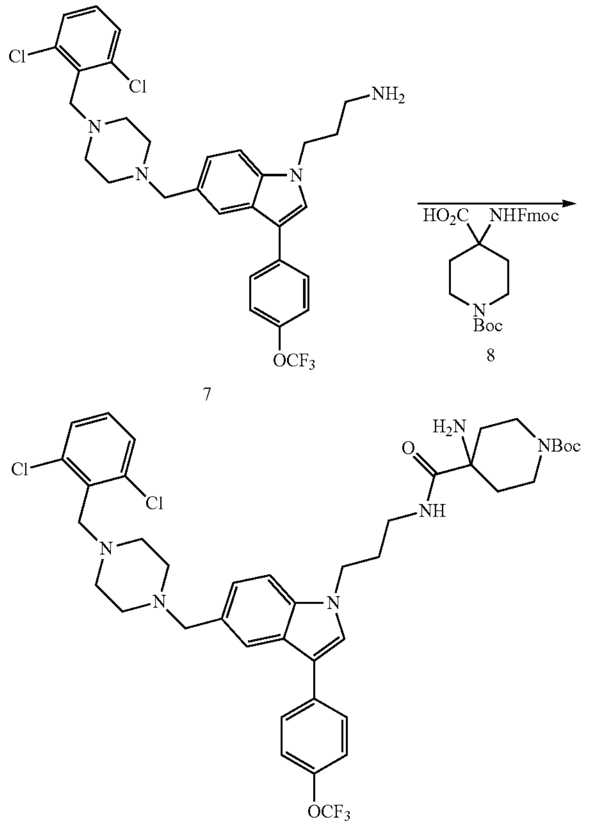

7 8 10 tert-butyl 4-amino-4-(3-(5-((4-(2,6-dichlorobenzyl)piperazin-1-yl)methyl)-3-(4-(trifluoromethoxy)phenyl)-1H-indol-1-yl)propylcarbamoyl)piperidine-1-carboxylate (Scheme 1, Compound 10)

HBTU (1.16 g, 3.05 mmol, 1.2 eq) was added to a solution of 4-(((9H-fluoren-9-yl)methoxy)carbonylamino)-1-(tert-butoxycarbonyl)piperidine-4-carboxylic acid (Scheme 1, compound 8) (1.42 g, 3.05 mmol, 1.2 eq) and EDIPA (530 μL, 3.05 mmol, 1.2 eq) in DMF (20 mL) at 0° C. and stirred for 30 minutes. A solution of 3-(5-((4-(2,6-dichlorobenzyl)piperazin-1-yl)methyl)-3-(4-(trifluoromethoxy)phenyl)-1H-indol-1-yl)propan-1-amine (Scheme 1, compound 7) (1.5 g, 2.54 mmol) in DMF (3 mL) was added and stirred for an additional 6 hours. Upon completion, the reaction was quenched with saturated aqueous $NaHCO_3$ and extracted 3 times with EtOAc. The combined organic layers were washed with brine, dried ($Na_2SO_4$), concentrated, and the crude material was purified by combiflash 0 to 5% MeOH in DCM. The slightly impure material (2.1 g) was suspended in DCM (15 mL) and piperidine (1.2 mL, 12.1 mmol, 6.0 eq) was added and stirred for 24 hours. Upon completion, the reaction was concentrated and purified directly by combiflash 0 to 5% MeOH in DCM, to yield tert-butyl 4-amino-4-(3-(5-((4-(2,6-dichlorobenzyl)piperazin-1-yl)methyl)-3-(4-(trifluoromethoxy)phenyl)-1H-indol-1-yl)propylcarbamoyl)piperidine-1-carboxylate (Scheme 1, compound 10) (0.89 g, 43% yield). $^1$H NMR (400 MHz, Methanol-$d_4$) δ 7.84 (d, J=1.6 Hz, 1H), 7.78-7.69 (m, 2H), 7.55 (s, 1H), 7.42 (d, J=8.5 Hz, 1H), 7.35-7.24 (m, 4H), 7.23-7.13 (m, 2H), 4.24 (t, J=6.7 Hz, 2H), 3.78 (dt, J=13.7, 4.2 Hz, 2H), 3.72 (d, J=6.3 Hz, 4H), 3.66 (s, 2H), 3.58-3.41 (m, 3H), 3.33 (p, J=1.7 Hz, 1H), 3.24 (t, J=6.6 Hz, 2H), 3.14 (s, 2H), 2.69-2.39 (m, 9H), 2.07 (dd, J=8.2, 5.2 Hz, 3H), 1.97-1.79 (m, 2H), 1.66 (d, J=5.4 Hz, 1H), 1.55 (dtd, J=11.3, 5.8, 3.5 Hz, 4H), 1.46 (d, J=3.4 Hz, 9H), 1.32-1.21 (m, 2H). $^{13}$C NMR (101 MHz, MeOD) 177.86, 173.27, 154.90, 154.76, 146.75, 136.51, 136.32, 134.73, 133.47, 128.98, 128.03, 127.82, 127.38, 126.62, 125.83, 123.84, 120.91, 120.53, 114.77, 109.36, 79.48, 62.74, 56.08, 55.57, 55.08, 52.23, 51.84, 48.10, 47.88, 47.67, 47.46, 47.25, 47.05, 47.03, 46.84, 43.69, 36.77, 35.75, 33.61, 29.21, 27.16, 25.76, 24.05. HRMS (m/z): [M+] cald for C41H49Cl2F3N6O4, 817.77. found 817.38.

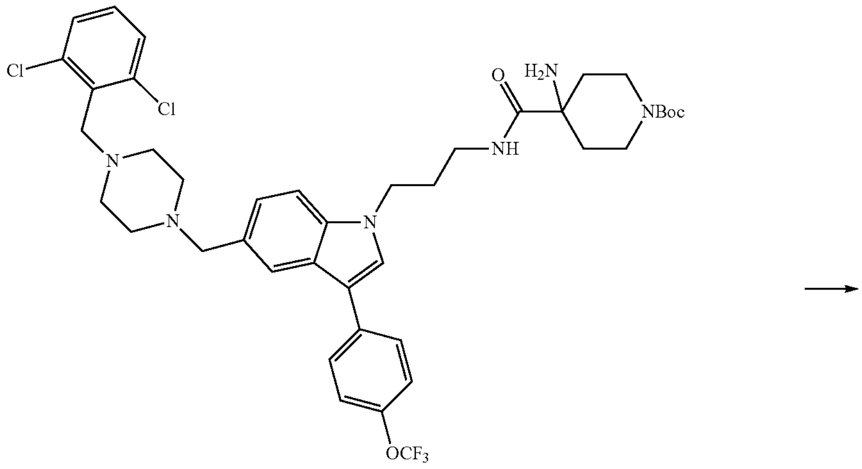

10

-continued

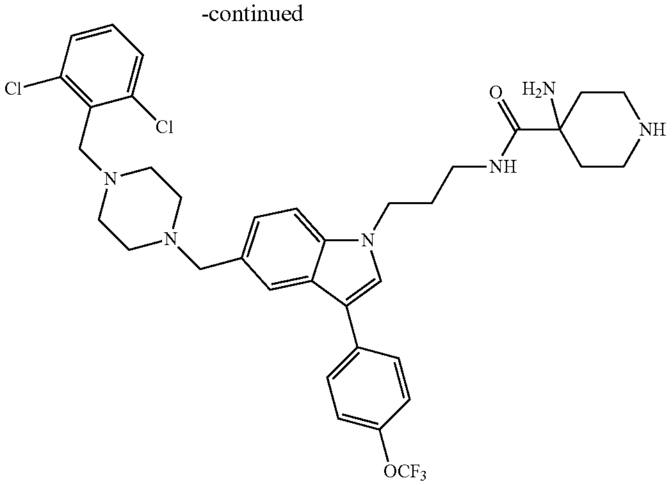

31MEW44

4-amino-N-(3-(5-((4-(2,6-dichlorobenzyl)piperazin-1-yl)methyl)-3-(4-(trifluoromethoxy)phenyl)-1H-indol-1-yl)propyl)piperidine-4-carboxamide: 31MEW44

Tert-butyl 4-amino-4-(3-(5-((4-(2,6-dichlorobenzyl)piperazin-1-yl)methyl)-3-(4-(trifluoromethoxy)phenyl)-1H-indol-1-yl)propylcarbamoyl)piperidine-1-carboxylate (Scheme 1, compound 10) (40 mg, 0.049 mmol) was dissolved in 1,4-dioxane (0.5 mL) before the addition of HCl in 1,4-dioxane (0.1 mL of a 4 M solution). The resulting mixture was stirred for 6 hours at 25° C. Upon completion, the 1,4-dioxane was removed, and the residue was resuspended in MeOH and solid $K_2CO_3$ (100 mg, XS) was added. The crude material was purified by preparative TLC (15% MeOH in DCM) to provide 31MEW44 (18 mg, 51%). $^1$H NMR (400 MHz, $d_4$-MeOD) δ 7.82 (s, 1H), 7.74 (d, J=8.7 Hz, 2H), 7.55 (s, 1H), 7.42 (d, J=8.4 Hz, 1H), 7.34 (d, J=8.0 Hz, 2H), 7.31 (d, J=8.2 Hz, 2H), 7.21 (dd, J=8.5, 7.5 Hz, 2H), 4.26 (t, J=6.7 Hz, 2H), 3.75 (s, 2H), 3.60 (s, 2H), 3.24 (t, J=6.6 Hz, 2H), 2.99-2.89 (m, 4H), 2.60 (brs, 4H), 2.49 (brs, 4H), 2.11-1.97 (m, 4H), 1.35 (brd, J=13.9 Hz, 2H). $^{13}$C NMR (100 MHz, $d_4$-MeOD) δ 179.4, 148.3, 138.1, 137.8, 136.4, 135.1, 130.5, 129.7, 129.6, 128.1, 127.4, 125.4, 122.5, 121.9, 116.3, 110.8, 64.5, 57.2, 56.2, 53.9, 53.7, 49.8, 45.2, 41.8, 38.3, 34.8, 30.8. HRMS (m/z): $[M+H]^+$ cald for $C_{36}H_{42}Cl_2F_3N_6O_2$, 717.2698. found 717.2675.

34MEW43

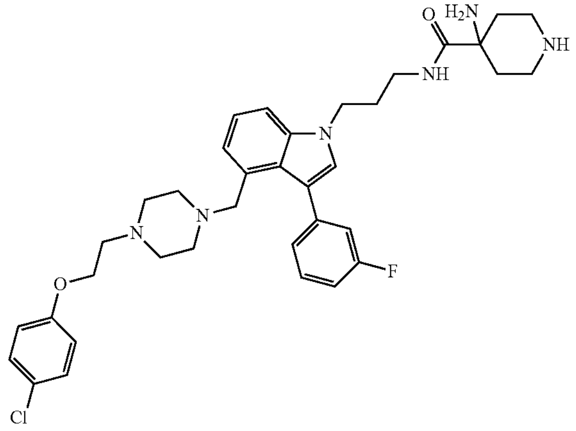

4-amino-N-(3-(4-((4-(2-(4-chlorophenoxy)ethyl)piperazin-1-yl)methyl)-3-(3-fluorophenyl)-1H-indol-1-yl)propyl)piperidine-4-carboxamide: 34MEW43

The compound was prepared according to the protocols for 31MEW44. 1 H-indole-4-carbaldehyde was used in place of compound 1, step a in scheme 1. For step c, 3-fluorophenyl boronic acid was used in place of 4-trifluoromethoxy phenyl boronic acid. For step d, 4-chorophenyl 2-bromo ether was used in place of 2,6-dichlorobenzylbromide, the resulting product was then used in step e. The subsequent steps are identical to the synthesis of 31MEW44. $^1$H NMR (400 MHz, Methanol-$d_4$) δ 7.44 (dd, J=8.4, 1.0 Hz, 1H), 7.38 (td, J=8.0, 6.1 Hz, 1H), 7.34-7.22 (m, 5H), 7.22-7.15 (m, 1H), 7.08-6.98 (m, 2H), 6.94-6.87 (m, 2H), 4.34-4.21 (m, 2H), 4.06 (t, J=5.5 Hz, 2H), 3.56 (s, 2H), 2.73 (t, J=5.5 Hz, 2H), 2.43 (s, 3H), 2.25-2.08 (m, 7H). $^{13}$C NMR (101 MHz, MeOD) 177.31, 163.55, 161.13, 136.91, 128.94, 127.83, 126.24, 125.39, 122.16, 121.08, 116.98, 116.77, 115.65, 112.55, 109.28, 59.49, 56.42, 53.71, 52.66, 51.31, 43.53, 39.68, 36.94, 31.10, 29.33. HRMS (m/z): [M+] cald for C36H44ClFN6O2, 647.22. found 647.34.

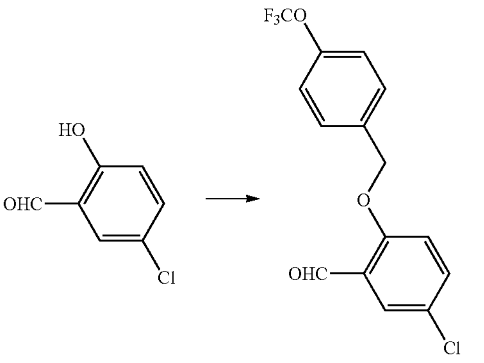 [SMILES: O=Cc1cc(Cl)ccc1O ; O=Cc1cc(Cl)ccc1OCc1ccc(OC(F)(F)F)cc1]

5-chloro-2-(4-(trifluoromethoxy)benzyloxy)benzaldehyde

To a solution of 5-chlorosalicylaldehyde (commercially available from Sigma, St. Louis, Mo.) (82 mg, 0.56 mmol) in DMF (1 mL), $K_2CO_3$ (87 mg, 0.63 mmol, 1.2 eq) was added and stirred for 10 minutes at 25° C. before the addition of 4-(trifluoromethoxy)benzyl bromide (commercially available from Sigma) (126 μL, 0.788 mmol, 1.4 eq). The resulting mixture was stirred at 25° C. for 12 hours. Upon completion, the reaction contents were diluted with saturated $NaHCO_3$ and extracted with EtOAc (three times). The combined organic layers were washed once with brine, dried ($Na_2SO_4$), concentrated and purified by combiflash 0 to 30% EtOAc to provide 5-chloro-2-(4-(trifluoromethoxy)benzyloxy)benzaldehyde (99 mg, 53% yield). $^1$H NMR (400 MHz, Chloroform-d) δ 10.49 (s, 1H), 7.84 (d, J=2.8 Hz, 1H), 7.55-7.45 (m, 3H), 7.34-7.23 (m, 3H), 7.01 (d, J=8.9 Hz, 1H), 5.20 (s, 2H). $^{13}$C NMR (101 MHz, $CDCl_3$) 188.13, 135.38, 128.78, 128.31, 121.32, 114.54, 70.03. HRMS (m/z): [M+] cald for C15H1OClF3O3, 330.69. found 329.02.

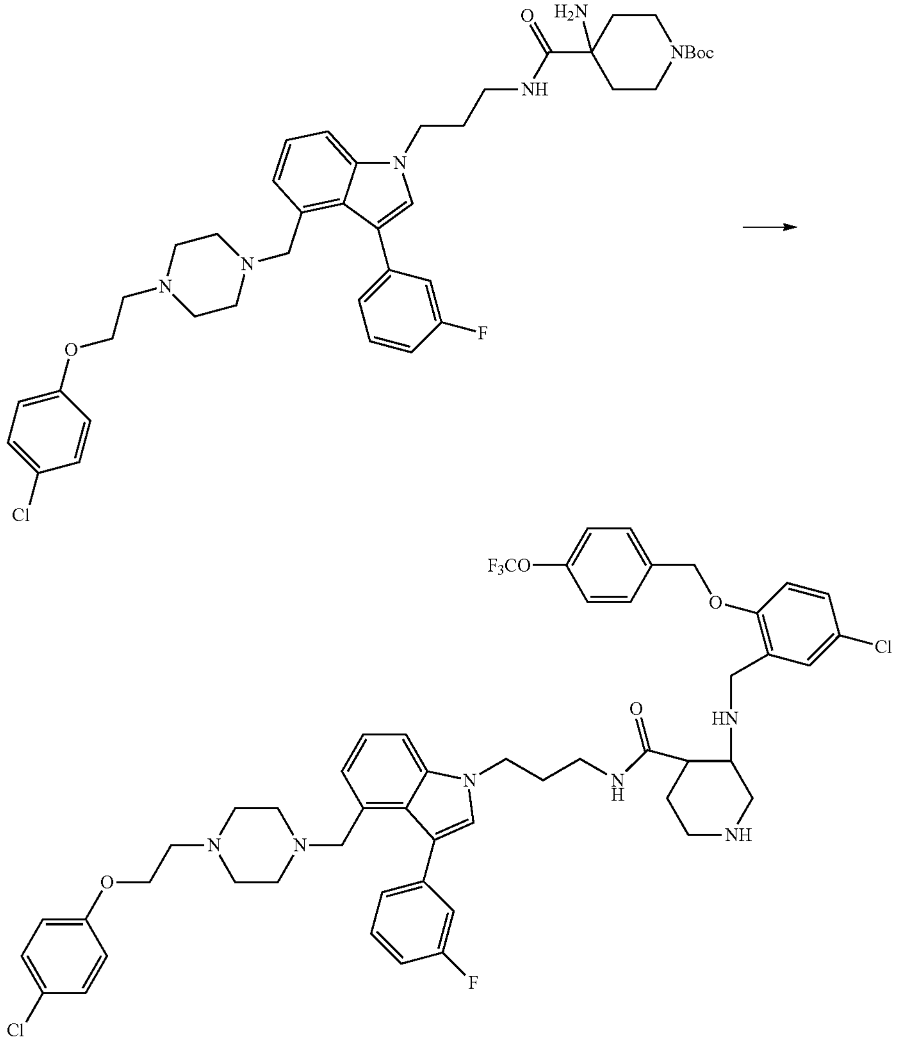

4-(5-chloro-2-(4-(trifluoromethoxy)benzyloxy)benzylamino)-N-(3-(4-((4-(2-(4-chlorophenoxy)ethyl)piperazin-1-yl)methyl)-3-(3-fluorophenyl)-1H-indol-1-yl)propyl)piperidine-4-carboxamide: 34MEW95

4-amino-4-(3-(4-((4-(2-(4-chlorophenoxy)ethyl)piperazin-1-yl)methyl)-3-(3-fluorophenyl)-1H-indol-1-yl)propylcarbamoyl)piperidine-1-carboxylate was synthesized using the methods described for 31MEW44 with modifications. 1H-indole-4-carbaldehyde was used in place of compound 1, step a in scheme 1. For step c, 3-fluorophenyl boronic acid was used in place of 4-trifluoromethoxy phenyl boronic acid. For step d, 4-chorophenyl 2-bromo ether was used in place of 2,6-dichlorobenzylbromide, the resulting product was then used in step e. The subsequent steps are identical to the synthesis of 31MEW44.

To a solution of tert-butyl 4-amino-4-(3-(4-((4-(2-(4-chlorophenoxy)ethyl)piperazin-1-yl)methyl)-3-(3-fluorophenyl)-1H-indol-1-yl)propylcarbamoyl)piperidine-1-carboxylate (29 mg, 0.0443 mmol) in DCE (1 mL), 5-chloro-2-(4-(trifluoromethoxy)benzyloxy)benzaldehyde (44 mg, 0.133 mmol, 3.0 eq), and $MgSO_4$ (10 mg) were added and stirred at 40° C. for 1 hour prior to the addition of sodium triacetoxyborohydride (19 mg, 0.0886 mmol, 2.0 eq). The resulting mixture was stirred for an additional 8 hours at 40° C. before being concentrated and purified directly by preparative TLC (2% MeOH in DCM). The Boc group of the product was then removed (using the protocol for 31MEW44) to provide 34MEW95 (14 mg, 33% yield over two steps). $^1H$ NMR (400 MHz, Methanol-$d_4$) δ 7.41-7.29 (m, 5H), 7.29-7.13 (m, 8H), 7.12-6.97 (m, 4H), 6.92-6.86 (m, 2H), 5.71 (s, 1H), 4.95 (q, J=11.1 Hz, 2H), 4.14 (q, J=7.1 Hz, 2H), 4.05 (t, J=5.5 Hz, 2H), 3.53 (s, 2H), 3.44 (ddd, J=14.7, 9.1, 6.3 Hz, 1H), 3.16 (dtd, J=27.2, 13.1, 11.7, 4.3 Hz, 3H), 3.00-2.80 (m, 2H), 2.72 (t, J=5.5 Hz, 2H), 2.09-1.79 (m, 5H), 1.71 (d, J=14.1 Hz, 1H). $^{13}C$ NMR (101 MHz, MeOD) 175.98, 157.45, 155.76, 136.79, 135.21, 130.37, 130.19, 129.73, 129.32, 128.89, 128.77, 128.68, 127.46, 126.16, 126.14, 126.01, 125.37, 125.29, 122.16, 121.13, 120.82, 116.95, 116.91, 116.74, 115.62, 113.99, 112.43, 112.22, 108.87, 69.47, 65.27, 59.72, 58.80, 56.68, 52.97, 51.76, 43.26, 40.50, 40.39, 38.38, 31.20, 29.71, 27.33. HRMS (m/z): [M+] cald for C51H54Cl2F4N6O4, 961.61. found 961.3.

Synthesis of Pharmacophore Compounds

Scheme 2-synthesis of 31MEW79:

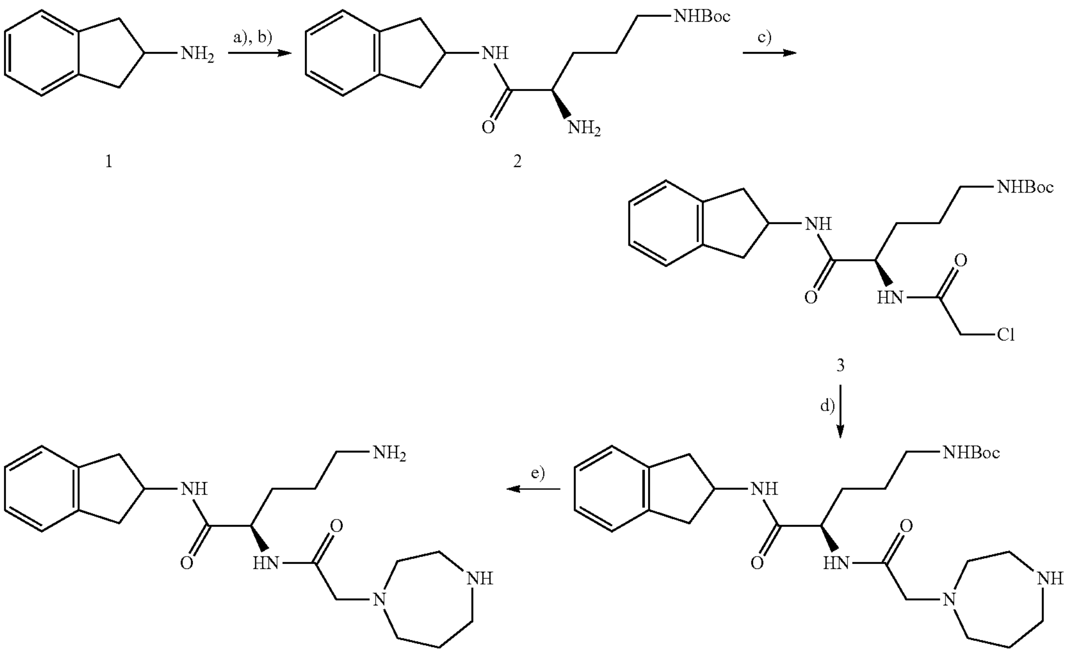

1 2 3 31MEW79 4 a) (R)-2-amino-5-(tert-butoxycarbonylamino)pentanoic acid (1.0 eq), EDIPA (1.2 eq), HBTU (1.2 eq), 0° C. THF, 30 min, then 2-aminoindan (1.5 eq), 25° C., 12 hr; b) piperdine (4.0 eq), 25° C., THF, 24 hr; c) EDIPA (1.1 eq), chloroacetyl chloride (1.1 eq), 0° C., THF, 6 hr; d) homopiperazine (6.0 eq), 0° C. to 25° C., THF, 12 hr; e) TFA (XS)

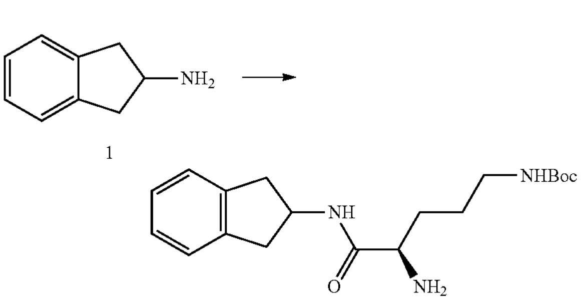

1

2

(R)-tert-butyl 4-amino-5-(2,3-dihydro-1H-inden-2-ylamino)-5-oxopentylcarbamate (Scheme 2, Compound 2)

To a solution of (R)-2-amino-5-(tert-butoxycarbonylamino)pentanoic acid (1.1 g, 2.42 mmol) and EDIPA (0.51 mL, 2.9 mmol, 1.2 eq) at 0° C. in THF (30 mL), HBTU (1.1 g, 2.9 mmol, 1.2 eq) was added. After 30 minutes of stirring 2-aminoindan (0.48 mL, 3.63 mmol, 1.5 eq) was added and the resulting mixture was slowly warmed to 25° C. and stirred for an additional 12 hours. After consumption of (R)-2-amino-5-(tert-butoxycarbonylamino) pentanoic acid, piperidine (0.95 mL, 9.68 mmol, 4.0 eq) was added to the crude reaction mixture and stirred for an additional 12 hours. Upon completion, the contents of the reaction were concentrated and purified by combiflash 0 to 20% MeOH in DCM to provide (R)-tert-butyl 4-amino-5-(2,3-dihydro-1H-inden-2-ylamino)-5-oxopentylcarbamate (Scheme 2, compound 2) (0.5 g, 59% yield). $^{1}$H NMR (400 MHz, Methanol-$d_4$) δ 7.35-7.13 (m, 4H), 4.66 (s, 1H), 3.46-2.67 (m, 6H), 1.89-1.51 (m, 2H), 1.44 (s, 9H). $^{13}$C NMR (101 MHz, MeOD) 157.16, 140.71, 140.68, 127.04, 126.41, 124.52, 124.24, 78.61, 39.59, 39.12, 38.97, 37.88, 27.47. HRMS (m/z): [M+] cald for C19H29N3O3, 347.45. found 348.2.

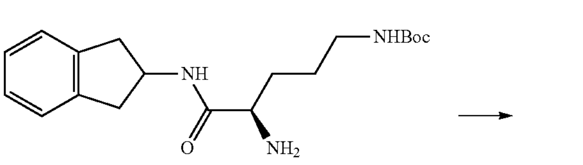

2

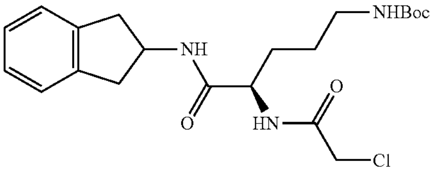

3

(R)-tert-butyl 4-(2-chloroethanamido)-5-(2,3-dihydro-1H-inden-2-ylamino)-5-oxopentylcarbamate (Scheme 2, Compound 3)

To a solution of (R)-tert-butyl 4-amino-5-(2,3-dihydro-1H-inden-2-ylamino)-5-oxopentylcarbamate (Scheme 2, compound 2) (0.5 g, 1.43 mmol) and EDIPA (0.25 mL, 1.58 mmol, 1.1 eq) at 0° C. in THF (30 mL) a solution of chloroacetyl chloride (0.126 mL, 1.58 mmol, 1.1 eq) in THF (3 mL) was added slowly dropwise. The resulting mixture was slowly warmed to 25° C. and stirred for an additional 6 hours. Upon completion, the reaction was diluted with saturated aqueous $NaHCO_3$ and extracted 3 times with ethyl acetate. The combined organic layers were dried ($Na_2SO_4$), concentrated, and the crude material was purified by combiflash 0 to 10% MeOH in DCM to provide (R)-tert-butyl 4-(2-chloroethanamido)-5-(2,3-dihydro-1H-inden-2-ylamino)-5-oxopentylcarbamate (Scheme 2, compound 3) (0.13 g, 0.306 mmol, 21% yield). $^{1}$H NMR (400 MHz, chloroform-d) δ 7.46 (d, J=8.3 Hz, 1H), 7.27-7.11 (m, 5H), 4.89 (t, J=6.2 Hz, 1H), 4.69 (dt, J=7.7, 5.4 Hz, 1H), 4.64-4.52 (m, 1H), 4.06-3.78 (m, 2H), 3.29 (tt, J=12.2, 6.8 Hz, 3H), 3.06 (dd, J=13.5, 6.4 Hz, 1H), 2.83 (dt, J=16.0, 6.3 Hz, 2H), 1.90-1.75 (m, 1H), 1.67 (dd, J=14.1, 7.1 Hz, 1H), 1.50 (p, J=7.0 Hz, 2H), 1.40 (s, 9H). $^{13}$C NMR (101 MHz, $CDCl_3$) 170.89, 166.25, 156.48, 140.73, 140.68, 126.79, 126.76, 124.71, 124.64, 79.29, 52.23, 50.55, 42.38, 39.85, 39.77, 39.36, 30.56, 28.41, 26.27. HRMS (m/z): [M+] cald for C21H30ClN3O4, 423.93. found 424.20.

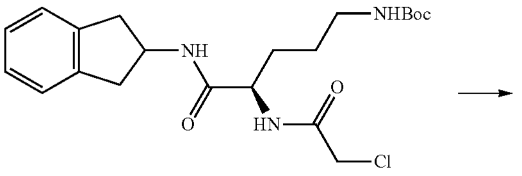

3

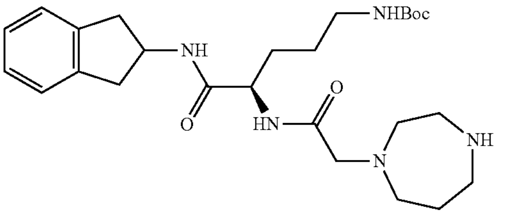

4

(R)-tert-butyl 4-(2-(1,4-diazepan-1-yl)ethanamido)-5-(2,3-dihydro-1H-inden-2-ylamino)-5-oxopentylcarbamate (Scheme 2, Compound 4)

To a solution of homopiperzine (92.1 mg, 0.920 mmol, 6.0 eq) in THF at 0° C., a solution of (R)-tert-butyl 4-(2-chloroethanamido)-5-(2,3-dihydro-1H-inden-2-ylamino)-5-oxopentylcarbamate (Scheme 2, compound 3) (0.153 mmol) in THF (3 mL) was added. The resulting mixture was slowly warmed to 25° C. and stirred for 24 hours. Upon completion, the reaction contents were concentrated and purified by combiflash 0 to 30% MeOH to provide (R)-tert-butyl 4-(2-(1,4-diazepan-1-yl)ethanamido)-5-(2,3-dihydro-1H-inden-2-ylamino)-5-oxopentylcarbamate (Scheme 2, compound 4) (70 mg, 93% yield). $^{1}$H NMR (400 MHz, Methanol-$d_4$) δ 7.22 (dd, J=5.4, 3.4 Hz, 2H), 7.16 (dt, J=5.1, 3.7 Hz, 2H), 4.60 (tt, J=7.4, 5.6 Hz, 1H), 4.40 (dd, J=8.2, 5.6 Hz, 1H), 3.60-3.47 (m, 1H), 3.33 (q, J=1.6 Hz, 3H), 3.31-3.18 (m, 4H), 3.06 (td, J=6.9, 2.1 Hz, 2H), 3.03-2.92 (m, 8H), 2.92-2.82 (m, 3H), 2.78 (dt, J=10.0, 5.6 Hz, 4H), 1.95-1.73 (m, 4H), 1.73-1.62 (m, 1H), 1.56-1.47 (m, 2H), 1.44 (s, 9H). $^{13}$C NMR (101 MHz, MeOD) 172.28, 171.92, 140.70, 140.67, 126.36, 124.19, 61.52, 56.63, 55.08, 52.33, 50.64, 48.94, 39.03, 38.83, 30.62, 29.96, 29.13, 27.40, 25.95. HRMS (m/z): [M+] cald for C26H41N5O4, 487.63. found 488.32.

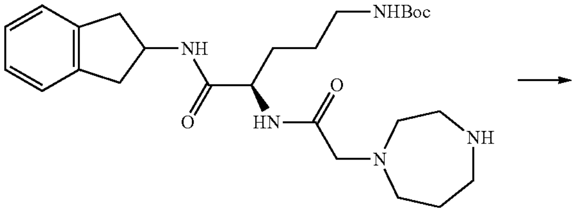

4

-continued

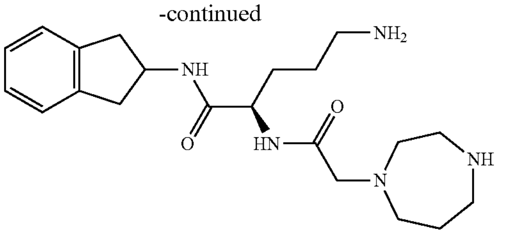

31MEW79

(R)-2-(2-(1,4-diazepan-1-yl)ethanamido)-5-amino-N-(2,3-dihydro-1H-inden-2-yl)pentanamide: 31MEW79

(R)-tert-butyl 4-(2-(1,4-diazepan-1-yl)ethanamido)-5-(2,3-dihydro-1H-inden-2-ylamino)-5-oxopentylcarbamate (Scheme 2, compound 4) (50 mg, 0.103 mmol) was dissolved in TFA (0.5 mL) and stirred for 12 hours at 25° C. Upon completion, the TFA was removed and the residue was re-suspended in MeOH and solid $K_2CO_3$ (100 mg, XS) was added. The crude material was purified by preparative TLC (15% MeOH in DCM) to provide 31MEW79 (28 mg, 70% yield). $^1$H NMR (400 MHz, Methanol-$d_4$) δ 7.22 (dt, J=7.6, 3.6 Hz, 2H), 7.19-7.09 (m, 2H), 4.59 (tt, J=7.3, 5.6 Hz, 1H), 4.43 (dd, J=8.1, 5.3 Hz, 1H), 3.31-3.17 (m, 4H), 2.97 (dt, J=8.4, 6.4 Hz, 4H), 2.93-2.72 (m, 4H), 2.04 (p, J=5.9 Hz, 2H), 1.92-1.81 (m, 1H), 1.74 (tdd, J=15.0, 8.8, 5.5 Hz, 3H). $^{13}$C NMR (101 MHz, MeOD) 126.39, 124.18, 61.00, 54.63, 52.05, 50.75, 45.88, 44.56, 38.92, 38.81, 29.38, 25.46, 23.57. HRMS (m/z): [M+] cald for C21H33N5O2, 387.52. found 388.27.

31MEW78

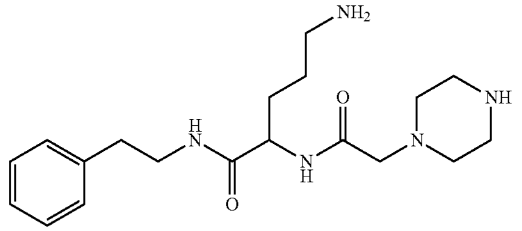

4-amino-N-(3-(4-((4-(2-(4-chlorophenoxy)ethyl)piperazin-1-yl)methyl)-3-(3-fluorophenyl)-1H-indol-1-yl)propyl)piperidine-4-carboxamide: 31MEW78

This compound was prepared using the protocols for 31MEW79. $^1$H NMR (400 MHz, Methanol-$d_4$) δ 7.34-7.15 (m, 4H), 4.40 (dd, J=8.2, 5.0 Hz, 1H), 3.54-3.37 (m, 2H), 3.31 (dd, J=10.3, 5.2 Hz, 4H), 3.19 (q, J=16.0 Hz, 2H), 2.94 (td, J=6.9, 3.2 Hz, 2H), 2.80 (q, J=6.7, 6.1 Hz, 5H), 1.92-1.78 (m, 1H), 1.69 (dq, J=19.4, 8.1, 6.5 Hz, 2H). $^{13}$C NMR (101 MHz, MeOD) 138.91, 128.47, 128.11, 126.01, 60.06, 52.30, 49.46, 43.21, 40.51, 38.78, 34.94, 29.02, 23.51. HRMS (m/z): [M+] cald for Cl9H31N5O2, 361.48. found 362.26.

36MEW3

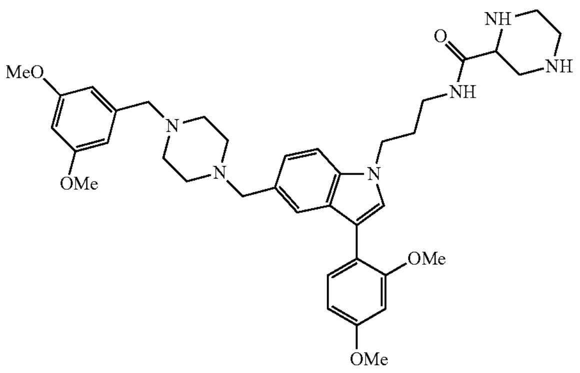

N-(3-(5-((4-(3,5-dimethoxybenzyl)piperazin-1-yl)methyl)-3-(2,4-dimethoxyphenyl)-1H-indol-1-yl)propyl)piperazine-2-carboxamide: 36MEW3

36MEW3 was synthesized according to the same procedure as 31MEW44 substituting the appropriate commercially available reagents. Nitrogen protected carboxy piperazine was substituted for compound 8. $^1$H NMR (400 MHz, Methanol-$d_4$) δ 7.62 (s, 1H), 7.50-7.40 (m, 3H), 7.20 (d, J=9.8 Hz, 1H), 6.68 (d, J=2.5 Hz, 1H), 6.64 (dd, J=8.3, 2.5 Hz, 1H), 6.52 (d, J=2.3 Hz, 2H), 6.40 (t, J=2.3 Hz, 1H), 4.55 (s, 3H), 4.29 (t, J=6.8 Hz, 2H), 3.87 (s, 3H), 3.82 (s, 3H), 3.77 (s, 6H), 3.73 (s, 2H), 3.53-3.48 (m, 3H), 3.16 (p, J=1.7 Hz, 1H), 2.77-2.48 (m, 11H), 2.36 (d, J=7.5 Hz, 1H), 2.11 (t, J=6.7 Hz, 2H), 0.95-0.84 (m, 4H).

34MEW45

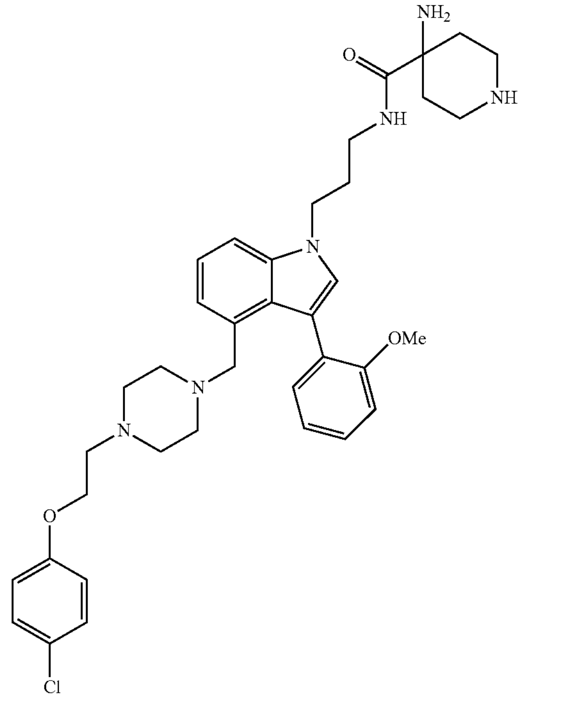

4-amino-N-(3-(4-((4-(2-(4-chlorophenoxy)ethyl)piperazin-1-yl)methyl)-3-(2-methoxyphenyl)-1H-indol-1-yl)propyl)piperidine-4-carboxamide: 34MEW45

34MEW45 was synthesized according to the same procedure as 34MEW95 substituting the appropriate commercially available reagents. $^1$H NMR (400 MHz, Methanol-$d_4$) δ 7.66 (d, J=1.5 Hz, 1H), 7.58 (dd, J=7.5, 1.7 Hz, 1H), 7.54 (s, 1H), 7.46 (d, J=8.4 Hz, 1H), 7.32-7.20 (m, 4H), 7.11 (dd, J=8.3, 1.1 Hz, 1H), 7.05 (td, J=7.5, 1.2 Hz, 1H), 6.96-6.88 (m, 2H), 4.32 (t, J=6.6 Hz, 2H), 4.12 (t, J=5.5 Hz, 2H), 3.86 (s, 3H), 3.71 (s, 2H), 3.25-3.17 (m, 4H), 2.83 (t, J=5.5 Hz, 2H), 2.66 (s, 7H), 2.20-2.07 (m, 4H), 1.49 (d, J=14.4 Hz, 2H).

32MEW56

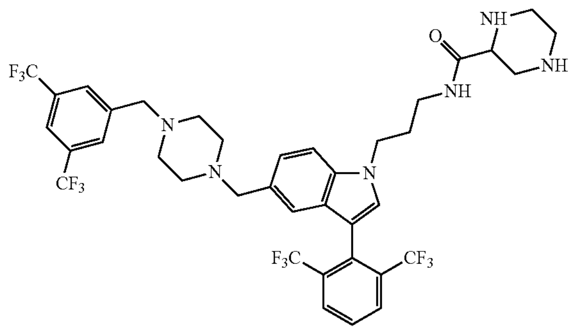

N-(3-(5-((4-(3,5-bis(trifluoromethyl)benzyl)piperazin-1-yl)methyl)-3-(2,6-bis(trifluoromethyl)phenyl)-1H-indol-1-yl)propyl)piperazine-2-carboxamide: 32MEW56

32MEW56 was synthesized according to the same procedure as 31MEW44 substituting the appropriate commercially available reagents. Nitrogen protected carboxy piperazine was substituted for compound 8. $^1$H NMR (400 MHz, Methanol-$d_4$) δ 8.23 (d, J=1.6 Hz, 1H), 7.97 (s, 1H), 7.93-7.83 (m, 2H), 7.56 (d, J=8.5 Hz, 1H), 7.32 (dd, J=8.5, 1.5 Hz, 1H), 4.35 (t, J=6.8 Hz, 1H), 3.86 (s, 1H), 3.73 (s, 1H), 3.61-3.46 (m, 1H), 3.16-2.83 (m, 3H), 2.67 (d, J=56.9 Hz, 4H), 2.15 (t, J=6.8 Hz, 1H).

43MEW63

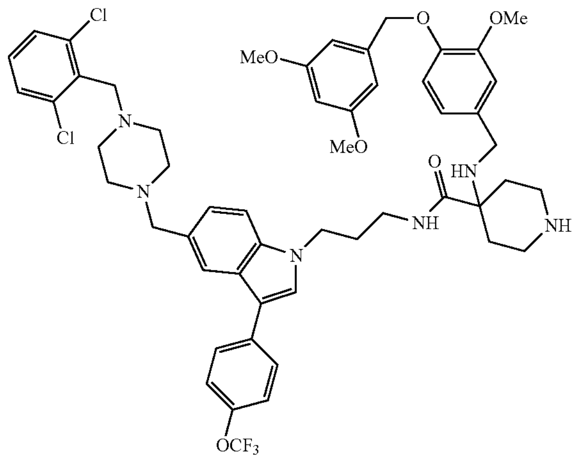

N-(3-(5-((4-(2,6-dichlorobenzyl)piperazin-1-yl)methyl)-3-(4-(trifluoromethoxy)phenyl)-1H-indol-1-yl)propyl)-4-((4-(3,5-dimethoxybenzyl)oxy)-3-methoxybenzyl)amino)piperidine-4-carboxamide: 43MEW63

43MEW63 was synthesized using the same procedures as 34MEW95 substituting the appropriate commercially available reagents. $^1$H NMR (400 MHz, Methanol-$d_4$) δ 7.84 (s, 1H), 7.74 (d, J=8.7 Hz, 2H), 7.49 (s, 1H), 7.43-7.29 (m, 5H), 7.29-7.17 (m, 2H), 6.96 (s, 1H), 6.90-6.80 (m, 2H), 6.59 (d, J=2.3 Hz, 2H), 6.40 (d, J=2.4 Hz, 1H), 5.00 (s, 2H), 4.25 (t, J=6.9 Hz, 2H), 3.81 (s, 3H), 3.79 (s, 2H), 3.75 (s, 6H), 3.62 (s, 2H), 3.53-3.47 (m, 3H), 3.19-2.91 (m, 6H), 2.63 (s, 4H), 2.50 (s, 4H), 2.16-1.96 (m, 5H), 1.75 (d, J=14.2 Hz, 2H).

43MEW65

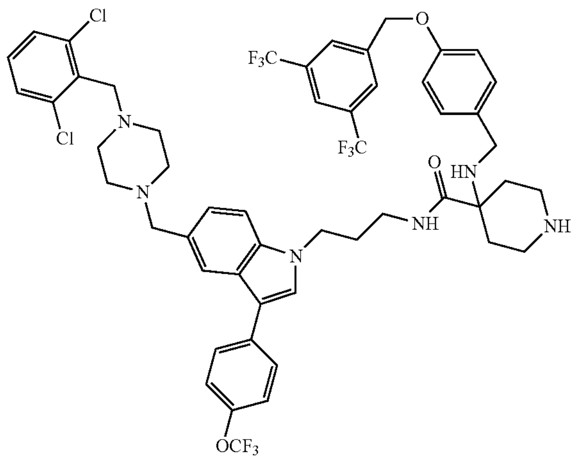

4-((4-((3,5-bis(trifluoromethyl)benzyl)oxy)benzyl)amino)-N-(3-(5-((4-(2,6-dichlorobenzyl)piperazin-1-yl)methyl)-3-(4-(trifluoromethoxy)phenyl)-1H-indol-1-yl)propyl)piperidine-4-carboxamide: 43MEW65

43MEW65 was synthesized using the same procedures as 34MEW95 substituting the appropriate commercially available reagents. $^1$H NMR (400 MHz, Methanol-$d_4$) δ 8.03 (s, 2H), 7.93 (s, 1H), 7.86-7.81 (m, 1H), 7.77-7.70 (m, 2H), 7.51 (s, 1H), 7.43 (d, J=8.5 Hz, 1H), 7.40-7.34 (m, 2H), 7.26 (dddd, J=23.7, 16.0, 8.2, 1.3 Hz, 7H), 7.00-6.93 (m, 2H), 5.20 (s, 2H), 4.27 (t, J=6.8 Hz, 2H), 3.78 (s, 2H), 3.62 (s, 2H), 3.48 (s, 3H), 3.11-2.99 (m, 2H), 2.99-2.89 (m, 2H), 2.63 (s, 4H), 2.50 (s, 4H), 2.11 (t, J=6.7 Hz, 2H), 1.99 (ddd, J=13.9, 9.7, 4.0 Hz, 2H), 1.70 (d, J=14.5 Hz, 2H).

43MEW73

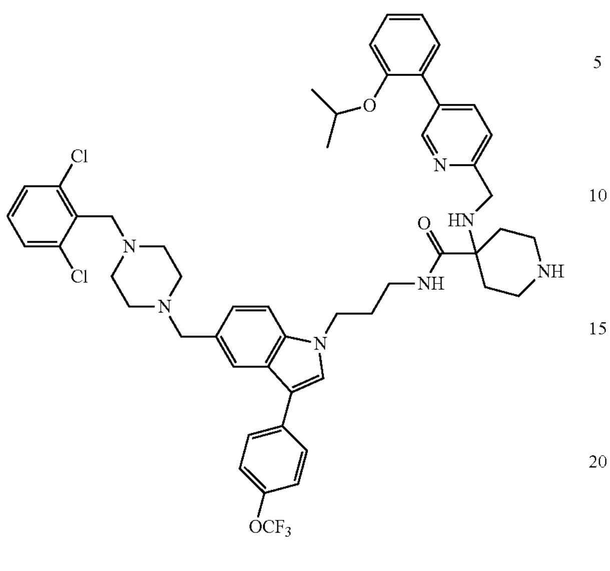

N-(3-(5-((4-(2,6-dichlorobenzyl)piperazin-1-yl)methyl)-3-(4-(trifluoromethoxy)phenyl)-1H-indol-1-yl)propyl)-4-(((5-(2-isopropoxyphenyl)pyridin-2-yl)methyl)amino)piperidine-4-carboxamide: 43MEW73

43MEW73was synthesized using the same procedures as 34MEW95 substituting the appropriate commercially available reagents. $^1$H NMR (400 MHz, Methanol-$d_4$) δ 8.65 (d, J=2.2 Hz, 1H), 7.91 (dd, J=8.1, 2.2 Hz, 1H), 7.85 (s, 1H), 7.76-7.69 (m, 2H), 7.53 (s, 1H), 7.47 (d, J=8.0 Hz, 1H), 7.42-7.33 (m, 4H), 7.33-7.22 (m, 4H), 7.21-6.99 (m, 4H), 4.59 (p, J=6.3 Hz, 1H), 4.30 (t, J=6.9 Hz, 2H), 3.79 (d, J=7.6 Hz, 4H), 3.69 (s, 2H), 2.61 (d, J=29.0 Hz, 8H), 2.28-2.08 (m, 4H), 1.94 (d, J=15.8 Hz, 3H), 1.31-1.21 (m, 3H), 1.20 (d, J=6.0 Hz, 5H).

4-((3-chloro-4-((4-fluorobenzyl)oxy)benzyl)amino)-N-(3-(4-((4-(2-(4-chlorophenoxy)ethyl)piperazin-1-yl)methyl)-3-(3-fluorophenyl)-1H-indol-1-yl)propyl)piperidine-4-carboxamide: 35MEW12

35MEW12 was synthesized according to the same procedures as 34MEW95 substituting the appropriate commercially available reagents. $^1$H NMR (400 MHz, Methanol-$d_4$) δ 7.51-7.41 (m, 3H), 7.41-7.28 (m, 3H), 7.28-7.20 (m, 4H), 7.20-7.13 (m, 2H), 7.13-7.06 (m, 2H), 7.06-6.98 (m, 3H), 6.93-6.86 (m, 2H), 5.11 (s, 2H), 4.26 (t, J=6.9 Hz, 2H), 4.06 (t, J=5.5 Hz, 2H), 3.56-3.49 (m, 4H), 3.33-3.08 (m, 10H), 2.72 (t, J=5.5 Hz, 2H), 2.41 (s, 3H), 2.12 (td, J=15.9, 13.5, 7.6 Hz, 8H), 1.89 (d, J=14.7 Hz, 2H).

Example 3

Results

The majority of cellular responses that oncogenic RAS proteins elicit are transduced by the effectors RAF, RALGDS, and PI3K (Downward et al., 2003). The analysis of the co-crystal structures of HRAS with PI3Kγ (PDB: 1HE8), with the C-RAF RAS-binding domain (RBD, PDB: 3KUD), and with RALGDS (PDB: 1 LFD) revealed conserved interactions between these effector proteins and a short stretch of amino acids on the switch 1 region (residues 36-39) of the RAS proteins, which are referred to as the D38 site (FIG. 1A-FIG. 1L). For example, I36 on RAS undergoes a conformational change when transitioning from the GDP-bound to the GTP-bound form (FIG. 1G-FIG. 1H) in which it adopts a solvent-exposed conformation (Hall et al., 2002). In this active form, each of the effector proteins has a complementary hydrophobic residue for interacting with I36, providing a favorable entropic gain. Mutation of D38A on HRAS completely prevents HRAS-mediated activation of these three effectors (Pacold et al., 2000). Similarly, mutation of the residue in the effector domain interacting with D38 on HRAS proteins results in the affinity being greatly diminished or completely eliminated (Pacold et al., 2000, Huang et al., 1998, Block et al., 1996). The sensitivity of this region to alterations in residues involved in effector binding suggests that it would be an ideal site to target, from a functional perspective, with small molecules. Additionally, the conformational changes adopted by this region may allow one to target RAS proteins selectively in their active state; this may be relevant as some small GTPases have been shown to transmit different signals in the GDP-bound state (Ho et al., 2008).

This goal was pursued using a pharmacophore strategy to test the notion that this site represents a viable pharmacological target; a pharmacophore is the spatial orientation of chemical features (hydrophobic regions, hydrogen bond donors and acceptors, cations, anions) that confer upon a small molecule its biological activity (Sun et al., 2008). Pharmacophore screening is an approach used primarily for lead optimization of small molecules; this involves construction of a model based on bioactive ligands and subsequent screening of virtual collections of molecules for their ability to match the pharmacophore features (Id.). Extending this strategy to lead discovery for protein-protein interactions (PPIs) was attempted by mapping key interactions at the interface of the RAS-effector complexes and building a pharmacophore model that captures these interactions (FIG. 1A-FIG. 1L, FIG. 2). Recognizing that the potential affinity of ligands to this site might ultimately be limited by its shallow nature, it was then sought to improve affinity of ligands to RAS proteins by designing compounds that extend into two adjacent shallow pockets near the D38 site, creating multivalent small molecule ligands.

Example 4

Pharmacophore Virtual Screening Yields Compounds that Bind to RAS Proteins

Figure 3:
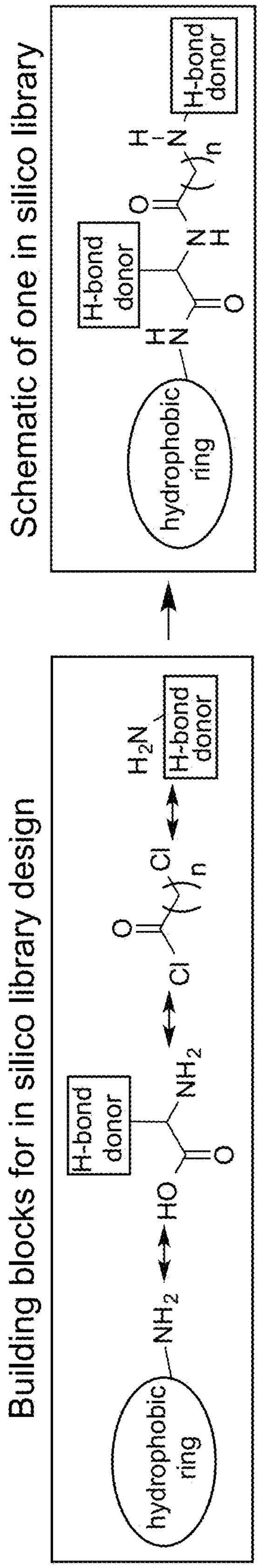
FIG. 3 shows retrosynthetic analysis and a schematic of one of the in silico libraries designed to match the properties in the pharmacophore model.

A pharmacophore model was constructed (using R.O.C.S., Openeye, Inc.) based on the residues on effector proteins that interact with the side chains and amide backbones of S39, D38, E37 and I36 on the human HRAS protein in the co-crystal structures (FIG. 1A-FIG. 1C, FIG. 2). The notion that a compound from readily available sources could meet the requirements of this pharmacophore model was then tested by screening a compound database of 4.7 million small molecules from the inventory of seven different chemical vendors; this yielded only relatively modest matches based on Tanimoto coefficient (about 0.8 maximum), confirming the suspicion that pre-assembled libraries of compounds would be insufficient for inhibiting RAS proteins. In order to identify compounds with a closer resemblance to the pharmacophore model, custom in silico libraries of synthetically accessible compounds (using Molecular Operating Environment (MOE) software, Chemical Computing Group, Inc.) specifically designed to match the model were created (FIG. 3).

Figure 4A:
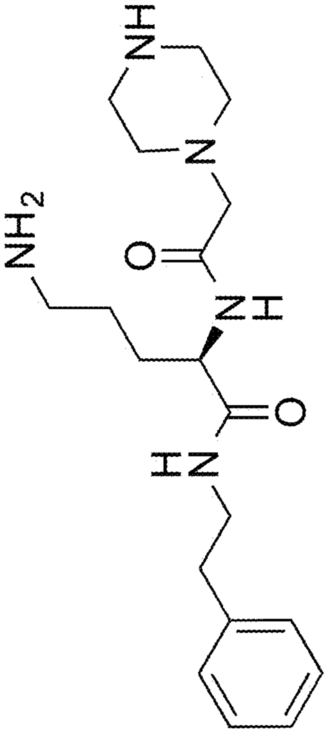
FIG. 4A shows structures of the two top pharmacophore hits.
Figure 4A:
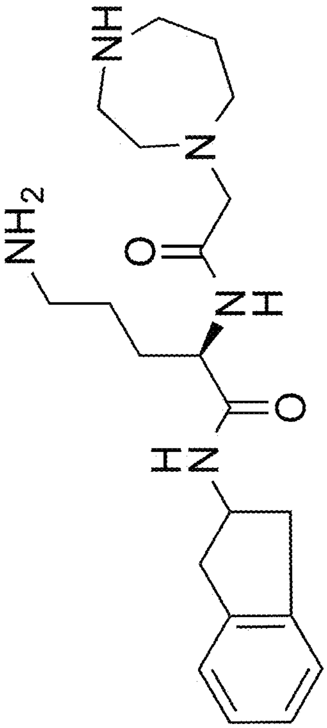
Figure 4C:
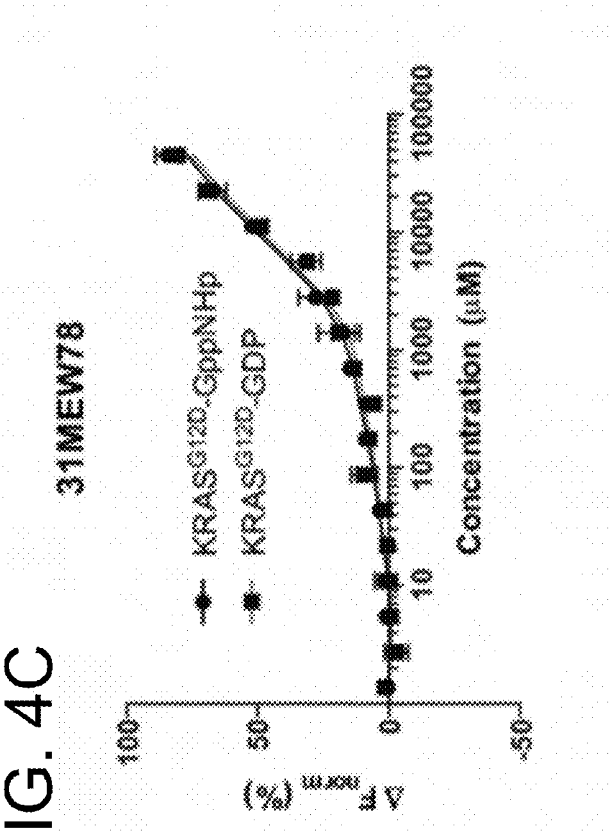
FIG. 4C shows binding of 31MEW78 to KRAS and measurement of dissociation constants. Dissociation constants were $K_D$=11 mM+/−0.50 mM for GppNHp-bound $KRAS^{G12D}$ and $K_D$=12 mM+/−0.43 mM for GDP-bound $KRAS^{G12D}$.
Figure 4B:
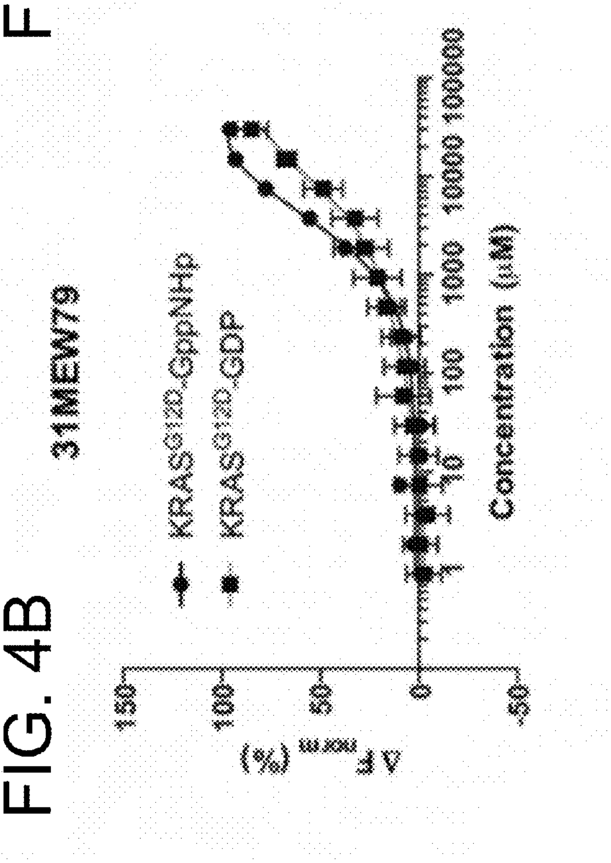
FIG. 4B shows binding of 31MEW79 to KRAS and measurement of dissociation constants. Dissociation constants were $K_D$=3.8 mM+/−0.13 mM for GppNHp-bound $KRAS^{G12D}$ and $K_D$=7.1 mM+/−0.68 mM for GDP-bound $KRAS^{G12D}$.
Figure 5:
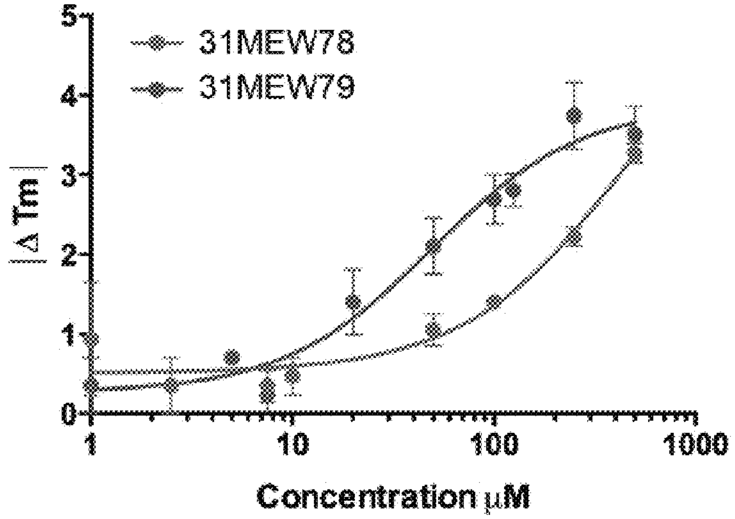
FIG. 5 shows differential scanning fluorimetry of 31MEW79 and 31MEW78 with 5 μM $KRAS^{G12D}$ in the presence of increasing concentration of compound. The ΔTm was calculated by subtracting the Tm of liganded $KRAS^{G12D}$ protein from unliganded $KRAS^{G12D}$ and is expressed as absolute value of the mean±standard error of the mean (sem).
Figure 6:
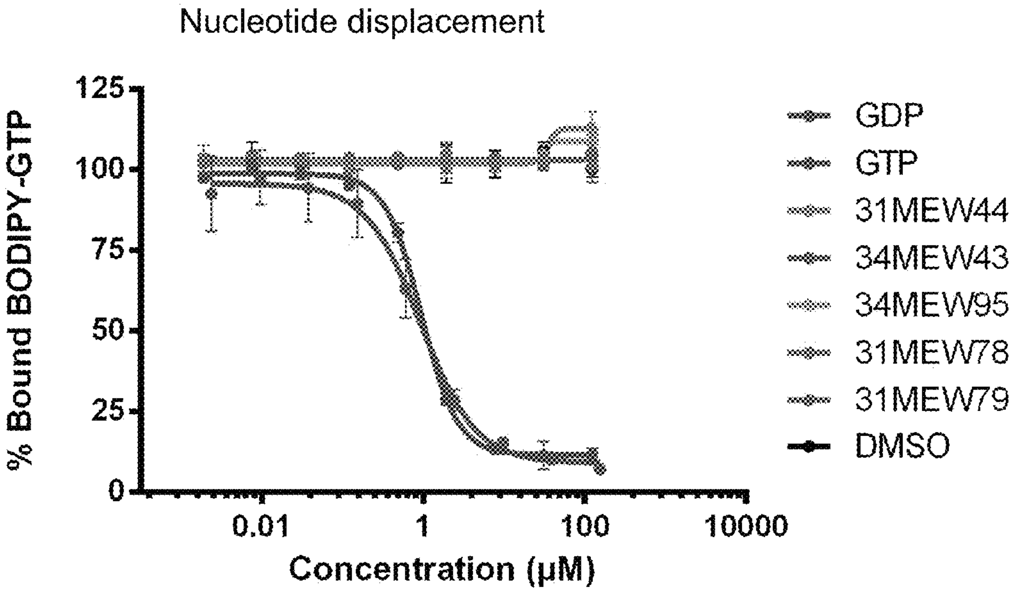
FIG. 6 shows that small-molecule inhibitors do not bind to the GTP-binding pocket on KRAS. A nucleotide displacement assay was performed in duplicate with 2.5 μM $KRAS^{G12D}$•BODIPY-GTP in the presence of increasing concentration of inhibitors or unlabeled GTP or GDP. Free unlabeled GTP and GDP can displace bound BODIPY-GTP from KRAS but the inhibitors cannot because they bind to a different site of $KRAS^{G12D}$.
Figure 7:
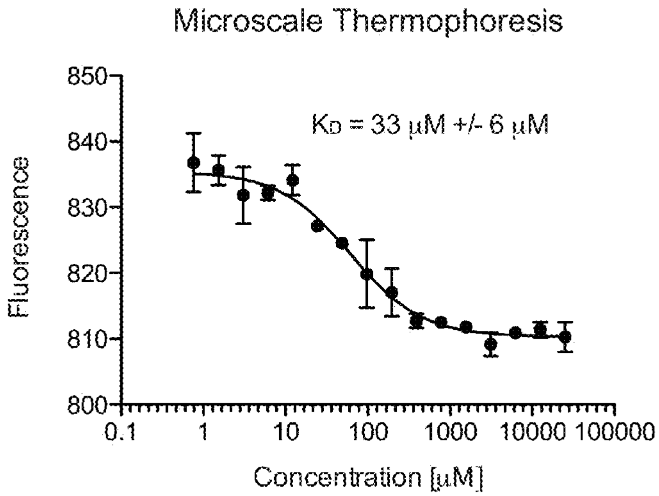
FIG. 7 shows results from microscale thermophoresis performed with 31MEW79 on GTP-loaded $KRAS^{G12D}$ in triplicate.
Figure 8:
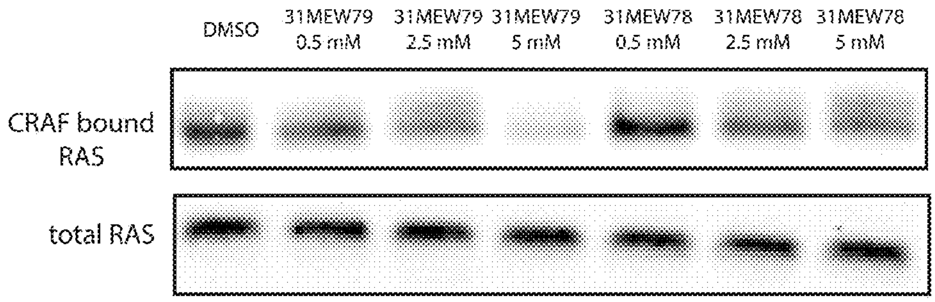
FIG. 8 shows pulldown of GTP-loaded $KRAS^{G12D}$ with the CRAF RBD in the presence of 31MEW79 and 31MEW78

A set of 45 of the closest matches (ranging from 0.85-0.97 Tanimoto coefficient) were synthesized (based on Scheme 2 with appropriate modifications) and tested for their ability to bind to $KRAS^{G12D}$ by differential scanning fluorimetry. Compounds 31MEW78 and 31MEW79 (FIG. 4A-FIG. 4B) both elicited a dose-dependent thermal shift in $KRAS^{G12D}$ stability (FIG. 5). In order to quantify the binding of the pharmacophore-derived compounds, GTP-loaded KRAS G12D was labeled with NT-647-maleimide and the binding to 31MEW79 was measured using microscale thermophoresis, which analyzes changes in the migration of macromolecules across a temperature gradient in the presence of small molecule ligands (Zheng et al., 2013). To account for the possibility of binding in the GTP pocket, 31MEW79 and 31MEW78 were tested in a nucleotide displacement assay with BODIPY-GTP. No displacement of the BODIPY nucleotide in the presence of either inhibitor was observed (FIG. 6). Microscale thermophoresis measurements on 31MEW79 yielded a calculated dissociation constant $K_D$ of 33 μM+/−6 μM (FIG. 7). To support the binding of 31MEW79 to the D38 site on KRAS, mutations in the predicted binding region were generated—$KRAS^{G12D\ D38A}$ and $KRAS^{G12D\ I36N}$. This yielded a 1.5 to 3.0 fold loss in affinity: $KRAS^{G12D\ D38A}$ $K_D$=83 μM+/−11 μM and $KRAS^{G12D\ I36N}$ $K_D$=47 μM+/−9 In order to test the ability of the compounds to prevent the interaction of $KRAS^{G12D}$ protein with its effector CRAF, an in vitro pull-down with GTP-loaded $KRAS^{G12D}$ was performed using CRAF RBD-GST, with glutathione beads (FIG. 8). A dose-dependent decrease in CRAF-bound $KRAS^{G12D}$ was observed for 31MEW79 and 31MEW78, indicating abrogation of this interaction.

Figure 9A:
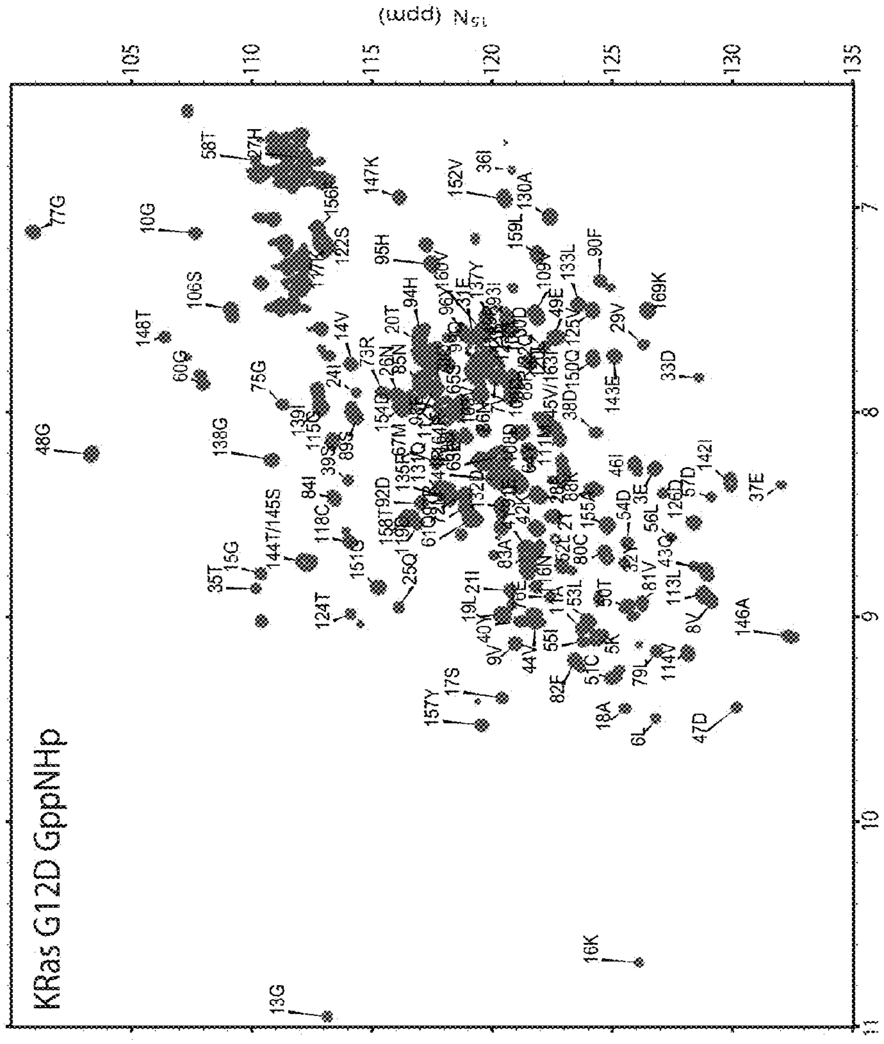
FIG. 9A-FIG. 9B shows NMR assignments of KRAS G12D loaded with a non-hydrolyzable GTP analog, GppNHp.
Figure 9B:
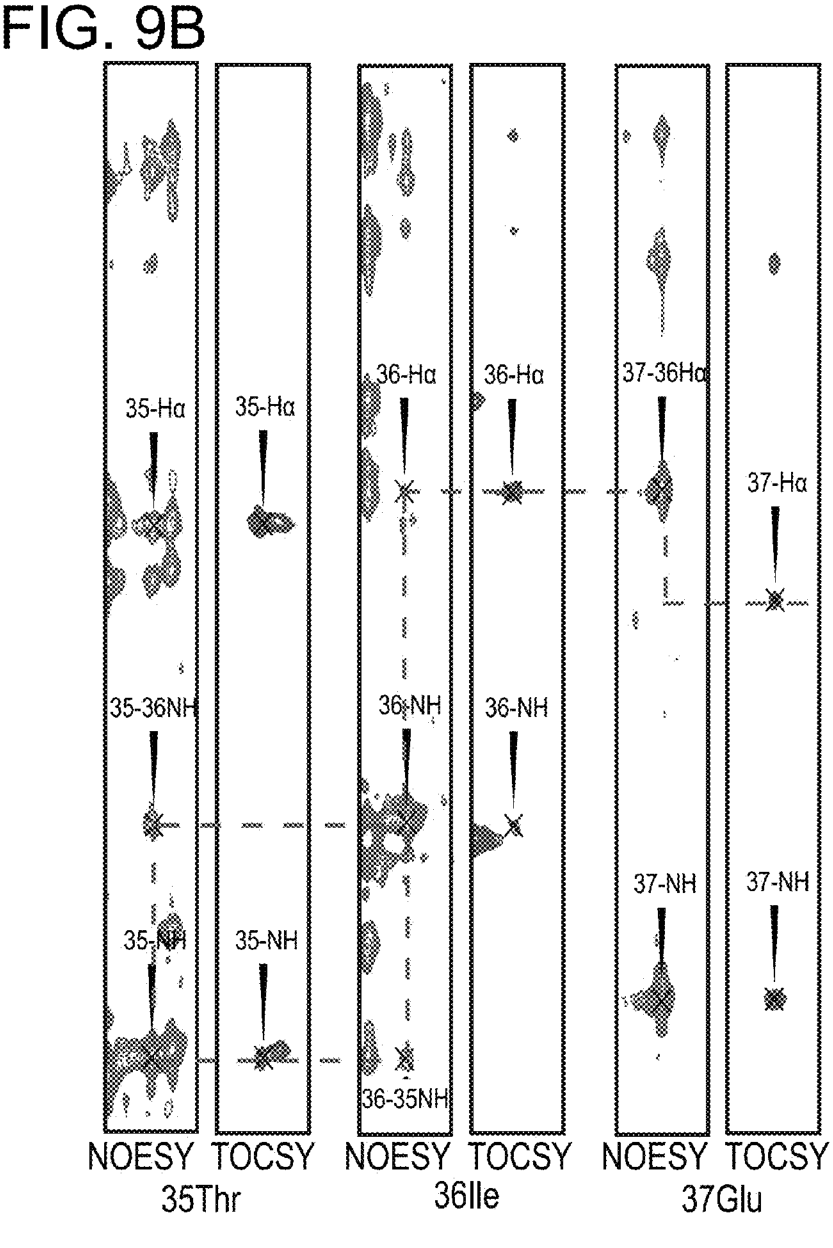
Figure 10:
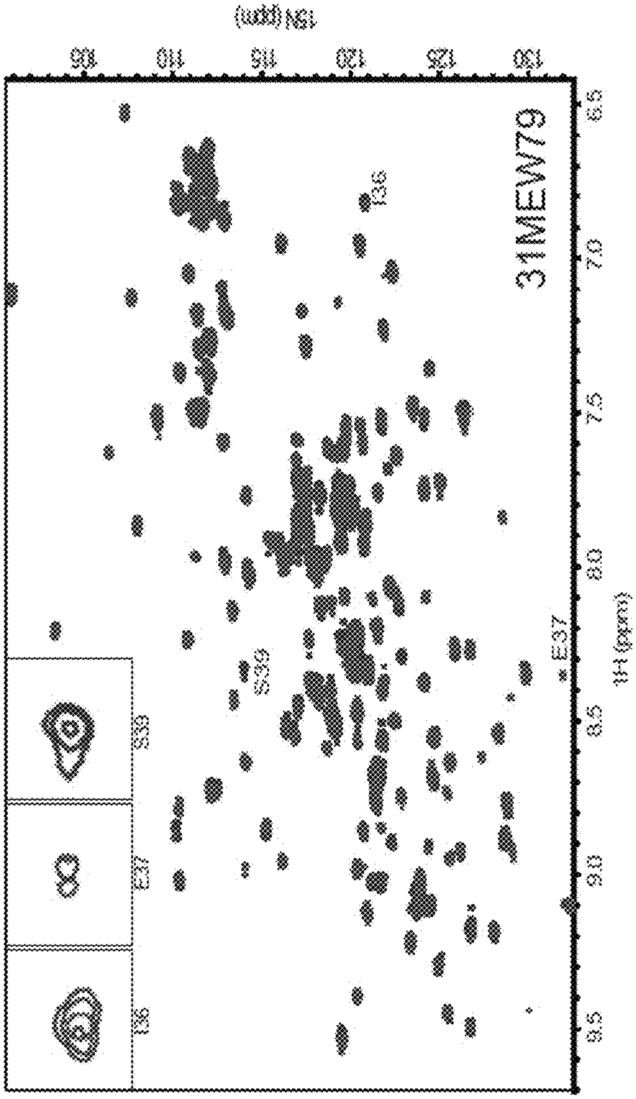
FIG. 10 shows $^1H$-$^{15}N$ HSQC spectrum of 50 μM $KRAS^{G12D}$ bound-to GppNHp in the absence (blue) and presence (red) of 250 μM inhibitor 31MEW79. Magnification of I36, E37 and S39 in the top left corner. These residues are shrinking (I36 and E37), or shifting (S39)-upon compound treatment.

To further investigate the binding site of these compounds with KRAS, 2D $^{1}H$-$^{15}N$ Heteronuclear Single Quantum Coherence (2D $^{1}H$-$^{15}N$ HSQC) experiments were performed on uniformly $^{15}N$-labeled $KRAS^{G12D}$ protein, with and without test compounds. The $^{1}H$-$^{15}N$ HSQC spectra of the $KRAS^{G12D}$ GDP-loaded protein and GppNHp-loaded protein were assigned using the previously published wild-type KRAS GDP assignments (Vo et al., 2013). To verify these assignments, 3D-$^{1}H$-$^{15}N$-$^{1}H$-NOESY-HSQC and 3D-$^{1}H$-$^{15}N$-$^{1}H$-TOCSY-HSQC experiments were performed on $KRAS^{G12D}$ protein loaded with either GDP or GppNHp (FIG. 9A-FIG. 9B). When $^{15}N$-labeled $KRAS^{G12D}$ protein was treated with 31MEW79, significant chemical shifts corresponding to the side chains of S39, E37, and I36 were observed, supporting the notion that binding occurs in the region that the compounds had been designed to interact with (FIG. 10).

Example 5

Computational Design of Three-Site Compounds

Figure 11A:
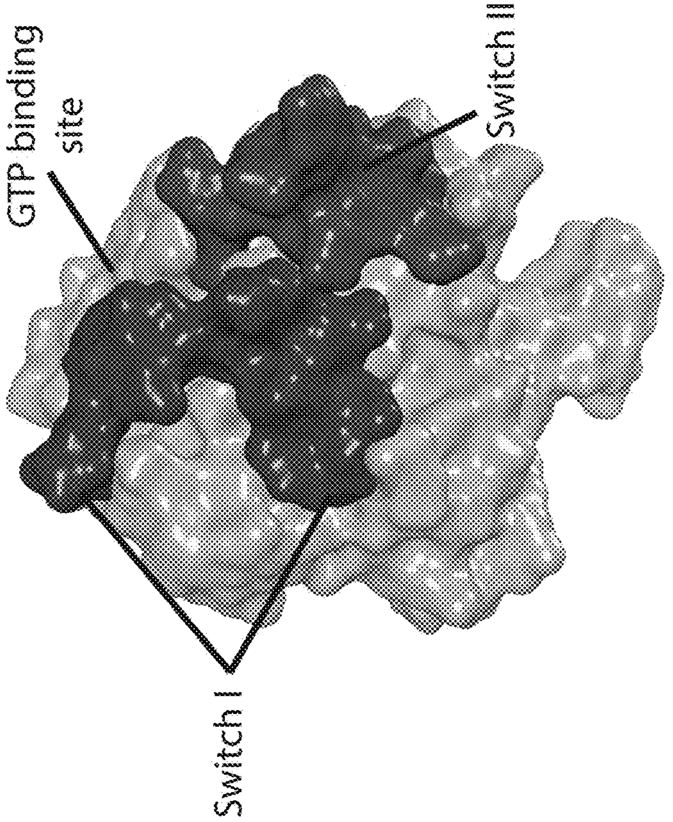
FIG. 11A-FIG. 11B show design of multivalent inhibitors.
Figure 11B:
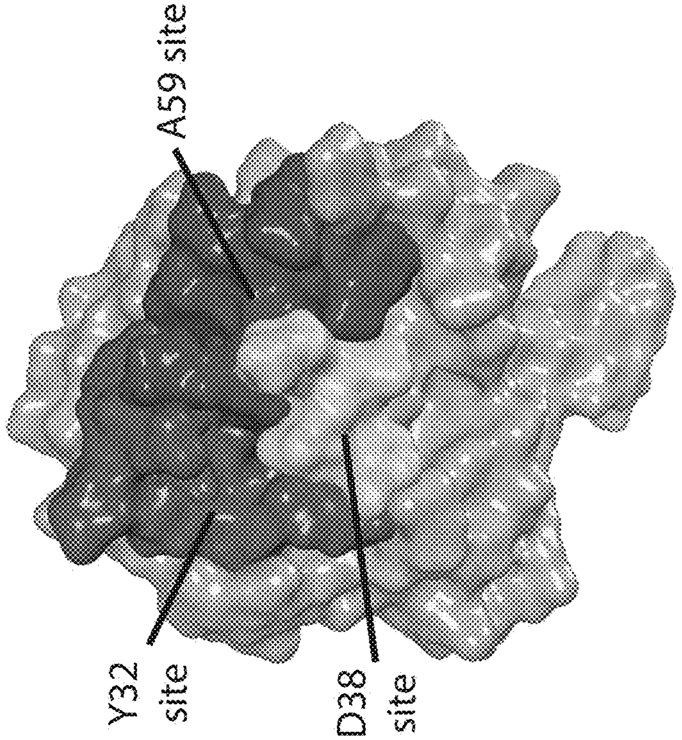
Figure 11C:
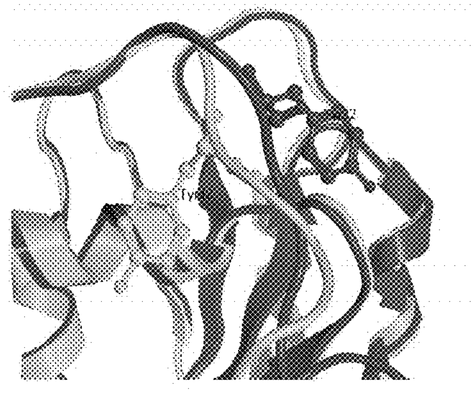
FIG. 11C-FIG. 11E show conformational change of Y32 going from the inactive to the active form of HRAS.
Figure 11D:
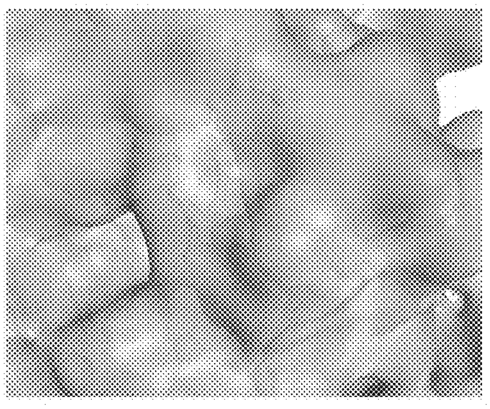
Figure 11E:
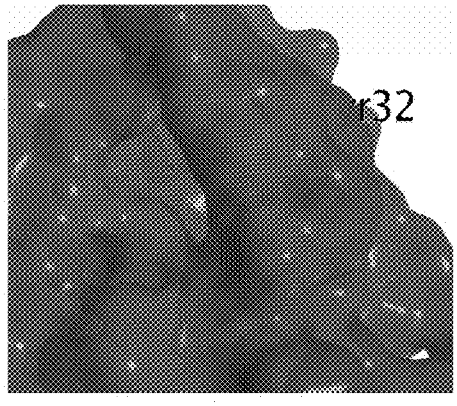

While this pharmacophore strategy yielded compounds capable of binding to RAS proteins and inhibiting their interaction with the C-RAF RBD in vitro, they did so with only moderate affinity, similar to previous attempts to identify small molecule ligands for RAS proteins (Maurer et al., 2012, Shima et al., 2013, Ostrem et al., 2013), highlighting the limits of single-site binding compounds. A strategy was thus sought for increasing small molecule ligand affinity. Analysis of the $KRAS^{G12D}$ (PDB: 4DSN) structure revealed two shallow pockets directly adjacent to the D38 site (FIG. 11A-FIG. 11B). One site, centered on A59, is located between the switch I and switch II regions (A59 site). On the other side of the D38 site, there exists a pocket present only in the active form of RAS, when Y32 undergoes a conformational change in which it flips over to the other end of the nucleotide-binding site and forms a hydrogen bond with the gamma phosphate of GTP. This change unveils a pocket (termed the Y32 site) that is not present in the GDP-bound form, allowing selective targeting of the active form (FIG. 11C-FIG. 11E).

Figure 12A:
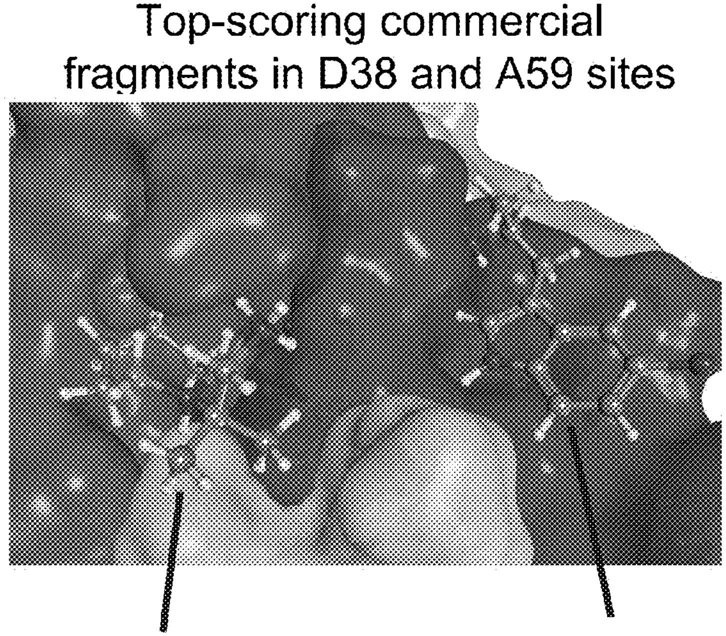
FIG. 12A-FIG. 12D show design of multivalent inhibitors.
Figure 12A:
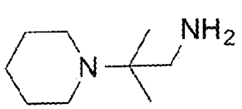
Figure 12A:
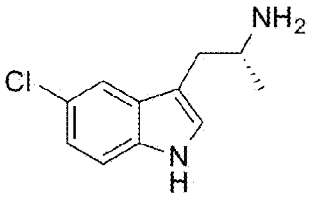

In order to produce compounds with improved affinity, a computational fragment-based approach to the design of multivalent ligands was adopted that could span the three shallow pockets described above; it was sought to extend from the D38 site to the adjacent A59 and Y32 sites. A library composed of 60,000 fragments filtered for lead-like properties (see Example 1) was docked (using Glide, Schrodinger Inc.) into each of these sites. Among the top-ranked fragments for the D38 site, a substantial number of aliphatic rings that contained protonated amines making electrostatic interactions with D38 and D33 was observed (FIG. 12A). Several of the top-scoring fragments in the A59 site contained an indole scaffold (FIG. 12A). These results inspired the design of novel in silico libraries based on these molecular architectures, with the hope of creating high-scoring multivalent ligands.

Figure 12B:
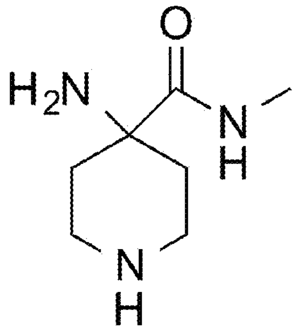
Figure 12B:
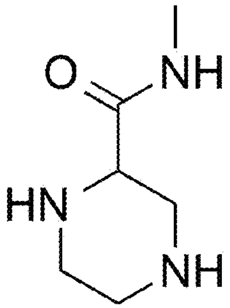
Figure 12C:
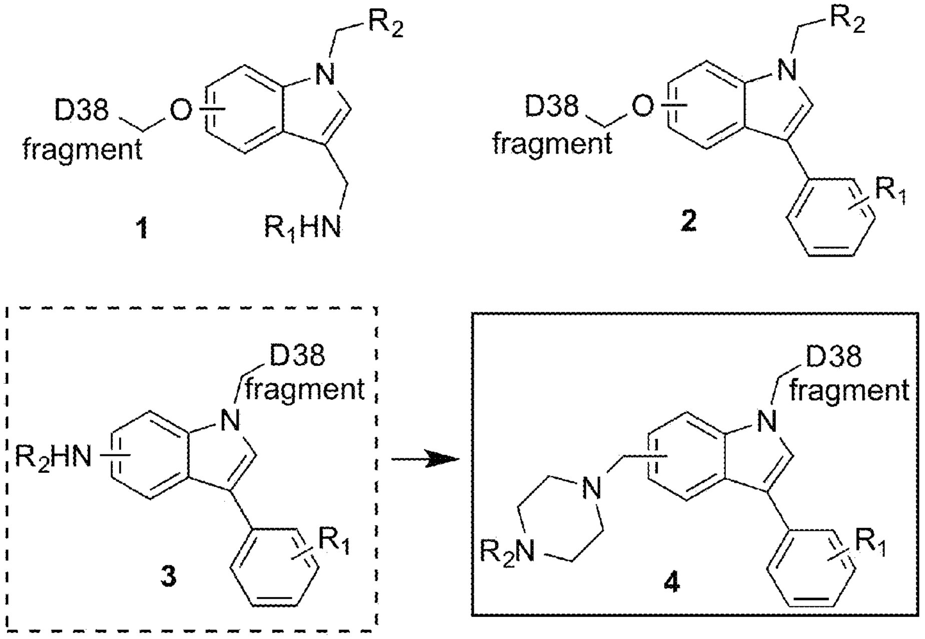
Figure 12D:
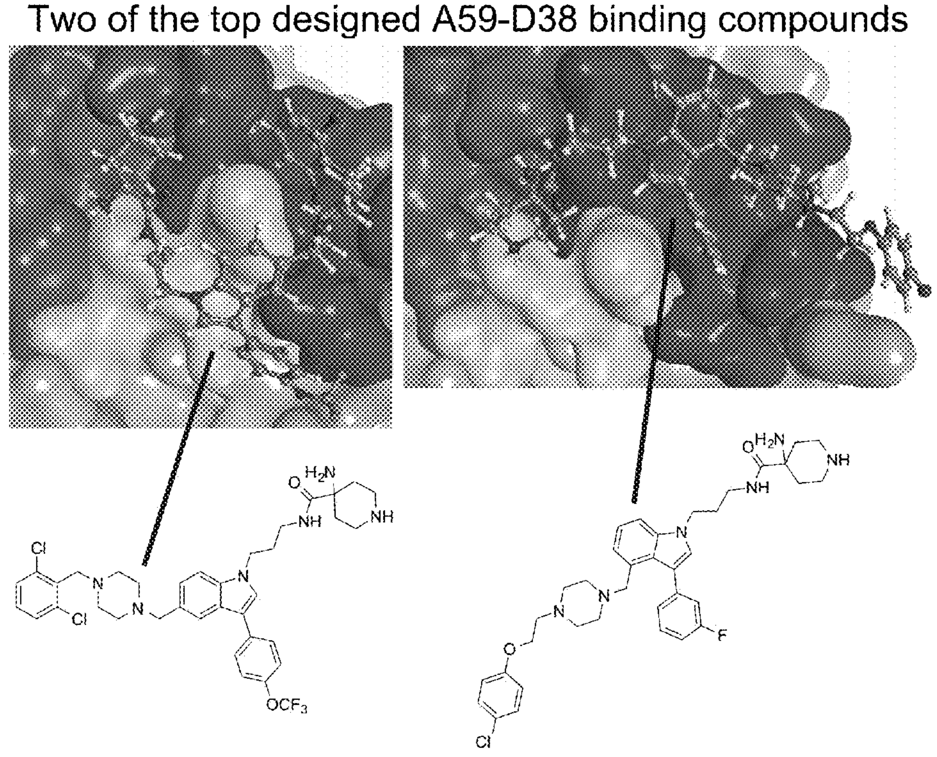

A library of compounds that contain an amine or a hydroxyl group for interacting with the aspartic acids in the center of the D38 site was designed, as well as a carboxylic acid moiety that could be used as a linking group for attachment of an adjacent fragment. Two of the fragments scored an order of magnitude better than the rest of the library, and were used to extend the compound to the A59 site (FIG. 12B). In silico libraries of synthetically accessible compounds based on the indole scaffold were then designed, with linkages to the two top-scoring fragments from the D38 site (FIG. 12C). Reliable chemical transformations were then used as the basis for points of diversity in order to accommodate a broad substrate range in the library and to minimize the degree of synthetic route optimization; for example, Suzuki couplings, nucleophillic substitutions, amine couplings, and reductive aminations were used. Extension into the A59 site from the D38 fragments resulted in an additional order of magnitude improvement in docking scores for the highest-ranked compounds (FIG. 12D).

Figure 13B:
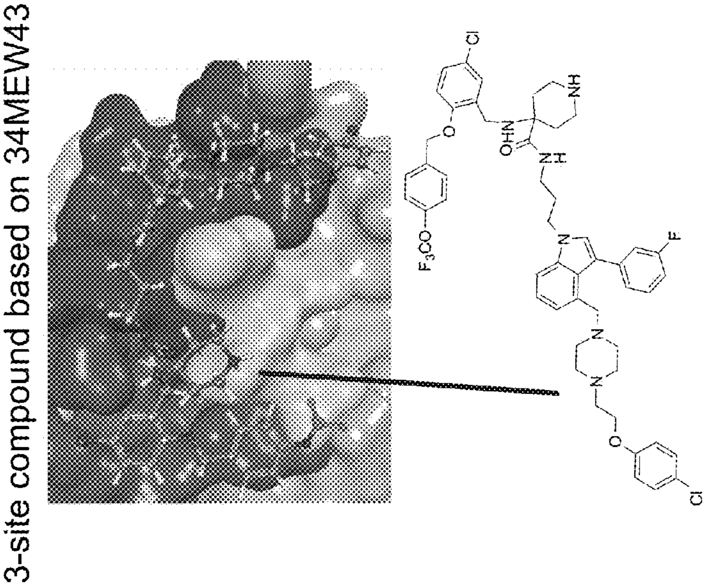
FIG. 13A-FIG. 13C show design of multivalent inhibitors.
Figure 13A:
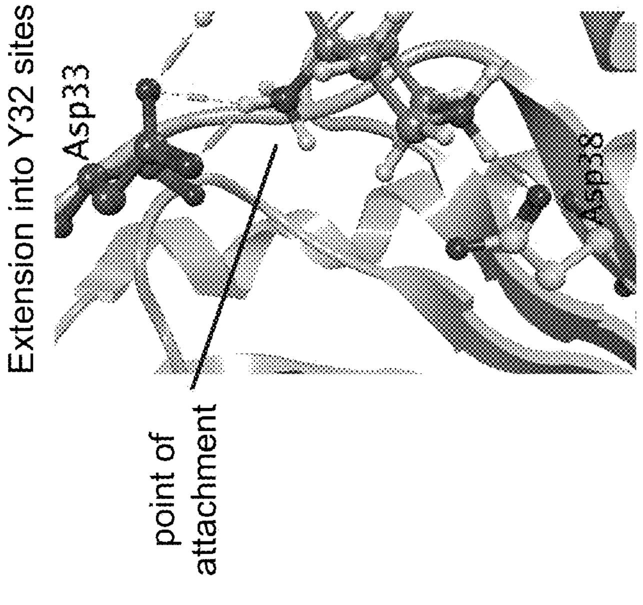
Figure 13C:
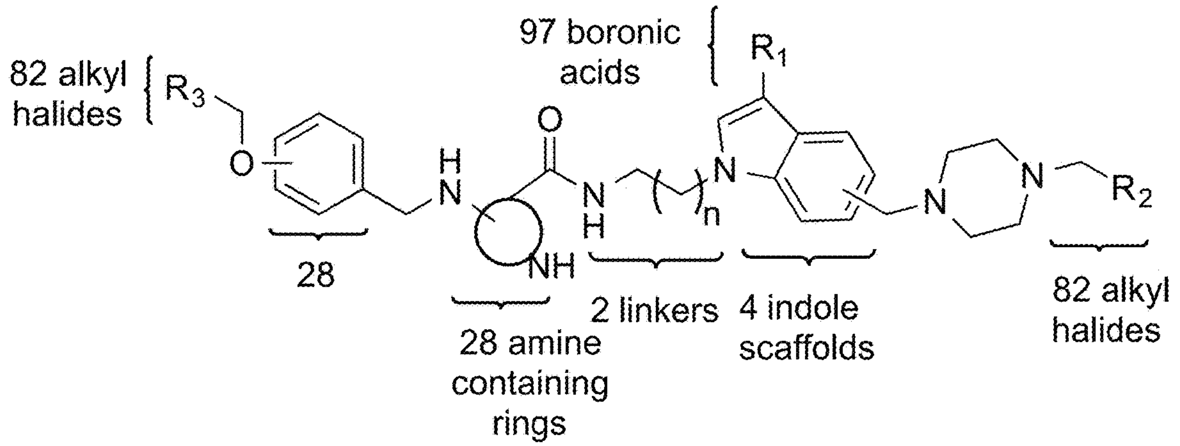

In order to retain the basic properties of amines within the D38-site-targeting fragments (FIG. 13A), it was sought to link to the Y32-site-targeting fragments via reductive amination. Libraries of synthetically accessible aldehydes were generated and linked to the A59-D38 compounds (FIG. 13B). This fragment design approach to create multivalent ligands was more computationally efficient compared to fully elaborating all possible compounds and docking them individually (FIG. 13C).

To support the notion that these compounds would be selective for the GTP-bound form, the potential inhibitors were docked into KRAS in its GDP-bound state (PDB: 4LPK) and a substantial decrease in docking scores of two to three orders of magnitude was observed (Table 4). Since GTPases have significant structural homology, these compounds were docked into a panel of GTPases in the GTP-bound form (RHO A, RHEB, RAC1, RAB3A, RAL A and CDC42) in order to predict the selectivity for RAS GTPases. The closest docking score to GTP-bound RAS was RAL A, which is still a full order of magnitude worse. Computationally, these compounds are predicted to be selective for GTP-bound RAS GTPases.

TABLE 4

| Docking Scores of 31MEW44, 34MEW43, and 34MEW95 Against a Panel of GTPases | | | | |
|---|---|---|---|---|
| PDB | Protein | 31MEW44 | 34MEW43 | 34MEW95 |
| 4DSN | KRAS G12D - GTP | −9.33 | −9.6 | −10 |
| 4LPK | KRAS wt - GDP | −6.1 | −6.95 | −7.62 |
| 1AB2 | RHO A - GTP | −6.31 | −6.98 | −6.85 |
| 1XTS | RHEB - GTP | −6.31 | −7.64 | −6.92 |
| 3TH5 | RAC1 - GTP | −7.24 | −7.69 | −8.86 |
| 3RAB | RAB3A - GTP | −6.66 | −6.34 | −7.05 |
| 1U8Y | RAL A - GTP | −8.65 | −8.335 | −8.79 |
| 2QRZ | CDC42 - GTP | −6.61 | −5.57 | −7.52 |

Note:
Docking scores were calculated using Glide (Schrodinger, Inc.).

With the molecular weight of these multivalent ligands deviating from the ideal range for marketed drugs, a computational analysis of the physical properties (using Qikprop, Schrodinger Inc.) was performed to determine how "drug-like" these molecules are, and if they could be candidates for in vivo testing (Table 5). While the number of hydrogen bond acceptors and donors for 31MEW44, 34MEW43 and 34MEW95 are compliant with Lipinski's rules, the predicted log P values were greater than 5 for 31MEW44 (predicted log P=6) and for 34MEW95 (predicted log P=9.2). However, the predicted human oral absorption (a descriptor that takes into account rotatable bonds, predicted log P, predicted aqueous solubility and predicted cell permeability) was favorable for all three molecules, with values of 57%-86%, suggesting they are viable candidates for in vivo studies.

TABLE 5

| Calculated Physiochemical Properties of 31MEW44, 34MEW43, and 34MEW95 | | | |
|---|---|---|---|
| | 31MEW44 | 34MEW43 | 34MEW95 |
| Molecular weight | 717.66 | 647.2 | 961.93 |
| H-bond donors | 3 | 3 | 3 |
| H-bond acceptors | 6 | 6 | 8 |
| log(P) | 6 | 4.8 | 9.2 |
| polar surface area (A^2) | 88.8 | 91.1 | 80.7 |
| Caco-2 (nm/sec) | 14.6 | 10.8 | 53.7 |
| % human oral absorption | 57% | 61% | 86% |

Note:
Properties were calculated using Qikprop (Schrodinger Inc.).

Example 6

Biochemical Evaluation of D38-A59 Two-Site Compounds

Figure 14A:
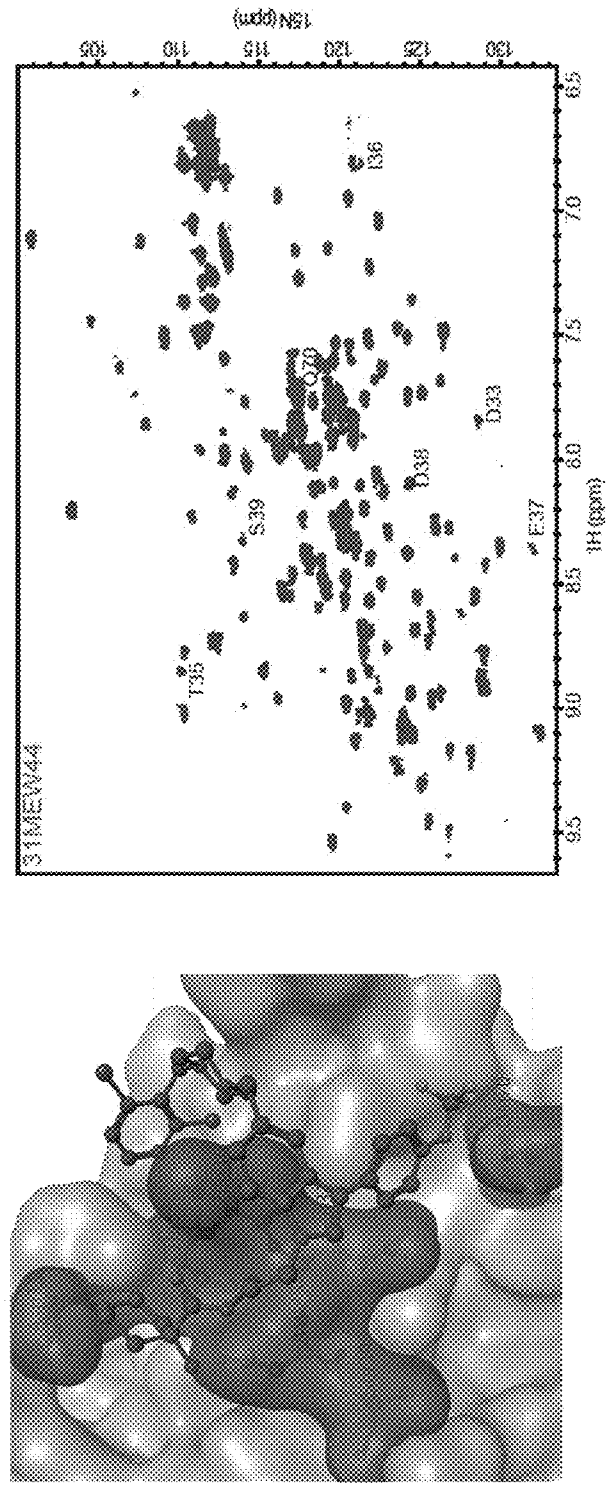
FIG. 14A-FIG. 14L show biochemical evaluation of D38-A59 two-site inhibitors.
Figure 14B:
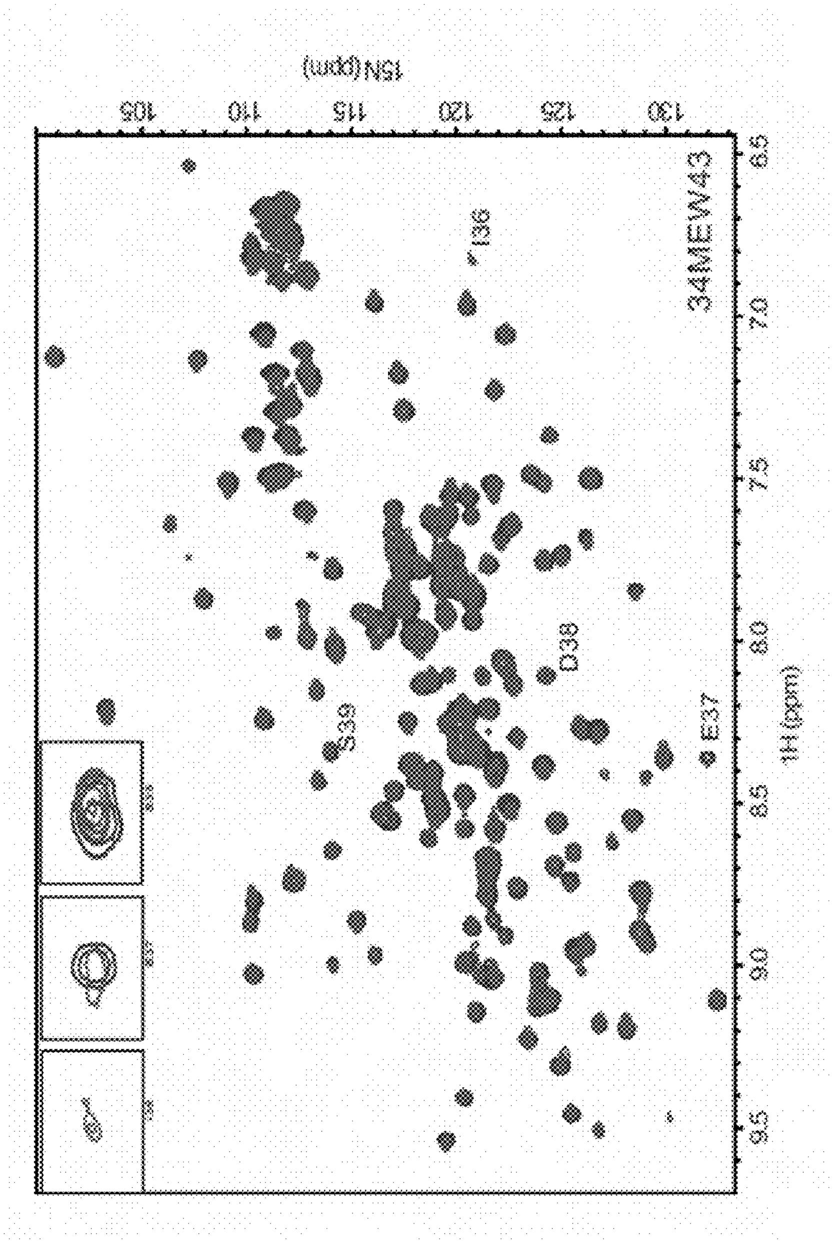
Figure 14C:
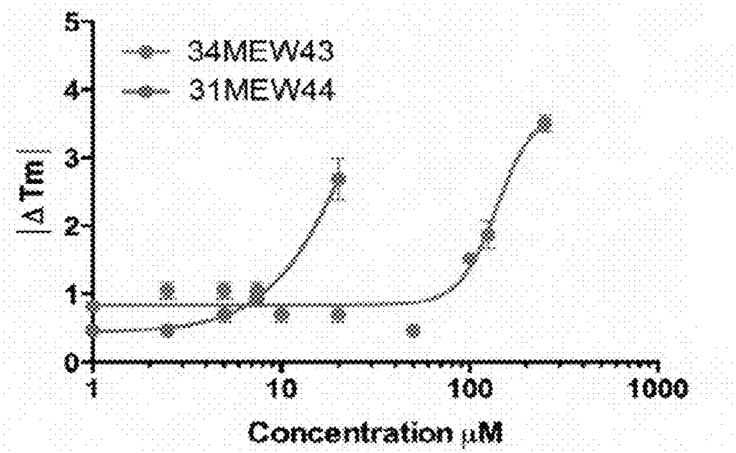

A set of 12 D38-A59 two-site multivalent compounds were synthesized initially (based on Scheme 1 with appropriate modifications) and evaluated by HSQC NMR for binding to $KRAS^{G12D}$. Two compounds (31MEW44 and 34MEW43) induced the largest chemical shifts among the ligands tested. The most dramatic shifts were observed in residues S39, D38, E37 and I36, consistent with the predicted docking pose (spectrum for 31MEW44, FIG. 14A; spectrum for 34MEW43, FIG. 14B). Both 31MEW44 and 34MEW43 demonstrated dose-dependent shifts by differential scanning fluorimetry (FIG. 14C). Measuring the affinity of 31MEW44 for the binding-site mutants revealed a 5-10 fold loss in binding affinity by microscale thermophoresis ($K_D$ $KRAS^{G12D\ D38A}$=1900 nM+/−200 nM, $K_D$ $KRAS^{G12D\ I36N}$=1100 nM+/−100 nM).

Figure 14D:
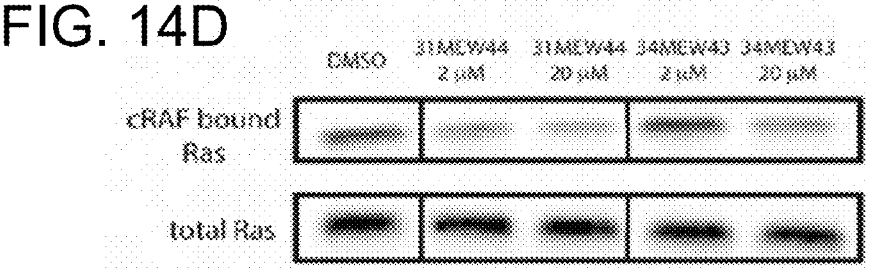
Figure 14E:
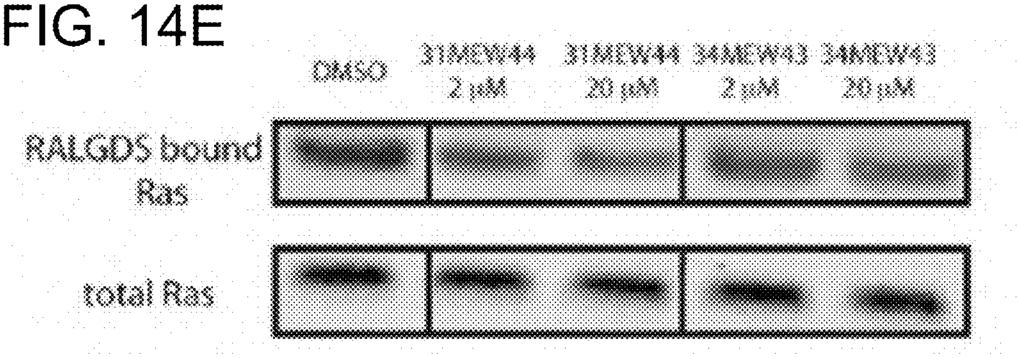
Figure 14F:
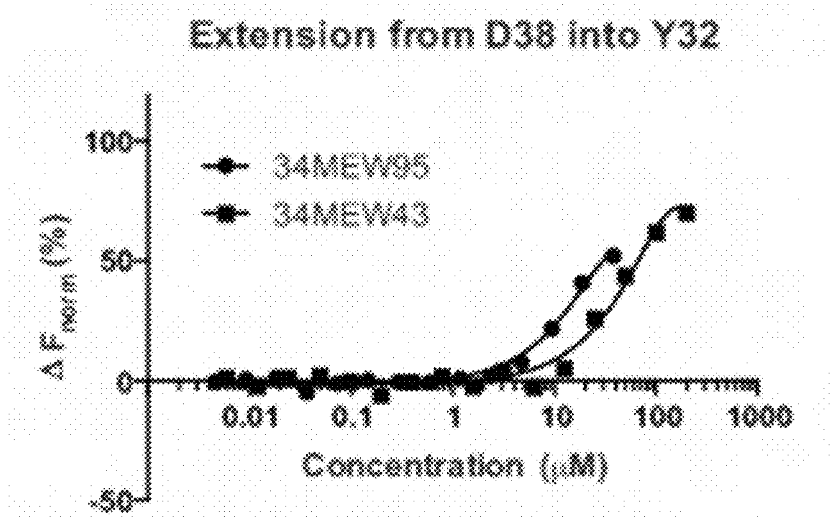
Figure 14G:
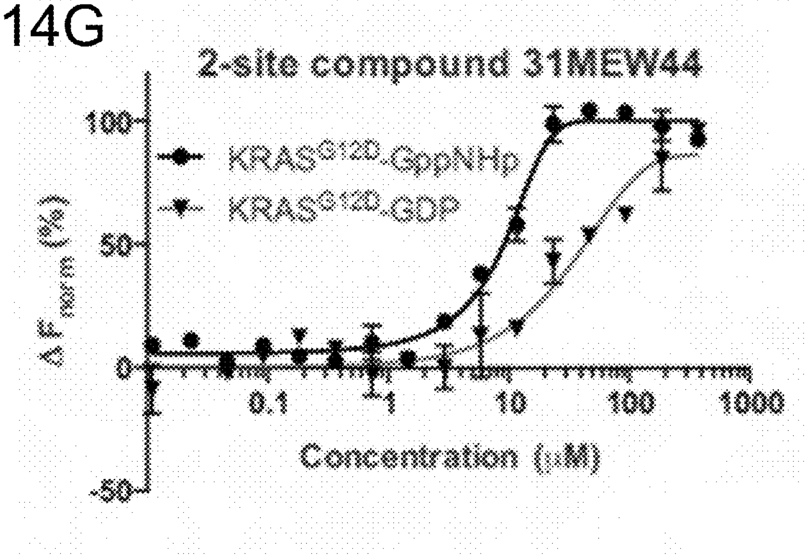

In another set of experiments, the top D38-A59 two-site multivalent compounds were evaluated by a RAS pulldown using the RAS binding domain of CRAF (the top two hits are shown in FIG. 14D). This abrogation of binding between RAS and its effector protein was also evident in the RAS-RALGDS interaction (FIG. 14E). To quantify the binding of the two-site compounds to RAS, MST was performed again using lysine NT-647-labeled, GppNHp-loaded $KRAS^{G12D}$. The low aqueous solubility of 34MEW43 prevented obtaining a full dose-response curve; the KD was estimated to be 73 μM+/−3.0 μM (FIG. 14F). The third (Y32) site was extended into (compound 34MEW95) using this scaffold. This three-site compound exhibited an estimated KD of 32 μM+/−0.85 μM (FIG. 14F); the low solubility of this larger compound again prevented a full dose-response curve and an accurate estimation of the dissociation constant. The more soluble two-site compound 31MEW44 also exhibited the highest potency among all tested compounds with a measured dissociation constant of 9.0 μM+/−1.1 μM (representing three biological replicates with three different synthesized batches of compound; a representative curve is shown in FIG. 14G); efforts at extending into the Y32 site using 31MEW44 did not yield a compound with a substantial improvement in binding affinity. The results with 31MEW44, which had the most ideal physiochemical properties along with the highest binding affinity, prompted a focus on extensive characterization of this compound.

Figure 14H:
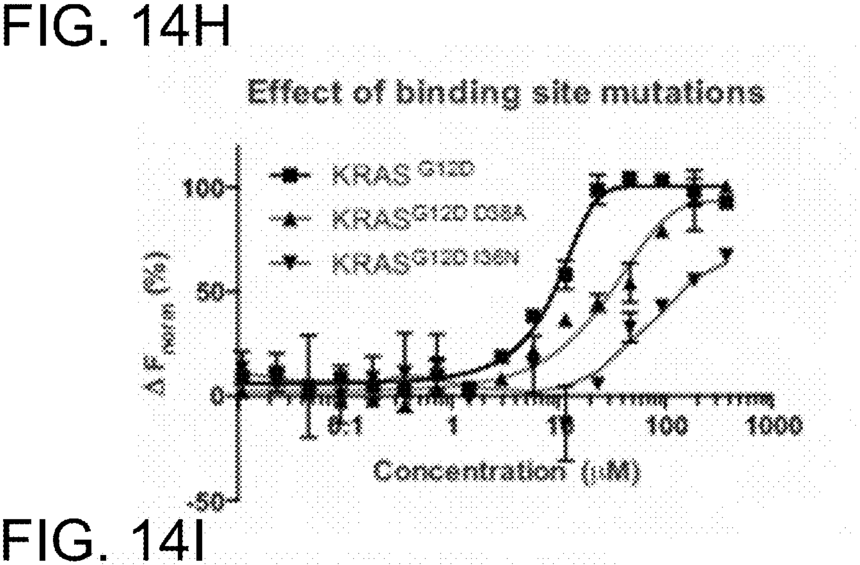

To test the hypothesis that 31MEW44 is selective for the GTP-bound form of RAS, we loaded $KRAS^{G12D}$ with GDP, and measured the binding affinity of 31MEW44 using MST: we observed a five-fold loss in affinity ($K_D$=45 μM+/−3.3 μM, FIG. 14G). To evaluate whether binding was in the predicted region of RAS, and interacting with the identified effector binding 'hot spot' residues, we performed MST on I36N and D38A mutants and observed a 3.5 to 21-fold loss in binding affinity (FIG. 14H, $KRAS^{G12D\ D38A}$ $K_D$=33+/−2.0 μM and $KRAS^{G12D\ I36N}$ $K_D$=200+/−19 μM).

Figure 14I:
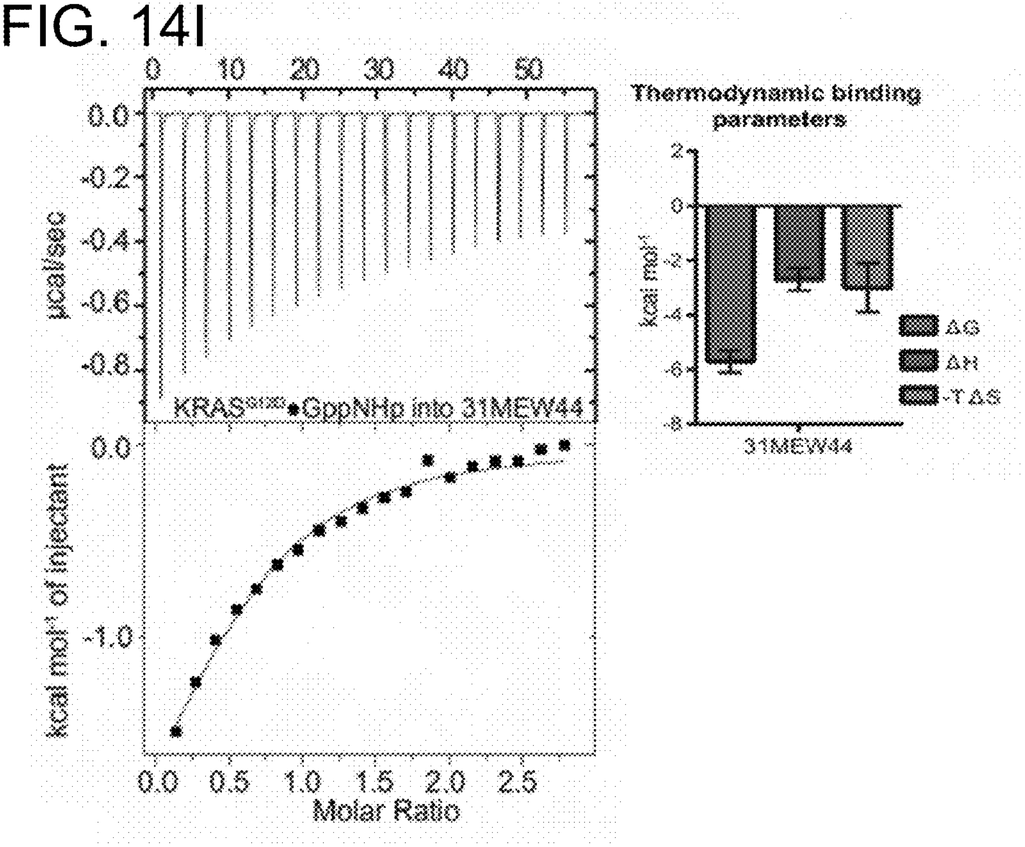

The binding site of 31MEW44 was further characterized by HSQC NMR using GppNHp-loaded $KRAS^{G12D}$ (see FIG. 9A and FIG. 9B for full 2D-1H-15N HSQC assignments and representative 3D-1H-15N-1H-NOESY-HSQC and 3D-1H-15N-1H-TOCSY-HSQC assignments on residues 35-37). The most dramatic shifts in amide resonances were observed in residues S39, D38, E37 and I36, consistent with the predicted docking pose (spectrum for 31MEW44, FIG. 14A; spectrum for 34MEW43, FIG. 14B). As a secondary measure of binding, we used isothermal titration calorimetry on GppNHp-loaded KRASG12D, and observed a dissociation constant of 34+/−24 μM (a representative trace shown in FIG. 14I).

Figure 14J:
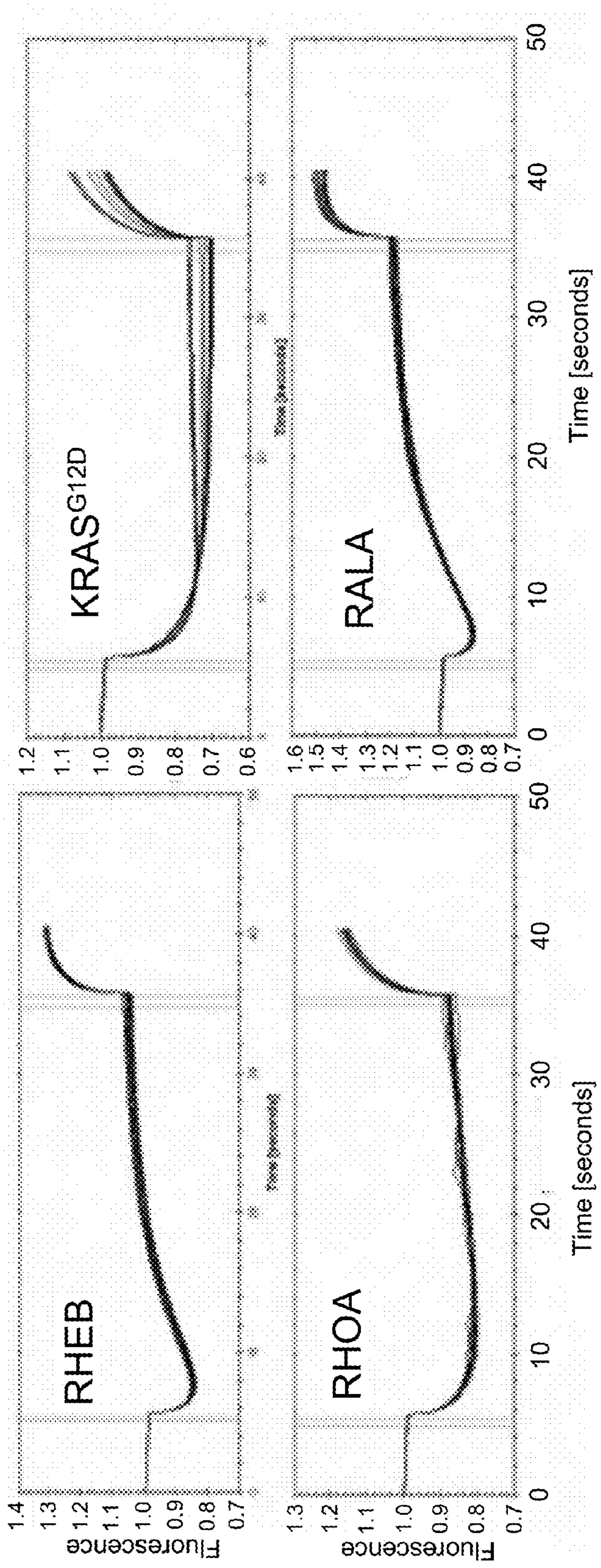
Figure 14K:
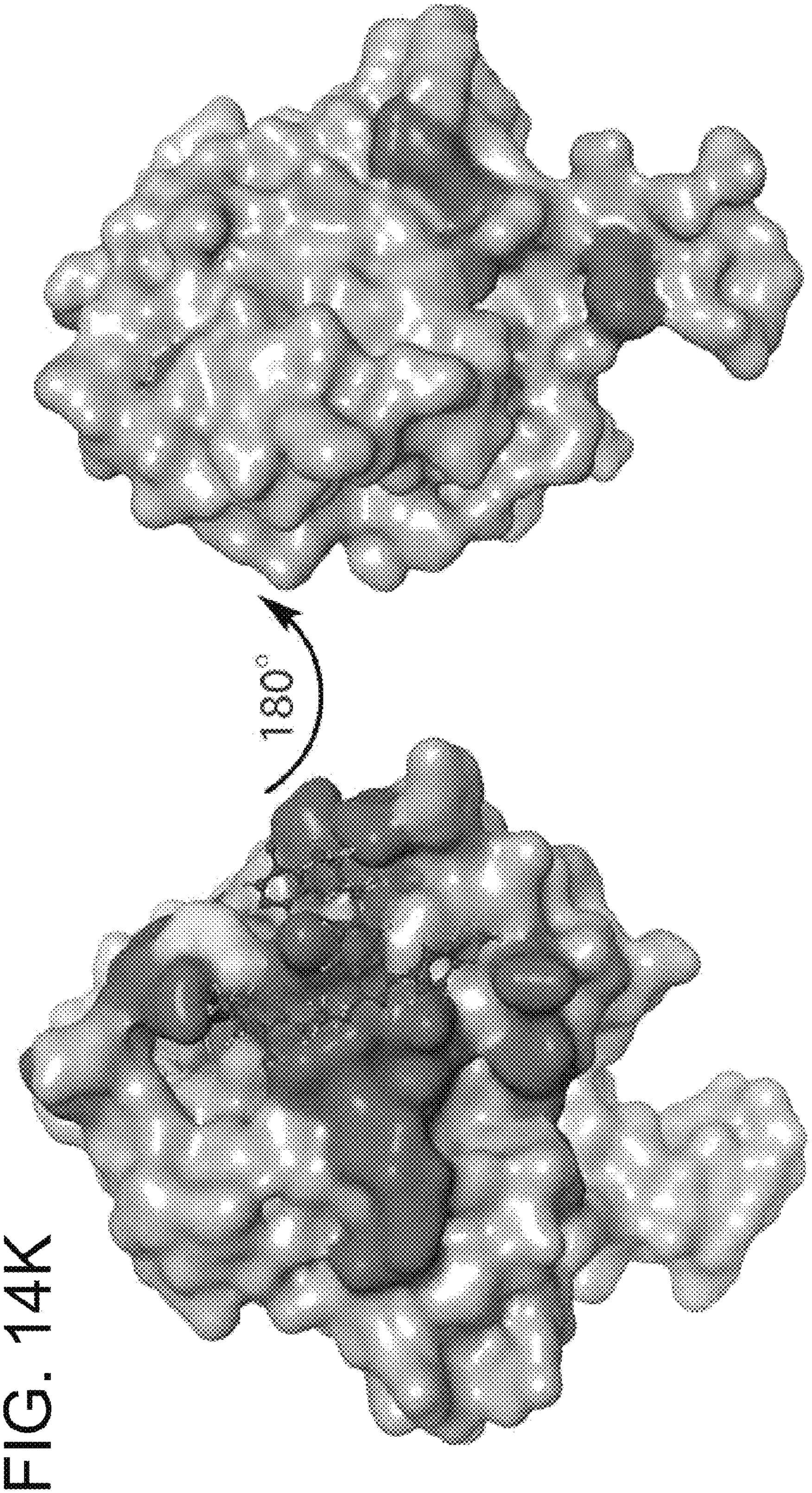
Figure 14L:
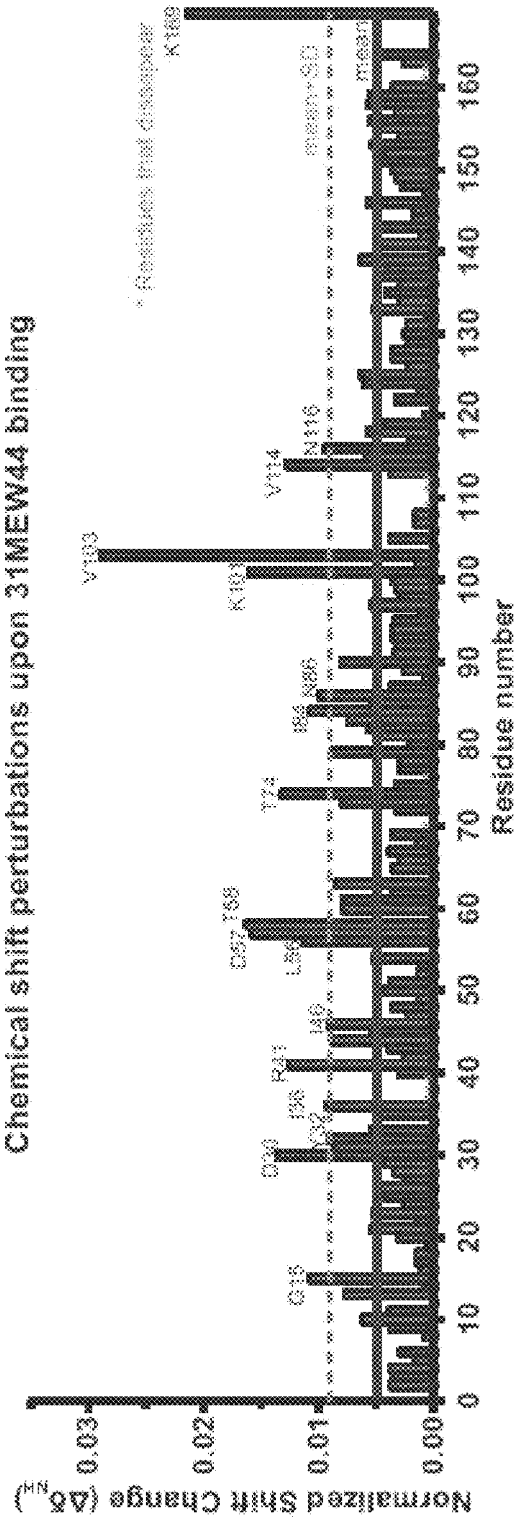

To provide evidence that the compound indeed was selective for RAS GTPases, MST binding measurements were performed on GppNHp-loaded RHEB, RHOA and RALA (FIG. 14J). Consistent with docking results, the compound was selective for RAS proteins; no binding was observed with up to 190 μM 31MEW44 to any of the other proteins.

Docking scores and dissociation constants for binding to GppNHp-bound $KRAS^{G12D}$ (PDB:4DSN) were measured as set forth above for additional 2- and 3-site compounds by microscale thermophoresis. The results are shown in Table 6.

TABLE 6

Docking Scores and $K_D$ values for additional 2- and 3-site compounds

| Compound | Docknig Score | $K_D$ (μM) |
|---|---|---|
| 36MEW3 | −10.02 | 230 +/− 9 |
| 34MEW45 | −8.96 | 1350 +/− 9 |
| 32MEW56 | −9.33 | >10000 |
| 43MEW65 | −10.0 | 7.9 +/− 1 |
| 43MEW63 | −10.6 | 26 +/− 1 |
| 43MEW73 | −10.1 | 24 +/− 1 |
| 35MEW12 | −9.88 | 36 +/− 2 |

Example 7

Figure 15A:
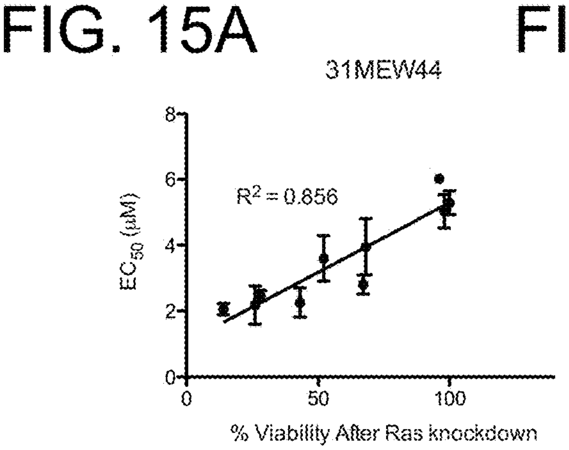
FIG. 15A-FIG. 15C show the effect of multivalent RAS inhibitors on cell viability and modulation of RAS signaling pathways. Measured inhibitor $EC_{50}$ values for a panel of cancer cell lines (across an 8-point dilution series for 24 hours) is shown as a function of cell viability after RAS knockdown using siRNA (FIG. 15A shows 31MEW44, FIG. 15B shows 34MEW43, and FIG. 15C shows 34MEW95). In each cell line, the mutant RAS isoform was knocked down, or the KRAS isoform if they consisted of wild-type RAS. $EC_{50}$ values were determined from three independent measurements performed on different days.
Figure 15B:
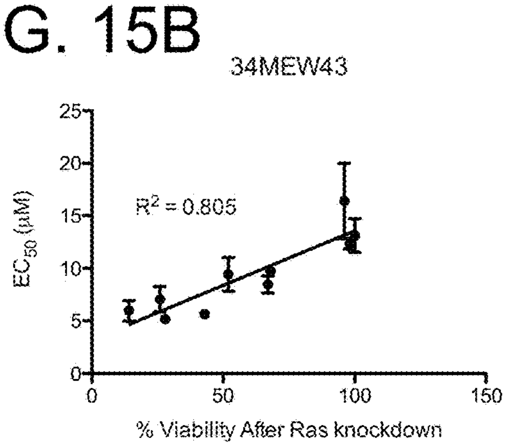
Figure 15C:
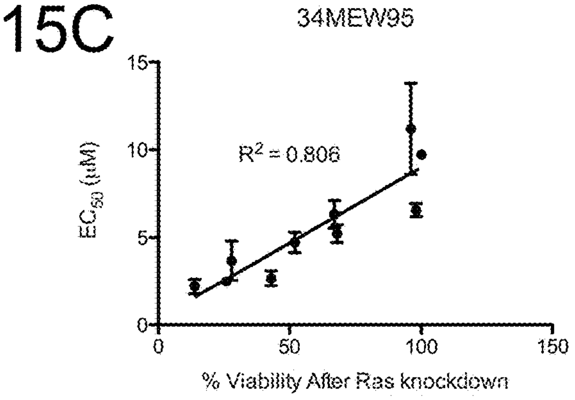

Evaluation of D38-A59 Two-Site and Y32-D38-A59 Three-Site Multivalent Ligands in Cell Lines with Oncogenic RAS Mutations In a first set of experiments, the two-site compounds 31MEW44 and 34MEW43 were tested in a panel of cancer cell lines, some with RAS gene mutations (Table 7). siRNA knockdown of the mutant RAS isoform or, in the absence of mutation, the KRAS isoform was performed in each of these cell lines, to examine their degree of dependency on RAS GTPases. Plotting the percent viability of each cell line after knockdown against $EC_{50}$ in each cell line for each compound yielded a high correlation ($R^2$=0.82-0.86), supporting the notion that the lethality of these compounds in cells is RAS-mediated within this concentration range (FIG. 15A-FIG. 15C).

TABLE 7

Potency of 31MEW44, 34MEW43, and 34MEW95 in a Panel of Cancer Cell Lines with the Viability Measured of Each Lines that was Subjected to a RAS Knockdown

| Primary Site | Cell Line (RAS mutation) | Viability after Ras KD | 31MEW44 EC50 (μM) | 34MEW43 EC50 (μM) | 34MEW95 EC50 (μM) |
|---|---|---|---|---|---|
| Pancreas | Panc-1 (KRAS G12D) | 14% | 2.06 +/− 0.17 | 5.96 +/− 0.97 | 2.20 +/− 0.42 |
| Colorectal | SW480 (KRAS G12V) | 26% | 2.18 +/− 0.58 | 7.06 +/− 1.2 | 2.49 +/− 0.050 |
| Fibrosarcoma | HT1080 (NRAS Q61K) | 28% | 2.47 +/− 0.16 | 5.17 +/− 0.22 | 3.68 +/− 1.12 |
| Breast | MDA-MB-231 (KRAS G13D) | 43% | 2.26 +/− 0.44 | 5.63 +/− 0.46 | 2.67 +/− 0.43 |
| Lung | Calu-1 (KRAS G12C) | 52% | 3.60 +/− 0.69 | 9.42 +/− 1.6 | 4.73 +/− 0.57 |
| Pancreas | MIA Paca-2 (KRAS G12C) | 67% | 2.81 +/− 0.29 | 8.45 +/− 0.80 | 6.33 +/− 0.79 |
| Skin fibroblast | BJeLR (HRAS G12V) | 68% | 3.95 +/− 0.85 | 9.71 +/− 0.36 | 5.23 +/− 0.50 |
| Pancreas | HPAFII (KRAS G12D) | 96% | 6.02 +/− 0.064 | 16.4 +/− 3.6 | 11.2 +/− 2.6 |
| Osteosarcoma | U2OS (WT) | 98% | 5.03 +/− 0.51 | 12.33 +/− 0.50 | 6.57 +/− 0.37 |
| Pancreas | BxPC-3 (WT) | 100% | 5.29 +/− 0.36 | 13.1 +/− 1.6 | 9.73 +/− 0.25 |

Note:
Cells were treated with compounds for 48 hours across an 8-point dilution series.

Comparing the lethal potency of these two-site compounds in KRAS-dependent (14% viability after KRAS knockdown) panc-1 cells to non-KRAS dependent (100% viability after KRAS knockdown) BxPC3 cells, a modest two-fold potency difference was observed. Based on these data and the 100% sequence conservation in the Y32-D38-A59 sites among the RAS isoforms, it was speculated that these compounds function as pan-RAS inhibitors. The relatively narrow selectivity window between these RAS mutant and RAS wild-type cell lines may be attributed, in part, to inhibition of the wild-type RAS isoforms, which is likely lethal to transformed cell lines lacking RAS mutations, such as BxPC3. Nonetheless, whether a pan-RAS inhibitor would have a therapeutic window is best addressed in primary patient samples and animal studies (see below).

A series of top-scoring compounds extending into the Y32 site were synthesized based on the 31MEW44 and 34MEW43 structures. 34MEW95, based on the 34MEW43 two-site compound, exhibited a three-fold improvement in potency and selectivity relative to 34MEW43. Thus, extending into a third site can improve compound potency and selectivity for RAS mutant cell lines.

Figure 16A:
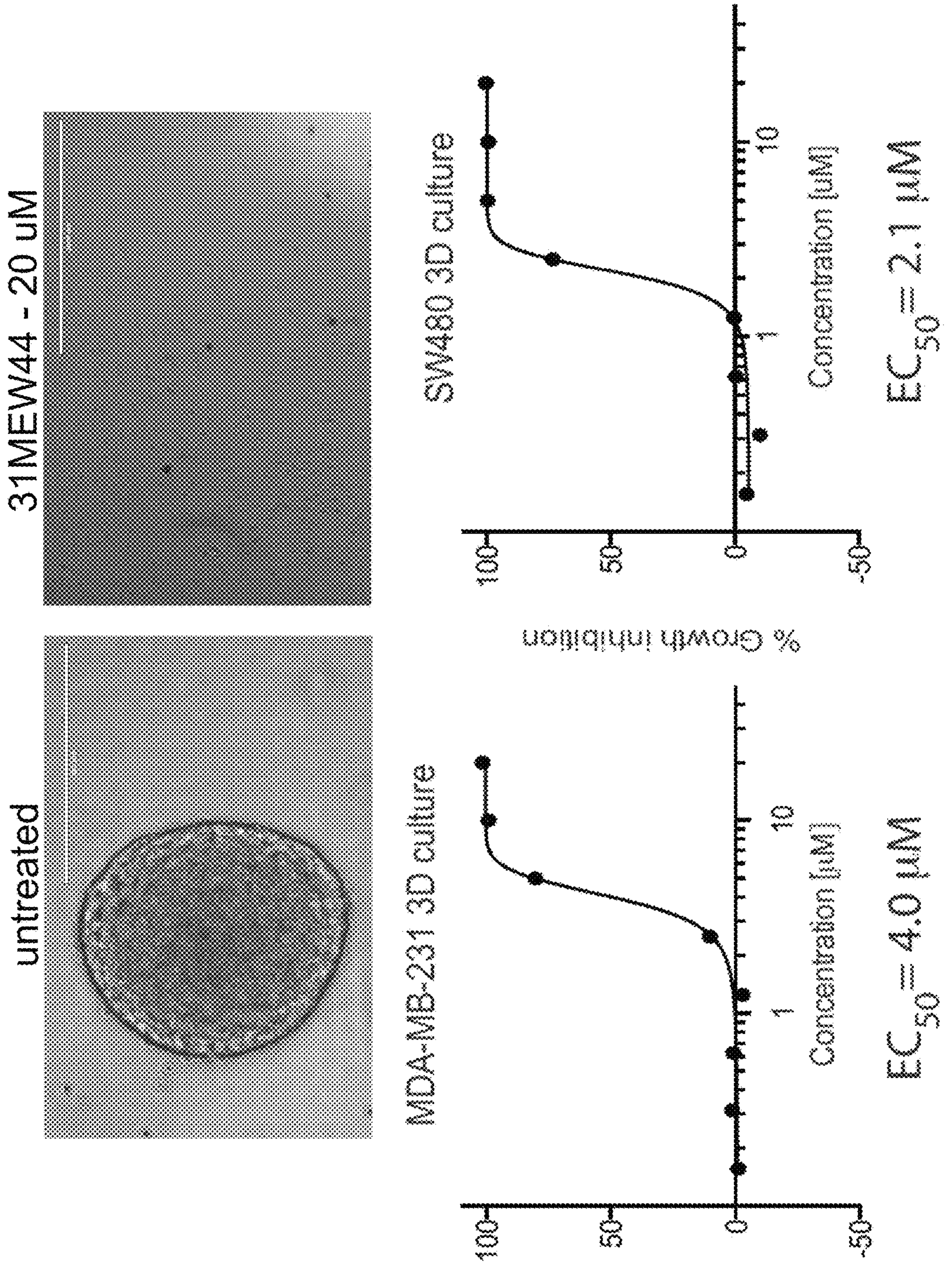
FIG. 16A-FIG. 16B show the effect of multivalent RAS inhibitors on cell viability and modulation of RAS signaling pathways, and the ability of 31MEW44 to prevent anchorage independent growth.
Figure 16B:
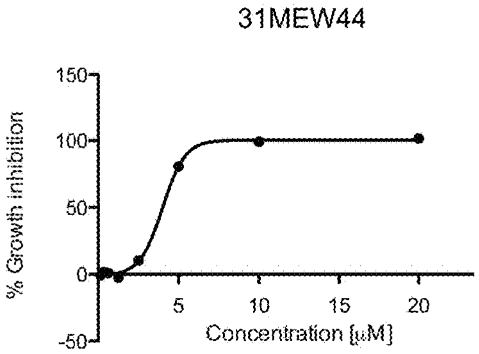
Figure 16B:
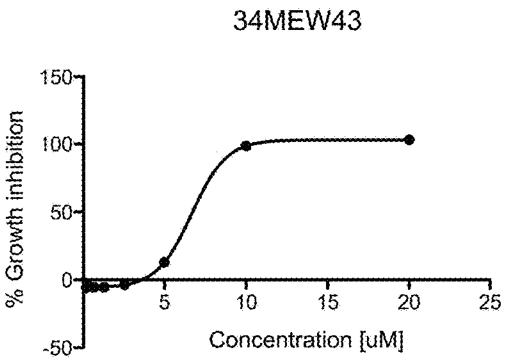
Figure 16B:
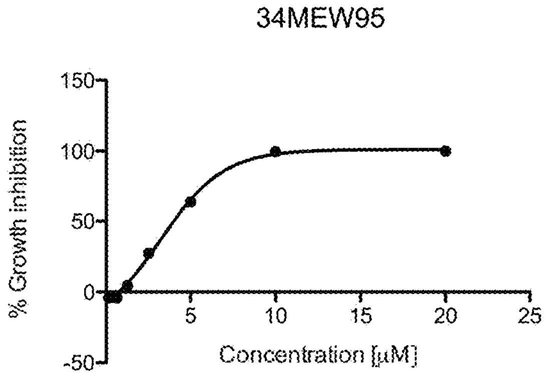

Next, whether these compounds were able to prevent tumor growth in an anchorage-independent fashion, which is a more physiologically relevant culture condition, was tested. The ability of 31MEW44, 34MEW43 and 34MEW95 to prevent anchorage-independent tumor cell growth was assessed by seeding the breast cancer MDA-MB-231 cell line (with $KRAS^{G13D}$) in low-adherence plates, resulting in aggregation into tumor-like spheres. Vehicle-treated cells grew into multicellular tumor spheroids (FIG. 16A-FIG. 16B) that decreased in size in a dose-dependent manner in the presence of each compound. Thus, these compounds are effective at inhibiting tumor cell growth in 3D cultures.

Figure 17A:
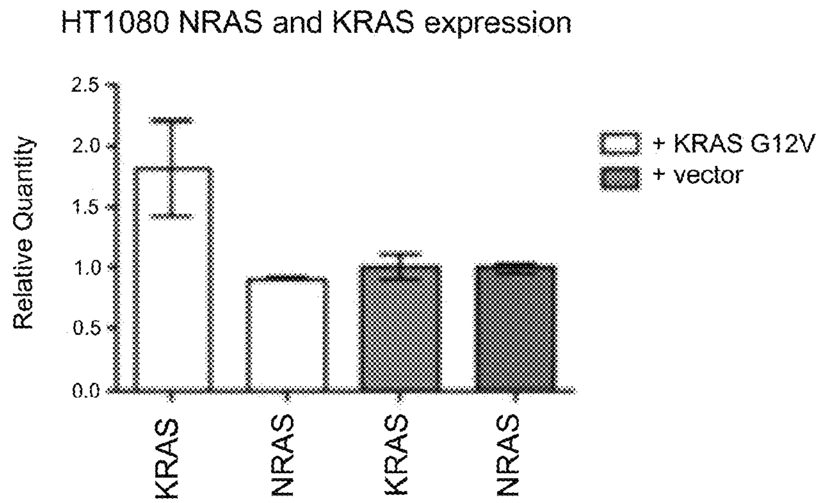
FIG. 17A-FIG. 17B show the effect of multivalent RAS inhibitors on cell viability and modulation of RAS signaling pathways. HT-1080 cells were retrovirally transfected with a pBABE-puro vector containing $KRAS^{G12V}$ or the empty vector. Following selection with puromycin (1 μg/mL treatment for 10 days) the RNA was extracted from the two cell lines and the expression of KRAS was quantified by qPCR (FIG. 17A). Transfected cells were then treated with 31MEW44, 34MEW43 and 34MEW95 at 5 μM for 24 hours (FIG. 17B). All measurements were performed in triplicate.
Figure 17B:
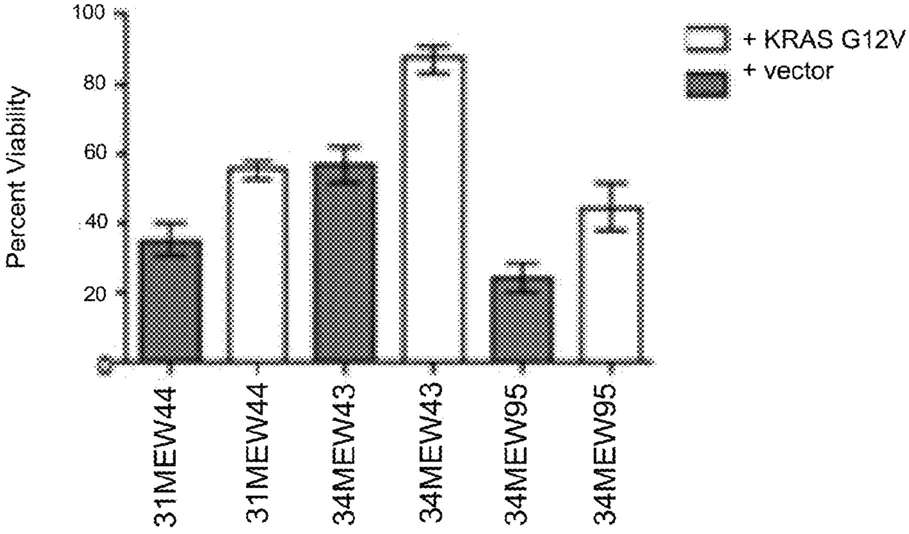

It was hypothesized that if these compounds were killing cells through RAS inhibition, overexpression of activated RAS would confer a degree of resistance to the inhibitors. HT-1080 cells ($NRAS^{Q61K}$) were transfected with a pBABE-puro-containing $KRAS^{G12V}$ or empty vector using a retrovirus. A 1.7-fold increase in KRAS expression in the vector containing $KRAS^{G12V}$ was observed relative to the vector alone following selection (FIG. 17A-FIG. 17B). The two lines were treated with 5 μM of each inhibitor for 24 hours. A corresponding 1.5-1.8 fold decrease in sensitivity (FIG. 17A-FIG. 17B) was observed, consistent with the idea that cell death is dependent on RAS, even with only a modest increase in activated RAS expression.

Figure 18:
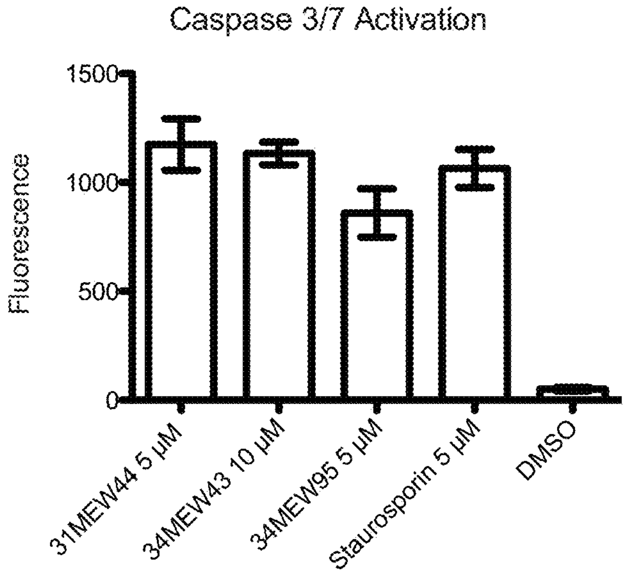
FIG. 18 shows HT-1080 cells treated with 31MEW44 (5 μM), 34MEW43 (10 μM), 34MEW95 (5 μM) and staurosporin for 24 hours. Cells were then lysed and treated with a pro-fluorescent caspase 3/7 substrate (rhodamine 110 bis-N-CBZ-L-aspartyl-L-gluramyl-L-valyl-aspartic acid amide) for 16 hours.

To test whether these compounds kill cells through caspase-dependent apoptosis, which has been suggested as the mechanism of lethality after loss of RAS expression, HT-1080 ($NRAS^{Q61K}$) cell lysates were incubated, after treatment of the cells with 31MEW44 (5 μM), 34MEW43 (10 μM), 34MEW95 (5 μM), or staurosporine (5 μM), with a pro-fluorescent substrate for caspases 3 and 7 (rhodamine 110 bis-N-CBZ-L-aspartyl-L-gluramyl-L-valyl-aspartic acid amide). Increased fluorescence of this substrate was observed, consistent with activation of caspases 3 and/or 7 activation in response to these compounds, similar to what was observed with the known apoptosis-inducing agent staurosporine (FIG. 18).

Figures 31A, 31B:
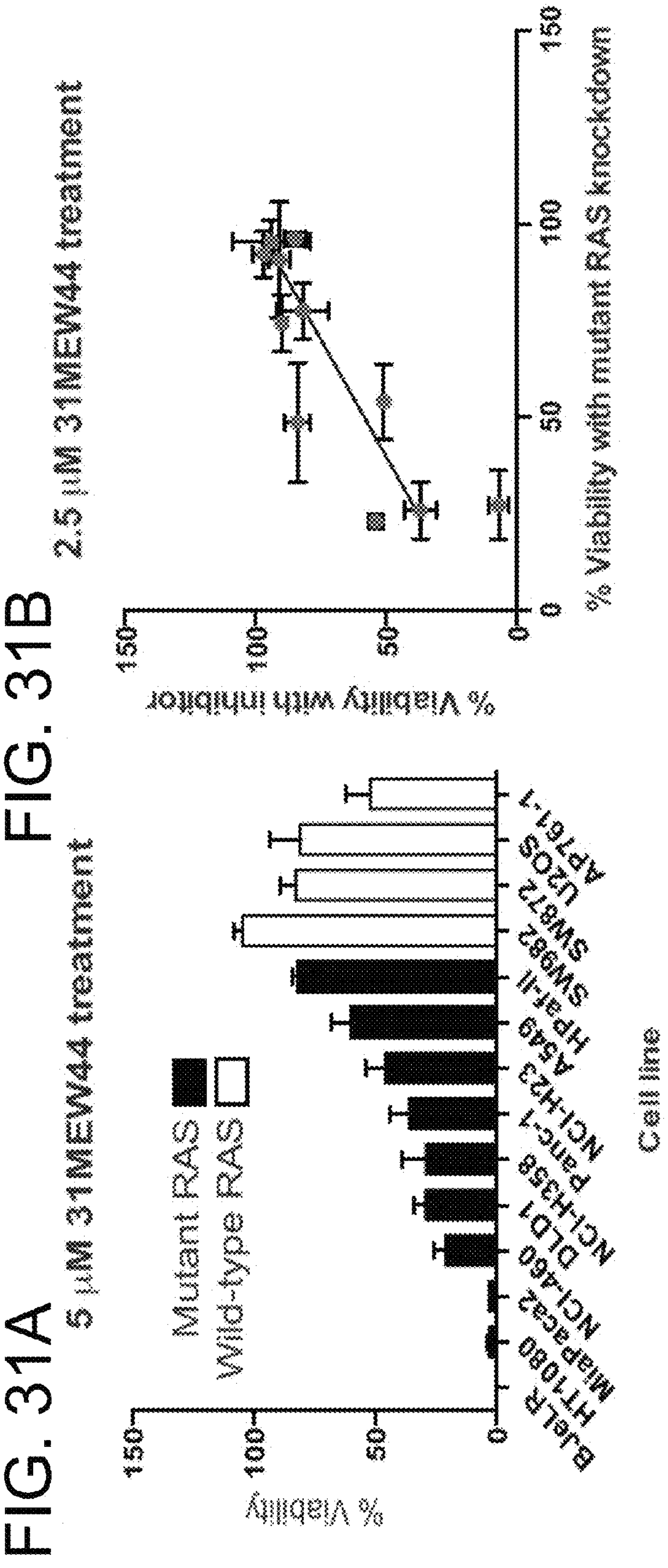
FIG. 31A-FIG. 31B show that 31MEW44 is selectively lethal to cell lines dependent on mutant RAS, induced caspase activation and prevention of anchorage independent growth.
Figure 32B:
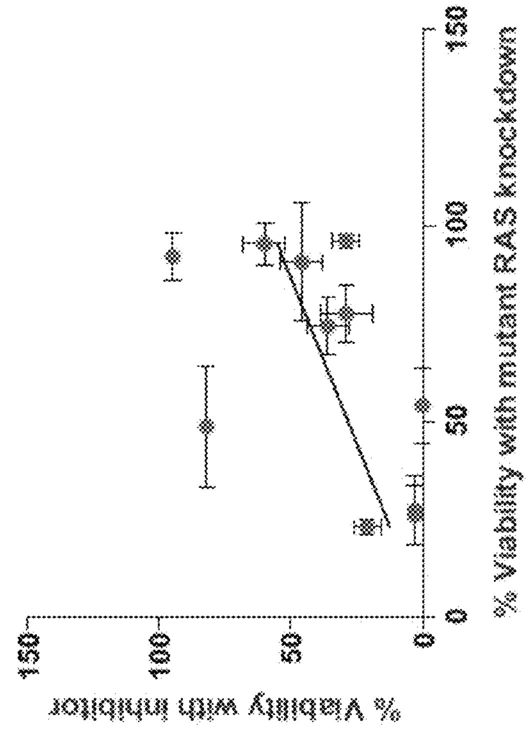
FIG. 32A-FIG. 32B show the sensitivity of a cell line panel to mutant RAS knockdown and the correlation of the sensitivity to the knockdown with the sensitivity to 31MEW44.
Figure 32A:
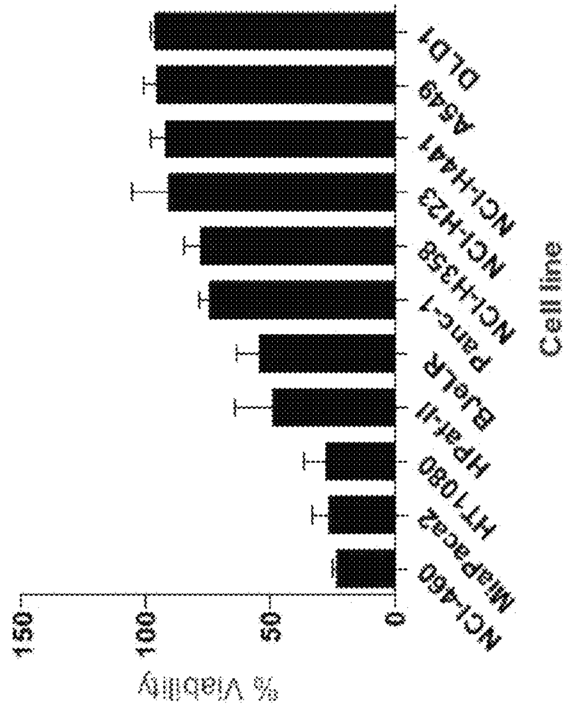

In a second set of experiments, 31MEW44 was evaluated in a panel of ten mutant RAS cell lines and four wild-type RAS cell lines (FIG. 31A, and Table 8 below, $EC_{50}$ values for 31MEW44, 34MEW43 and 34MEW95). Based on the near identical sequences in the D38 and A59 sites among the RAS isoforms, it was speculated that 31MEW44 would function as a pan-RAS inhibitor. Consistent with the idea that the compound is acting through RAS inhibition, the two most resistant lines, SW982 and SW872, both possess mutant BRAFV600E, which is downstream of RAS and would therefore would be expected to cause resistance to RAS inhibition. A range of sensitivity was observed in the mutant RAS lines, which was hypothesized to be due to their degree of dependency on mutant RAS. To test if this was indeed the case, a knockdown of the mutant isoform was performed and the viability plotted following knockdown against the viability following inhibitor treatment. With 2.5 μM 31MEW44, a strong correlation in RAS dependency and compound lethality was observed, suggesting this concentration is likely acting on-target ($R^2$=0.70, FIG. 31B). At 5 μM 31MEW44, the correlation was still present, but lower (FIG. 32B). An interpretation of these data is that 2.5 μM is more functionally equivalent to the knockdown of a single RAS isoform, whereas the higher concentrations would cause inhibition of the other active isoforms and be more reflective of inhibiting total GTP-bound RAS, revealing a lower correlation with knockdown of one isoform.

TABLE 8

Measured $EC_{50s}$ of inhibitors in a panel of mutant RAS cell lines. Cells were treated with inhibitors in 384-well format and viability was measured after 48 hours of treatment using alamar blue.

| primary site | cell line (RAS mutation) | 31MEW44 EC50 (μM) | 34MEW43 EC50 (μM) | 34MEW95 EC50 (μM) |
|---|---|---|---|---|
| pancreas | panc-1 ($KRAS^{G12D}$) | 5.1 | 6.0 | 2.2 |
| colorectal | SW480 ($KRAS^{G12V}$) | 2.2 | 7.1 | 2.5 |
| fibroscarcoma | HT1080 ($NRAS^{Q61K}$) | 1.1 | 5.2 | 3.7 |
| breast | MDA-MB-231 ($KRAS^{G13O}$) | 2.3 | 5.6 | 2.7 |
| lung | calu-1 ($KRAS^{G12C}$) | 3.6 | 9.4 | 4.7 |
| pancreas | Mia Paca-2 ($KRAS^{G12C}$) | 3.2 | 8.5 | 6.3 |
| skin fibroblast | BJeLR ($HRAS^{G12V}$) | 4.0 | 9.7 | 5.2 |
| pancreas | HPAFII ($KRAS^{G12D}$) | 5.2 | 16 | 11 |
| lung | A549 ($KRAS^{G12S}$) | 4.8 | | |
| lung | H441 ($KRAS^{G12V}$) | 4.9 | | |
| lung | H358 ($KRAS^{G12C}$) | 2.8 | | |
| lung | H23 ($KRAS^{G12C}$) | 2.4 | | |
| lung | DLD1 ($KRAS^{Q61H}$) | 8.8 | | |
| lung | H460 ($KRAS^{Q61H}$) | 4.9 | | |

Figure 33A:
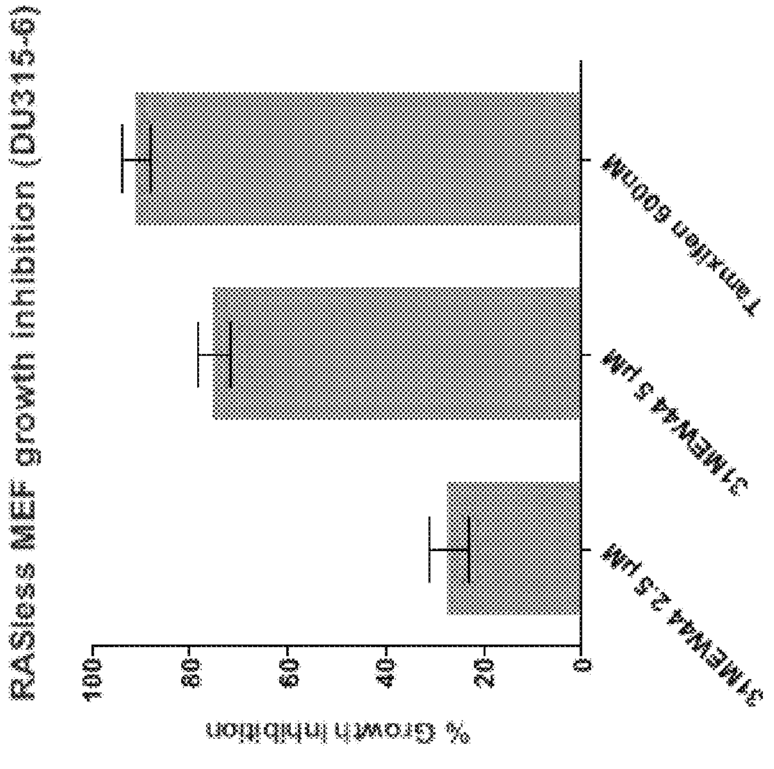
FIG. 33A shows the effect of 31MEW44 on the growth inhibition of MEFs containing a floxed allele of Kras compared to induction of CRE recombinase by 4OHT. Cells were treated in 6-well format with 31MEW44 at 2.5 μM, 5 μM, or DMSO for 24 hours. In parallel, cells were treated with DMSO or 4OHT at 600 nM for 6 days.
Figure 33B:
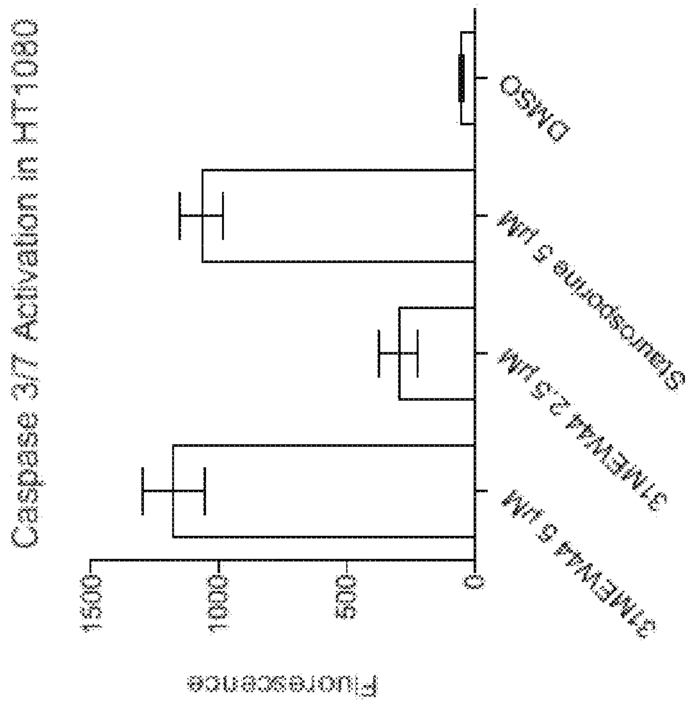
FIG. 33B shows the induction of caspase 3/7 activation by 31MEW44. HT-1080 cells treated were with 31MEW44 or staurosporin for 24 hours. Cells were then lysed and treated with a pro-fluorescent caspase 3/7 substrate (rhodamine 110 bis-N-CBZ-L-aspartyl-L-gluramyl-L-valyl-aspartic acid amide) for 16 hours and measured.

Mouse embryonic fibroblasts (MEFs) have been generated to contain null Hras and Nras alleles, along with a floxed Kras locus that can be excised using a knocked in, inducible Cre recombinase (Drosten et al., 2010). Induction of Cre effectively renders these cells "RASless", and unable to proliferate. It was demonstrated that complete elimination of K-Ras occurs from 7 to 14 days of treatment with 4-hydroxytamoxifen (4OHT) (Drosten et al., 2010). Experiences with 31MEW44 have shown that cell death by RAS inhibition occurs within 24 hours of compound treatment, indicating faster kinetics than the combination of 4OHT induction and excision of Kras by Cre. To see whether 31MEW44 treatment compares with 4OHT treatment, these cells were treated with 31MEW44 (24 hours) or 4OHT (6 days) and compared the effect on growth inhibition to vehicle (DMSO) treatment (FIG. 33B). The results revealed 91% growth inhibition with 600 nM 4OHT compared to 75% with up to 5 μM 31MEW44, indicating a similar inhibitory effect on proliferation. Indeed, the fact that a significant number of RASless MEFS remained after treatment indicates that 31MEW44 was not killing all the cells, but was likely inhibiting their growth, similar to 4OHT.

To test whether 31MEW44 kills sensitive RAS-addicted tumor cells through caspase-dependent apoptosis, which has been suggested as the mechanism of lethality after loss of RAS expression, HT-1080 ($NRAS^{Q61K}$) cell lysates were incubated, after treatment of the cells with 31MEW44 (2.5 and 5 μM), or staurosporine (5 μM), with a pro-fluorescent substrate for caspases 3 and 7 (rhodamine 110 bis-N-CBZ-L-aspartyl-L-gluramyl-L-valyl-aspartic acid amide). Increased fluorescence associated with cleavage of this substrate was observed, consistent with activation of caspases 3 and/or 7 in response to 31MEW44, similar to what was seen with staurosporine, a known apoptosis-inducing agent, at 5 μM (FIG. 33B, see FIG. 18 for 34MEW43 and 34MEW95 results).

Figure 34A:
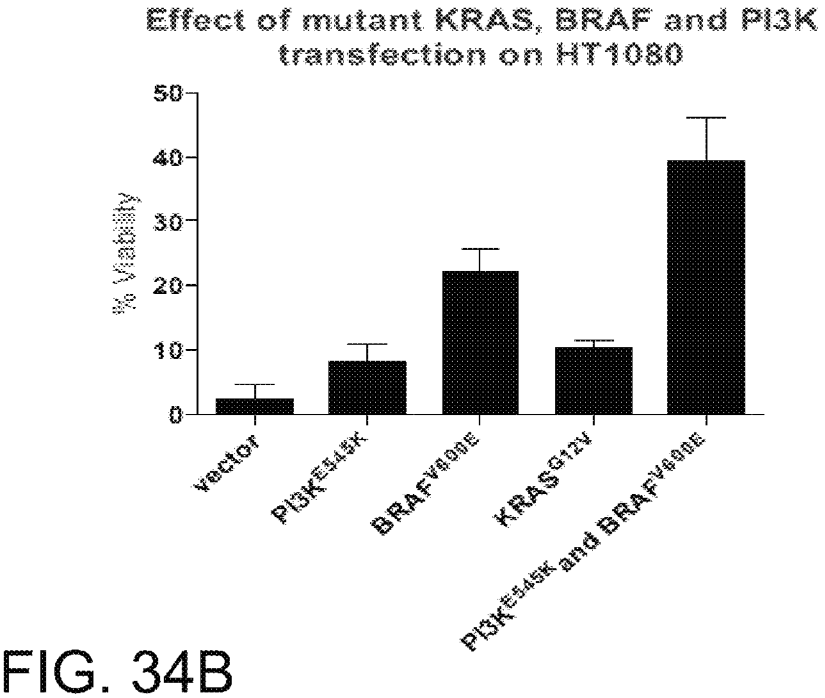
FIG. 34A shows the effect of KRAS and effector over-expression on 31MEW44 sensitivity. HT-1080 cells were retrovirally transfected with a pBABE-puro empty vector or vector containing $KRAS^{G12V}$, $PI3K^{E545K}$, or $BRAF^{V600E}$. Following selection with puromycin, a population of the $PI3K^{E545K}$ transfected cells were transfected a second time with a pBABE-neo-$BRAF^{V600E}$ vector and selected a second time with geneticin. Stable cell lines were then treated with 31MEW44 for 24 hours in 6-well format. Cell lysates were analyzed by western blotting for levels of downstream phosphorylated ERK and AKT.
Figure 35A:
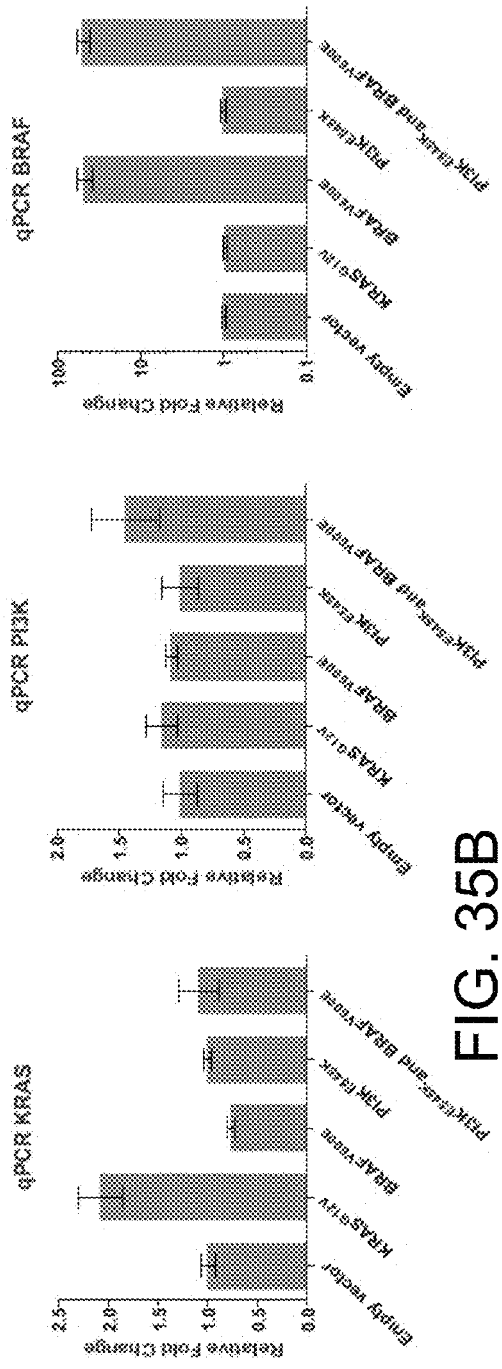
FIG. 35A-FIG. 35B show validation of the efficacy of the transfection of mutant KRAS, PI3K, and BRAF.
Figure 35B:
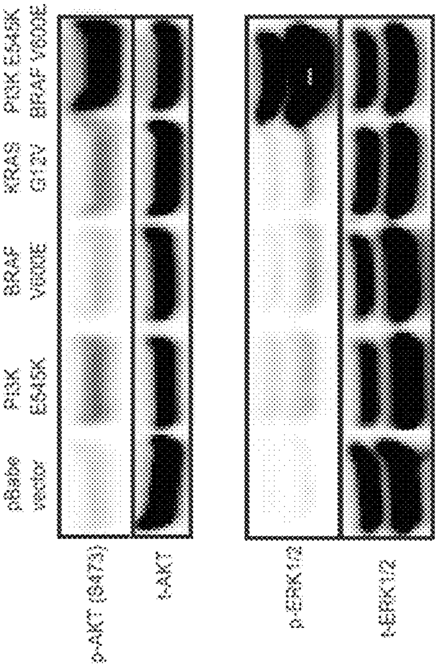

It was hypothesized that if 31MEW44 was killing these cells through RAS inhibition, overexpression of activated RAS and two of its effectors most commonly associated with the oncogenic phenotype (PI3K and RAF) would confer a degree of resistance to the inhibitors. To test this, HT-1080 cells ($NRAS^{Q61K}$) were transfected with pBABE-puro-containing $KRAS^{G12V}$, $PI3K^{E545K}$, $BRAF^{V600E}$ or empty vector. In the $PI3K^{E545K}$-transfected line, a second transfection was performed with pBABEneo $BRAF^{V600E}$. After 5 μM treatment for 24 h, resistance was indeed observed in all cases, with the most resistant cells being the those with $BRAF^{V600E}$ and $PI3K^{E545K}$ co-transfected, followed by the BRAFv600E transfected cells (FIG. 34A). Overexpression of these proteins was verified by qPCR and their function activity was measured by western blot of downstream phosphorylated ERK and AKT (FIG. 35).

Figure 34B:
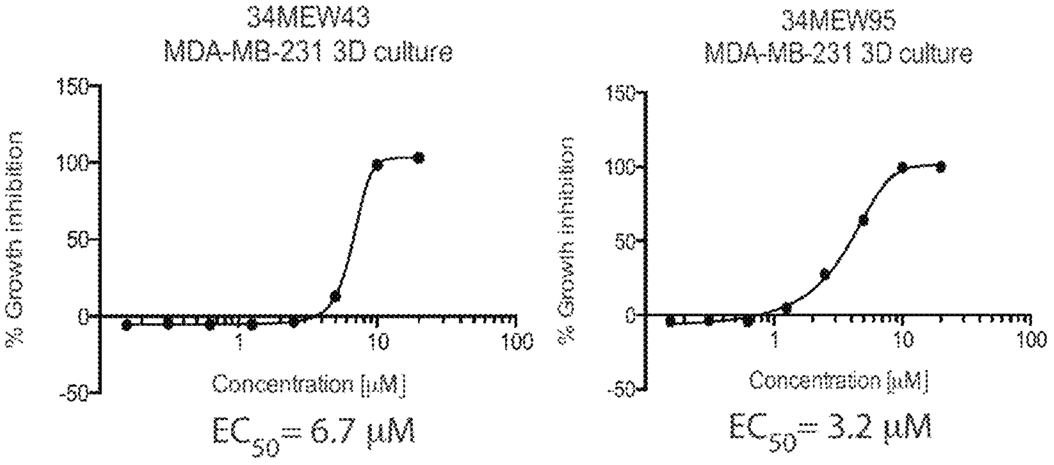
FIG. 34B shows a dose-response curve of 34MEW43 and the 3-site compound 34MEW95 in 3D cell culture of MDA-MB-231 cells.

The next test determined whether 31MEW44 was able to prevent tumor growth in an anchorage-independent fashion, which is a more physiologically relevant culture condition. The activity of 31MEW44 was assessed by seeding the breast cancer MDA-MB-231 cell line ($KRAS^{G13D}$) and the colorectal cancer SW480 ($KRAS^{G12V}$) in low-adherence plates, resulting in aggregation into tumor-like spheres. Vehicle-treated cells grew into multicellular tumor spheroids (FIG. 16A) that decreased in size in a dose-dependent manner in the presence of the inhibitor (34MEW43 and 34MEW95, FIG. 34B). Thus, these compounds are effective at inhibiting tumor cell growth in 3D cultures.

Example 8

Inhibition of RAS Signaling by Multivalent Ligands

Figure 19A:
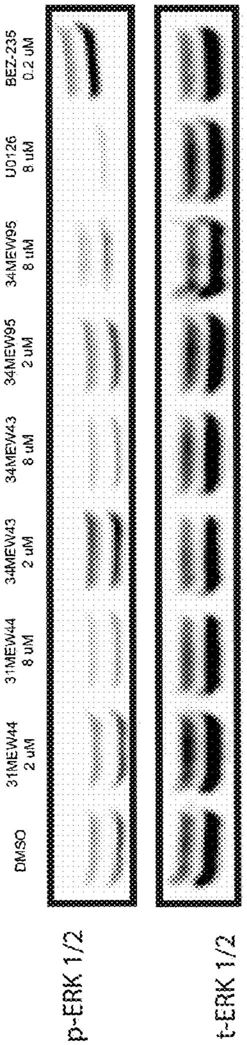
FIG. 19A-FIG. 19B show BJeLR cells were treated with DMSO, RAS inhibitor at 2 μM and 8 μM, U0126 at 8 μM, or BEZ-235 at 0.2 μM for 24 hours under serum free conditions. Cells were then lysed and the lysate was subjected to detection of phosphorylated Erk and total Erk by western blotting (FIG. 19A). Three independent experiments yielded essentially equivalent results. The quantification is shown in FIG. 19B.
Figure 19B:
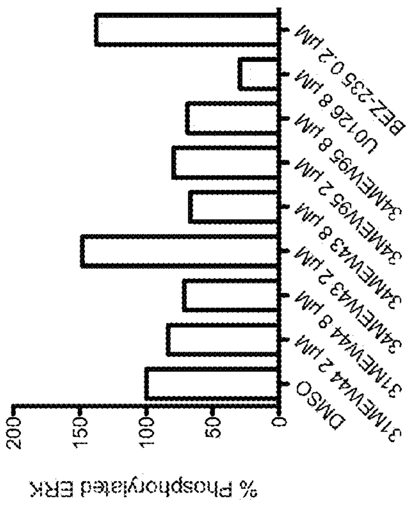
Figure 20A:
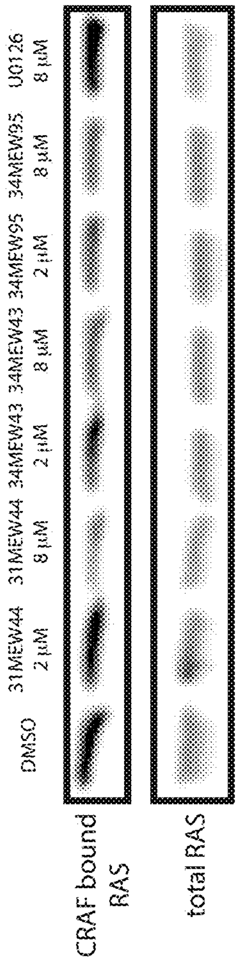
FIG. 20A-FIG. 20B show BJeLR cells were treated as described in FIG. 19A-FIG. 19B and the lysate was incubated with CRAF-RBD bound agarose beads. The beads were then washed three times with PBS to remove any unbound RAS and the bound fraction was then denatured and subjected to detection by western blotting using a pan-RAS antibody (FIG. 20A). The quantification is shown in FIG. 20B.
Figure 20B:
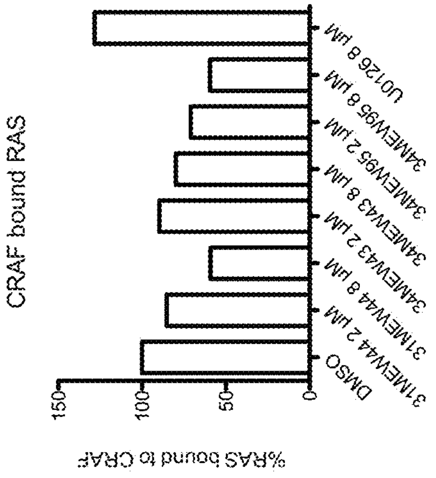
Figure 21A:
FIG. 21A-FIG. 21B show BJeLR cells were treated as described in FIG. 19A-FIG. 19B and the lysate was subjected to detection of phosphorylated AKT (ser 437) and total AKT by western blotting (FIG. 21A). The quantification is shown in FIG. 21B).
Figure 21B:
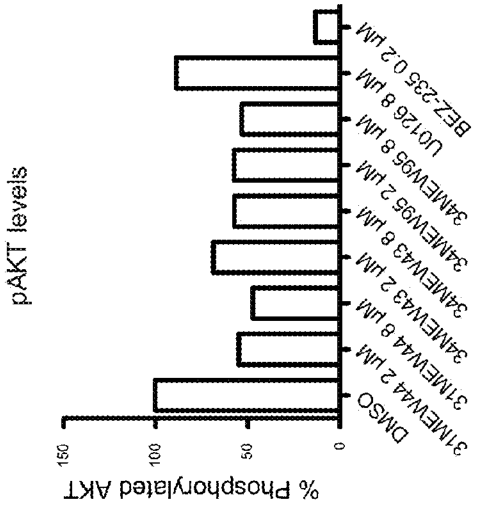

The ability of 31MEW44, 34MEW43, and 34MEW95 to disrupt RAS-RAF-MEK-ERK signaling was examined by measuring phosphorylated ERK abundance upon compound treatment. All three compounds effectively decreased pERK abundance in a dose-dependent manner (FIG. 19A-FIG. 19B) in BJeLR ($HRAS^{G12V}$), to levels comparable to those caused by the MEK 1/2 inhibitor U0126. This decrease was confirmed to correlate with disruption of the interaction between HRAS and RAF in cells through a RAS pulldown assay, which yielded a dose-dependent decrease in CRAF-RBD-bound RAS (FIG. 20A-FIG. 20B). This inhibitory effect was evident as well on the RAS-PI3K-AKT pathway, which exhibited a dose-dependent decrease in phosphorylated AKT (FIG. 21A-FIG. 21B).

Figure 36A:
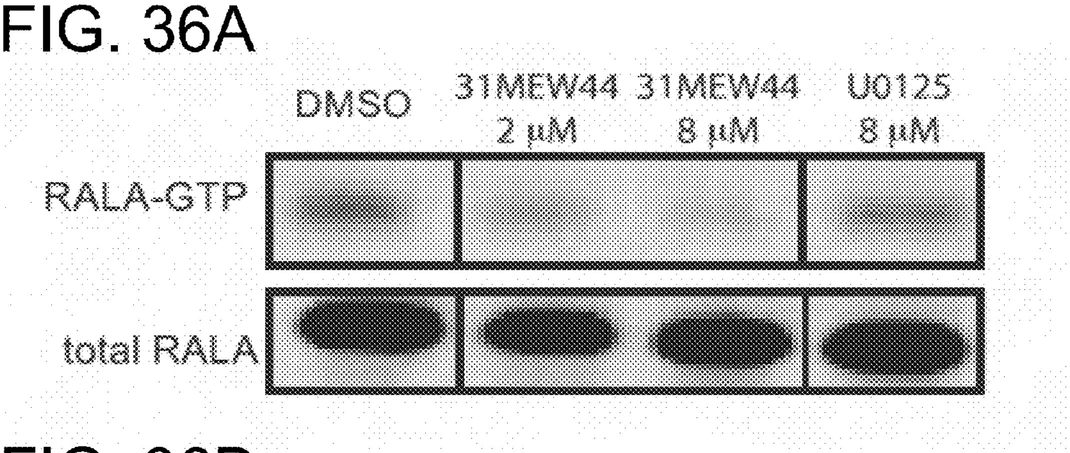
FIG. 36A-FIG. 36B show the effect of 31MEW44 on the RAS-RALGDS pathway.
Figure 36B:
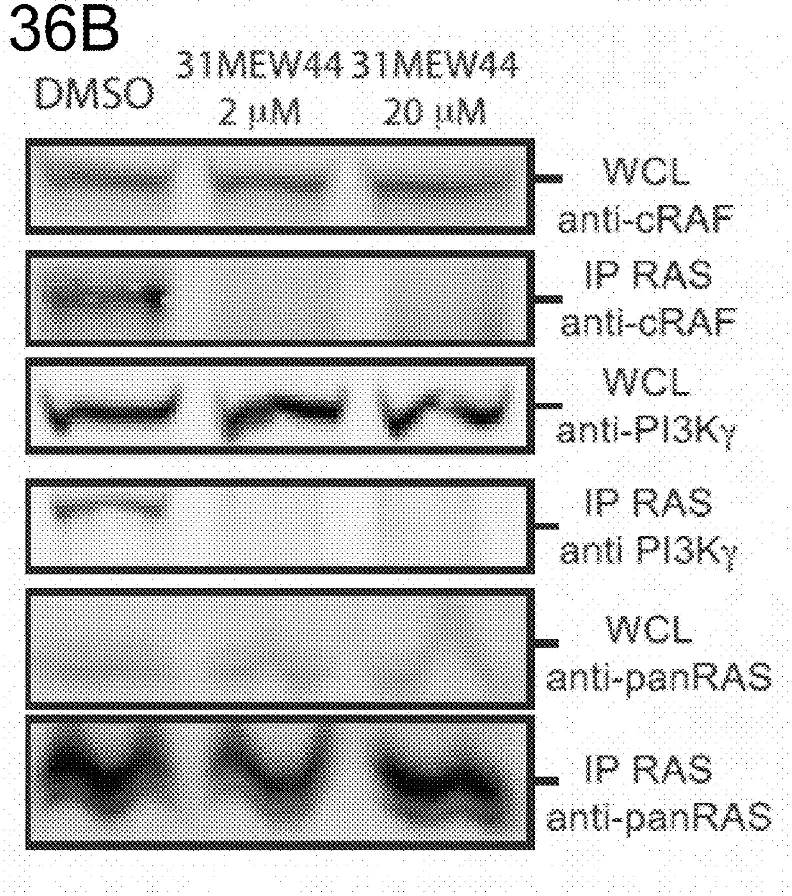

To test if 31MEW44 was capable of preventing the interaction between RAS and RALGDS (a guanine dissociation stimulator of RALA), a RALA activation assay was performed using RALBP1. Consistent with preventing the RAS-RALGDS interaction, decreased levels of active GTP-bound RALA were observed in a dose-dependent manner (FIG. 36A). To provide further confirmation of direct disruption of RAS-RAF and RAS-PI3K, we performed immunoprecipitation using an HRAS antibody and blotted for cRAF and PI3Kgamma. Compound administration decreased levels of co-immunoprecipitated cRAF and PI3K, indicative of direct inhibition (FIG. 36B).

Figures 22A, 22B, 22C, 22D, 22E, 22F:
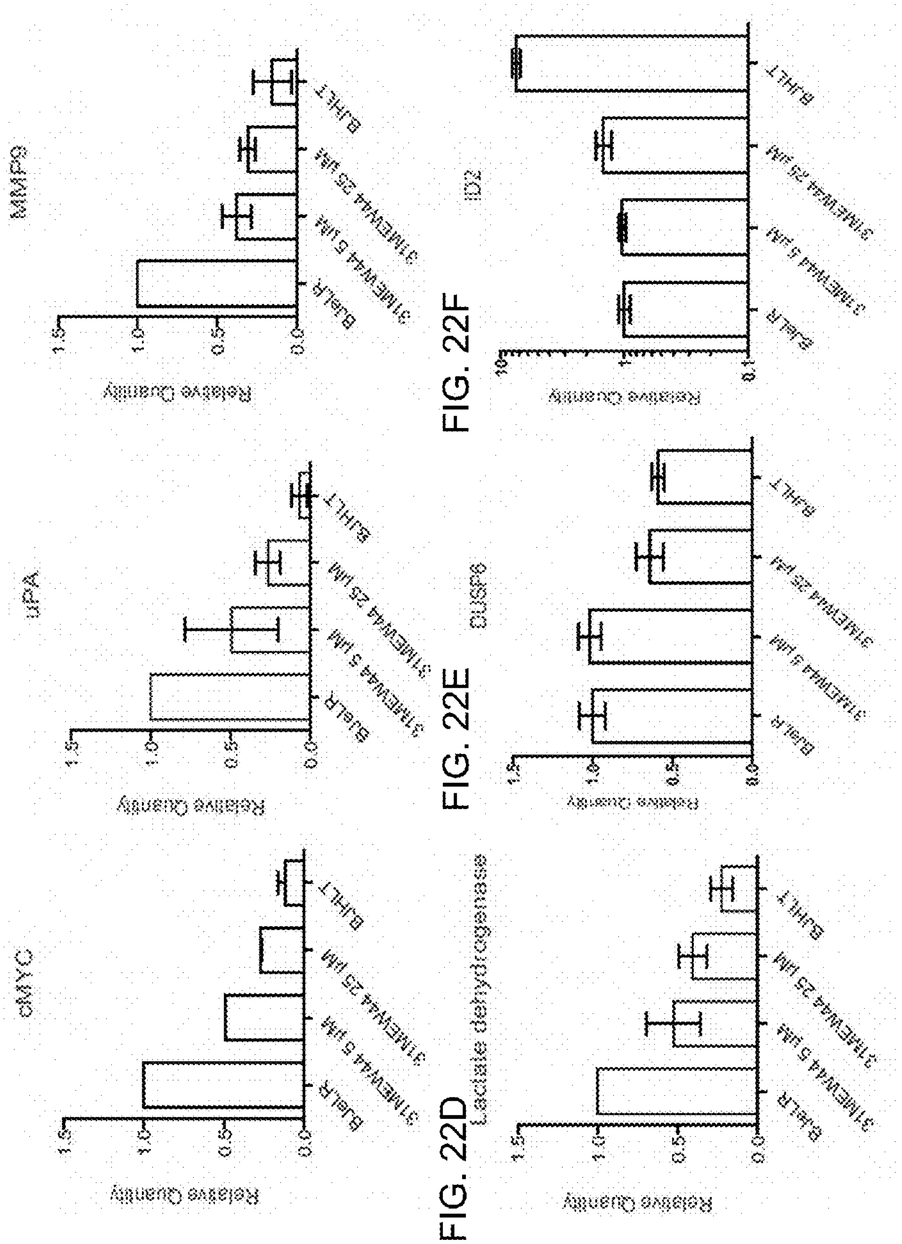
FIG. 22A-FIG. 22D show BJeLR cells were treated with DMSO, 31 MEW44 at 5 μM and/or 25 μM alongside BJHLT treated with DMSO for one hour. Cells were lysed and the RNA was extracted, converted to cDNA and quantified by qPCR.
FIG. 22E shows relative quantity of DUSP6 RNA.
FIG. 22F shows relative quantity of ID2 RNA.
Figure 23A:
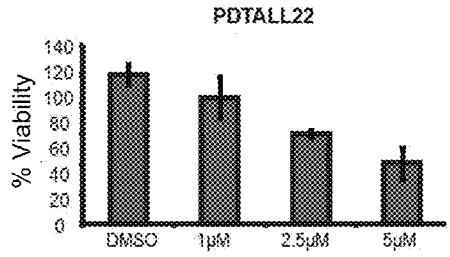
FIG. 23A-FIG. 23F shows efficacy of 31MEW44 in patient-derived T-ALL samples cultured in vitro. PDTALL22 (FIG. 23A) has $NRAS^{G13V}$ and PDTALL26 (FIG. 23B) has $NRAS^{G13D}$, while PDTALL6, 9, 13 and 19 (FIG. 23C-FIG. 23F, respectively) all have wild-type NRAS. Mutation status was verified by sequencing.
Figure 23B:
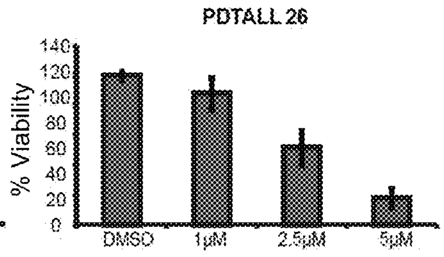
Figure 23C:
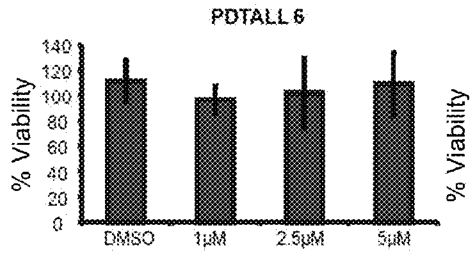
Figure 23D:
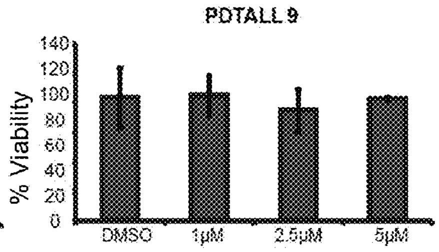
Figure 23E:
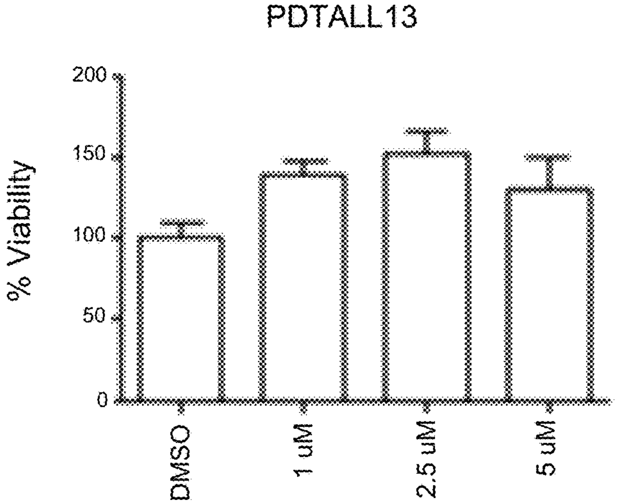
Figure 23F:
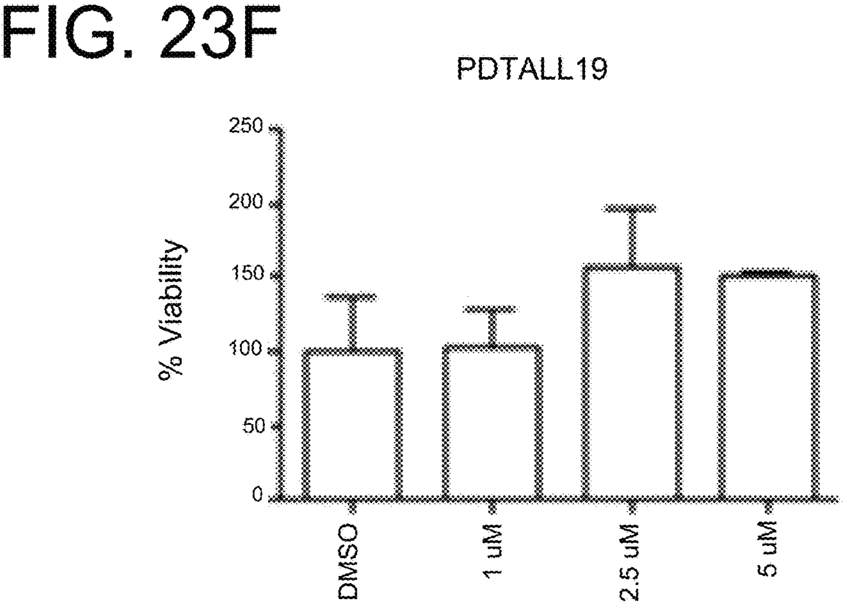

Next, the consequences of these RAS inhibitors were investigated at the transcriptional level. Focus was shifted to 31MEW44, which had the most drug-like properties as well as similar potency in 2D cell culture and in the multicellular spheroid assay to the 3-site compound 34MEW95 (based on the 34MEW43 2-site compound). To determine mRNA expression differences manifest upon RAS activation, BJeLR ($HRAS^{G12V}$) and BJeHLT (wt HRAS) engineered isogenic fibroblasts that differ only by $HRAS^{G12V}$ overexpression in BJeLR cells were utilized. The expression of urokinase-type plasminogen activator (uPA) is associated with invasion, metastasis and angiogenesis via breakdown of various components of the extracellular matrix (Pakneshan et al., 2005, Pulayeva-Gupta et al., 2011); uPA overexpression is facilitated by RAS activation through the RAS-RALGDS-RAL pathway (Id.). Inhibition of this cascade was tested for by analyzing uPA expression levels, via qPCR, in BJeLR (DMSO treated) versus BJeLR (31MEW44 treated at 5 μM and 25 μM) and BJHLT (DMSO treated); a dose-dependent decrease in uPA expression upon 31MEW44 treatment was found, similar to the levels found in BJeHLT cells (FIG. 22A). Another RAS effector is the GEF TIAM1, which subsequently activates the small GTPase RAC (Kerkhoff et al., 1998). RAC activation leads to overexpression of matrix metalloprotease 9 (MMP9) that plays a key role in metastasis and the invasive phenotype (Pulayeva-Gupta et al., 2011, Shin et al., 2005). Downregulation of MMP9 expression was observed upon 31MEW44 treatment (FIG. 22B). The proliferative status of cells is strongly correlated with the levels of the transcription factor CMYC (Pulayeva-Gupta et al., 2011, Kerkhoff et al., 1998). The RAS-RAF signaling cascade is known to be a key regulator of CMYC expression (Pakneshan et al., 2005, Kerkhoff et al., 1998). Upon 31MEW44 treatment of BJeLR cells, a dose-dependent reduction in CMYC mRNA was observed (FIG. 22C). Finally, the metabolic shift of transformed cells to the aerobic metabolism of glucose is well established (Pulayeva-Gupta et al., 2011, Chiaradonna et al., 2006). Associated with this change is the upregulation of lactate dehydrogenase (LDH), which converts the end product of glycolysis (pyruvate) into lactate, a change that has been observed in RAS transformed cells (Chiaradonna et al., 2006). Treatment of 31MEW44, indeed, decreased these elevated levels of LDH, dose-dependently, in BJeLR cells (FIG. 22D). Thus, 31MEW44 reverses the transcriptional changes associated with RAS activation, consistent with the notion that it is a RAS inhibitor. Activation of ERK signaling has been shown to be associated with the induction of expression of dual specificity-phosphatase (DUSP6) (Joseph et al., 2010), while the same study indicated that downregulation of isocitrate dehydroganse-2 (IDH2) is linked to active Erk (Id.). Treatment of BJeLR cells with 31MEW44 at 5 μM and 25 μM again showed a profile characteristic of decreased activation of RAS signaling (FIG. 22E-FIG. 22F).

Figure 37:
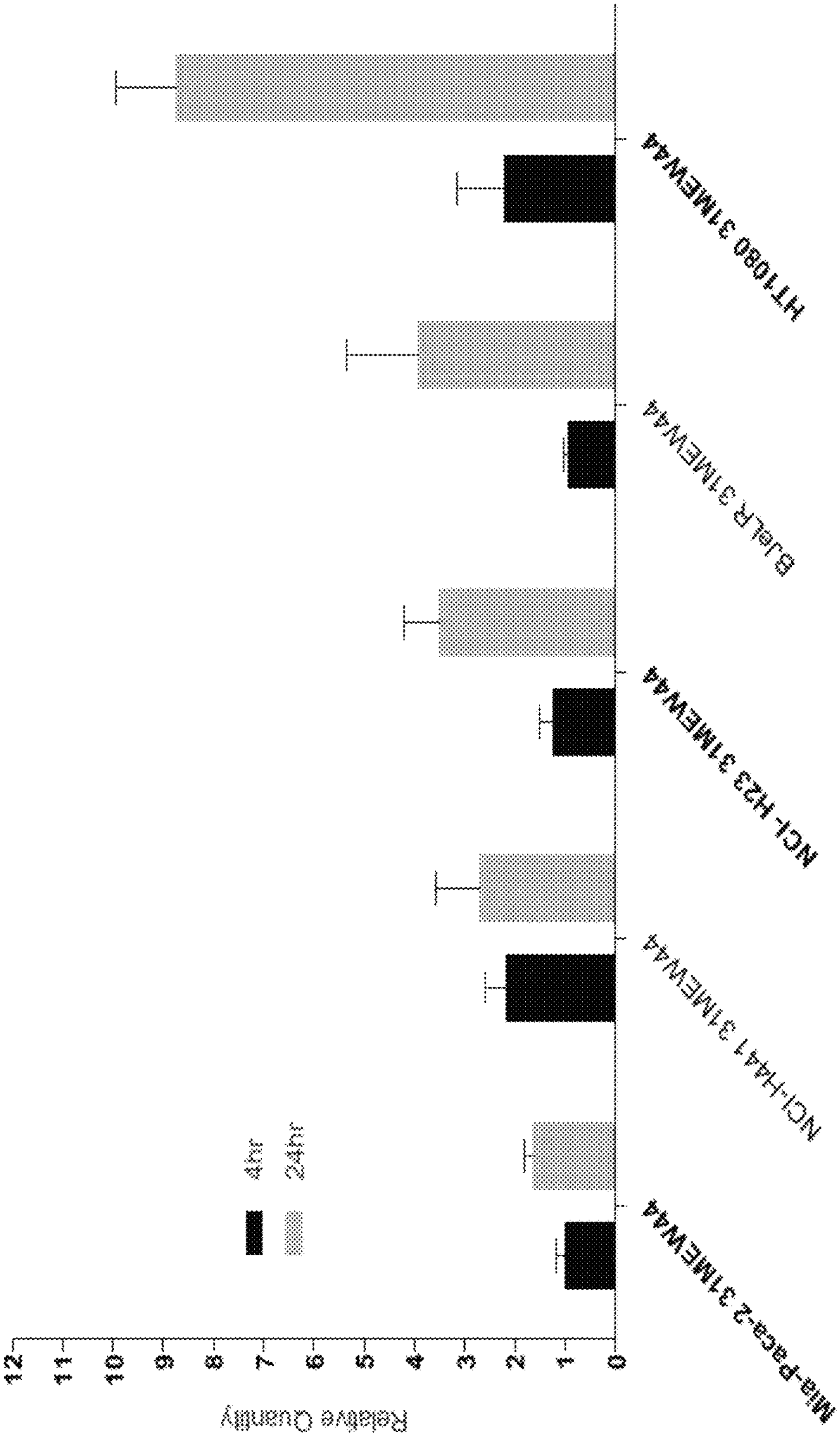
FIG. 37 shows expression levels of mutant RAS with 31MEW44 and doxorubicin treatment. Each cell line indicated was treated with 10 μM 31MEW44 for 4 hours or 24 hours before being lysed and analyzed for expression of the mutant RAS isoform by qPCR. Samples were normalized to DMSO treatment.

In addition to altering genes associated with RAS activation, it was hypothesized that upon inhibitor treatment, cells would attempt to compensate by expressing additional RAS proteins. To examine this, five cell lines were treated with 31MEW44 at 4 and 24 hours, Mia-Paca2 ($KRAS^{G12C}$), NCI-H441 ($KRAS^{G12V}$), NCI-H23 ($KRAS^{G12C}$) BJeLR ($HRAS^{G12V}$), and HT1080 ($NRAS^{Q61K}$). In all cell lines, a time-dependent increase of RAS expression was observed (FIG. 37).

Example 9

Effects of Multivalent RAS Inhibitors on Primary Patient Samples in Mouse Xenograft Tumors Although these multivalent pan-RAS compounds do not possess selective inhibitory activity towards mutated RAS proteins, there is ample evidence that tumors with mutated RAS proteins are addicted to these oncogenic isoforms. Thus, it was speculated that pan-RAS inhibitors such as 31MEW44 might have an acceptable therapeutic index in patient cells and in vivo. First, 31MEW44 was evaluated in primary patient-derived T-cell acute lymphoblastic leukemia (T-ALL) cells cultured in vitro to determine the potency and selectivity in a more clinically relevant model. 31MEW44 was tested in two samples containing mutant NRAS (G13V and G13D) as well as four samples possessing wild-type NRAS (FIG. 23A-FIG. 23F). A high degree of selectivity was observed with the cell lines, with mutant NRAS cells retaining only 20-40% viability after 5 μM 31MEW44 treatment, while no observed decrease in viability was observed in the four cell lines tested with wild-type NRAS. This indicated that 31MEW44 could be a viable therapeutic agent in NRAS mutated T-ALL.

Figure 24:
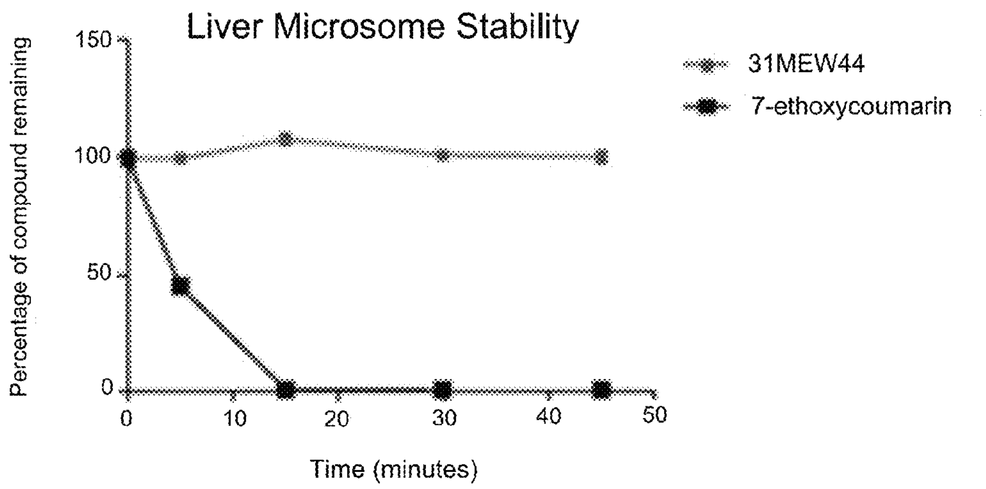
FIG. 24 shows stability of 31MEW44 and 7-ethoxycoumarin incubated with mouse liver microsomes.
Figure 25:
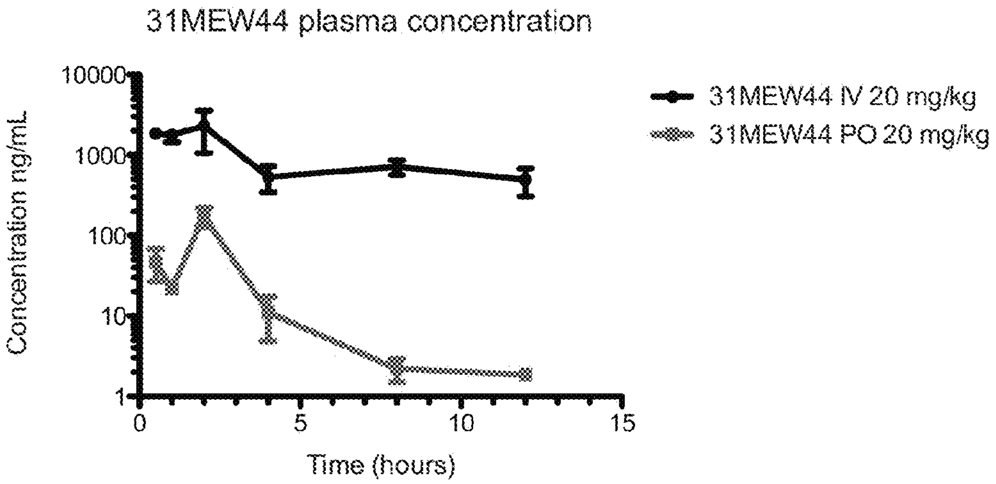
FIG. 25 shows a total of 42 male C57 adult mice were dosed with 31MEW44 in 10% NMP/90% PEG-400 at 30 mg/kg. Shown is the concentration of 31MEW44 measured in the plasma over 12 hours after dosing intravenously or orally. All measurements were performed in triplicate.

It was then sought to determine if 31MEW44 was sufficiently metabolically stable for in vivo testing. To see if 31MEW44 was susceptible to metabolism by cytochrome P450 enzymes, the compound was incubated with purified mouse liver microsomes and its degradation was followed by LC-MS. The positive control compound, 7-ethoxycoumarin was determined to have a half-life of 3.9 minutes, while all of 31MEW44 remained after a 45 minute incubation (FIG. 24). Encouraged by the stability of 31MEW44 in the microsome assay, it was sought to determine its in vivo pharmacokinetics by analyzing plasma samples of male C57BL6 adult mice with the compound administered both orally (PO) and intravenously (IV). After monitoring the concentration of 31MEW44 over 12 hours, oral delivery yielded a half-life of 3.1 hours, while intravenous delivery showed no elimination, suggesting a half-life >12 hours (FIG. 25). From these experiments, it was concluded that 31MEW44 is a suitable candidate for in vivo testing.

Figure 26:
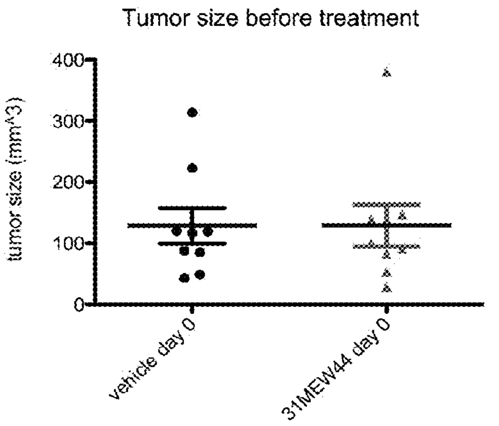
FIG. 26 shows tumor sizes of the vehicle and 31MEW44 treatment groups at day 0 after 8 week old female nude mice were injected with 8 million MD-MB-231 cells to generate tumor xenografts.
Figure 27:
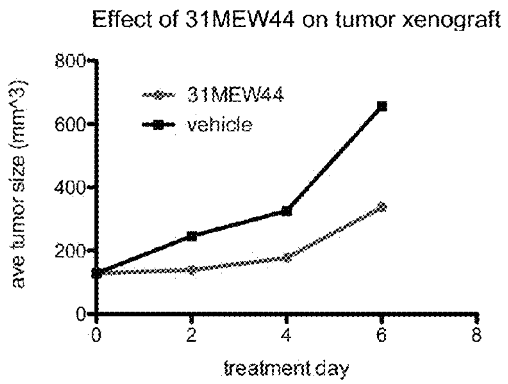
FIG. 27 shows average tumor size in the tumor xenograft of FIG. 26 that were treated with 31MEW44 (8 mg/mL, 5% DMSO in HBSS at pH 4) dosed at 20 mg/kg once per day or vehicle.
Figure 28:
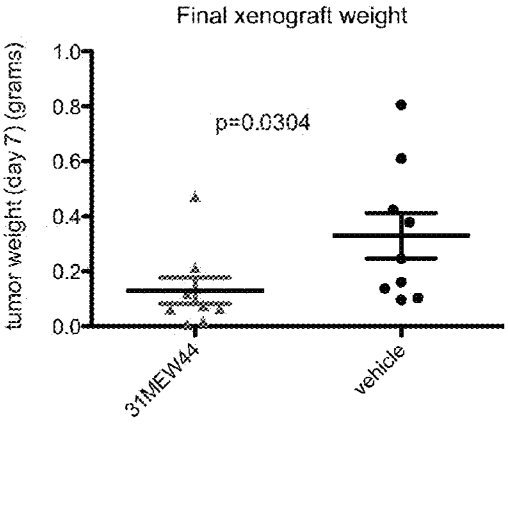
FIG. 28 shows tumor weight of dissected xenografts from the mice of FIG. 26 on day 7.
Figure 29A:
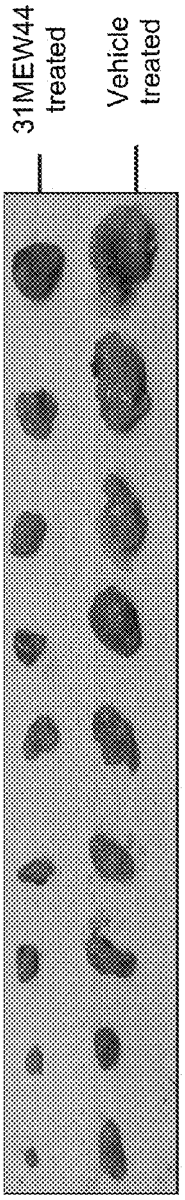
FIG. 29A-FIG. 29B shows the effect of 31MEW44 on MDA-MB-231 xenografts.
Figure 29B:
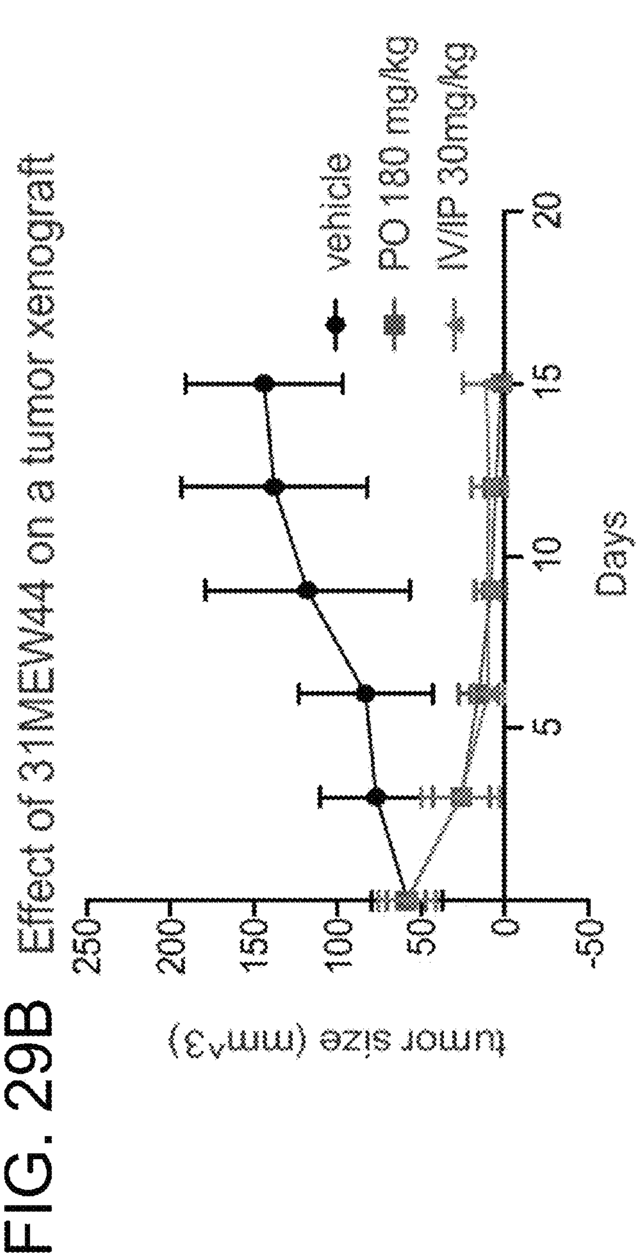
Figure 30A:
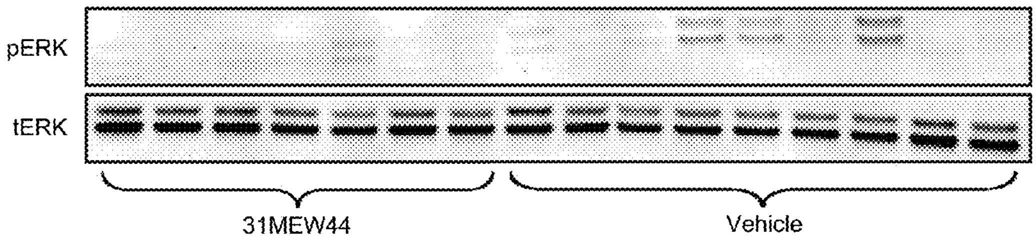
FIG. 30A-FIG. 30B show a western blot of phosphorylated ERK performed on xenograft samples (FIG. 30A) with the quantification (FIG. 30B).
Figure 30B:
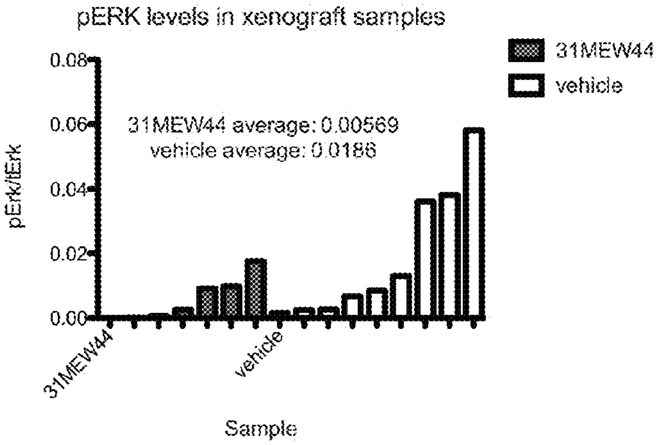

The in vivo efficacy and toxicity of 31MEW44 was assessed in a xenograft mouse tumor model using the aggressive MDA-MB-231 cell line in 8-week-old nude mice. Once tumor xenografts reached an average size of about 58 mm$^3$, mice were separated into treatment groups receiving vehicle, or 31MEW44, either orally or via a combination of intravenous and intraperitoneal injections. Both treatments resulted in an almost complete elimination of the tumor (FIG. 29B). To see if 31MEW44 was indeed inhibiting RAS signaling in vivo, an additional short pharmacodynamic study was performed. In this study, mice were injected in the right flank subcutaneously with 8 million MDA-MB-231 cells. A population of xenograft sizes was visible just three days following injection, indicating a rapidly growing tumor. Mice were separated into treatment groups of equal xenograft population and average size (about 128 cubic millimeters, FIG. 26). Each group was dosed daily by intraperitoneal injection with 31MEW44 at 30 mg/kg or vehicle only (5% DMSO in HBSS at pH 4). No overt toxicity was apparent following daily injections. Following six days of treatment, 31MEW44-treated tumors exhibited a 60% reduction in growth relative to the vehicle-treated group (FIG. 27). The tumors were dissected and weighed (FIG. 28 and FIG. 29A). Segments of the xenografts were lysed by sonication, and analyzed for phosphorylated ERK levels by Western blotting (FIG. 30A-FIG. 30B). On average, 31MEW44-treated mice exhibited tumor pERK levels about 70% lower than those of the vehicle-treated mouse tumors, indicating the 31MEW44 was able to significantly reduce RAS activation of pERK in these tumors.

Figure 38A:
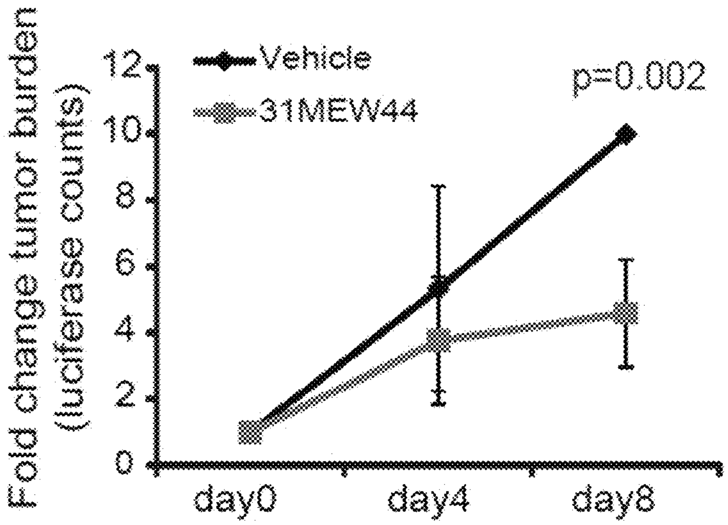
FIG. 38A-FIG. 38D show 31MEW44 activity in a patient derived T-ALL xenograft.
Figure 38B:
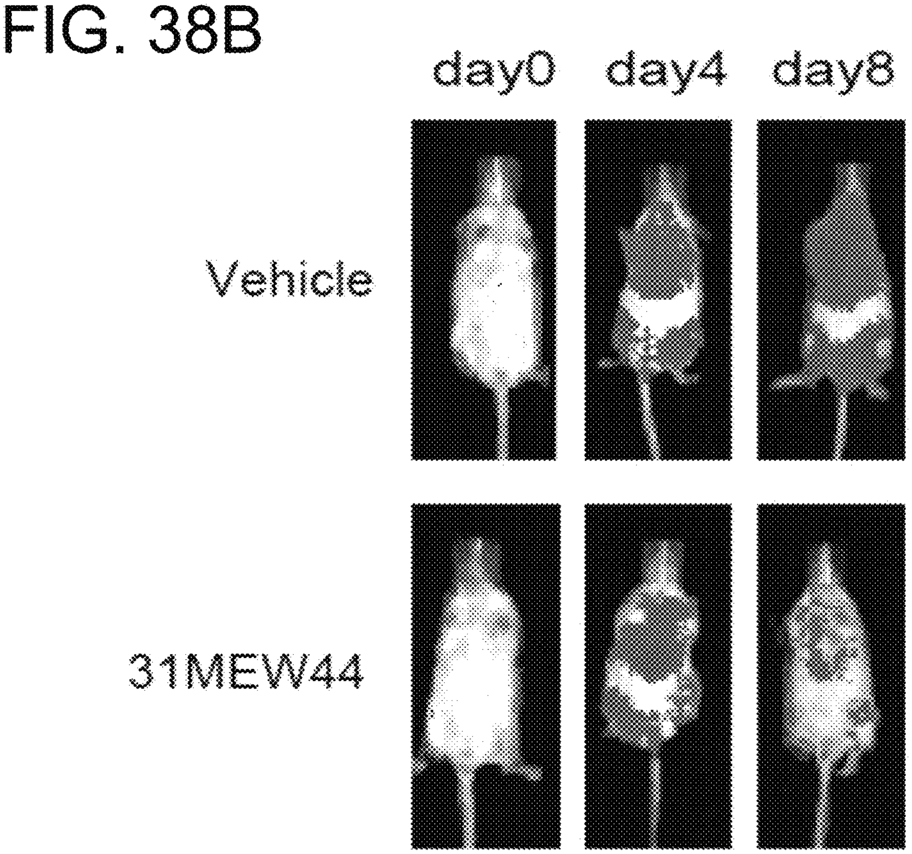
Figure 38C:
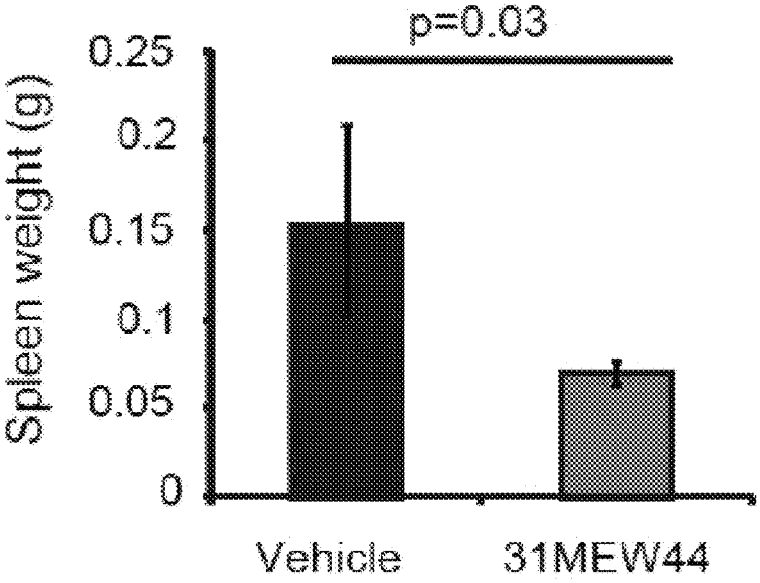
Figure 38D:
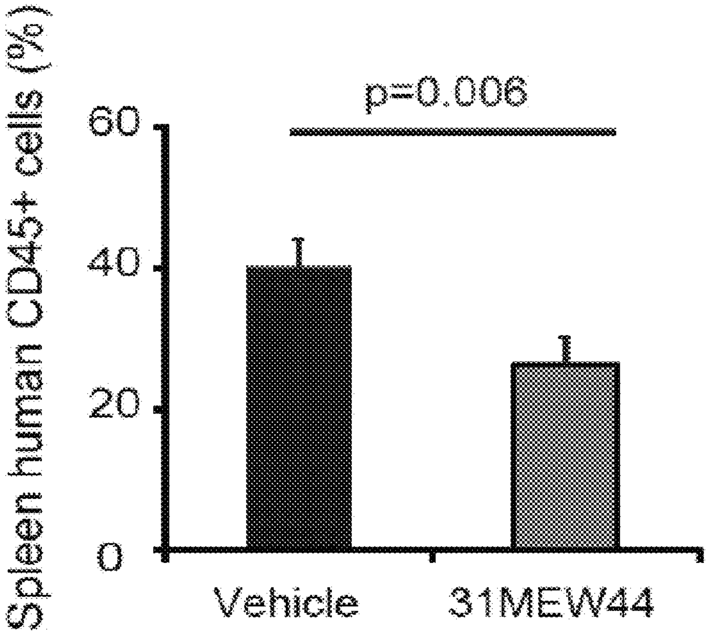

The PDTALL22 patient sample was then used as a luciferase expressing patient-derived xenograft. Mice were imaged after 4 and 8 days of treatment, and a significant decrease in tumor burden was observed (FIG. 38A-FIG. 38D). Consistent with the overall decrease in tumor burden, examination of the spleen revealed a decrease in size with inhibitor treatment, as well as a significant reduction in the percent of human CD45$^+$ cells indicating a decrease in the number of human xenografted cells infiltrating into the spleen upon compound treatment (FIG. 38D). Thus, this approach to designing multivalent ligands yielded a compound with affinity to RAS proteins that can reduce the tumor burden of RAS mutated tumors in mouse xenografts models.

Figure 39A:
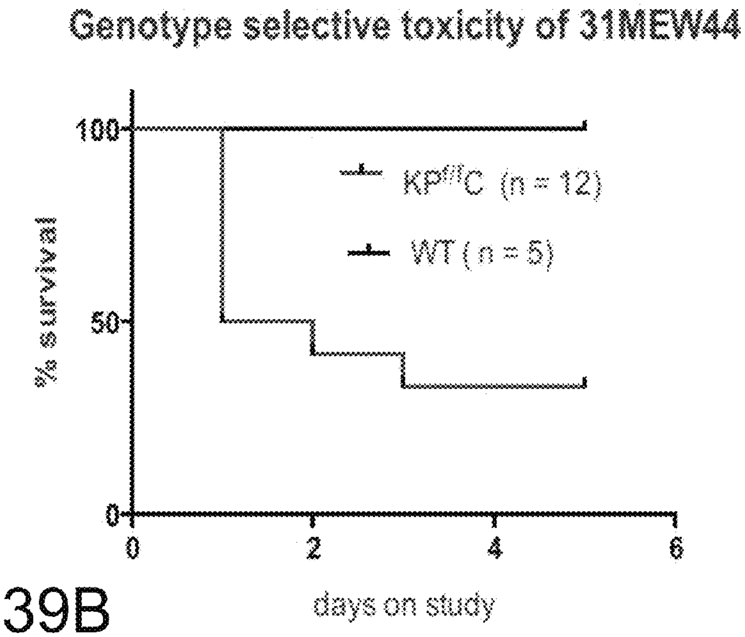
FIG. 39A-FIG. 39F show that 31MEW44 displays genotype selective toxicity.
Figure 39B:
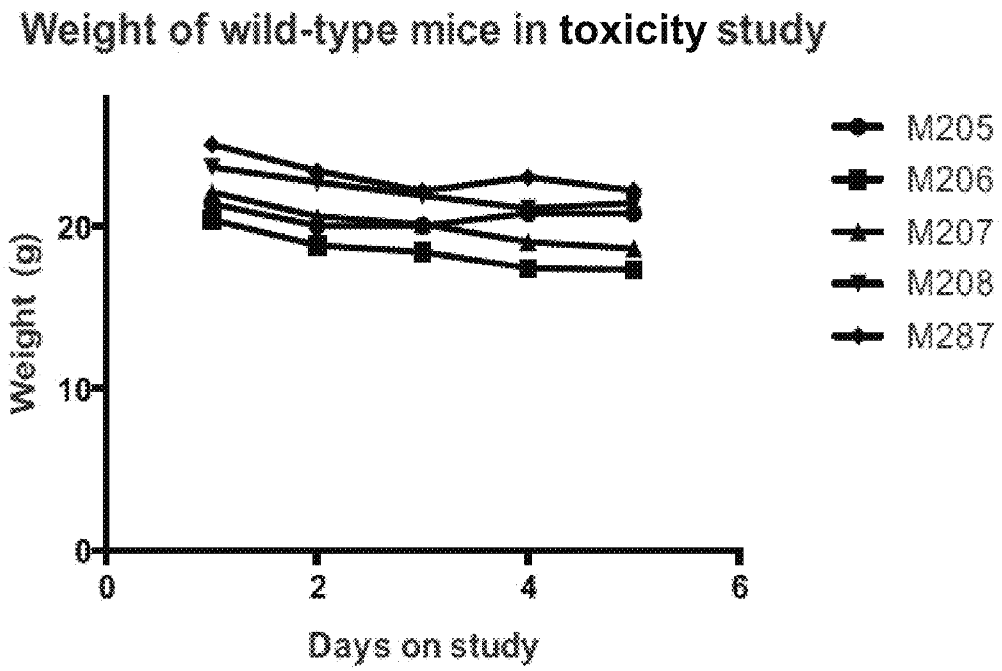
Figure 39C:
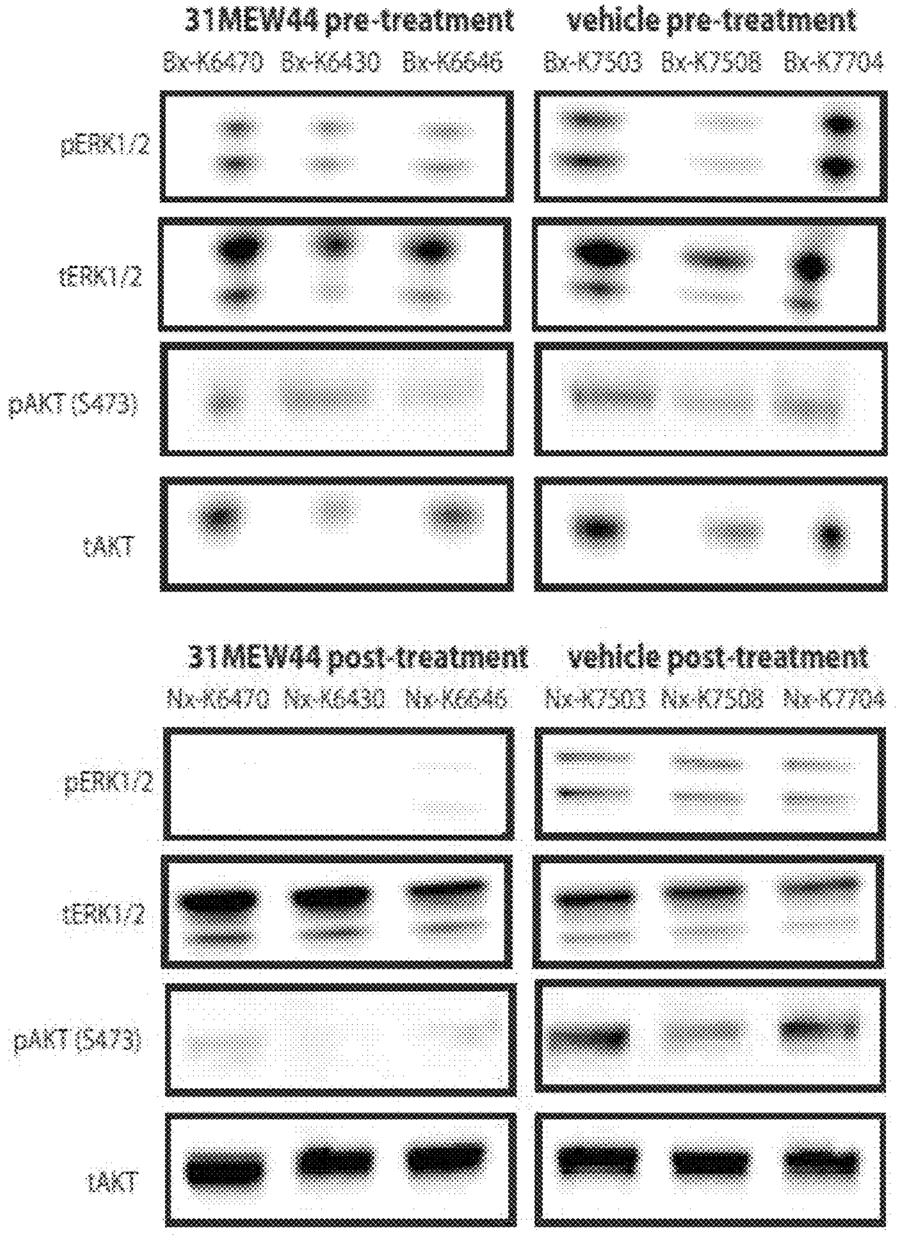
Figure 39D:
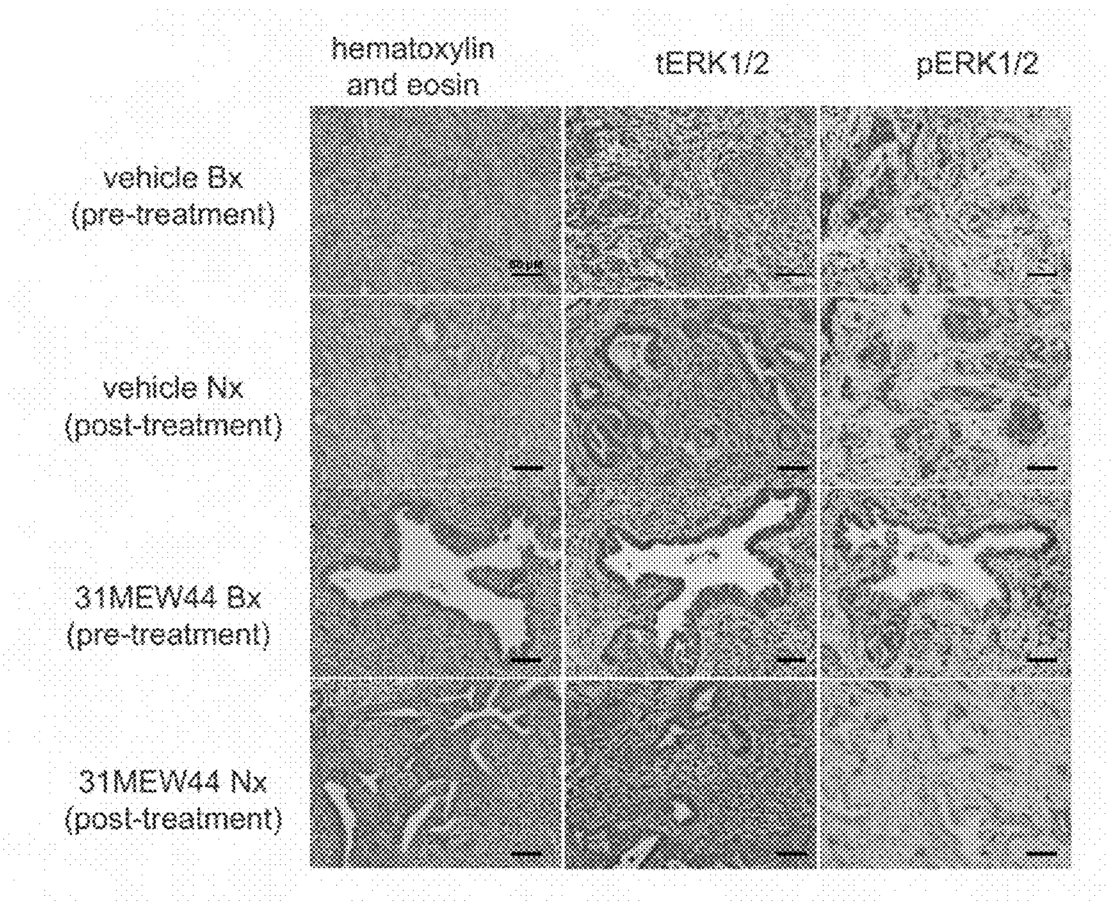
Figure 39E:
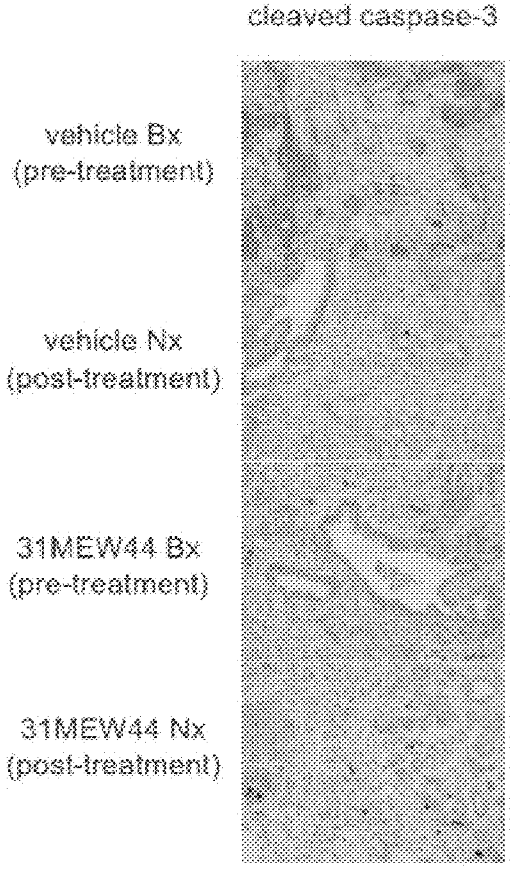
Figure 39F:
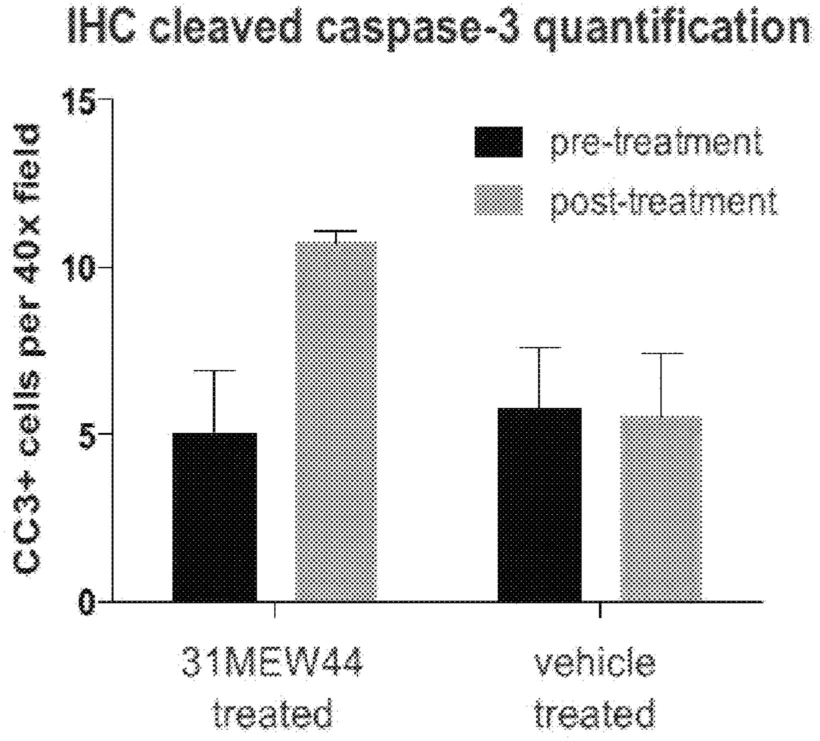

Mutations in the RAS genes are found in 90% of pancreatic cancers (Hopkins et al., 2002). Pancreatic ductal adenocarcinoma is particularly resistant to chemotherapy, as it is known to have a dense, desmoplastic stroma that can limit drug delivery (Oberstein et al., 2013). The most commonly used therapeutic agent, gemcitabine, extends patient survival by only a few weeks (Burris et al., 1997). To see if 31MEW44 could be a potential therapeutic agent for pancreatic cancers, the Kras$^{LSL.G12D/+}$Tp53$^{fl/fl}$Pdx1-Cre (KP$^{f/f}$C) mouse model was used (Bardeesy et al., 2006), which allows for both pancreas-specific expression of Kras$^{G12D}$ and the deletion of p53. Pre-treatment biopsies were acquired from each mouse by abdominal laparotomy, followed by a day of recovery and treatment with 30 mg/kg 31MEW44, once daily, i.p. Interestingly, toxicity was observed in the KP$^{f/f}$C mice, but not in wild-type mice enrolled in the study (FIG. 39A-FIG. 39B). The increased sensitivity of these mice was attributed to their lack of one functional Kras allele, suggesting due to this artificial condition, RAS inhibitors cannot be fully evaluated for efficacy in this model. Nonetheless, comparison of pre- and post-treatment tumor samples showed a substantial decrease for both phosphorylated AKT (S473) and phosphorylated ERK1/2, indicating that 31MEW44 was infiltrating the tumor and abrogating the RAS-PI3K and RAS-RAF signaling pathways, respectively (FIG. 39C-FIG. 39D), suggesting that such compounds can indeed be candidate therapeutic agents for pancreatic cancers. A modest increase in cleaved caspase-3 was also observed, showing that even in this exacting model, 31MEW44 has the capacity to kill RAS-mutant tumor cells (FIG. 39E-FIG. 39F).

Over the past two years, compounds that bind to RAS proteins have been identified by several groups, despite the historical challenge of identifying direct ligands for RAS proteins. Maurer et al. (Maurer et al., 2012) described compounds that bind to RAS-GDP and prevent SOS-mediated nucleotide exchange. Treatment with an inhibitor of this type would be applicable in cancers that require activation of wild-type RAS through SOS for proliferation; mutated RAS remains unaffected by this class of compounds. Shima et al. (Shima et al., 2013) described compounds that inhibit the interaction of RAS with its effector proteins with inhibitor constants ($K_i$) ranging from 46 to 733 µM; the modest potency of these compounds likely precludes further development and may impede their use as probes. Ostrem et al. (Ostrem et al., 2013) reported covalent inhibitors from a fragment screening approach, tethering, which selectively target KRAS$^{G12C}$ by exploiting the reactive cysteine present in the mutant. While this represents an important advance for addressing some RAS malignancies, it is only applicable to this specific mutant; present in only about one in eight KRAS mutated samples (Downward et al., 2014). In the panel of cell lines tested with this compound, the selective inhibition of growth in KRAS$^{G12C}$ cells ranged from three-fold, in the most sensitive cell line, to no selectivity. This narrow window may be attributable to the reactive electrophile present in the inhibitors.

This longstanding problem of the fundamental challenge of protein druggability was approached using the concept of multivalent ligand design. Analysis of protein structures in the Protein Data Bank suggests only about 12% of proteins encoded in the genome possess a cavity with the necessary properties for the tight binding of small molecules, based on extrapolation from current drugs; similar analyses suggest that about 3,000 druggable proteins exist, compared to the about 20,000 protein-coding human genes (Hopkins et al., 2002, Verdine et al., 2007). To tap into the vast landscape of challenging, but disease-modifying, therapeutic targets, new strategies may be needed. It is suggested that structure-based design of multivalent ligands for specific proteins may be one such strategy. This strategy has resulted in the creation of pan-RAS inhibitors that have a viable therapeutic index in primary patient samples and in a murine xenograft tumor model; thus, this approach may ultimately be one means of disrupting the oncogenic functions of RAS proteins in human tumors. Moreover, it may be possible to extend this approach to other small GTPases in the RAS superfamily, as well as other challenging protein targets.

DOCUMENTS

ARMSTRONG, F. et al. NOTCH is a key regulator of human T-cell acute leukemia initiating cell activity. Blood 113, 1730-40 (2009).

BARDEESY, N. et al. Both p16(Ink4a) and the p19(Arf)-p53 pathway constrain progression of pancreatic adenocarcinoma in the mouse. Proc Natl Acad Sci USA 103 (15): p. 5947-52 (2006).

BLOCK, C. et al. Quantitative structure activity analysis correlating RAS/RAF interaction in vitro to RAF activation in vivo. Nature Structural Biology 3, 244-251 (1996).

BURRIS H. A. et al. Improvements in survival and clinical benefit with gemcitabine as first-line therapy for patients with advanced pancreas cancer: a randomized trial. *J. of Clinical Oncology* 15, 2403-2413 (1997).

CHIANG, M. Y. et al. Leukemia-associated NOTCH1 alleles are weak tumor initiators but accelerate K-ras-initiated leukemia. The Journal of Clinical Investigation 118, 3181-3194 (2008).

CHIARADONNA, F. et al. RAS dependent carbon metabolism and transformation in mouse fibroblasts. Oncogene 25, 5391-5404 (2006).

DOWNWARD, J. RAS's cloak of invincibility splits at last? Cancer Cell 25, 5-6 (2014).

DOWNWARD, J. Targeting RAS signaling pathways in cancer therapy. Nat. Rev. Cancer 3, 11-22 (2003).

DROSTEN, M. et al. Genetic analysis of Ras signalling pathways in cell proliferation, migration and survival. EMBO J. 29, 1091-1104 (2010).

HALL, B. E. et al. The structural basis of the transition from RAS-GTP to RAS-GDP. PNAS 99, 12138-12142 (2002).

HO, T. T. et al. RhoA-GDP regulates RhoB protein stability. Potential involvement of RhoGDIalpha. JBC. 283, 21588-98 (2008).

HOPKINS, A. L. et al. The druggable Genome Nat Rev Drug Discov 1, 727-30 (2002).

HUANG, L. et al. Structural basis for the interaction of RAS with RalGDS. Nature Structural Biology 5, 422-426 (1998).

JOHN, J. et al. Kinetics of interaction of nucleotides with nucleotide free HRAS p21. Biochemistry 29, 6058-6065 (1990).

JOSEPH, E. W. et al. The RAF inhibitor PLX4032 inhibits ERK signaling and tumor cell proliferation in a V600E BRAF-selective manner. PNAS 103, 14903-14908 (2010).

KERKHOFF, E. et al. Cell cycle targets of RAS/RAF signaling. Oncogene 16, 211-216 (1998).

MAURER, T. et al. Small molecule ligands bind to a distinct pocket in RAS and inhibit SOS mediated nucleotide exchange activity. PNAS 109, 5299-5304 (2012).

NERO, T. L. et al. Oncogenic protein interfaces: small molecules, big challenges Nat. Rev. Canc. 14, 248-262 (2014).

OBERSTEIN, P. E, and Olive, K. P. Pancreatic cancer: why is it so hard to treat? Therapeutic Advances in Gastroenterology 6, 321-3337 (2013).

OSTREM, J. et al. KRAS G12C inhibits allosterically controlled GTP affinity and effector interactions. Nature 503, 548-551 (2013).

PACOLD, M. E. et al. Structure and functional analysis of RAS binding to its effector phosphoinositide 3-kinase. Cell 103, 931-943 (2000).

PAKNESHAN, P. et al. Methylation and inhibition of expression of uPA by the RAS oncogene: divergence of growth control and invasion in breast cancer cells. Carcinogenesis 26, 557-564 (2005).

PARIKH, C. et al. Oncogenic NRAS, KRAS, and HRAS exhibit different leukemogenic potentials in mice. Cancer Res 67(15): 7139-46 (2007).

PIOVAN, E. et al. Direct reversal of glucocorticoid resistance by AKT inhibition in acute lymphoblastic leukemia. Cancer cell 24, 766-776 (2013).

PULAYEVA-GUPTA, Y. et al. RAS oncogenes: weaving a tumorigenic web. Nat. Rev. Cancer 11, 761-774 (2011).

SASTRA, S. A. et al., Acquisition of Mouse Tumor Biopsies through Abdominal Laparotomy. Cold Spring Harb Protoc 2014(1) (2014).

SHIMA, F. et al. In silico discovery of small molecule RAS inhibitors that display antitumor activity by blocking the RAS effector interaction. PNAS 20, 8182-8187 (2013).

SHIN, I. et al. HRAS specific activation of RAC-MMK3/6-p38 pathway: it's critical role in invasion and migration of breast cancer epithelial cells. J. Bio. Chem. 280, 14675-14683 (2005).

SUN, H. Pharmacophore based virtual screening. Curr. Med. Chem. 15, 1018-1024 (2008).

VALENCIA, Alfonso, et al. "The ras protein family: evolutionary tree and role of conserved amino acids." Biochemistry 30.19 (1991): 4637-4648.

VASSILEV, L. T. et al. In vivo activation of the p53 pathway by small molecules antagonists of MDM2. Science 303, 844-848 (2004).

VERDINE, G. L. et al. The challenge of drugging undruggable targets in cancer: lessons learned from targeting the BCL-2 family members. Clin. Cancer Res. 13, 7264-7270 (2007).

VO, U. et al. 1H 13C and 15N resonance assignments for the human KRAS at physiological pH. Biomol. NMR Assign. 7, 215-219 (2013).

WEINSTEIN, B. et al. Oncogene Addiction. Cancer Res. 68, 3077-3080 (2008).

ZHENG, Y. et al. Triazole-dithiocarbamate based selective lysine specific demethylase 1 (LSD1) inactivators inhibit gastric cancer cell growth, invasion and migration. J. Med. Chem. 56, 8543-8560 (2013).

All documents cited in this application are hereby incorporated by reference as if recited in full herein.

Although illustrative embodiments of the present invention have been described herein, it should be understood that the invention is not limited to those described, and that various other changes or modifications may be made by one skilled in the art without departing from the scope or spirit of the invention.

What is claimed is:

1. A compound having the structure:

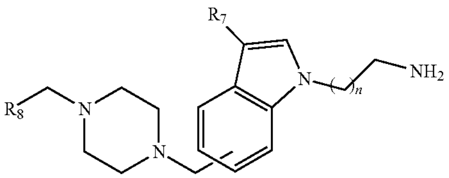

wherein:

$R_7$ is aryl, wherein the aryl is optionally substituted with one or more groups consisting of halide, $C_{1-4}$alkyl, —O—$C_{1-4}$alkyl and a combination thereof, wherein the alkyl is optionally substituted with one or more halide;

$R_8$ is selected from the group consisting of H, alkyl, aryl, and $C_{1-4}$alkyl-O-aryl wherein the alkyl is optionally substituted with halide, and the aryl is optionally substituted with one or more groups consisting of halide, $C_{1-4}$alkyl, and a combination thereof; and n is selected from the group consisting of an integer between 0-5, or a hydrate or pharmaceutically acceptable salt thereof.

2. The compound of claim 1, wherein $R_7$ is aryl substituted with one —O—$C_{1-4}$alkyl, and wherein the alkyl is optionally substituted with one or more halide.

3. The compound of claim 1, wherein $R_8$ is aryl substituted with one or more groups consisting of halide, $C_{1-4}$alkyl, and a combination thereof.

4. The compound of claim 1, wherein $R_8$ is H.

5. The compound of claim 1, wherein the compound is:

7

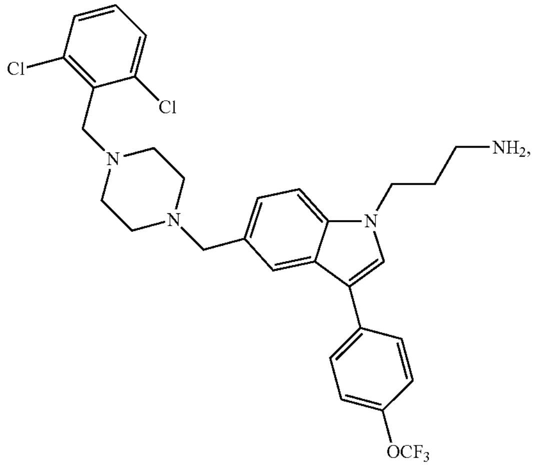

or a hydrate or pharmaceutically acceptable salt thereof.

6. A pharmaceutical composition comprising a pharmaceutically acceptable carrier and a compound having the structure:

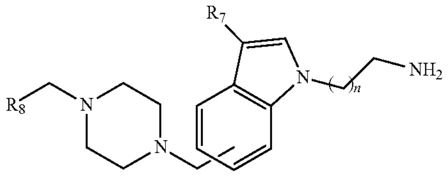

wherein:

$R_7$ is aryl, wherein the aryl is optionally substituted with one or more groups consisting of halide, $C_{1-4}$alkyl, —O—$C_{1-4}$alkyl and a combination thereof, wherein the alkyl is optionally substituted with one or more halide;

$R_8$ is selected from the group consisting of H, alkyl, aryl, and $C_{1-4}$alkyl-O-aryl wherein the alkyl is optionally substituted with halide, and the aryl is optionally substituted with one or more groups consisting of halide, $C_{1-4}$alkyl, and a combination thereof; and n is selected from the group consisting of an integer between 0-5, or a hydrate or pharmaceutically acceptable salt thereof.

7. The pharmaceutical composition of claim 6, wherein $R_7$ is aryl substituted with one —O—$C_{1-4}$alkyl, and wherein the alkyl is optionally substituted with one or more halide.

8. The pharmaceutical composition of claim 6, wherein $R_8$ is aryl substituted with one or more groups consisting of halide, $C_{1-4}$alkyl, and a combination thereof.

9. The pharmaceutical composition of claim 6, wherein $R_8$ is H.

10. The pharmaceutical composition of claim 6, wherein the compound is:

7

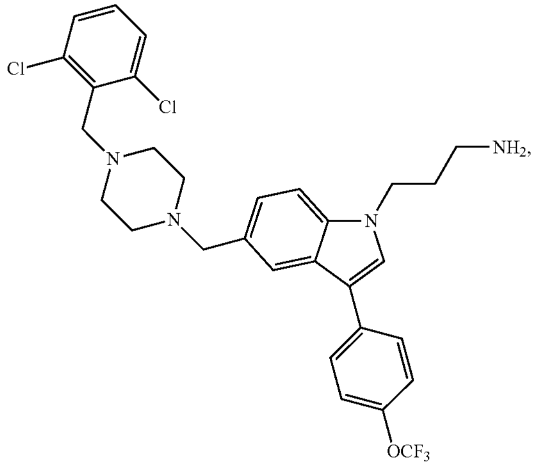

or a hydrate or pharmaceutically acceptable salt thereof.

* * * * *

SEQUENCE LISTING

<160> NUMBER OF SEQ ID NOS: 69

<210> SEQ ID NO 1
<211> LENGTH: 1061
<212> TYPE: DNA
<213> ORGANISM: Homo sapiens

<400> SEQUENCE: 1
tgccctgcgc ccgcaacccg agccgcaccc gccgcggacg gagcccatgc gcggggcgaa 60
ccgcgcgccc ccgcccccgc cccgccccgg cctcggcccc ggccctggcc ccgggggcag 120
tcgcgcctgt gaacggtggg gcaggagacc ctgtaggagg accccgggcc gcaggcccct 180
gaggagcgat gacggaatat aagctggtgg tggtgggcgc cggcggtgtg ggcaagagtg 240
cgctgaccat ccagctgatc cagaaccatt ttgtggacga atacgacccc actatagagg 300
attcctaccg gaagcaggtg gtcattgatg gggagacgtg cctgttggac atcctggata 360
ccgccggcca ggaggagtac agcgccatgc gggaccagta catgcgcacc ggggagggct 420
tcctgtgtgt gtttgccatc aacaacacca agtcttttga ggacatccac cagtacaggg 480
agcagatcaa acgggtgaag gactcggatg acgtgcccat ggtgctggtg gggaacaagt 540
gtgacctggc tgcacgcact gtggaatctc ggcaggctca ggacctcgcc cgaagctacg 600
gcatccccta catcgagacc tcggccaaga cccggcaggg agtggaggat gccttctaca 660
cgttggtgcg tgagatccgg cagcacaagc tgcggaagct gaaccctcct gatgagagtg 720
gccccggctg catgagctgc aagtgtgtgc tctcctgacg cagcacaagc tcaggacatg 780
gaggtgccgg atgcaggaag gaggtgcaga cggaaggagg aggaaggaag gacggaagca 840
aggaaggaag gaagggctgc tggagcccag tcaccccggg accgtgggcc gaggtgactg 900
cagaccctcc cagggaggct gtgcacagac tgtcttgaac atcccaaatg ccaccggaac 960
cccagccctt agctcccctc ccaggcctct gtgggccctt gtcgggcaca gatgggatca 1020
cagtaaatta ttggatggtc ttgaaaaaaa aaaaaaaaaa a 1061

<210> SEQ ID NO 2
<211> LENGTH: 1251
<212> TYPE: DNA
<213> ORGANISM: Homo sapiens

<400> SEQUENCE: 2
tgccctgcgc ccgcaacccg agccgcaccc gccgcggacg gagcccatgc gcggggcgaa 60
ccgcgcgccc ccgcccccgc cccgccccgg cctcggcccc ggccctggcc ccgggggcag 120
tcgcgcctgt gaacggtggg gcaggagacc ctgtaggagg accccgggcc gcaggcccct 180
gaggagcgat gacggaatat aagctggtgg tggtgggcgc cggcggtgtg ggcaagagtg 240
cgctgaccat ccagctgatc cagaaccatt ttgtggacga atacgacccc actatagagg 300
attcctaccg gaagcaggtg gtcattgatg gggagacgtg cctgttggac atcctggata 360
ccgccggcca ggaggagtac agcgccatgc gggaccagta catgcgcacc ggggagggct 420
tcctgtgtgt gtttgccatc aacaacacca agtcttttga ggacatccac cagtacaggg 480
agcagatcaa acgggtgaag gactcggatg acgtgcccat ggtgctggtg gggaacaagt 540
gtgacctggc tgcacgcact gtggaatctc ggcaggctca ggacctcgcc cgaagctacg 600
gcatccccta catcgagacc tcggccaaga cccggcaggg cagccgctct ggctctagct 660
ccagctccgg gaccctctgg gaccccccgg gacccatgtg acccagcggc ccctcgcgct 720
ggagtggagg atgccttcta cacgttggtg cgtgagatcc ggcagcacaa gctgcggaag 780
ctgaaccctc ctgatgagag tggccccggc tgcatgagct gcaagtgtgt gctctcctga 840
cgcaggtgag gggactccc agggcggccg ccacgcccac cggatgaccc cggctccccg 900
cccctgccgg tctcctggcc tgcggtcagc agcctccctt gtgccccgcc cagcacaagc 960
tcaggacatg gaggtgccgg atgcaggaag gaggtgcaga cggaaggagg aggaaggaag 1020
gacggaagca aggaaggaag gaagggctgc tggagcccag tcaccccggg accgtgggcc 1080
gaggtgactg cagaccctcc cagggaggct gtgcacagac tgtcttgaac atcccaaatg 1140
ccaccggaac cccagccctt agctcccctc ccaggcctct gtgggccctt gtcgggcaca 1200
gatgggatca cagtaaatta ttggatggtc ttgaaaaaaa aaaaaaaaaa a 1251

<210> SEQ ID NO 3
<211> LENGTH: 1169
<212> TYPE: DNA
<213> ORGANISM: Homo sapiens

<400> SEQUENCE: 3
tgccctgcgc ccgcaacccg agccgcaccc gccgcggacg gagcccatgc gcggggcgaa 60
ccgcgcgccc ccgcccccgc cccgccccgg cctcggcccc ggccctggcc ccgggggcag 120
tcgcgcctgt gaacggtggg gcaggagacc ctgtaggagg accccgggcc gcaggcccct 180
gaggagcgat gacggaatat aagctggtgg tggtgggcgc cggcggtgtg ggcaagagtg 240
cgctgaccat ccagctgatc cagaaccatt ttgtggacga atacgacccc actatagagg 300
attcctaccg gaagcaggtg gtcattgatg gggagacgtg cctgttggac atcctggata 360
ccgccggcca ggaggagtac agcgccatgc gggaccagta catgcgcacc ggggagggct 420
tcctgtgtgt gtttgccatc aacaacacca agtcttttga ggacatccac cagtacaggg 480
agcagatcaa acgggtgaag gactcggatg acgtgcccat ggtgctggtg gggaacaagt 540
gtgacctggc tgcacgcact gtggaatctc ggcaggctca ggacctcgcc cgaagctacg 600
gcatccccta catcgagacc tcggccaaga cccggcaggg agtggaggat gccttctaca 660
cgttggtgcg tgagatccgg cagcacaagc tgcggaagct gaaccctcct gatgagagtg 720
gccccggctg catgagctgc aagtgtgtgc tctcctgacg caggtgaggg ggactcccag 780
ggcggccgcc acgcccaccg gatgaccccg gctccccgcc cctgccggtc tcctggcctg 840
cggtcagcag cctcccttgt gccccgccca gcacaagctc aggacatgga ggtgccggat 900
gcaggaagga ggtgcagacg gaaggaggag gaaggaagga cggaagcaag gaaggaagga 960
agggctgctg gagcccagtc accccgggac cgtgggccga ggtgactgca gaccctccca 1020
gggaggctgt gcacagactg tcttgaacat cccaaatgcc accggaaccc cagcccttag 1080
ctcccctccc aggcctctgt gggcccttgt cgggcacaga tgggatcaca gtaaattatt 1140
ggatggtctt gaaaaaaaaa aaaaaaaaa 1169

<210> SEQ ID NO 4
<211> LENGTH: 189
<212> TYPE: PRT
<213> ORGANISM: Homo sapiens

<400> SEQUENCE: 4

Met Thr Glu Tyr Lys Leu Val Val Val Gly Ala Gly Gly Val Gly Lys
1 5 10 15

Ser Ala Leu Thr Ile Gln Leu Ile Gln Asn His Phe Val Asp Glu Tyr
20 25 30

```
Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His Gln Tyr
                85                  90                  95

Arg Glu Gln Ile Lys Arg Val Lys Asp Ser Asp Asp Val Pro Met Val
            100                 105                 110

Leu Val Gly Asn Lys Cys Asp Leu Ala Ala Arg Thr Val Glu Ser Arg
        115                 120                 125

Gln Ala Gln Asp Leu Ala Arg Ser Tyr Gly Ile Pro Tyr Ile Glu Thr
    130                 135                 140

Ser Ala Lys Thr Arg Gln Gly Val Glu Asp Ala Phe Tyr Thr Leu Val
145                 150                 155                 160

Arg Glu Ile Arg Gln His Lys Leu Arg Lys Leu Asn Pro Pro Asp Glu
                165                 170                 175

Ser Gly Pro Gly Cys Met Ser Cys Lys Cys Val Leu Ser
            180                 185


<210> SEQ ID NO 5
<211> LENGTH: 170
<212> TYPE: PRT
<213> ORGANISM: Homo sapiens

<400> SEQUENCE: 5

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His Gln Tyr
                85                  90                  95

Arg Glu Gln Ile Lys Arg Val Lys Asp Ser Asp Asp Val Pro Met Val
            100                 105                 110

Leu Val Gly Asn Lys Cys Asp Leu Ala Ala Arg Thr Val Glu Ser Arg
        115                 120                 125

Gln Ala Gln Asp Leu Ala Arg Ser Tyr Gly Ile Pro Tyr Ile Glu Thr
    130                 135                 140

Ser Ala Lys Thr Arg Gln Gly Ser Arg Ser Gly Ser Ser Ser Ser Ser
145                 150                 155                 160

Gly Thr Leu Trp Asp Pro Pro Gly Pro Met
                165                 170


<210> SEQ ID NO 6
<211> LENGTH: 2043
<212> TYPE: DNA
<213> ORGANISM: Mus musculus

<400> SEQUENCE: 6
```

-continued

```
cgagcgcggg cccggccaag tccccgccgt ccgctcccgg cgcccgcagc ccgagccgca      60

cccgccgcgg acggagctca tgcgcgggcc cagccggcgc ccgtccgcgc ccccgccctg     120

ccccggcccc ggccccggcc ccgggggcag tcgcgccagc aagcggtggg gcaggagctc     180

ctggattggc agccgctgta gaagctatga cagaatacaa gcttgtggtg gtgggcgctg     240

gaggcgtggg aaagagtgcc ctgaccatcc agctgatcca gaaccacttt gtggacgagt     300

atgatcccac tatagaggac tcctaccgga aacaggtggt cattgatggg gagacatgtc     360

tactggacat cttagacaca gcaggtcaag aagagtatag tgccatgcgg gaccagtaca     420

tgcgcacagg ggagggcttc ctctgtgtat ttgccatcaa caacaccaag tccttcgagg     480

acatccatca gtacagggag cagatcaagc gggtgaaaga ttcagatgat gtgccaatgg     540

tgctggtggg caacaagtgt gacctggctg ctcgcactgt tgagtctcgg caggcccagg     600

accttgctcg cagctatggc atcccctaca ttgaaacatc agccaagacc cggcagggcg     660

tggaggatgc cttctataca ctagtccgtg agattcggca gcataaattg cggaaactga     720

acccacccga tgagagtggt cctggctgca tgagctgcaa atgtgtgctg tcctgacacc     780

aggctcagga catggaggtg ccggatgcag ggaggaggtg ccgacggaag gaaggaaaga     840

ggcgggaagg aaggaaacgg tgctggagcc aggccagtcc agggatggtg gacagatgtg     900

accaagacct tcgcatggac aatttgaaca gactgtcatg aactgtccct gttgccactg     960

gcacccaagt cctccacccc tctcagttcc ctccgggcgc ctgcctgtga gggcacacgt    1020

tgcatcacag taaattattt gatggtcttg acttgtctct ggctggaagt aggaggtgca    1080

ctgcctgtgg cctcacagaa gatgctgggc acctggggtc catcatctgc cttgctcctg    1140

tgctagaaga ggctggggag gctggcctgg gacctcggac tatacagccc ttcccttctg    1200

cctgtcccaa ctgtcttgtg tttgctgcag aaagttatag gcaacacaag gatagtcagg    1260

tgatatgacc tattgtcctt taactaatgg gaggaggagg gctctgagag taagagggta    1320

tcccttgtct ccagcaggaa acacatttcc tgcattctgg gatccatgaa atacagcctc    1380

aagagtgaca gagtgtaaga tttgccctga cccaacatcc tgcagccctc tgacctggga    1440

tggagattct aggactatgg aaatagggcc ctgatgttat ctgtgtagcc tcgggtccca    1500

ctggtgccta gggcctggca tcacaactcc ctgagagggt agaaagtgcc tcactggttg    1560

ctccctcttc tctgaggtgt acagatgttc ttctccaagt cacctgtatg gccttgagag    1620

gcacgtgcag gtcagatggc tgctcactgc gtgcttcctt ctggctctag tcatggctac    1680

aggagggtcc atctgcttat cctgctcctc ttcctggcca ctggggccca tggtgggtgc    1740

cctttatact ttccagactc gagtggaatt gggtgaagtc cctctgttta gggcacttga    1800

aatgcaagga gcctccaata gacatgatgt agagcctgct gctgagtggc tgggcagtgc    1860

gacaccacag ttgctctctt ccacagcagc caaatgttca gcttcccttg tctgtgtgta    1920

tctggggctc ctgaggtatc atctggagcg tcagtgacac cttcggagcc ttgttggtca    1980

tgaacttaag gtgggtggga gatagtgtct gctacactag gagttgtccc tggccctgtt    2040

tga                                                                  2043
```

<210> SEQ ID NO 7
<211> LENGTH: 2272
<212> TYPE: DNA
<213> ORGANISM: Mus musculus

<400> SEQUENCE: 7

```
cgagcgcggg cccggccaag tccccgccgt ccgctcccgg cgcccgcagc ccgagccgca      60
```

```
cccgccgcgg acggagctca tgcgcgggcc cagccggcgc ccgtccgcgc ccccgccctg    120

ccccggcccc ggccccggcc ccgggggcag tcgcgccagc aagcggtggg gcaggagctc    180

ctggattggc agccgctgta gaagctatga cagaatacaa gcttgtggtg gtgggcgctg    240

gaggcgtggg aaagagtgcc ctgaccatcc agctgatcca gaaccacttt gtggacgagt    300

atgatcccac tatagaggac tcctaccgga aacaggtggt cattgatggg gagacatgtc    360

tactggacat cttagacaca gcaggtcaag aagagtatag tgccatgcgg gaccagtaca    420

tgcgcacagg ggagggcttc ctctgtgtat ttgccatcaa caacaccaag tccttcgagg    480

acatccatca gtacagggag cagatcaagc gggtgaaaga ttcagatgat gtgccaatgg    540

tgctggtggg caacaagtgt gacctggctg ctcgcactgt tgagtctcgg caggcccagg    600

accttgctcg cagctatggc atcccctaca ttgaaacatc agccaagacc cggcagggca    660

gccgctctgg ctccagctcc gggaccctct gggatccccc ctcccccggg acccatgtga    720

cccagcggcc ctcaagctgg cgtggaggat gccttctata cactagtccg tgagattcgg    780

cagcataaat tgcggaaact gaacccaccc gatgagagtg gtcctggctg catgagctgc    840

aaatgtgtgc tgtcctgaca ccaggtgagg cagggaccag cgagacgtct ggggcagtga    900

cctcagctag ccagatgaac ttcatatcca ctctgatgtc cttgctcccc caattctgcc    960

aatcccccc gcctgcagtc agtcatgtcc tttgtgcccg tcccggcaca ggctcaggac    1020

atggaggtgc cggatgcagg gaggaggtgc cgacggaagg aaggaaagag gcgggaagga    1080

aggaaacggt gctggagcca ggccagtcca gggatggtgg acagatgtga ccaagacctt    1140

cgcatggaca atttgaacag actgtcatga actgtccctg ttgccactgg cacccaagtc    1200

ctccacccct ctcagttccc tccgggcgcc tgcctgtgag ggcacacgtt gcatcacagt    1260

aaattatttg atggtcttga cttgtctctg gctggaagta ggaggtgcac tgcctgtggc    1320

ctcacagaag atgctgggca cctggggtcc atcatctgcc ttgctcctgt gctagaagag    1380

gctggggagg ctggcctggg acctcggact atacagccct tcccttctgc ctgtcccaac    1440

tgtcttgtgt ttgctgcaga aagttatagg caacacaagg atagtcaggt gatatgacct    1500

attgtccttt aactaatggg aggaggaggg ctctgagagt aagagggtat cccttgtctc    1560

cagcaggaaa cacatttcct gcattctggg atccatgaaa tacagcctca agagtgacag    1620

agtgtaagat ttgccctgac ccaacatcct gcagccctct gacctgggat ggagattcta    1680

ggactatgga aatagggccc tgatgttatc tgtgtagcct cgggtcccac tggtgcctag    1740

ggcctggcat cacaactccc tgagagggta gaaagtgcct cactggttgc tccctcttct    1800

ctgaggtgta cagatgttct tctccaagtc acctgtatgg ccttgagagg cacgtgcagg    1860

tcagatggct gctcactgcg tgcttccttc tggctctagt catggctaca ggagggtcca    1920

tctgcttatc ctgctcctct tcctggccac tggggcccat ggtgggtgcc ctttatactt    1980

tccagactcg agtggaattg ggtgaagtcc ctctgtttag ggcacttgaa atgcaaggag    2040

cctccaatag acatgatgta gagcctgctg ctgagtggct gggcagtgcg acaccacagt    2100

tgctctcttc cacagcagcc aaatgttcag cttcccttgt ctgtgtgtat ctggggctcc    2160

tgaggtatca tctggagcgt cagtgacacc ttcggagcct tgttggtcat gaacttaagg    2220

tgggtgggag atagtgtctg ctacactagg agttgtccct ggccctgttt ga            2272
```

<210> SEQ ID NO 8
<211> LENGTH: 2190
<212> TYPE: DNA

-continued

<213> ORGANISM: Mus musculus

<400> SEQUENCE: 8

```
cgagcgcggg cccggccaag tccccgccgt ccgctcccgg cgcccgcagc ccgagccgca      60
cccgccgcgg acggagctca tgcgcgggcc cagccggcgc ccgtccgcgc ccccgccctg     120
ccccggcccc ggccccggcc ccgggggcag tcgcgccagc aagcggtggg gcaggagctc     180
ctggattggc agccgctgta gaagctatga cagaatacaa gcttgtggtg gtgggcgctg     240
gaggcgtggg aaagagtgcc ctgaccatcc agctgatcca gaaccacttt gtggacgagt     300
atgatcccac tatagaggac tcctaccgga aacaggtggt cattgatggg gagacatgtc     360
tactggacat cttagacaca gcaggtcaag aagagtatag tgccatgcgg gaccagtaca     420
tgcgcacagg ggagggcttc ctctgtgtat ttgccatcaa caacaccaag tccttcgagg     480
acatccatca gtacagggag cagatcaagc gggtgaaaga ttcagatgat gtgccaatgg     540
tgctggtggg caacaagtgt gacctggctg ctcgcactgt tgagtctcgg caggcccagg     600
accttgctcg cagctatggc atcccctaca ttgaaacatc agccaagacc cggcagggcg     660
tggaggatgc cttctataca ctagtccgtg agattcggca gcataaattg cggaaactga     720
acccacccga tgagagtggt cctggctgca tgagctgcaa atgtgtgctg tcctgacacc     780
aggtgaggca gggaccagcg agacgtctgg ggcagtgacc tcagctagcc agatgaactt     840
catatccact ctgatgtcct tgctccccca attctgccaa tcccccccgc ctgcagtcag     900
tcatgtcctt tgtgcccgtc ccggcacagg ctcaggacat ggaggtgccg gatgcaggga     960
ggaggtgccg acggaaggaa ggaaagaggc gggaaggaag gaaacggtgc tggagccagg    1020
ccagtccagg gatggtggac agatgtgacc aagaccttcg catggacaat ttgaacagac    1080
tgtcatgaac tgtccctgtt gccactggca cccaagtcct ccacccctct cagttccctc    1140
cgggcgcctg cctgtgaggg cacacgttgc atcacagtaa attatttgat ggtcttgact    1200
tgtctctggc tggaagtagg aggtgcactg cctgtggcct cacagaagat gctgggcacc    1260
tggggtccat catctgcctt gctcctgtgc tagaagaggc tggggaggct ggcctgggac    1320
ctcggactat acagcccttc ccttctgcct gtcccaactg tcttgtgttt gctgcagaaa    1380
gttataggca acacaaggat agtcaggtga tatgacctat tgtcctttaa ctaatgggag    1440
gaggagggct ctgagagtaa gagggtatcc cttgtctcca gcaggaaaca catttcctgc    1500
attctgggat ccatgaaata cagcctcaag agtgacagag tgtaagattt gccctgaccc    1560
aacatcctgc agccctctga cctgggatgg agattctagg actatggaaa tagggccctg    1620
atgttatctg tgtagcctcg ggtcccactg gtgcctaggg cctggcatca caactccctg    1680
agagggtaga aagtgcctca ctggttgctc cctcttctct gaggtgtaca gatgttcttc    1740
tccaagtcac ctgtatggcc ttgagaggca cgtgcaggtc agatggctgc tcactgcgtg    1800
cttccttctg gctctagtca tggctacagg agggtccatc tgcttatcct gctcctcttc    1860
ctggccactg gggcccatgg tgggtgccct ttatactttc cagactcgag tggaattggg    1920
tgaagtccct ctgtttaggg cacttgaaat gcaaggagcc tccaatagac atgatgtaga    1980
gcctgctgct gagtggctgg gcagtgcgac accacagttg ctctcttcca cagcagccaa    2040
atgttcagct tcccttgtct gtgtgtatct ggggctcctg aggtatcatc tggagcgtca    2100
gtgacacctt cggagccttg ttggtcatga acttaaggtg ggtgggagat agtgtctgct    2160
acactaggag ttgtccctgg ccctgtttga                                    2190
```

```
<210> SEQ ID NO 9
<211> LENGTH: 189
<212> TYPE: PRT
<213> ORGANISM: Mus musculus

<400> SEQUENCE: 9

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His Gln Tyr
                85                  90                  95

Arg Glu Gln Ile Lys Arg Val Lys Asp Ser Asp Asp Val Pro Met Val
            100                 105                 110

Leu Val Gly Asn Lys Cys Asp Leu Ala Ala Arg Thr Val Glu Ser Arg
        115                 120                 125

Gln Ala Gln Asp Leu Ala Arg Ser Tyr Gly Ile Pro Tyr Ile Glu Thr
    130                 135                 140

Ser Ala Lys Thr Arg Gln Gly Val Glu Asp Ala Phe Tyr Thr Leu Val
145                 150                 155                 160

Arg Glu Ile Arg Gln His Lys Leu Arg Lys Leu Asn Pro Pro Asp Glu
                165                 170                 175

Ser Gly Pro Gly Cys Met Ser Cys Lys Cys Val Leu Ser
            180                 185


<210> SEQ ID NO 10
<211> LENGTH: 188
<212> TYPE: PRT
<213> ORGANISM: Mus musculus

<400> SEQUENCE: 10

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His Gln Tyr
                85                  90                  95

Arg Glu Gln Ile Lys Arg Val Lys Asp Ser Asp Asp Val Pro Met Val
            100                 105                 110

Leu Val Gly Asn Lys Cys Asp Leu Ala Ala Arg Thr Val Glu Ser Arg
        115                 120                 125

Gln Ala Gln Asp Leu Ala Arg Ser Tyr Gly Ile Pro Tyr Ile Glu Thr
    130                 135                 140

Ser Ala Lys Thr Arg Gln Gly Ser Arg Ser Gly Ser Ser Ser Gly Thr
```

145 150 155 160

Leu Trp Asp Pro Pro Ser Pro Gly Thr His Val Thr Gln Arg Pro Ser
165 170 175

Ser Trp Arg Gly Gly Cys Leu Leu Tyr Thr Ser Pro
180 185

<210> SEQ ID NO 11
<211> LENGTH: 1246
<212> TYPE: DNA
<213> ORGANISM: Rattus norvegicus

<400> SEQUENCE: 11
gcccggcgcc cgcagcccga gccgcacccg ccgcggacgg agcccatgcg cgggcccagt 60
cggcgcccgt ccgcgccccc gccctgcccc ggccccggcc ccgggggcag tcgcgccagc 120
aagcggtggg gcaggagctc ctggtttggc agcccctgta gaagcgatga cagaatacaa 180
gcttgtggtg gtgggcgctg gaggcgtggg aaagagtgcc ctgaccatcc agctgatcca 240
gaaccatttt gtggacgagt atgatcccac tatagaggac tcctaccgga aacaggtagt 300
cattgatggg gagacgtgtt tactggacat cttagacaca gcaggtcaag aagagtatag 360
tgccatgcgg gaccagtaca tgcgcacagg ggagggcttc ctctgtgtat ttgccatcaa 420
caacaccaag tcctttgaag acatccatca gtacagggag cagatcaagc gggtgaaaga 480
ttcagatgat gtgccaatgg tgctggtggg caacaagtgt gacctggccg ctcgcactgt 540
tgagtctcgg caggcccagg accttgctcg cagctatggc atcccctaca ttgaaacatc 600
agccaagacc cggcagggtg tggaggatgc cttctacaca ctagtacgtg agattcggca 660
gcataaactg cggaaactga acccgcctga tgagagtggc cctggctgca tgagctgcaa 720
gtgtgtgctg tcctgacacc aggctcagga cgaggaggtg ccggatgcag ggaggaggtg 780
ctgtcggaag gaaggaaaga ggagggaagg aaggaaacga tgctggagcc agtccagtcc 840
agggatggtg gacagatgtg accaagacct tcgcatggac aatttgaaca gactgtcatg 900
aactatccct gttgccactg gcacccaagt cctccgcccc tctcagctcc cttgggcgcc 960
tatgagggca catgttgaat cacagtaaat tatttgatgg tcttgacttg tctctggctg 1020
gaagtaggag gtgtagtgcc tgtggcctca cagaagatac tggggacctg ggatctatca 1080
tctgccttgt tcctgtttct agaagaggct ggggaggctg gcctgggacc tgggactgtg 1140
cagcccttct cttctgcctg cctcaactgt cttgtgtttc ctgcagaaag ttataaataa 1200
cacaagaata gtcaggtgat atgaaaaaaa aaaaaaaaaa aaaaaa 1246

<210> SEQ ID NO 12
<211> LENGTH: 1392
<212> TYPE: DNA
<213> ORGANISM: Rattus norvegicus

<400> SEQUENCE: 12
gcccggcgcc cgcagcccga gccgcacccg ccgcggacgg agcccatgcg cgggcccagt 60
cggcgcccgt ccgcgccccc gccctgcccc ggccccggcc ccgggggcag tcgcgccagc 120
aagcggtggg gcaggagctc ctggtttggc agcccctgta gaagcgatga cagaatacaa 180
gcttgtggtg gtgggcgctg gaggcgtggg aaagagtgcc ctgaccatcc agctgatcca 240
gaaccatttt gtggacgagt atgatcccac tatagaggac tcctaccgga aacaggtagt 300
cattgatggg gagacgtgtt tactggacat cttagacaca gcaggtcaag aagagtatag 360
tgccatgcgg gaccagtaca tgcgcacagg ggagggcttc ctctgtgtat ttgccatcaa 420

```
caacaccaag tcctttgaag acatccatca gtacagggag cagatcaagc gggtgaaaga    480

ttcagatgat gtgccaatgg tgctggtggg caacaagtgt gacctggccg ctcgcactgt    540

tgagtctcgg caggcccagg accttgctcg cagctatggc atcccctaca ttgaaacatc    600

agccaagacc cggcagggtg tggaggatgc cttctacaca ctagtacgtg agattcggca    660

gcataaactg cggaaactga acccgcctga tgagagtggc cctggctgca tgagctgcaa    720

gtgtgtgctg tcctgacacc aggtgaggca gggaccagca agacatctgg ggcagtgacc    780

tcagctagcc agatgaactt catatccact ttgatgtccc tgctccccca attctgccaa    840

tccccctgcc tgcagtcagt catgtccttt gtgcccgtcc cggcacaggc tcaggacgag    900

gaggtgccgg atgcagggag gaggtgctgt cggaaggaag gaaagaggag ggaaggaagg    960

aaacgatgct ggagccagtc cagtccaggg atggtggaca gatgtgacca agaccttcgc   1020

atggacaatt tgaacagact gtcatgaact atccctgttg ccactggcac ccaagtcctc   1080

cgcccctctc agctcccttg ggcgcctatg agggcacatg ttgaatcaca gtaaattatt   1140

tgatggtctt gacttgtctc tggctggaag taggaggtgt agtgcctgtg gcctcacaga   1200

agatactggg gacctgggat ctatcatctg ccttgttcct gtttctagaa gaggctgggg   1260

aggctggcct gggacctggg actgtgcagc ccttctcttc tgcctgcctc aactgtcttg   1320

tgtttcctgc agaaagttat aaataacaca agaatagtca ggtgatatga aaaaaaaaaa   1380

aaaaaaaaaa aa                                                       1392
```

```
<210> SEQ ID NO 13
<211> LENGTH: 189
<212> TYPE: PRT
<213> ORGANISM: Rattus norvegicus

<400> SEQUENCE: 13

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His Gln Tyr
                85                  90                  95

Arg Glu Gln Ile Lys Arg Val Lys Asp Ser Asp Asp Val Pro Met Val
            100                 105                 110

Leu Val Gly Asn Lys Cys Asp Leu Ala Ala Arg Thr Val Glu Ser Arg
        115                 120                 125

Gln Ala Gln Asp Leu Ala Arg Ser Tyr Gly Ile Pro Tyr Ile Glu Thr
    130                 135                 140

Ser Ala Lys Thr Arg Gln Gly Val Glu Asp Ala Phe Tyr Thr Leu Val
145                 150                 155                 160

Arg Glu Ile Arg Gln His Lys Leu Arg Lys Leu Asn Pro Pro Asp Glu
                165                 170                 175

Ser Gly Pro Gly Cys Met Ser Cys Lys Cys Val Leu Ser
            180                 185
```

-continued

<210> SEQ ID NO 14
<211> LENGTH: 938
<212> TYPE: DNA
<213> ORGANISM: Canis lupus familiaris

<400> SEQUENCE: 14
agcaggtggg acaggagacc tcgttggcgt cctgtgctgc gtcccgtgag gagccatgac 60
ggagtataag ctggtggtgg tgggcgctgg aggcgtgggc aagagcgccc tgaccatcca 120
gctcatccag aaccacttcg tggatgagta cgaccccacc atcgaggact cctatcggaa 180
gcaagtggtc atcgacgggg agacgtgcct gctggacatc ctggacacag cgggccagga 240
ggagtacagc gccatgcggg accagtacat gcgcacgggg gagggctttc tctgtgtatt 300
tgccatcaac aacaccaagt cctttgagga catccaccag tacagggagc agatcaagcg 360
agtgaaggac tctgacgacg tgcccatggt gctggtgggg aacaagtgtg acctggctgc 420
tcgcaccgtg gagtcccggc aggcgcagga cctcgcccgc agctacggca tcccctacat 480
cgagacgtca gccaagacgc gccagggcgt ggaggatgcc ttctacacgc tggtgcgaga 540
gattcgacag cacaaggtgc gcaagctgag cccgcccgac gagggaggcc caggctgcat 600
gagctgcaag tgcctgctgt cctgacgtcc cctccagggc cacgttggca gccccgctgg 660
tcctctgtgc cccaggcgca caggctcggg gcgaggaggt gccggaagct gggaggaggc 720
gcggaaggag gaaggaggag ggcgaggaag gaaggaagcg cccccggggc ccggccagcc 780 caggcccccct ggacaggggg agcacggacc tcccagggcg ctttgcacag actgtcgtga 840
actgaggcca cgggcccccc cggctgtcac tctcccccag tcccgtcctt gcccgcgggg 900
caaaggctga gtcgcagtaa attatttgat ggtcttga 938

<210> SEQ ID NO 15
<211> LENGTH: 1020
<212> TYPE: DNA
<213> ORGANISM: Canis lupus familiaris

<400> SEQUENCE: 15
agcaggtggg acaggagacc tcgttggcgt cctgtgctgc gtcccgtgag gagccatgac 60
ggagtataag ctggtggtgg tgggcgctgg aggcgtgggc aagagcgccc tgaccatcca 120
gctcatccag aaccacttcg tggatgagta cgaccccacc atcgaggact cctatcggaa 180
gcaagtggtc atcgacgggg agacgtgcct gctggacatc ctggacacag cgggccagga 240
ggagtacagc gccatgcggg accagtacat gcgcacgggg gagggctttc tctgtgtatt 300
tgccatcaac aacaccaagt cctttgagga catccaccag tacagggagc agatcaagcg 360
agtgaaggac tctgacgacg tgcccatggt gctggtgggg aacaagtgtg acctggctgc 420
tcgcaccgtg gagtcccggc aggcgcagga cctcgcccgc agctacggca tcccctacat 480
cgagacgtca gccaagacgc gccagggcag ccggtctggc tctggctcca gctccgggac 540
cctctgggac cctccgggac ccccgtgacc cagcggcccc tagcgctggc gtggaggatg 600
ccttctacac gctggtgcga gagattcgac agcacaaggt gcgcaagctg agcccgcccg 660
acgagggagg cccaggctgc atgagctgca agtgcctgct gtcctgacgt cccctccagg 720
gccacgttgg cagccccgct ggtcctctgt gccccaggcg cacaggctcg gggcgaggag 780
gtgccggaag ctgggaggag gcgcggaagg aggaaggagg agggcgagga aggaaggaag 840
cgcccccggg gcccggccag cccaggcccc ctggacaggg ggagcacgga cctcccaggg 900
cgctttgcac agactgtcgt gaactgaggc cacgggcccc cccggctgtc actctccccc 960

-continued agtcccgtcc ttgcccgcgg ggcaaaggct gagtcgcagt aaattatttg atggtcttga 1020

<210> SEQ ID NO 16
<211> LENGTH: 189
<212> TYPE: PRT
<213> ORGANISM: Canis lupus familiaris

<400> SEQUENCE: 16

Met Thr Glu Tyr Lys Leu Val Val Val Gly Ala Gly Gly Val Gly Lys
1 5 10 15

Ser Ala Leu Thr Ile Gln Leu Ile Gln Asn His Phe Val Asp Glu Tyr
20 25 30

Asp Pro Thr Ile Glu Asp Ser Tyr Arg Lys Gln Val Val Ile Asp Gly
35 40 45

Glu Thr Cys Leu Leu Asp Ile Leu Asp Thr Ala Gly Gln Glu Glu Tyr
50 55 60

Ser Ala Met Arg Asp Gln Tyr Met Arg Thr Gly Glu Gly Phe Leu Cys
65 70 75 80

Val Phe Ala Ile Asn Asn Thr Lys Ser Phe Glu Asp Ile His Gln Tyr
85 90 95

Arg Glu Gln Ile Lys Arg Val Lys Asp Ser Asp Asp Val Pro Met Val
100 105 110

Leu Val Gly Asn Lys Cys Asp Leu Ala Ala Arg Thr Val Glu Ser Arg
115 120 125

Gln Ala Gln Asp Leu Ala Arg Ser Tyr Gly Ile Pro Tyr Ile Glu Thr
130 135 140

Ser Ala Lys Thr Arg Gln Gly Val Glu Asp Ala Phe Tyr Thr Leu Val
145 150 155 160

Arg Glu Ile Arg Gln His Lys Val Arg Lys Leu Ser Pro Pro Asp Glu
165 170 175

Gly Gly Pro Gly Cys Met Ser Cys Lys Cys Leu Leu Ser
180 185

<210> SEQ ID NO 17
<211> LENGTH: 170
<212> TYPE: PRT
<213> ORGANISM: Canis lupus familiaris

<400> SEQUENCE: 17

Met Thr Glu Tyr Lys Leu Val Val Val Gly Ala Gly Gly Val Gly Lys
1 5 10 15

Ser Ala Leu Thr Ile Gln Leu Ile Gln Asn His Phe Val Asp Glu Tyr
20 25 30

Asp Pro Thr Ile Glu Asp Ser Tyr Arg Lys Gln Val Val Ile Asp Gly
35 40 45

Glu Thr Cys Leu Leu Asp Ile Leu Asp Thr Ala Gly Gln Glu Glu Tyr
50 55 60

Ser Ala Met Arg Asp Gln Tyr Met Arg Thr Gly Glu Gly Phe Leu Cys
65 70 75 80

Val Phe Ala Ile Asn Asn Thr Lys Ser Phe Glu Asp Ile His Gln Tyr
85 90 95

Arg Glu Gln Ile Lys Arg Val Lys Asp Ser Asp Asp Val Pro Met Val
100 105 110

Leu Val Gly Asn Lys Cys Asp Leu Ala Ala Arg Thr Val Glu Ser Arg
115 120 125

```
Gln Ala Gln Asp Leu Ala Arg Ser Tyr Gly Ile Pro Tyr Ile Glu Thr
    130                 135                 140

Ser Ala Lys Thr Arg Gln Gly Ser Arg Ser Gly Ser Gly Ser Ser Ser
145                 150                 155                 160

Gly Thr Leu Trp Asp Pro Pro Gly Pro Pro
                165                 170
```

<210> SEQ ID NO 18
<211> LENGTH: 962
<212> TYPE: DNA
<213> ORGANISM: Gallus gallus

<400> SEQUENCE: 18

```
gggttgatgg ccggaccgtc gattccctga cgactacgag cacctacacc tgaggtggtg     60

gtgctcctgg aggccctgag ctggggtcag ctggaagatg accgagtaca agctggtggt    120

agtgggagct ggaggtgtcg ggaagagcgc tttgacgata cagctcattc agaaccattt    180

tgttgatgag tacgacccca caatagagga ttcctacaga aagcaagtcg tcatcgatgg    240

agagacctgt ttgctggaca tcctggatac ggcggggcag gaggagtaca gtgccatgcg    300

agaccagtac atgagaacgg gggaaggatt cctgtgcgtc tttgccatta acaacaccaa    360

gtcctttgag gacatccacc agtacaggga gcagatcaag agggtgaaag actcagatga    420

tgtccccatg gtgctggtgg gaaataaatg tgatctgcca gcacggacag tggagacccg    480

gcaagcgcag gacctggccc ggagttacgg gatcccctac atagaaacgt cggccaaaac    540

cagacagggc gtcgaagatg ccttctatac cttagtgcgg gagatccgtc agcataaact    600

gcgcaagctg aacccaccag atgagagtgg ccctggctgc atgaactgta aatgcgtgat    660

atcgtgactg tgctgactgg accctgactt ggagaggtgt ccgctgtgca gagcacaagg    720

aaagaggtga tgcgaaggaa gaaacaaatg gattcagggg aggagtggag ggggagggag    780

agaggaagaa gaggacggga ggagtgccag cccctccaag gactatctcg cacttcaccc    840

aggccggcag cagatgactt ttggttcttt ccccatcccc tcctcctttg gcctcctcca    900

ccccggcaac tgtacaaagc cacagattga atcacagtaa attattattt gatggtctcg    960

ac                                                                   962
```

<210> SEQ ID NO 19
<211> LENGTH: 189
<212> TYPE: PRT
<213> ORGANISM: Gallus gallus

<400> SEQUENCE: 19

```
Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His Gln Tyr
                85                  90                  95

Arg Glu Gln Ile Lys Arg Val Lys Asp Ser Asp Asp Val Pro Met Val
            100                 105                 110
```

```
Leu Val Gly Asn Lys Cys Asp Leu Pro Ala Arg Thr Val Glu Thr Arg
        115                 120                 125

Gln Ala Gln Asp Leu Ala Arg Ser Tyr Gly Ile Pro Tyr Ile Glu Thr
    130                 135                 140

Ser Ala Lys Thr Arg Gln Gly Val Glu Asp Ala Phe Tyr Thr Leu Val
145                 150                 155                 160

Arg Glu Ile Arg Gln His Lys Leu Arg Lys Leu Asn Pro Pro Asp Glu
                165                 170                 175

Ser Gly Pro Gly Cys Met Asn Cys Lys Cys Val Ile Ser
            180                 185


<210> SEQ ID NO 20
<211> LENGTH: 978
<212> TYPE: DNA
<213> ORGANISM: Bos taurus

<400> SEQUENCE: 20

ccgccgcgga cgggacccat gcgtcgggcg agccctgcgc cccggccccg gcccctgccg      60

ccgccccgc tccggccccg gcccgggggg cagtcgagcc agtgagcggt gggaccggcg      120

accactgcag cgcctcgtgc tgcggtctct tgaggagcaa tgacggagta taagctcgtg     180

gtggtgggcg ccggtggcgt ggggaagagc gccctgacta tccagctcat tcagaatcac     240

ttcgtggacg agtacgaccc caccatcgag gactcctacc ggaagcaagt ggtcatcgat     300

ggggagacgt gcctgctgga catcctggac acagcgggcc aggaggaata cagcgccatg     360

cgagaccagt acatgcgcac cggggagggc tttctctgcg tgtttgctat caaccacgtc     420

aagtccttcg aggacatcca ccagtaccgg gagcagatca agcgggtgaa ggactcggat     480

gacgtgccca tggtgttggt tgggaacaag tgcgacctgg ccgcgcgcac cgtggagtct     540

cggcaggccc aggacctcgc ccgcagctac ggcatcccgt acatcgagac ctccgccaag     600

acccgccagg gcgtggagga tgctttctac accctggtgc gcgagatccg gcagcacaag     660

gtgcgcaagc tgagcccgcc ggacgagggc ggccccggct gcctgagctg caggtgcctg     720

ctctcctgac ggcagcgtgg gcgcggagcg ctgggtgcca tgcaggaggc ggcgcagcag     780

gggtggaggg aggtgccgcc agagcccagc cccccaggcc agtgggcagt gcccgcgggc     840

ctcccgggac gcttcgcaca gactctggtg aactgatgct gctggccccc agcctcgctc     900

tcctccagcc ctgtcctggc ccagcgggcg caggccgagt cgcagtaaat tatttcatgg     960

tcttgaaaaa aaaaaaaa                                                   978


<210> SEQ ID NO 21
<211> LENGTH: 1060
<212> TYPE: DNA
<213> ORGANISM: Bos taurus

<400> SEQUENCE: 21

ccgccgcgga cgggacccat gcgtcgggcg agccctgcgc cccggccccg gcccctgccg      60

ccgccccgc tccggccccg gcccgggggg cagtcgagcc agtgagcggt gggaccggcg      120

accactgcag cgcctcgtgc tgcggtctct tgaggagcaa tgacggagta taagctcgtg     180

gtggtgggcg ccggtggcgt ggggaagagc gccctgacta tccagctcat tcagaatcac     240

ttcgtggacg agtacgaccc caccatcgag gactcctacc ggaagcaagt ggtcatcgat     300

ggggagacgt gcctgctgga catcctggac acagcgggcc aggaggaata cagcgccatg     360

cgagaccagt acatgcgcac cggggagggc tttctctgcg tgtttgctat caaccacgtc     420
```

```
aagtccttcg aggacatcca ccagtaccgg gagcagatca agcgggtgaa ggactcggat    480

gacgtgccca tggtgttggt tgggaacaag tgcgacctgg ccgcgcgcac cgtggagtct    540

cggcaggccc aggacctcgc ccgcagctac ggcatcccgt acatcgagac ctccgccaag    600

acccgccagg gcagccgctc tggctctggc tccagctccg ggaccctctg ggaccctccg    660

ggacccccgt gacccagccg cccctctcgc tggcgtggag gatgctttct acaccctggt    720

gcgcgagatc cggcagcaca aggtgcgcaa gctgagcccg ccggacgagg gcggccccgg    780

ctgcctgagc tgcaggtgcc tgctctcctg acggcagcgt gggcgcggag cgctgggtgc    840

catgcaggag gcggcgcagc aggggtggag ggaggtgccg ccagagccca gccccccagg    900

ccagtgggca gtgcccgcgg gcctcccggg acgcttcgca cagactctgg tgaactgatg    960

ctgctggccc ccagcctcgc tctcctccag ccctgtcctg gcccagcggg cgcaggccga   1020

gtcgcagtaa attatttcat ggtcttgaaa aaaaaaaaaa                         1060
```

<210> SEQ ID NO 22
<211> LENGTH: 189
<212> TYPE: PRT
<213> ORGANISM: Bos taurus

<400> SEQUENCE: 22

```
Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn His Val Lys Ser Phe Glu Asp Ile His Gln Tyr
                85                  90                  95

Arg Glu Gln Ile Lys Arg Val Lys Asp Ser Asp Asp Val Pro Met Val
            100                 105                 110

Leu Val Gly Asn Lys Cys Asp Leu Ala Ala Arg Thr Val Glu Ser Arg
        115                 120                 125

Gln Ala Gln Asp Leu Ala Arg Ser Tyr Gly Ile Pro Tyr Ile Glu Thr
    130                 135                 140

Ser Ala Lys Thr Arg Gln Gly Val Glu Asp Ala Phe Tyr Thr Leu Val
145                 150                 155                 160

Arg Glu Ile Arg Gln His Lys Val Arg Lys Leu Ser Pro Pro Asp Glu
                165                 170                 175

Gly Gly Pro Gly Cys Leu Ser Cys Arg Cys Leu Leu Ser
            180                 185
```

<210> SEQ ID NO 23
<211> LENGTH: 170
<212> TYPE: PRT
<213> ORGANISM: Bos taurus

<400> SEQUENCE: 23

```
Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
```

```
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn His Val Lys Ser Phe Glu Asp Ile His Gln Tyr
                85                  90                  95

Arg Glu Gln Ile Lys Arg Val Lys Asp Ser Asp Asp Val Pro Met Val
            100                 105                 110

Leu Val Gly Asn Lys Cys Asp Leu Ala Ala Arg Thr Val Glu Ser Arg
        115                 120                 125

Gln Ala Gln Asp Leu Ala Arg Ser Tyr Gly Ile Pro Tyr Ile Glu Thr
    130                 135                 140

Ser Ala Lys Thr Arg Gln Gly Ser Arg Ser Gly Ser Gly Ser Ser Ser
145                 150                 155                 160

Gly Thr Leu Trp Asp Pro Pro Gly Pro Pro
                165                 170


<210> SEQ ID NO 24
<211> LENGTH: 5889
<212> TYPE: DNA
<213> ORGANISM: Homo sapiens

<400> SEQUENCE: 24

tcctaggcgg cggccgcggc ggcggaggca gcagcggcgg cggcagtggc ggcggcgaag      60

gtggcggcgg ctcggccagt actcccggcc cccgccattt cggactggga gcgagcgcgg     120

cgcaggcact gaaggcggcg gcggggccag aggctcagcg gctcccaggt gcgggagaga     180

ggcctgctga aaatgactga atataaactt gtggtagttg gagctggtgg cgtaggcaag     240

agtgccttga cgatacagct aattcagaat cattttgtgg acgaatatga tccaacaata     300

gaggattcct acaggaagca agtagtaatt gatggagaaa cctgtctctt ggatattctc     360

gacacagcag gtcaagagga gtacagtgca atgagggacc agtacatgag gactggggag     420

ggctttcttt gtgtatttgc cataaataat actaaatcat ttgaagatat tcaccattat     480

agagaacaaa ttaaaagagt taaggactct gaagatgtac ctatggtcct agtaggaaat     540

aaatgtgatt tgccttctag aacagtagac acaaaacagg ctcaggactt agcaagaagt     600

tatggaattc cttttattga aacatcagca aagacaagac agagagtgga ggatgctttt     660

tatacattgg tgagggagat ccgacaatac agattgaaaa aaatcagcaa agaagaaaag     720

actcctggct gtgtgaaaat taaaaaatgc attataatgt aatctgggtg ttgatgatgc     780

cttctataca ttagttcgag aaattcgaaa acataaagaa aagatgagca aagatggtaa     840

aaagaagaaa aagaagtcaa agacaaagtg tgtaattatg taaatacaat ttgtactttt     900

ttcttaaggc atactagtac aagtggtaat ttttgtacat tacactaaat tattagcatt     960

tgttttagca ttacctaatt tttttcctgc tccatgcaga ctgttagctt ttaccttaaa    1020

tgcttatttt aaaatgacag tggaagtttt tttttcctct aagtgccagt attcccagag    1080

ttttggtttt tgaactagca atgcctgtga aaaagaaact gaatacctaa gatttctgtc    1140

ttggggtttt tggtgcatgc agttgattac ttcttatttt tcttaccaat tgtgaatgtt    1200

ggtgtgaaac aaattaatga agcttttgaa tcatccctat tctgtgtttt atctagtcac    1260
```

-continued

```
ataaatggat taattactaa tttcagttga gaccttctaa ttggttttta ctgaaacatt   1320
gagggaacac aaatttatgg gcttcctgat gatgattctt ctaggcatca tgtcctatag   1380
tttgtcatcc ctgatgaatg taaagttaca ctgttcacaa aggttttgtc tcctttccac   1440
tgctattagt catggtcact ctccccaaaa tattatattt tttctataaa aagaaaaaaa   1500
tggaaaaaaa ttacaaggca atggaaacta ttataaggcc atttcctttt cacattagat   1560
aaattactat aaagactcct aatagctttt cctgttaagg cagacccagt atgaaatggg   1620
gattattata gcaaccattt tggggctata tttacatgct actaaatttt tataataatt   1680
gaaaagattt taacaagtat aaaaaattct cataggaatt aaatgtagtc tccctgtgtc   1740
agactgctct ttcatagtat aactttaaat cttttcttca acttgagtct ttgaagatag   1800
ttttaattct gcttgtgaca ttaaaagatt atttgggcca gttatagctt attaggtgtt   1860
gaagagacca aggttgcaag gccaggccct gtgtgaacct ttgagctttc atagagagtt   1920
tcacagcatg gactgtgtcc ccacggtcat ccagtgttgt catgcattgg ttagtcaaaa   1980
tggggaggga ctagggcagt ttggatagct caacaagata caatctcact ctgtggtggt   2040
cctgctgaca aatcaagagc attgcttttg tttcttaaga aaacaaactc tttttttaaaa   2100
attactttta aatattaact caaaagttga gattttgggg tggtggtgtg ccaagacatt   2160
aatttttttt ttaaacaatg aagtgaaaaa gttttacaat ctctaggttt ggctagttct   2220
cttaacactg gttaaattaa cattgcataa acacttttca agtctgatcc atatttaata   2280
atgctttaaa ataaaaataa aaacaatcct tttgataaat ttaaaatgtt acttatttta   2340
aaataaatga agtgagatgg catggtgagg tgaaagtatc actggactag gaagaaggtg   2400
acttaggttc tagataggtg tcttttagga ctctgatttt gaggacatca cttactatcc   2460
atttcttcat gttaaaagaa gtcatctcaa actcttagtt tttttttttt acaactatgt   2520
aatttatatt ccatttacat aaggatacac ttatttgtca agctcagcac aatctgtaaa   2580
tttttaacct atgttacacc atcttcagtg ccagtcttgg gcaaaattgt gcaagaggtg   2640
aagtttatat ttgaatatcc attctcgttt taggactctt cttccatatt agtgtcatct   2700
tgcctcccta ccttccacat gccccatgac ttgatgcagt tttaatactt gtaattcccc   2760
taaccataag atttactgct gctgtggata tctccatgaa gttttcccac tgagtcacat   2820
cagaaatgcc ctacatctta tttcctcagg gctcaagaga atctgacaga taccataaag   2880
ggatttgacc taatcactaa ttttcaggtg gtggctgatg ctttgaacat ctctttgctg   2940
cccaatccat tagcgacagt aggatttttc aaacctggta tgaatagaca gaaccctatc   3000
cagtggaagg agaatttaat aaagatagtg ctgaaagaat tccttaggta atctataact   3060
aggactactc ctggtaacag taatacattc cattgtttta gtaaccagaa atcttcatgc   3120
aatgaaaaat actttaattc atgaagctta cttttttttt ttggtgtcag agtctcgctc   3180
ttgtcaccca ggctggaatg cagtggcgcc atctcagctc actgcaacct ccatctccca   3240
ggttcaagcg attctcgtgc ctcggcctcc tgagtagctg ggattacagg cgtgtgccac   3300
tacactcaac taatttttgt atttttagga gagacggggt ttcaccctgt tggccaggct   3360
ggtctcgaac tcctgacctc aagtgattca cccaccttgg cctcataaac ctgttttgca   3420
gaactcattt attcagcaaa tatttattga gtgcctacca gatgccagtc accgcacaag   3480
gcactgggta tatggtatcc ccaaacaaga gacataatcc cggtccttag gtagtgctag   3540
tgtggtctgt aatatcttac taaggccttt ggtatacgac ccagagataa cacgatgcgt   3600
attttagttt tgcaaagaag ggtttggtc tctgtgccag ctctataatt gttttgctac   3660
```

```
gattccactg aaactcttcg atcaagctac tttatgtaaa tcacttcatt gttttaaagg   3720
aataaacttg attatattgt ttttttattt ggcataactg tgattctttt aggacaatta   3780
ctgtacacat taaggtgtat gtcagatatt catattgacc caaatgtgta atattccagt   3840
tttctctgca taagtaatta aaatatactt aaaaattaat agttttatct gggtacaaat   3900
aaacaggtgc ctgaactagt tcacagacaa ggaaacttct atgtaaaaat cactatgatt   3960
tctgaattgc tatgtgaaac tacagatctt tggaacactg tttaggtagg gtgttaagac   4020
ttacacagta cctcgtttct acacagagaa agaaatggcc atacttcagg aactgcagtg   4080
cttatgaggg gatatttagg cctcttgaat ttttgatgta gatgggcatt tttttaaggt   4140
agtggttaat tacctttatg tgaactttga atggtttaac aaaagatttg tttttgtaga   4200
gattttaaag gggagaattt ctagaaataa atgttaccta attattacag ccttaaagac   4260
aaaaatcctt gttgaagttt ttttaaaaaa agctaaatta catagactta ggcattaaca   4320
tgtttgtgga agaatatagc agacgtatat tgtatcattt gagtgaatgt tcccaagtag   4380
gcattctagg ctctatttaa ctgagtcaca ctgcatagga atttagaacc taacttttat   4440
aggttatcaa aactgttgtc accattgcac aattttgtcc taatatatac atagaaactt   4500
tgtggggcat gttaagttac agtttgcaca agttcatctc atttgtattc cattgatttt   4560
tttttcttc taaacatttt ttcttcaaac agtatataac tttttttagg ggattttttt    4620
ttagacagca aaaactatct gaagatttcc atttgtcaaa aagtaatgat ttcttgataa   4680
ttgtgtagta atgtttttta gaacccagca gttaccttaa agctgaattt atatttagta   4740
acttctgtgt taatactgga tagcatgaat tctgcattga gaaactgaat agctgtcata   4800
aaatgaaact ttctttctaa agaaagatac tcacatgagt tcttgaagaa tagtcataac   4860
tagattaaga tctgtgtttt agtttaatag tttgaagtgc ctgtttggga taatgatagg   4920
taatttagat gaatttaggg gaaaaaaaag ttatctgcag atatgttgag ggcccatctc   4980
tccccccaca cccccacaga gctaactggg ttacagtgtt ttatccgaaa gtttccaatt   5040
ccactgtctt gtgttttcat gttgaaaata cttttgcatt tttcctttga gtgccaattt   5100
cttactagta ctatttctta atgtaacatg tttacctgga atgtatttta actatttttg   5160
tatagtgtaa actgaaacat gcacattttg tacattgtgc tttcttttgt gggacatatg   5220
cagtgtgatc cagttgtttt ccatcatttg gttgcgctga cctaggaatg ttggtcatat   5280
caaacattaa aaatgaccac tcttttaatt gaaattaact tttaaatgtt tataggagta   5340
tgtgctgtga agtgatctaa aatttgtaat atttttgtca tgaactgtac tactcctaat   5400
tattgtaatg taataaaaat agttacagtg actatgagtg tgtatttatt catgaaattt   5460
gaactgtttg ccccgaaatg gatatggaat actttataag ccatagacac tatagtatac   5520
cagtgaatct tttatgcagc ttgttagaag tatcctttat ttctaaaagg tgctgtggat   5580
attatgtaaa ggcgtgtttg cttaaactta aaaccatatt tagaagtaga tgcaaaacaa   5640
atctgccttt atgacaaaaa aataggataa cattatttat ttatttcctt ttatcaaaga   5700
aggtaattga tacacaacag gtgacttggt tttaggccca aaggtagcag cagcaacatt   5760
aataatggaa ataattgaat agttagttat gtatgttaat gccagtcacc agcaggctat   5820
ttcaaggtca gaagtaatga ctccatacat attatttatt tctataacta catttaaatc   5880
attaccagg                                                            5889
```

<210> SEQ ID NO 25

-continued

<211> LENGTH: 5765
<212> TYPE: DNA
<213> ORGANISM: Homo sapiens

<400> SEQUENCE: 25

```
tcctaggcgg cggccgcggc ggcggaggca gcagcggcgg cggcagtggc ggcggcgaag     60
gtggcggcgg ctcggccagt actcccggcc cccgccattt cggactggga gcgagcgcgg    120
cgcaggcact gaaggcggcg gcggggccag aggctcagcg gctcccaggt gcgggagaga    180
ggcctgctga aaatgactga atataaactt gtggtagttg gagctggtgg cgtaggcaag    240
agtgccttga cgatacagct aattcagaat cattttgtgg acgaatatga tccaacaata    300
gaggattcct acaggaagca agtagtaatt gatggagaaa cctgtctctt ggatattctc    360
gacacagcag gtcaagagga gtacagtgca atgagggacc agtacatgag gactggggag    420
ggctttcttt gtgtatttgc cataaataat actaaatcat ttgaagatat tcaccattat    480
agagaacaaa ttaaaagagt taaggactct gaagatgtac ctatggtcct agtaggaaat    540
aaatgtgatt tgccttctag aacagtagac acaaaacagg ctcaggactt agcaagaagt    600
tatggaattc cttttattga aacatcagca aagacaagac agggtgttga tgatgccttc    660
tatacattag ttcgagaaat tcgaaaacat aaagaaaaga tgagcaaaga tggtaaaaag    720
aagaaaaaga agtcaaagac aaagtgtgta attatgtaaa tacaatttgt actttttttct    780
taaggcatac tagtacaagt ggtaattttt gtacattaca ctaaattatt agcatttgtt    840
ttagcattac ctaatttttt tcctgctcca tgcagactgt tagcttttac cttaaatgct    900
tattttaaaa tgacagtgga agttttttt tcctctaagt gccagtattc ccagagtttt    960
ggtttttgaa ctagcaatgc ctgtgaaaaa gaaactgaat acctaagatt tctgtcttgg   1020
ggtttttggt gcatgcagtt gattacttct tatttttctt accaattgtg aatgttggtg   1080
tgaaacaaat taatgaagct tttgaatcat ccctattctg tgttttatct agtcacataa   1140
atggattaat tactaatttc agttgagacc ttctaattgg tttttactga aacattgagg   1200
gaacacaaat ttatgggctt cctgatgatg attcttctag gcatcatgtc ctatagtttg   1260
tcatccctga tgaatgtaaa gttacactgt tcacaaaggt tttgtctcct ttccactgct   1320
attagtcatg gtcactctcc ccaaaatatt atatttttc tataaaaaga aaaaaatgga   1380
aaaaaattac aaggcaatgg aaactattat aaggccattt ccttttcaca ttagataaat   1440
tactataaag actcctaata gcttttcctg ttaaggcaga cccagtatga aatggggatt   1500
attatagcaa ccattttggg gctatattta catgctacta aatttttata ataattgaaa   1560
agattttaac aagtataaaa aattctcata ggaattaaat gtagtctccc tgtgtcagac   1620
tgctctttca tagtataact ttaaatcttt tcttcaactt gagtctttga agatagtttt   1680
aattctgctt gtgacattaa aagattattt gggccagtta tagcttatta ggtgttgaag   1740
agaccaaggt tgcaaggcca ggccctgtgt gaacctttga gctttcatag agagtttcac   1800
agcatggact gtgtccccac ggtcatccag tgttgtcatg cattggttag tcaaaatggg   1860
gagggactag ggcagtttgg atagctcaac aagatacaat ctcactctgt ggtggtcctg   1920
ctgacaaatc aagagcattg cttttgtttc ttaagaaaac aaactctttt ttaaaaatta   1980
cttttaaata ttaactcaaa agttgagatt ttggggtggt ggtgtgccaa gacattaatt   2040
tttttttaa acaatgaagt gaaaaagttt tacaatctct aggtttggct agttctctta   2100
acactggtta aattaacatt gcataaacac ttttcaagtc tgatccatat ttaataatgc   2160
tttaaaataa aaataaaaac aatccttttg ataaatttaa aatgttactt attttaaaat   2220
```

```
aaatgaagtg agatggcatg gtgaggtgaa agtatcactg gactaggaag aaggtgactt   2280
aggttctaga taggtgtctt ttaggactct gattttgagg acatcactta ctatccattt   2340
cttcatgtta aaagaagtca tctcaaactc ttagtttttt tttttacaa ctatgtaatt   2400
tatattccat ttacataagg atacacttat ttgtcaagct cagcacaatc tgtaaatttt   2460
taacctatgt tacaccatct tcagtgccag tcttgggcaa aattgtgcaa gaggtgaagt   2520
ttatatttga atatccattc tcgttttagg actcttcttc catattagtg tcatcttgcc   2580
tccctacctt ccacatgccc catgacttga tgcagtttta atacttgtaa ttcccctaac   2640
cataagattt actgctgctg tggatatctc catgaagttt tcccactgag tcacatcaga   2700
aatgccctac atcttatttc ctcagggctc aagagaatct gacagatacc ataaagggat   2760
ttgacctaat cactaatttt caggtggtgg ctgatgcttt gaacatctct ttgctgccca   2820
atccattagc gacagtagga tttttcaaac ctggtatgaa tagacagaac cctatccagt   2880
ggaaggagaa tttaataaag atagtgctga aagaattcct taggtaatct ataactagga   2940
ctactcctgg taacagtaat acattccatt gttttagtaa ccagaaatct tcatgcaatg   3000
aaaaatactt taattcatga agcttacttt tttttttgg tgtcagagtc tcgctcttgt   3060
cacccaggct ggaatgcagt ggcgccatct cagctcactg caacctccat ctcccaggtt   3120
caagcgattc tcgtgcctcg gcctcctgag tagctgggat tacaggcgtg tgccactaca   3180
ctcaactaat ttttgtattt ttaggagaga cggggtttca ccctgttggc caggctggtc   3240
tcgaactcct gacctcaagt gattcaccca ccttggcctc ataaacctgt tttgcagaac   3300
tcatttattc agcaaatatt tattgagtgc ctaccagatg ccagtcaccg cacaaggcac   3360
tgggtatatg gtatccccaa acaagagaca taatcccggt ccttaggtag tgctagtgtg   3420
gtctgtaata tcttactaag gcctttggta tacgacccag agataacacg atgcgtattt   3480
tagttttgca aagaaggggt ttggtctctg tgccagctct ataattgttt tgctacgatt   3540
ccactgaaac tcttcgatca agctacttta tgtaaatcac ttcattgttt taaaggaata   3600
aacttgatta tattgttttt ttatttggca taactgtgat tcttttagga caattactgt   3660
acacattaag gtgtatgtca gatattcata ttgacccaaa tgtgtaatat tccagttttc   3720
tctgcataag taattaaaat atacttaaaa attaatagtt ttatctgggt acaaataaac   3780
aggtgcctga actagttcac agacaaggaa acttctatgt aaaaatcact atgatttctg   3840
aattgctatg tgaaactaca gatctttgga acactgttta ggtagggtgt taagacttac   3900
acagtacctc gtttctacac agagaaagaa atggccatac ttcaggaact gcagtgctta   3960
tgaggggata tttaggcctc ttgaattttt gatgtagatg ggcatttttt taaggtagtg   4020
gttaattacc tttatgtgaa ctttgaatgg tttaacaaaa gatttgtttt tgtagagatt   4080
ttaaaggggg agaattctag aaataaatgt tacctaatta ttacagcctt aaagacaaaa   4140
atccttgttg aagttttttt aaaaaaagct aaattacata gacttaggca ttaacatgtt   4200
tgtggaagaa tatagcagac gtatattgta tcatttgagt gaatgttccc aagtaggcat   4260
tctaggctct atttaactga gtcacactgc ataggaattt agaacctaac ttttataggt   4320
tatcaaaact gttgtcacca ttgcacaatt ttgtcctaat atatacatag aaactttgtg   4380
gggcatgtta agttacagtt tgcacaagtt catctcattt gtattccatt gattttttt   4440
ttcttctaaa cattttttct tcaaacagta tataactttt tttaggggat ttttttttag   4500
acagcaaaaa ctatctgaag atttccattt gtcaaaaagt aatgatttct tgataattgt   4560
```

-continued

```
gtagtaatgt tttttagaac ccagcagtta ccttaaagct gaatttatat ttagtaactt   4620

ctgtgttaat actggatagc atgaattctg cattgagaaa ctgaatagct gtcataaaat   4680

gaaactttct ttctaaagaa agatactcac atgagttctt gaagaatagt cataactaga   4740

ttaagatctg tgttttagtt taatagtttg aagtgcctgt ttgggataat gataggtaat   4800

ttagatgaat ttaggggaaa aaaaagttat ctgcagatat gttgagggcc catctctccc   4860

cccacacccc cacagagcta actgggttac agtgttttat ccgaaagttt ccaattccac   4920

tgtcttgtgt tttcatgttg aaaatacttt tgcatttttc ctttgagtgc caatttctta   4980

ctagtactat ttcttaatgt aacatgttta cctggaatgt attttaacta tttttgtata   5040

gtgtaaactg aaacatgcac attttgtaca ttgtgctttc ttttgtggga catatgcagt   5100

gtgatccagt tgttttccat catttggttg cgctgaccta ggaatgttgg tcatatcaaa   5160

cattaaaaat gaccactctt ttaattgaaa ttaactttta aatgtttata ggagtatgtg   5220

ctgtgaagtg atctaaaatt tgtaatattt ttgtcatgaa ctgtactact cctaattatt   5280

gtaatgtaat aaaaatagtt acagtgacta tgagtgtgta tttattcatg aaatttgaac   5340

tgtttgcccc gaaatggata tggaatactt tataagccat agacactata gtataccagt   5400

gaatctttta tgcagcttgt tagaagtatc ctttatttct aaaaggtgct gtggatatta   5460

tgtaaaggcg tgtttgctta aacttaaaac catatttaga agtagatgca aaacaaatct   5520

gcctttatga caaaaaaata ggataacatt atttatttat ttccttttat caaagaaggt   5580

aattgataca caacaggtga cttggtttta ggcccaaagg tagcagcagc aacattaata   5640

atggaaataa ttgaatagtt agttatgtat gttaatgcca gtcaccagca ggctatttca   5700

aggtcagaag taatgactcc atacatatta tttatttcta taactacatt taaatcatta   5760

ccagg                                                               5765
```

```
<210> SEQ ID NO 26
<211> LENGTH: 189
<212> TYPE: PRT
<213> ORGANISM: Homo sapiens

<400> SEQUENCE: 26

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Arg Val Glu Asp Ala Phe Tyr Thr Leu Val
145                 150                 155                 160
```

```
Arg Glu Ile Arg Gln Tyr Arg Leu Lys Lys Ile Ser Lys Glu Glu Lys
                165                 170                 175

Thr Pro Gly Cys Val Lys Ile Lys Lys Cys Ile Ile Met
            180                 185


<210> SEQ ID NO 27
<211> LENGTH: 188
<212> TYPE: PRT
<213> ORGANISM: Homo sapiens

<400> SEQUENCE: 27

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
            180                 185


<210> SEQ ID NO 28
<211> LENGTH: 4670
<212> TYPE: DNA
<213> ORGANISM: Mus musculus

<400> SEQUENCE: 28

aggcggcggc cgcggcggct gaggcggcag cgctgtggcg gcggctgaga cggcagggga      60

aggcggcggc ggctcggccc ggagtcccgc tcccgcgcca tttcggaccc ggagcgagcg     120

cggcgcgggc ctgaaggcgg cggcgggagc ctgaggcgcg gcggctccgc ggcgcggaga     180

gaggcctgct gaaaatgact gagtataaac ttgtggtggt tggagctggt ggcgtaggca     240

agagcgcctt gacgatacag ctaattcaga atcactttgt ggatgagtat gaccctacga     300

tagaggactc ctacaggaaa caagtagtaa ttgatggaga aacctgtctc ttggatattc     360

tcgacacagc aggtcaagag gagtacagtg caatgaggga ccagtacatg agaactgggg     420

agggctttct ttgtgtattt gccataaata atactaaatc atttgaagat attcaccatt     480

atagagaaca aattaaaaga gtaaaggact ctgaagatgt gcctatggtc ctggtaggga     540

ataagtgtga tttgccttct agaacagtag acacgaaaca ggctcaggag ttagcaagga     600
```

-continued

```
gttacgggat tccgttcatt gagacctcag caaagacaag acagggtgtt gacgatgcct    660
tctatacatt agtccgagaa attcgaaaac ataaagaaaa gatgagcaaa gatgggaaga    720
agaagaagaa gaagtcaagg acaaggtgta cagttatgtg aatactttgt actctttctt    780
aaggcacact taagtaaaag tgtgattttt gtacattaca ctaaattatt agcatttgtt    840
ttagcattac ctaatctttt tttttcttct gttcgtgcaa actgtcagct tttatctcaa    900
atgcttattt taaaagaaca gtggaaacct tctttttttct aagtgccagt attccctggg    960
ttttggactt aaactagcaa tgcctgtgga agagactaaa gacctgagac tctgtcttgg   1020
gatttggtgc atgcagttga ttccttgcta gttctcttac caactgtgaa cactgatggg   1080
aagcaggata atgaagcttc cggaccatcc ctgctctgtg tccatctact catccaatgg   1140
agtcattagc agtcaatcgc cgcttcactg gacactgagg ggtcacagac ttaggctccc   1200
tttgagtcgc gtccagcgtg tcctagactt tatcatcttt cagaggcgta ggcagactgt   1260
tcacaaaggc tttctgtagc tttccactgc aattaatctt ggtcactccc tcaaatagta   1320
tattttttct agaaaagggg aaaaatggaa aaaaaaaggc aatggaaaat gttgaaatcc   1380
attcagtttc catgttagct aaattactgt aagattccta taatagcttt tcctggtaag   1440
gcagacccag tatgaaatag taataaccat ttgggctata tttacatgct actaaatttt   1500
tgtaataatt caaacaactt tagcatatat aaaaagttct cataagaatt aagtacaatt   1560
cccctttgtc agattgttct tatcctaact ttcaagtctt ttttgaattt ctgttgttga   1620
aagtagtttt aatggttgtg aagctgaaga tgatctgaga cagttatagc ttggcaggtg   1680
ttgaggagac cagagttgca gggttgggcc ttacgtgaac ctgtgacgaa cgctactggg   1740
ttttgcagca ctgctgcatt caatgttggc gacgcattgt ttggtcaaca taggggataa   1800
ggagactttg atggcttagt ataatgcatt ctcaccatgt aacagtccta ctgacaaatc   1860
aagaaatttg tttataataa taaaaaattt ttaaaaattt cgatgttcgc ttcaaggttg   1920
agattttggg gtaggaggct acaacaagag taaatcttaa agcaaggttt taagaaggtt   1980
tgaaaatgca ggtttgacta gtctctcaac tctagctaaa caaacattcc caagtacttc   2040
ccaaatctga taggtattta aaattatcta atgctttaag aatagttaac aggaaaaaaa   2100
tctcctcagt gcacttaaag caacccttca catcatttga aatgagatgg aaatatcact   2160
ggactatgag gactggatgt ctgtctgatt ttaagcaaat cactgtctgc ttggttttga   2220
atcatctcaa agacattaac ctcccagccg tgtaacatag tttacatgtt gacacaccta   2280
gttatcaagc tcagcacaat ctgtaactgt tttacatgga ttaacatctt cactgccagt   2340
cttgggcaaa ttgtgcaaga ggtaaaattt atatttcagt atccattctc ccatttcagg   2400
actcccctcc aacattatgc tggctttcag cctgtctctc acctgcccat cacttagtgt   2460
agttttaata atttccccca cttcaaactt tgtttccact atggacaact tcatgaactt   2520
tgcccactaa ggtaggtaca tcaaagctgc cctatggctt tcttccccgg gactgaaaat   2580
aacagacacc atagtgggat ttaaactaat agatggtttt cagggccact acaacaattc   2640
aatctcaatc ctttggactt cattcctgct gcccaggcca ctggtgcctc agtaggaatt   2700
ttcaaaatta gtgtgaacag acagagcaca gtccagtgga aggtgagctt aatcttcatc   2760
tagccatcat catggtaagt gatagattct attgttttaa taaatacagt ctaacaatga   2820
aaaacacttc gaagtttcaa tcataaagct gtctttttaa aaattttatt tactcaacat   2880
ttattcagtg cttgtcatat tctgggaatt acactaggca ctcagggtgc ggtgtcctca   2940
atccttggcc agtggtatgt agcatgatct gtaataccac taaataaggc atatagcata   3000
```

-continued

```
tgacttagac ataatgaaat acatgatttg agttttgcag agaggagttt gggtttgtac   3060
attcccttcc cccccagttt agcaagaatt gtttgctgtg aatccaatgc aacttttaaa   3120
tcaaactact ttatataatt atttcatttt tctaaaggaa cagaagtacc ctaaactatt   3180
tttttgaaat gttctaaact gtacatattc atagaacatt ctttgggtga attttaagtc   3240
ttaaaatgca attagtaata cttctcattt ctattcagag gaacaggtgt acttcaaaag   3300
ctgcagtgta taatcagata tttttaatgg acaatgtgtt aaagaagtgg taattaccac   3360
tatgtaaatt tgaattgtgt tacactttgg ttaacaaaag gggaaagaat cctagaaaca   3420
aatatgttat ctagttactg cagccttaaa gtccttgttg aagttaaaaa gcaatgctaa   3480
gttacagtca taggcattaa catgtttatg ggaaggatat agtaggcaaa tacaatttga   3540
gtaaatattt tcagtaggga attttaggct ctactgactg agtcacactg cataggaatt   3600
tagatcttaa cttttatagg ttatcgacct ttgccaccat tgcacaattt tgtcctaaca   3660
taaatacaag ttctgtgagg catgtcaaaa gttacagttt gcataaattc atctcatttt   3720
gtattccact gattttacat tttcctcaaa catacataca tacatacata caacacacac   3780
acactcacac atgaagggtt tttttttgt aggcaataaa aatttaacta atttccattt   3840
gttaaaaagt agtgatttat tgagaattat gcagtcattt tttaaaccca aaagttattt   3900
aaaggtgaat ttatactcaa taacttctgt gtaatactgg gtagcatgaa ttctgcattg   3960
aaaaattgaa cagataatac caatagctgt aaattctgtc aaaacatgaa aattatttct   4020
aaagaagtac attagttttc aaagaacagt tattagaatc agatctgtgg tttagttcaa   4080
taatttgaag tgcctgtttg ggatggtggt aggcatttta gatgaatttg ggaaaaataa   4140
agttctgcag aaatgccagt ttcagacccc gctaacccgc tgagtgggct gtgtgctgtg   4200
ttagctccag tgccccaatc ccgtttcatg tcttcatgtt gaaacacttc tgcattttta   4260
tttgagtgcc aatttcttac tagtgctatt tcttagtgta acatgtttac ctgggatgta   4320
ttttaactat ttttgtatag tgtaaactga aacatgcaca ttttgtacat tgtgctttcc   4380
ttctttccat tccttttctt tctgttttgt ttgtttgttt gtttgtttgt ttgttatggg   4440
acatatgcag tgtgatccag ttgttttcca tcctttggtt gcgctgacct agggaatgtt   4500
ggtcatatca aacattaaat ttaaaagtga ccactcttaa ttaaaattaa cttttaaatg   4560
tttataggag tacgtgctgt gaagtgatct gaaatttgta atatttttgt catgaaccgt   4620
actgctccta atcattgtaa tgtaataaaa atagttatgg tgactatgaa             4670
```

<210> SEQ ID NO 29
<211> LENGTH: 188
<212> TYPE: PRT
<213> ORGANISM: Mus musculus

<400> SEQUENCE: 29

```
Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80
```

-continued

```
Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Glu Leu Ala Arg Ser Tyr Gly Ile Pro Phe Ile Glu Thr
    130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Arg Thr Arg Cys Thr Val Met
            180                 185
```

<210> SEQ ID NO 30
<211> LENGTH: 661
<212> TYPE: DNA
<213> ORGANISM: Rattus norvegicus

<400> SEQUENCE: 30

```
atgactgagt ataaacttgt ggtagttgga gctggtggcg taggcaagag tgccttgacg     60

atacagctaa ttcagaatca ctttgtggat gaatatgatc ctacgataga ggactcctac    120

aggaaacaag tagtaattga tggagaaacc tgtctcttgg atattctcga cacagcaggt    180

caagaggagt acagtgcaat gagggaccag tacatgagaa ctggggaggg ctttctttgt    240

gtatttgcca taaataatac taaatcattt gaagatattc accattatag agaacaaatt    300

aaaagagtaa aggactctga agatgtgcct atggtcctag tagggaataa gtgtgacttg    360

ccttctagaa cagtagacac gaaacaggct caggagttag caaggagtta tgggattcca    420

ttcattgaga cctcagcgaa gacaagacag ggtgttgacg atgccttcta tacattagtc    480

cgagaaattc gaaaacataa agaaaagatg agcaaagatg ggaaaaagaa gaagaagaag    540

tcaaggacaa ggtgtatagt catgtgaata gtttgtactc tttcttaagg cacacttaag    600

taaagtgtga tttttgtaca ttacactaaa ttattagcat ttgttttagc attacctaat    660

c                                                                    661
```

<210> SEQ ID NO 31
<211> LENGTH: 188
<212> TYPE: PRT
<213> ORGANISM: Rattus norvegicus

<400> SEQUENCE: 31

```
Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95
```

-continued

Arg Glu Gln Ile Lys Arg Val Lys Asp Ser Glu Asp Val Pro Met Val
100 105 110

Leu Val Gly Asn Lys Cys Asp Leu Pro Ser Arg Thr Val Asp Thr Lys
115 120 125

Gln Ala Gln Glu Leu Ala Arg Ser Tyr Gly Ile Pro Phe Ile Glu Thr
130 135 140

Ser Ala Lys Thr Arg Gln Gly Val Asp Asp Ala Phe Tyr Thr Leu Val
145 150 155 160

Arg Glu Ile Arg Lys His Lys Glu Lys Met Ser Lys Asp Gly Lys Lys
165 170 175

Lys Lys Lys Lys Ser Arg Thr Arg Cys Ile Val Met
180 185

<210> SEQ ID NO 32
<211> LENGTH: 4993
<212> TYPE: DNA
<213> ORGANISM: Canis lupus familiaris

<400> SEQUENCE: 32
gctgaaaatg actgaatata aacttgtggt agttggagct ggtggcgtag gcaagagtgc 60
cttgacgata cagctaattc agaatcactt tgtggatgaa tatgatccta caatagagga 120
ttcctacagg aaacaagtag taattgatgg agaaacctgt ctcttggata ttctcgacac 180
agcaggtcaa gaggagtaca gtgcaatgag ggaccagtac atgaggactg ggagggctt 240 tctttgtgta tttgccataa ataatactaa atcatttgaa gatattcacc attatagaga 300
acaaattaaa agagttaaag actctgaaga tgtacctatg gtcctagtag gaaataaatg 360
tgatttgcct tctagaacag tagacacaaa acaggctcag gacttagcaa gaagttatgg 420
aattcctttt attgaaacat cagcaaagac aagacagaga gtggaggatg ctttttatac 480
attggtgaga gagatccgac aatacagatt gaaaaaaatc aacaaagaag aaaagactcc 540
tggctgtgtg aaaattaaaa aatgcattgt aatgggtgtt gacgatgcct tctatacatt 600
agttcgagaa attcgaaaac ataaagaaaa gatgagcaaa gatggtaaaa agaagaaaaa 660
gaagtcaaag acaaagtgta taattatgta aatacaattt gtactttttt cttaaggcat 720
acttaagtaa aagtggtaat ttttgtacat tacactaaat tattagcatt tgttttagca 780
ttacctaatt ttctgctcca tccaaactgt tagcttttat cttgaatgct tattttaaaa 840
tgacagtgga aactttttcc tctaagtgcc agtattccct gagttttggt tttgaactag 900
caatgcctgt gaaaaagaaa ctgaatacct gagatttctg tcttggggtt tttggtgcat 960
gcagttgatt acttcctatt tttcttacca attgtgaact ttggtgtgaa acaaattaat 1020
gaagctttcg aatcatccct attctgtgtt ttacctagtc acatacatgg attaattact 1080
aattataact tcagttgata tttcatgatt ggttttactg aaacattgag ggaacatgaa 1140
tttatgggct gcttcttata ggtataatgt cctatagttt cagtcaccct taatgaatgt 1200
aaagctacac tgttcacaaa ggttttctcc atcttttcac tgctatttgt catagccacg 1260
ctcccaaaaa tattatattt tttctataaa aaagggaaaa aatagaaaaa aatacaaggc 1320
aatggaaaat attaaaaggc atttactttc catattagat aaattcctat aatactctga 1380
atagcttttc ctgttaaggc agacccagta tgtaatgagg attatagcaa ccattttggg 1440
gctatattta catgctacta aatttttgta ttaattgaaa aagttttaac atgtataaaa 1500
aattcccata ggaattaaat atagtctccc tgtgtcagat tgctctttct tagcataact 1560

-continued

```
ttaaatcttt tcttgatctt caatcttaga aaatagtttt aattcttgta gtgatgttaa   1620
agattatttg ggccagttag tttttaatag atgttaaaga gaccacagtt ccaaggccag   1680
gccttgtgtg aacctttaag cttcattaag agtttcatag tacagactgc atccctgtgg   1740
tctcccaggg tcatcatgca ttgattgggt ggtcaaaagt ggggacaaag agtgtttaga   1800
taagatgcat cctcactgta tggtggtcct gctgacagat caggaccatc acttttgttt   1860
tttaaaaaac caacagagct ttttaaaaac attatttaaa atgagatttt tgggggcagg   1920
gggtggcaag acttgaattt tttttaaaca atgaagtaaa aaggtttcaa aatctctagt   1980
gttggctagt tctcaacatt ggctaaagta acatttcata aacactttac aagtattggt   2040
ccatatttaa gaatatctaa tgcttaaata atagattaat aacaattctt tcagtgcatt   2100
taaaatgtat ttttaaatat ctgaagtgag atggtgtgtt gaggtgaaaa tatcactgga   2160
ctaggaggaa ggtgacttag attctagtta cgtgtctttt acaacttcag ttttgggcaa   2220
atcactcact atccatttct tcatgttaag tcatctcaaa ggctatatct agcatcaact   2280
atgtgattta cattcagttt acataaggat atacctattt gtcaatctca gcacaatctg   2340
taacttttta cctatgttct cttcagcgcc agtcttaggc aaagttgtgc aagaggtgag   2400
gtttattttt gagaatctga tctccggtag caggtactcc tctcccatgt tagtgtcatc   2460
ttgcctgcct accttctaca tgccccatga cttgatgctt tctaattccc cgaacctcaa   2520
gatgtagtgc tgctttggat atctccatga ggtaataagt cacattagtc aggctcaaca   2580
taatctgaca gatactgtag tgggatttga tctaatagct aattttcagg tggtaactgt   2640
atcaatttaa ttttgatctt ttgaacatca tctctgctac ctggtccatt agtgactaag   2700
taggaaaagt aggaatttc atatctgtga tgtgtagaca gaccctatcc agtagaagaa    2760
tttaataaat ttaattaata aatactgaaa gatttcctta gataatccaa aactaggact   2820
agccctggta acggtgatac attccattat tttaataagt aaaatcttct tacaatgaaa   2880
aatactttaa aatttaattc ataaagctta ctttttagca gaattcattt attcaacaaa   2940
tacttgagtg cctgctagat gccaggttct acacaaggca ccggggatat tatggtattc   3000
ccaacaaggg acataatccc tatccttaag tagtactgtt attttagagt ggtctgtagt   3060
atattagtga ggcatttggc acatgaccca gagataatat aatgcatatt ttagttttgc   3120
acagaaggga tatggtctct aaggtttttt ccagctctaa aataattgtt cgctctgatt   3180
ccaataaact gtttaatcaa gctactttat ataaatcact ttacttcatt attttaaaga   3240
agtaaacttg actatattgt tttttatttg ggataattat gtgattctgt tgggatactt   3300
atatagtaca cattaaattg tatgtcagat gataacatta aaattcccaa gtgtaatatt   3360
ctacttggtc tctgtgtatc ataattaaaa tagatttaaa tattgagttc aaaaatagtt   3420
ttatttatct gggtgtgaat aaacagatgc ctgaactaat tcacagaaaa ggaaacttct   3480
gtgtaaaaag tcagtccaat ttctgaaatg ctatgctaaa ctacaggttt atggaacatt   3540
agatagggtg ttaagacttt atatagtact tcctcttgtt tctatacaag agaaagaaat   3600
ggccatactt caggaattgc agtgcataac tgagggattt ttaggactct tgaatttttg   3660
atgtagccgg gcaacttttt ttaggcagtg gtaattatcc tttattatgt gaattttgaa   3720
tggtttgaca aaacgtttgt ttttgtagag attttaaaag gggagcgcta atcctagaaa   3780
taaatattat gtaattatta cggccttaaa gataaaaatc cttgttgaaa gttgaaaaaa   3840
attgctaaat tacatagtct tagacattaa catgtttgtg gaagaatgta gcagaggtat   3900
gtagtataat ttgagtgaat attcccaatt aggaattcta ggctctagtt taactgagtc   3960
```

acactgcata ggaatttaga acctaacttc taggttatca aaatctttgc caccattgca 4020
caattttgtc ctaatatata gagaaacttt gtgaggcatg ttcagttgcg gtttgcacaa 4080
gttcatctca tttgtattcc agtgattttt tttcttctaa ccattttttt aaacaacatg 4140
tacacattgt ttttttggt aggcaatgaa aactgtcatt tccattgtca aacagtaatt 4200
cctcgataac tgtattaatg gtttttaaaa aaccatcagt tactttaaaa ctgaatttat 4260
atttaataac ttctgtatta gtattgggta gcatgaaatc tctattgaga aattgaacag 4320
catacaacta gtagctgtaa attccttcag aaagtgaaaa ttatttcttc ctaaagatat 4380
cttgacatca gtgcttgaag aatagtcata actagattaa taattgtttt agttaaacag 4440
ttttaagtgc ctgtttcaga tgatgatagg caatttagat gaatttagga aaaatcaaag 4500
tttttacttg cagaaatgtc cattataggg ggcccccctc ctcatagagc tgaatgggtt 4560
atgtaatgtt ttatccaaaa gtttccaatt ccactgtctt gtgttttcat gttgaaaata 4620
cttttgcatt tttcctttga gtgccaattt cttactagta ctatttctta atgtaacatg 4680
tttacctgga atgtatttta actatttttg tatagtgtaa actgaaacat gcacattttg 4740
tacattgtgc tttttttgt gggacatatg cagtgtgatc cagttgtttt ccatcatttg 4800
gttgcgctga cctaggaatg ttggtcatat caaacattaa atttaaaaat gaccactctt 4860
ttaattaaaa ttaactttta aatgtttata ggagtatgtg ctgtgaagtg atctgaaatt 4920
tgtaatattt ttgtcatgaa ctgtactgct cctaattatt gtaatgtaat aaaaatagtt 4980
atggtgacta tga 4993

<210> SEQ ID NO 33
<211> LENGTH: 4876
<212> TYPE: DNA
<213> ORGANISM: Canis lupus familiaris

<400> SEQUENCE: 33
gctgaaaatg actgaatata aacttgtggt agttggagct ggtggcgtag gcaagagtgc 60
cttgacgata cagctaattc agaatcactt tgtggatgaa tatgatccta caatagagga 120
ttcctacagg aaacaagtag taattgatgg agaaacctgt ctcttggata ttctcgacac 180
agcaggtcaa gaggagtaca gtgcaatgag ggaccagtac atgaggactg gggagggctt 240
tctttgtgta tttgccataa ataatactaa atcatttgaa gatattcacc attatagaga 300
acaaattaaa agagttaaag actctgaaga tgtacctatg gtcctagtag gaaataaatg 360
tgatttgcct tctagaacag tagacacaaa acaggctcag gacttagcaa gaagttatgg 420
aattcctttt attgaaacat cagcaaagac aagacagggt gttgacgatg ccttctatac 480
attagttcga gaaattcgaa aacataaaga aaagatgagc aaagatggta aaaagaagaa 540
aaagaagtca aagacaaagt gtataattat gtaaatacaa tttgtacttt tttcttaagg 600
catacttaag taaaagtggt aatttttgta cattacacta aattattagc atttgtttta 660
gcattaccta attttctgct ccatccaaac tgttagcttt tatcttgaat gcttatttta 720
aaatgacagt ggaaactttt tcctctaagt gccagtattc cctgagtttt ggttttgaac 780
tagcaatgcc tgtgaaaaag aaactgaata cctgagattt ctgtcttggg gtttttggtg 840
catgcagttg attacttcct atttttctta ccaattgtga actttggtgt gaaacaaatt 900
aatgaagctt tcgaatcatc cctattctgt gttttaccta gtcacataca tggattaatt 960
actaattata acttcagttg atatttcatg attggtttta ctgaaacatt gagggaacat 1020

-continued

```
gaatttatgg gctgcttctt ataggtataa tgtcctatag tttcagtcac ccttaatgaa   1080
tgtaaagcta cactgttcac aaaggttttc tccatctttt cactgctatt tgtcatagcc   1140
acgctcccaa aaatattata ttttttctat aaaaaaggga aaaaatagaa aaaaatacaa   1200
ggcaatggaa aatattaaaa ggcatttact ttccatatta gataaattcc tataatactc   1260
tgaatagctt ttcctgttaa ggcagaccca gtatgtaatg aggattatag caaccatttt   1320
ggggctatat ttacatgcta ctaaattttt gtattaattg aaaaagtttt aacatgtata   1380
aaaaattccc ataggaatta aatatagtct ccctgtgtca gattgctctt tcttagcata   1440
actttaaatc ttttcttgat cttcaatctt agaaaatagt tttaattctt gtagtgatgt   1500
taaagattat ttgggccagt tagtttttaa tagatgttaa agagaccaca gttccaaggc   1560
caggccttgt gtgaaccttt aagcttcatt aagagtttca tagtacagac tgcatccctg   1620
tggtctccca gggtcatcat gcattgattg ggtggtcaaa agtggggaca aagagtgttt   1680
agataagatg catcctcact gtatggtggt cctgctgaca gatcaggacc atcacttttg   1740
tttttttaaaa aaccaacaga gctttttaaa aacattattt aaaatgagat ttttgggggc   1800
agggggtggc aagacttgaa tttttttttaa acaatgaagt aaaaaggttt caaaatctct   1860
agtgttggct agttctcaac attggctaaa gtaacatttc ataaacactt tacaagtatt   1920
ggtccatatt taagaatatc taatgcttaa ataatagatt aataacaatt ctttcagtgc   1980
atttaaaatg tatttttaaa tatctgaagt gagatggtgt gttgaggtga aaatatcact   2040
ggactaggag gaaggtgact tagattctag ttacgtgtct tttacaactt cagttttggg   2100
caaatcactc actatccatt tcttcatgtt aagtcatctc aaaggctata tctagcatca   2160
actatgtgat ttacattcag tttacataag gatataccta tttgtcaatc tcagcacaat   2220
ctgtaacttt ttacctatgt tctcttcagc gccagtctta ggcaaagttg tgcaagaggt   2280
gaggtttatt tttgagaatc tgatctccgg tagcaggtac tcctctccca tgttagtgtc   2340
atcttgcctg cctaccttct acatgcccca tgacttgatg ctttctaatt ccccgaacct   2400
caagatgtag tgctgctttg gatatctcca tgaggtaata agtcacatta gtcaggctca   2460
acataatctg acagatactg tagtgggatt tgatctaata gctaattttc aggtggtaac   2520
tgtatcaatt taattttgat cttttgaaca tcatctctgc tacctggtcc attagtgact   2580
aagtaggaaa agtaggaatt ttcatatctg tgatgtgtag acagacccta tccagtagaa   2640
gaatttaata aatttaatta ataaatactg aaagatttcc ttagataatc caaaactagg   2700
actagccctg gtaacggtga tacattccat tattttaata agtaaaatct tcttacaatg   2760
aaaaatactt taaaatttaa ttcataaagc ttacttttta gcagaattca tttattcaac   2820
aaatacttga gtgcctgcta gatgccaggt tctacacaag gcaccgggga tattatggta   2880
ttcccaacaa gggacataat ccctatcctt aagtagtact gttattttag agtggtctgt   2940
agtatattag tgaggcattt ggcacatgac ccagagataa tataatgcat attttagttt   3000
tgcacagaag ggatatggtc tctaaggttt tttccagctc taaaataatt gttcgctctg   3060
attccaataa actgtttaat caagctactt tatataaatc actttacttc attattttaa   3120
agaagtaaac ttgactatat tgttttttat ttgggataat tatgtgattc tgttgggata   3180
cttatatagt acacattaaa ttgtatgtca gatgataaca ttaaaattcc caagtgtaat   3240
attctacttg gtctctgtgt atcataatta aaatagattt aaatattgag ttcaaaaata   3300
gttttattta tctgggtgtg aataaacaga tgcctgaact aattcacaga aaaggaaact   3360
tctgtgtaaa aagtcagtcc aatttctgaa atgctatgct aaactacagg tttatggaac   3420
```

-continued

```
attagatagg gtgttaagac tttatatagt acttcctctt gtttctatac aagagaaaga   3480

aatggccata cttcaggaat tgcagtgcat aactgaggga tttttaggac tcttgaattt   3540

ttgatgtagc cgggcaactt tttttaggca gtggtaatta tcctttatta tgtgaatttt   3600

gaatggtttg acaaaacgtt tgtttttgta gagattttaa aaggggagcg ctaatcctag   3660

aaataaatat tatgtaatta ttacggcctt aaagataaaa atccttgttg aaagttgaaa   3720

aaaattgcta aattacatag tcttagacat taacatgttt gtggaagaat gtagcagagg   3780

tatgtagtat aatttgagtg aatattccca attaggaatt ctaggctcta gtttaactga   3840

gtcacactgc ataggaattt agaacctaac ttctaggtta tcaaaatctt tgccaccatt   3900

gcacaatttt gtcctaatat atagagaaac tttgtgaggc atgttcagtt gcggtttgca   3960

caagttcatc tcatttgtat tccagtgatt ttttttcttc taaccatttt tttaaacaac   4020

atgtacacat tgtttttttt ggtaggcaat gaaaactgtc atttccattg tcaaacagta   4080

attcctcgat aactgtatta atggttttta aaaaaccatc agttacttta aaactgaatt   4140

tatatttaat aacttctgta ttagtattgg gtagcatgaa atctctattg agaaattgaa   4200

cagcatacaa ctagtagctg taaattcctt cagaaagtga aaattatttc ttcctaaaga   4260

tatcttgaca tcagtgcttg aagaatagtc ataactagat taataattgt tttagttaaa   4320

cagttttaag tgcctgtttc agatgatgat aggcaattta gatgaattta ggaaaaatca   4380

aagtttttac ttgcagaaat gtccattata gggggccccc ctcctcatag agctgaatgg   4440

gttatgtaat gttttatcca aaagtttcca attccactgt cttgtgtttt catgttgaaa   4500

atacttttgc atttttcctt tgagtgccaa tttcttacta gtactatttc ttaatgtaac   4560

atgtttacct ggaatgtatt ttaactattt ttgtatagtg taaactgaaa catgcacatt   4620

ttgtacattg tgcttttttt tgtgggacat atgcagtgtg atccagttgt tttccatcat   4680

ttggttgcgc tgacctagga atgttggtca tatcaaacat taaatttaaa aatgaccact   4740

cttttaatta aaattaactt ttaaatgttt ataggagtat gtgctgtgaa gtgatctgaa   4800

atttgtaata tttttgtcat gaactgtact gctcctaatt attgtaatgt aataaaaata   4860

gttatggtga ctatga                                                   4876
```

<210> SEQ ID NO 34
<211> LENGTH: 227
<212> TYPE: PRT
<213> ORGANISM: Canis lupus familiaris

<400> SEQUENCE: 34

```
Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110
```

```
Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Arg Val Glu Asp Ala Phe Tyr Thr Leu Val
145                 150                 155                 160

Arg Glu Ile Arg Gln Tyr Arg Leu Lys Lys Ile Asn Lys Glu Glu Lys
                165                 170                 175

Thr Pro Gly Cys Val Lys Ile Lys Lys Cys Ile Val Met Gly Val Asp
            180                 185                 190

Asp Ala Phe Tyr Thr Leu Val Arg Glu Ile Arg Lys His Lys Glu Lys
        195                 200                 205

Met Ser Lys Asp Gly Lys Lys Lys Lys Lys Lys Ser Lys Thr Lys Cys
    210                 215                 220

Ile Ile Met
225
```

<210> SEQ ID NO 35
<211> LENGTH: 188
<212> TYPE: PRT
<213> ORGANISM: Canis lupus familiaris

<400> SEQUENCE: 35

```
Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Ile Ile Met
            180                 185
```

<210> SEQ ID NO 36
<211> LENGTH: 1112
<212> TYPE: DNA
<213> ORGANISM: Gallus gallus

<400> SEQUENCE: 36

```
caggtctgct aaaaaatgac agagtataag cttgttgtcg ttggagctgg tggtgtgggc     60
```

-continued

```
aagagcgcct tgacaataca gctcattcag aaccactttg tggatgagta tgaccctacc    120
atagaggatt cctacagaaa gcaagtagta attgatgggg aaacctgtct cttggatatt    180
cttgatacag caggtcaaga agaatatagt gcaatgaggg accaatatat gagaacagga    240
gaaggctttc tgtgtgtttt tgctataaac aatacaaaat cttttgaaga tattcaccat    300
tatagggaac aaataaagag agttaaagac tctgaagatg tcccaatggt gctagtagga    360
aacaaatgtg atttgccttc cagaacagta gatacaaaac aagctcagga tttagcaaga    420
agttatggaa ttccttttat tgaaacatca gcaaagacaa gacagggtgt tgatgatgcc    480
ttctatacat tagttcgaga aatcagaaaa cacaaagaga agatgagcaa agatggtaaa    540
aagaagaaaa agaagacaaa gacaaagtgt ataattatgt aaatacaatg tatccttatt    600
cttaagacgt actgaagtaa tttttgtaca ttacactaaa ttattagcat ttgtttttag    660
cattacttta ctttctgctt catgatcctg ttagctttac ctgaatgctt gttttaaatg    720
acagtggaaa cttcattcct cttaaagtgc cagtattctt tgagtgttgg ttcttgaact    780
agcaatgcct gtgaagaaaa ataaaaacaa atgaaaaaaa aaaaaacaca caaaaacctg    840
agaactgtct taggactctt tggtgcatgc acagttgcta acttcctatt tttcttactg    900
attgtgaact tctgttccgt gcgtaaacaa aacaatgaaa cgatctacac gttctaacat    960
ccccccttcat ttgtactctc ttattttta catctggttg ggaaaacgga ccagttagtg   1020
acaaagactt tattttcaga cttccttcta atttcgactg actgcaatat agagagacca   1080
gaagccttta tagtcttcct gtagattttg ct                                 1112
```

```
<210> SEQ ID NO 37
<211> LENGTH: 188
<212> TYPE: PRT
<213> ORGANISM: Gallus gallus

<400> SEQUENCE: 37

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Thr Lys Thr Lys Cys Ile Ile Met
            180                 185
```

<210> SEQ ID NO 38
<211> LENGTH: 2144
<212> TYPE: DNA
<213> ORGANISM: Bos taurus

<400> SEQUENCE: 38
ggcggtggcg gcggcggcgg cggtggcggt ggcggttcgg ccagtactcc cggcccccgc 60
catttctgac tgggagcgag cgcggcgcag gcactgaagg cagcggcggg ggccagaggc 120
tcggcggctc ccaggtgagg gagagaggcc tgctgaaaat gactgaatat aaacttgtgg 180
tagttggagc tggtggcgta ggcaagagtg ccttgacgat acagctaatt cagaatcact 240
ttgtggatga atatgatcct acgatagagg attcctacag gaaacaagta gtaattgatg 300
gagaaacctg tctcttggat attctcgaca cagcaggtca agaggagtac agtgcaatga 360
gggaccagta catgaggact ggggagggct ttctttgtgt atttgccata aataatacta 420
aatcatttga agatattcac cattatagag aacaaataaa aagagttaaa gactctgaag 480
atgtacctat ggttctagta ggaaataaat gtgatttgcc ttctagaaca gtagacacaa 540
aacaggctca ggacttagca agaagttatg gaattccttt tattgaaaca tcagcaaaga 600
caagacaggg tgttgacgat gccttctata cattagttcg agaaattcga aaacataaag 660
aaaagatgag caaagatggt aaaaagaaga aaaagaagtc aaagacaaag tgtataatta 720
tgtaaataca atttgtactt ttttcttaag gcatacttaa gtaaaagtgg taatttttgt 780
atattacact aaattattag catttgtttt agcattatct aattttcttt ctgctccatc 840
catactgtta gcttttatct tgaatgctta ttttaaaatg acagtggaaa ctttttttcct 900 ctaagtgcca gtattccctg cgttttggtt tttgaactag caatgcctgt gaaaaagaaa 960
ctgaacaccc aagatttttg tcttggggtt tttggtgcat gcagttgatt acttcctatt 1020
tttcttatca attgtgaact ttagtgtgaa acaaattaat gaggctttca aatcatccct 1080
attgtattgt tttatctagt cacacacatg gattaattac taattataac ttcagttgag 1140
atttcatgat tggttttact gaaacatcga gggaacatga atttatgggc ttcctatagt 1200
ttcatcttgt aggtatcatt gtcctatagt ttcagttacc cttaatgaat gtcaggttac 1260
actgttcaca aaggttttct tctttccact gctatttgtc aaatggtcac gttccctaaa 1320
atactatatt ttttctataa aaaaaagaaa aaaatggaaa aaaatacaag gcaatggaaa 1380
atattaaaag gccacttact ttccacatta ggtaaattcc tataatgctc tgaatagctt 1440
tttatgttaa ggcagaccca gtaggtaatg aggattagaa caagcatttt gggactatat 1500
ttacatgctt taaatttttg taataacaaa aaaattttaa catgtataaa gaattctcat 1560
aggaattaaa tacagtctcc ctgtgtcaga ttgctctttc ttagcataaa tctttttctt 1620
gaacttcaat ctttaaaagt agttttaatt ctactgatag tgatgtaaaa gattatttgg 1680
gccagttagc ttggtaggtg ttacagagac cagggtggca tagccgggcc ttgtgtgaac 1740
ctttaagcta catggagagt ttcacagtgt ggactgcatc cctgtggtct tccattgttg 1800
ccatgccttg gttggtcaaa aacaaggact tgcagagaga ttgaatagct cagcaaggta 1860
cattctcatt atgtcgtagt cctactcagg aacatcactt ttttaaaata aaaaaccccca 1920 aaaaacagaa cttaaaaaaa aaaacaacat tattttaaat gagattttcg gtggggtgga 1980
aagattttaa tttttttttaa acgatgaaat gaaaaaatgt caaaatcttg agtattggct 2040
agttctcttt aacactggct aaagtaacat ttttgtaaac acttcagtac agtctggtcc 2100
attattaaga atatctaatg cttatacaat aaagtaatgc taac 2144

<210> SEQ ID NO 39
<211> LENGTH: 188
<212> TYPE: PRT
<213> ORGANISM: Bos taurus

<400> SEQUENCE: 39

Met Thr Glu Tyr Lys Leu Val Val Val Gly Ala Gly Gly Val Gly Lys
1 5 10 15

Ser Ala Leu Thr Ile Gln Leu Ile Gln Asn His Phe Val Asp Glu Tyr
20 25 30

Asp Pro Thr Ile Glu Asp Ser Tyr Arg Lys Gln Val Val Ile Asp Gly
35 40 45

Glu Thr Cys Leu Leu Asp Ile Leu Asp Thr Ala Gly Gln Glu Glu Tyr
50 55 60

Ser Ala Met Arg Asp Gln Tyr Met Arg Thr Gly Glu Gly Phe Leu Cys
65 70 75 80

Val Phe Ala Ile Asn Asn Thr Lys Ser Phe Glu Asp Ile His His Tyr
85 90 95

Arg Glu Gln Ile Lys Arg Val Lys Asp Ser Glu Asp Val Pro Met Val
100 105 110

Leu Val Gly Asn Lys Cys Asp Leu Pro Ser Arg Thr Val Asp Thr Lys
115 120 125

Gln Ala Gln Asp Leu Ala Arg Ser Tyr Gly Ile Pro Phe Ile Glu Thr
130 135 140

Ser Ala Lys Thr Arg Gln Gly Val Asp Asp Ala Phe Tyr Thr Leu Val
145 150 155 160

Arg Glu Ile Arg Lys His Lys Glu Lys Met Ser Lys Asp Gly Lys Lys
165 170 175

Lys Lys Lys Lys Ser Lys Thr Lys Cys Ile Ile Met
180 185

<210> SEQ ID NO 40
<211> LENGTH: 4454
<212> TYPE: DNA
<213> ORGANISM: Homo sapiens

<400> SEQUENCE: 40
gaaacgtccc gtgtgggagg ggcgggtctg ggtgcggcct gccgcatgac tcgtggttcg 60
gaggcccacg tggccggggc ggggactcag gcgcctgggg cgccgactga ttacgtagcg 120
ggcggggccg gaagtgccgc tccttggtgg gggctgttca tggcggttcc ggggtctcca 180
acatttttcc cggctgtggt cctaaatctg tccaaagcag aggcagtgga gcttgaggtt 240
cttgctggtg tgaaatgact gagtacaaac tggtggtggt tggagcaggt ggtgttggga 300
aaagcgcact gacaatccag ctaatccaga accactttgt agatgaatat gatcccacca 360
tagaggattc ttacagaaaa caagtggtta tagatggtga aacctgtttg ttggacatac 420
tggatacagc tggacaagaa gagtacagtg ccatgagaga ccaatacatg aggacaggcg 480
aaggcttcct ctgtgtattt gccatcaata atagcaagtc atttgcggat attaacctct 540
acagggagca gattaagcga gtaaaagact cggatgatgt acctatggtg ctagtgggaa 600
acaagtgtga tttgccaaca aggacagttg atacaaaaca agcccacgaa ctggccaaga 660
gttacgggat tccattcatt gaaacctcag ccaagaccag acagggtgtt gaagatgctt 720
tttacacact ggtaagagaa atacgccagt accgaatgaa aaaactcaac agcagtgatg 780

-continued

```
atgggactca gggttgtatg ggattgccat gtgtggtgat gtaacaagat acttttaaag    840
ttttgtcaga aaagagccac tttcaagctg cactgacacc ctggtcctga cttccctgga    900
ggagaagtat tcctgttgct gtcttcagtc tcacagagaa gctcctgcta cttccccagc    960
tctcagtagt ttagtacaat aatctctatt tgagaagttc tcagaataac tacctcctca   1020
cttggctgtc tgaccagaga atgcacctct tgttactccc tgttattttt ctgccctggg   1080
ttcttccaca gcacaaacac acctctgcca ccccaggttt ttcatctgaa aagcagttca   1140
tgtctgaaac agagaaccaa accgcaaacg tgaaattcta ttgaaaacag tgtcttgagc   1200
tctaaagtag caactgctgg tgattttttt tttcttttta ctgttgaact tagaactatg   1260
ctaattttttg gagaaatgtc ataaattact gttttgccaa gaatatagtt attattgctg   1320
tttggtttgt ttataatgtt atcggctcta ttctctaaac tggcatctgc tctagattca   1380
taaatacaaa aatgaatact gaattttgag tctatcctag tcttcacaac tttgacgtaa   1440
ttaaatccaa ctttcacagt gaagtgcctt tttcctagaa gtggtttgta gacttccttt   1500
ataatatttc agtggaatag atgtctcaaa aatccttatg catgaaatga atgtctgaga   1560
tacgtctgtg acttatctac cattgaagga aagctatatc tatttgagag cagatgccat   1620
tttgtacatg tatgaaattg gttttccaga ggcctgtttt ggggctttcc caggagaaag   1680
atgaaactga aagcacatga ataatttcac ttaataattt ttacctaatc tccacttttt   1740
tcataggtta ctacctatac aatgtatgta atttgtttcc cctagcttac tgataaacct   1800
aatattcaat gaacttccat ttgtattcaa atttgtgtca taccagaaag ctctacattt   1860
gcagatgttc aaatattgta aaactttggt gcattgttat ttaatagctg tgatcagtga   1920
ttttcaaacc tcaaatatag tatattaaca aattacattt tcactgtata tcatggtatc   1980
ttaatgatgt atataattgc cttcaatccc cttctcaccc caccctctac agcttccccc   2040
acagcaatag gggcttgatt atttcagttg agtaaagcat ggtgctaatg gaccagggtc   2100
acagtttcaa aacttgaaca atccagttag catcacagag aaagaaattc ttctgcattt   2160
gctcattgca ccagtaactc cagctagtaa ttttgctagg tagctgcagt tagccctgca   2220
aggaaagaag aggtcagtta gcacaaaccc tttaccatga ctggaaaact cagtatcacg   2280
tatttaaaca tttttttttc ttttagccat gtagaaactc taaattaagc caatattctc   2340
atttgagaat gaggatgtct cagctgagaa acgttttaaa ttctctttat tcataatgtt   2400
ctttgaaggg tttaaaacaa gatgttgata aatctaagct gatgagtttg ctcaaaacag   2460
gaagttgaaa ttgttgagac aggaatggaa aatataatta attgatacct atgaggattt   2520
ggaggcttgg cattttaatt tgcagataat accctggtaa ttctcatgaa aaatagactt   2580
ggataacttt tgataaaaga ctaattccaa aatggccact ttgttcctgt ctttaatatc   2640
taaatactta ctgaggtcct ccatcttcta tattatgaat tttcatttat taagcaaatg   2700
tcatattacc ttgaaattca gaagagaaga aacatatact gtgtccagag tataatgaac   2760
ctgcagagtt gtgcttctta ctgctaattc tgggagcttt cacagtactg tcatcatttg   2820
taaatggaaa ttctgctttt ctgtttctgc tccttctgga gcagtgctac tctgtaattt   2880
tcctgaggct tatcacctca gtcatttctt ttttaaatgt ctgtgactgg cagtgattct   2940
ttttcttaaa aatctattaa atttgatgtc aaattaggga gaaagatagt tactcatctt   3000
gggctcttgt gccaatagcc cttgtatgta tgtacttaga gttttccaag tatgttctaa   3060
gcacagaagt ttctaaatgg ggccaaaatt cagacttgag tatgttcttt gaatacctta   3120
```

-continued

```
agaagttaca attagccggg catggtggcc cgtgcctgta gtcccagcta cttgagaggc   3180

tgaggcagga gaatcacttc aacccaggag gtggaggtta cagtgagcag agatcgtgcc   3240

actgcactcc agcctgggtg acaagagaga cttgtctcca aaaaaaaagt tacacctagg   3300

tgtgaatttt ggcacaaagg agtgacaaac ttatagttaa aagctgaata acttcagtgt   3360

ggtataaaac gtggttttta ggctatgttt gtgattgctg aaaagaattc tagtttacct   3420

caaaatcctt ctctttcccc aaattaagtg cctggccagc tgtcataaat tacatattcc   3480

ttttggtttt tttaaaggtt acatgttcaa gagtgaaaat aagatgttct gtctgaaggc   3540

taccatgccg gatctgtaaa tgaacctgtt aaatgctgta tttgctccaa cggcttacta   3600

tagaatgtta cttaatacaa tatcatactt attacaattt ttactatagg agtgtaatag   3660

gtaaaattaa tctctatttt agtgggccca tgtttagtct ttcaccatcc tttaaactgc   3720

tgtgaatttt tttgtcatga cttgaaagca aggatagaga aacactttag agatatgtgg   3780

ggttttttta ccattccaga gcttgtgagc ataatcatat ttgctttata tttatagtca   3840

tgaactccta agttggcagc tacaaccaag aaccaaaaaa tggtgcgttc tgcttcttgt   3900

aattcatctc tgctaataaa ttataagaag caaggaaaat tagggaaaat attttatttg   3960

gatggtttct ataaacaagg gactataatt cttgtacatt atttttcatc tttgctgttt   4020

ctttgagcag tctaatgtgc cacacaatta tctaaggtat ttgttttcta taagaattgt   4080

tttaaaagta ttcttgttac cagagtagtt gtattatatt tcaaaacgta agatgatttt   4140

taaaagcctg agtactgacc taagatggaa ttgtatgaac tctgctctgg agggagggga   4200

ggatgtccgt ggaagttgta agacttttat ttttttgtgc catcaaatat aggtaaaaat   4260

aattgtgcaa ttctgctgtt taaacaggaa ctattggcct ccttggccct aaatggaagg   4320

gccgatattt taagttgatt attttattgt aaattaatcc aacctagttc tttttaattt   4380

ggttgaatgt tttttcttgt taaatgatgt ttaaaaaata aaaactggaa gttcttggct   4440

tagtcataat tctt                                                     4454
```

<210> SEQ ID NO 41
<211> LENGTH: 189
<212> TYPE: PRT
<213> ORGANISM: Homo sapiens

<400> SEQUENCE: 41

```
Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Ser Lys Ser Phe Ala Asp Ile Asn Leu Tyr
                85                  90                  95

Arg Glu Gln Ile Lys Arg Val Lys Asp Ser Asp Asp Val Pro Met Val
            100                 105                 110

Leu Val Gly Asn Lys Cys Asp Leu Pro Thr Arg Thr Val Asp Thr Lys
        115                 120                 125

Gln Ala His Glu Leu Ala Lys Ser Tyr Gly Ile Pro Phe Ile Glu Thr
```

```
    130                 135                 140

Ser Ala Lys Thr Arg Gln Gly Val Glu Asp Ala Phe Tyr Thr Leu Val
145                 150                 155                 160

Arg Glu Ile Arg Gln Tyr Arg Met Lys Lys Leu Asn Ser Ser Asp Asp
                165                 170                 175

Gly Thr Gln Gly Cys Met Gly Leu Pro Cys Val Val Met
            180                 185


<210> SEQ ID NO 42
<211> LENGTH: 4470
<212> TYPE: DNA
<213> ORGANISM: Mus musculus

<400> SEQUENCE: 42

gggactgggg cgccttgggc gcctagtgat tacgtagcgg gtggggccgg aagtgccgct      60

ccctggcggg ggctgttcat ggcggtttcg gggtctccaa cagcttctca ggttgaagtc     120

caaaagcctc ccgaggcggg gtctgcggag tttgaggttt ttgctggtgt gaaatgactg     180

agtacaaact ggtggtggtt ggagcaggtg gtgttgggaa aagcgccttg acgatccagc     240

taatccagaa ccactttgtg gatgaatatg atcccaccat agaggattct taccgaaagc     300

aagtggtgat tgatggtgag acctgcctgc tggacatact ggacacagct ggacaagagg     360

agtacagtgc catgagagac cagtacatga ggacaggcga agggttcctc tgtgtatttg     420

ccatcaataa tagcaaatca tttgcagata ttaacctcta cagggagcaa attaagcgtg     480

tgaaagattc tgatgatgtc cccatggtgc tggtaggcaa caagtgtgac ttgccaacaa     540

ggacagttga cacaaagcaa gcccacgaac tggccaagag ttacggaatt ccattcattg     600

agacctcagc caagacccga cagggtgtgg aggatgcctt ttacacactg gtaagggaga     660

tacgccagta ccgaatgaaa aagctcaaca gcagtgacga tggcactcaa ggttgtatgg     720

ggctgccctg tgtgctgatg tagtaagaca ctttgaaagt tctgtcatca gaaaagagcc     780

actttgaagc tgcactgatg ccctggttct gacatccctg gaggagacct gttcctgctg     840

ctctctgcat ctcagagaag ctcctgcttc ctgcttcccc gactcagtta ctgagcacag     900

ccatctaacc tgagacctct tcagaataac tacctcctca ctcggctgtc tgaccagaga     960

aatagacctg tctctcccgg tcgttctctg ccctgggttc ccctagaaac agacacagcc    1020

tccagctggc tttgtcctct gaaaagcagt ttacattgat gcagagaacc aaactagaca    1080

tgccattctg ttgacaacag tttcttatac tctaaggtaa caactgctgg tgattttccc    1140

ctgcccccaa ctgttgaact tggccttgtt ggtttggggg gaaaatgtca taaattactt    1200

tcttcccaaa atataattag tgttgctgat tgatttgtaa tgtgatcagc tatattccat    1260

aaactggcat ctgctctgta ttcataaatg caaacacgaa tactctcaac tgcatgcaat    1320

taaatccaac attcacaaca aagtgccttt ttcctaaaag tgctctgtag gctccattac    1380

agtttgtaat tggaatagat gtgtcaagaa ccattgtata ggaaagtgac tctgagccat    1440

ctacctttga gggaaaggtg tatgtacctg atggcagatg ctttgtgtat gcacatgaag    1500

atagtttccc tgtctgggat tctcccagga gaaagatgga actgaaacaa ttacaagtaa    1560

tttcatttaa ttctagctaa tctttttttt ttttttttt tttttggta gactatcacc    1620

tataaatatt tggaatatct tctagcttac tgataatcta ataattaatg agcttccatt    1680

ataatgaatt ggttcatacc aggaagccct ccatttatag tatagatact gtaaaaattg    1740

gcatgttgtt actttatagc tgtgattaat gattcctcag accttgctga gatatagtta    1800
```

-continued

```
ttagcagaca ggttatatct ttgctgcata gtttcttcat ggaatatata tctatctgta   1860
tgtggagaga acgtggccct cagttccctt ctcagcatcc ctcatctctc agcctagaga   1920
agttcgagca tcctagaggg gcttgaacag ttatctcggt taaaccatgg tgctaatgga   1980
ccgggtcatg gtttcaaaac ttgaacaagc cagttagcat cacagagaaa cagtccatcc   2040
atatttgctc cctgcctatt attcctgctt acagactttt gcctgatgcc tgctgttagt   2100
gctacaagga taaagcttgt gtggttctca ccaggactgg aagtacctgg tgagctctgg   2160
ggtaagccta gatatcttta cattttcaga cccttattct tagccacgtg gaaactgaag   2220
ccagagtcca tacctccatc tccttccccc cccaaaaaaa ttagattaat gttctttata   2280
tagcttttt aaagtattta aaacatgtct ataagttagg ctgccaacta acaaaagctg   2340
atgtgtttgt tcaaataaag aggtatcctt cgctactcga gagaagaatg taaaatgcca   2400
ttgattgttg tcacttggag gcttgatgtt tgccctgata attcattagt gggttttgtt   2460
tgtcacatga tacctaagat gtaactcagc tcagtaattc taatgaaaac ataaattgga   2520
taccttaatt gaaaaaagca aacctaattc caaaatggcc attttctctt ctgatcttgt   2580
aatacctaaa attctgaggt ccttgggatt cttttgttta taacaggatc ttgctgtgta   2640
gtcctagctg gcctcaaact cacaatactc ttcctggatc aatctcccaa gtgctgggat   2700
tacaggcaca ttccaccaca cacacctgac tgagctcgtt cctaatgagt tttcattaag   2760
caaattcccc atcaccttga aactaatcag aagggggaag aaacatttgc tatgctcctg   2820
agtgctaaca ctgggatcat tcacatgggg tttgcattcc taggcaaact aaactgctgc   2880
cttttacaac aaggctcagt catcttcctg aagctgctga gaccagcact tggtcttgtt   2940
ttgttttaat atgtctatat gactggtggt ggatccctaa atagtttatt aattaaactc   3000
cagttaagga gaaagttact caccttgacc cgtttgacca tatcccgtgt gtgtgtgtgt   3060
gtgtgtgtgt gtgtgtgtgt gtgtgtgtgt gtgcacgcgt atgtacgtac gtatgtatgt   3120
aggtatgtag gtggtttcca gtataaacac agaaacaaat ggagccaatt caggtttcag   3180
atgcccttac taacatatat tcccacgggg tgtgggtttt ggcacaacag tgacaaactt   3240
aaaagccaag taagagccgg gcgtggtggc gcacgccttt aatcccagca cttgggaggc   3300
agaggcaggc ggatttctga gttctaggcc atcctggtct acagtgagtt ccaggacagc   3360
cagtgctaca cagagaaacc ctgtctcgaa aagccaaaaa aaaaaaaaaa aaaaaaaaaa   3420
aaaagccaag taggtccagt tggtatagta tcaaagtgtt tttagagtaa ttagtgaagg   3480
tctgctttac ctcaaagttg cagagcctct cttcctgagt ttaagtgcct ggccggcagt   3540
cacaaattaa catgttgctg taaggcagtt agttgaagct ttgttcacac attggagagt   3600
atgaaaataa agtgttctaa gagcgctgat actggatctg tgtaaacctg gtaaatgccg   3660
tttgtccagg acttagcgtg tgtgagttgg tagctcagta cgagtttact agttccgcag   3720
tgtgtacaat ggaggcgggt ttgttttagc tggccacctg tagaatcagc ctttaaactg   3780
ctgtgaactt tgtcatgact tgaatatgaa gatagacaaa aactctgtaa agacaaatgt   3840
ttgttttccc ccttacagaa cgtgtgagct tggttttatc ttcctttgta tttagtcata   3900
acctctcaag ctggcagctc cgaccaagga tcagaagctg tgtgcgttcc acctggtgga   3960
attagctcag ctctatatga gaagtggagt taatggaaaa cgtgttgact gggtggtttc   4020
tatttaaaag agtgatgata attcttgaac agtagttttt attttgctat ttctttaagc   4080
tgactgatgt gccacaaaat tattttaagg tatttgtgtt ttaagagtgt tctcatgaga   4140
ttagttgtag atatttttta aaatacaact ggtttttaaa atctgagtat tgctctaagc   4200
```

```
aagtgtttag actcttacgg gaaggtgggt ggaagttgtt tggcttccgt atttccatgc   4260

gtgccgtcag acataggtca gaacgccaac tgtgcatcct gctgtttaaa gacctcttgg   4320

cctctgtgac cctcatgaag ggctgatat tttaagttga ctgtttgatt gtaaattaat   4380

cctttctaat ttttaaagac ttgcttgact gttttccttg ttaaataatt ttaaaaaaat   4440

aaaaaactgg aagttctttg cttaactgta                                  4470


<210> SEQ ID NO 43
<211> LENGTH: 189
<212> TYPE: PRT
<213> ORGANISM: Mus musculus

<400> SEQUENCE: 43

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Ser Lys Ser Phe Ala Asp Ile Asn Leu Tyr
                85                  90                  95

Arg Glu Gln Ile Lys Arg Val Lys Asp Ser Asp Asp Val Pro Met Val
            100                 105                 110

Leu Val Gly Asn Lys Cys Asp Leu Pro Thr Arg Thr Val Asp Thr Lys
        115                 120                 125

Gln Ala His Glu Leu Ala Lys Ser Tyr Gly Ile Pro Phe Ile Glu Thr
    130                 135                 140

Ser Ala Lys Thr Arg Gln Gly Val Glu Asp Ala Phe Tyr Thr Leu Val
145                 150                 155                 160

Arg Glu Ile Arg Gln Tyr Arg Met Lys Lys Leu Asn Ser Ser Asp Asp
                165                 170                 175

Gly Thr Gln Gly Cys Met Gly Leu Pro Cys Val Leu Met
            180                 185


<210> SEQ ID NO 44
<211> LENGTH: 1326
<212> TYPE: DNA
<213> ORGANISM: Rattus norvegicus

<400> SEQUENCE: 44

gccgttcatg gcggtttcgg ggtctccaac agcttctcag gttgaaatcc aaaagcctcc     60

cgaggcgggg tctgcggagt ttgagatttt tgcaggtgtg aaatgactga gtacaaactg    120

gtggtggttg gagcaggtgg cgttgggaaa agtgctttga caatccagct aatccagaac    180

cactttgtgg atgaatatga tcccaccata gaggattctt accgaaaaca agtggtgatt    240

gacggtgaga cctgtctact ggacatactg gacacagctg gacaagagga gtacagtgcc    300

atgagagacc aatacatgag gacaggcgaa gggttcctct gtgtgtttgc catcaataat    360

agcaaatcct ttgcagatat taacctctac agggagcaaa ttaagcgcgt gaaagactct    420

gatgatgtac ccatggtgct ggtagggaac aagtgtgact tgccaacaag gacagttgac    480
```

-continued

```
acaaagcaag cccacgagct ggccaagagt tatggaattc cattcattga aacctcagcc    540

aagacccgac agggtgtgga ggatgccttt tacacgcttg taagggagat acgccagtac    600

cggatgaaga agctcaacag cagtgaggat ggcactcaag gctgtatggg gctgccctgt    660

gtggtgatgt agtaagaccc tttaaaagtt ctgtcatcag aaacgagcca ctttcaagcc    720

tcactgatgc cctggttctg acatccctgg aggagacgtg tttctgctgc tctctgcatc    780

tcagagaagc tcctgcttcc tgcttcccca acttagttac tgagcacagc catctaacct    840

gagacctctt cagaataact acctcctcac tcggctgtcc gaccagagaa atgaacctgt    900

ttctccccag tagttctctg ccctgggttt cccctagaaa caaacacacc tgccagctgg    960

ctttgtcctc cgaaaagcag tttacattga tgcagagaac caaactatag acaagcaatt   1020

ctgttgtcaa cagtttctta agctctaagg taacaattgc tggtgatttc cccctttgcc   1080

cccaactgtt gaacttggcc ttgttagttt tgggggaaat gtcaaaaatt aatctcttcc   1140

cgagaataga attagtgttg ctgattgcct gatttgcaat gtgatcagct atattctata   1200

agctggcgtc tgctctgtat tcataaatgc aaacatgagt actgacgtaa gtgcatccct   1260

agtcttctca gctgcatgca attaaatcca acgttcacaa caaaaaaaaa aaaaaaaaaa   1320

aaaaaa                                                              1326
```

```
<210> SEQ ID NO 45
<211> LENGTH: 189
<212> TYPE: PRT
<213> ORGANISM: Rattus norvegicus

<400> SEQUENCE: 45

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Ser Lys Ser Phe Ala Asp Ile Asn Leu Tyr
                85                  90                  95

Arg Glu Gln Ile Lys Arg Val Lys Asp Ser Asp Asp Val Pro Met Val
            100                 105                 110

Leu Val Gly Asn Lys Cys Asp Leu Pro Thr Arg Thr Val Asp Thr Lys
        115                 120                 125

Gln Ala His Glu Leu Ala Lys Ser Tyr Gly Ile Pro Phe Ile Glu Thr
    130                 135                 140

Ser Ala Lys Thr Arg Gln Gly Val Glu Asp Ala Phe Tyr Thr Leu Val
145                 150                 155                 160

Arg Glu Ile Arg Gln Tyr Arg Met Lys Lys Leu Asn Ser Ser Glu Asp
                165                 170                 175

Gly Thr Gln Gly Cys Met Gly Leu Pro Cys Val Val Met
            180                 185


<210> SEQ ID NO 46
<211> LENGTH: 1253
<212> TYPE: DNA
<213> ORGANISM: Canis lupus familiaris
```

<400> SEQUENCE: 46

```
ggcggttccg gggtctccaa cctttctcct agttgtggtc ctaaatacgt cggaagcgga     60
ggcggcgaag cttgaggttc ttgctggtgt gaaatgactg agtacaaact ggtggtggtt    120
ggagcaggtg gtgttgggaa aagcgcactg acaatccagc taatccagaa ccactttgta    180
gatgaatatg atcccaccat agaggattct taccgaaaac aggtggttat agacggtgaa    240
acctgtctgt tggatatact ggatacagct ggtcaagaag agtacagtgc catgagagac    300
caatacatga ggacaggcga aggcttcctc tgtgtatttg ccatcaataa tagcaaatca    360
tttgcagaca ttaacctcta cagggaacag attaagcgag taaaagattc agatgatgta    420
cctatggtgc tagtaggaaa caagtgtgat ttgccaacaa ggacagttga cacaaaacaa    480
gcccatgaac tggccaagag ttatgggatt ccattcattg aaacctcagc caagaccaga    540
cagggtgtcg aggatgcctt ttacacactg gtaagagaaa tacgtcagta ccgaatgaag    600
aaactcaaca gcagtgatga tgggactcaa ggttgtatgg ggttaccatg tgtggtgatg    660
taacaagaca cttttaaagt tctagcatca gaaaagagcc actgtcaagc tgcactgaca    720
ccctggtcct gacttccctg gaggagaagt attcctgttg ctatcttcag tctcacaaag    780
aagctcctgc tacttcccca actctcagta gatcagtaca atgttctcta tttgagaagt    840
tctccgaaca actacctcct cacttggttg tctgaccaga gaaatgaacc tcttgttcct    900
tcccgctgtt tttccaccct gaattctccc ccaacacaca taaacaaacc tctgccatcc    960
caggtttttc atctgaaaaa taattcatgc tctgaaacag agaacaaaac tgtagacatg   1020
aaattctgta ggaaacaagg tcttgagctc aaaagtagca actgctggtg acctttttt   1080
cccccctttt tactgttgaa cttggaacta tgttggtttt tggagaaatg tcataagtta   1140
ctgttttgct gagaatatag ttaagttgac atttggtttg tttgtaatat cattagctat   1200
tttctataaa ttggcatctg ctctgcattc ataaatacac gagtgaattc tga          1253
```

<210> SEQ ID NO 47
<211> LENGTH: 189
<212> TYPE: PRT
<213> ORGANISM: Canis lupus familiaris

<400> SEQUENCE: 47

```
Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Ser Lys Ser Phe Ala Asp Ile Asn Leu Tyr
                85                  90                  95

Arg Glu Gln Ile Lys Arg Val Lys Asp Ser Asp Asp Val Pro Met Val
            100                 105                 110

Leu Val Gly Asn Lys Cys Asp Leu Pro Thr Arg Thr Val Asp Thr Lys
        115                 120                 125

Gln Ala His Glu Leu Ala Lys Ser Tyr Gly Ile Pro Phe Ile Glu Thr
    130                 135                 140
```

Ser Ala Lys Thr Arg Gln Gly Val Glu Asp Ala Phe Tyr Thr Leu Val
145 150 155 160

Arg Glu Ile Arg Gln Tyr Arg Met Lys Lys Leu Asn Ser Ser Asp Asp
165 170 175

Gly Thr Gln Gly Cys Met Gly Leu Pro Cys Val Val Met
180 185

<210> SEQ ID NO 48
<211> LENGTH: 4825
<212> TYPE: DNA
<213> ORGANISM: Gallus gallus

<400> SEQUENCE: 48
gcgccgggac cggaagccgg aagctttgca gaagggtgtt ccgcgttcgc ggtgcgggag 60
cggtcagccg gggtggcggg gctggggccg gccggggcag gcggctccgc gctccgcact 120
gggccgctgg gagggcgatg actgaataca agctggtggt ggtgggagct ggcggcgtcg 180
ggaagagcgc gttgaccatc cagctcatcc agaaccactt cgtggacgag tacgacccca 240
ccatcgagga ttcgtacaga aagcaggttg tcatcgatgg agagacgtgc ttgttggaca 300
ttctggacac tgcaggacag gaagaataca gtgctatgcg tgatcagtac atgagaactg 360
gggaaggatt cctttgtgtg tttgccatta acaacagtaa atcattcgct gatattaacc 420
tttacagaga gcaaatcaag agagtgaaag attcagacga tgtgccaatg gtgctggtgg 480
ggaataagtg cgatttgcca acaaggacag tagacaccaa acaggctcaa gagttagcaa 540
aaagctacgg cattcccttc atagagacat cagccaaaac gagacagggt gtggaagatg 600
cgttttacac actggtgagg gagattcggc agtaccggat gaaaaagctc aacagcaacg 660
aagatgggaa tcagggctgt atggggttgt cctgcattgt gatgtgataa gatgccaggt 720
tcagatgtag ctgctggaca agtctcgatg ctactgtatt gtgtctcatg ctgatgccct 780
gcagtatttt ggtgccagcg accagactct tggtaccagt taattagctc aggatccttt 840
cctgtgctcc atctgaagaa aacatctctg gtatctacct ccttgctcag ctcacagagc 900
agtcatatct cttggtgtac tgggattctt ttctagctgt gttgtctggg tttgttcaag 960
aagaaaacca gtcacaagaa aagtgaatta cagagactaa atgctgtgaa aaagatcaca 1020
ctttacctcc agagtaaaag ctagaagtgg cgtttgaccc ctttgcattg gattcagatt 1080
tgcggtgttg tcagaggagt ggcagaagta attttgccat tacaaaggtt tctgtcacca 1140
gtcggattgg tatctgctgt ctgtgcaccc acacagtgta tctgcaacat ctgcattgtg 1200
ccagaagtat cacttaactg atgaactgat cctttatttt tctgtaataa aaaggagata 1260
tctttgctaa cttaagtgcc tgtttgctca gaaggttgga ggttgtatgc tgttcccttg 1320
ggctgaggag aaccccaagg atgaatttct tgggtgctca ttgtcttgag caggcaagtt 1380
ttgtgtgggt gatctctttt catggcagga tattaaaatg ggaatttgta gtctggaaga 1440
tggagcagct gtttgtgaga ctcttgagtt agggagagaa atgtatacca cgtctgttct 1500
cgatccatca gaatggatcc atccacctct ttgtgtgtgg aactgtgtat agtctgtatt 1560
ggttttctac agcacttgga tctctttgga ccaaattagc gagctgttca ttttaacata 1620
actgccagta tttatagaca atttcttacg gacagataat gaatttagaa actggaggtt 1680
actttgggca gctgttcctc agctctgtct gtaacttgca aattattctg agttattttc 1740
tgcagaacct ccttccttat cacgggagga gcctgggagt tgaggttgac tgtaattggg 1800
tcaatggttg tcacagactt aaggtgtcca ggctgattgg aggaggcact gagccctaac 1860

-continued

```
agagcactga gctgacttct aattgcagca tccttgcaaa atgaggaagg gagttcagtg   1920
atgtctgcac tgaagatgta tgatacactg atagcagttc tgggtatgtt gtaacagctt   1980
caaagtagaa ccgcagtact gcgtgagctg tgtgacttct tcctagaaca cagcactgtc   2040
accccatatg gttgggacgt gcaggtgaga ccaacaccta ccaggttccc tggcgtaccg   2100
tggccttctc agttcttgtg ccagtgatac tgggttctgt tctgtggtgt cagacagcgt   2160
cctgtagcaa agctgaattc ccacttagtc tggtgagaga ataaagagcc atcagccaac   2220
agagggagcg ttcattctgc tggagcagtg cgagctgtaa gcattacgag aggcgtagtt   2280
tcagtttgtt gcagtcaggt tcctatattt tcaaagctga aatcagaaat aagtaaatac   2340
ggagaaaata agctgttgct tttaatgctc tttcctccac taattgtact cttaattttc   2400
ttcttgggag gccgaggatc catctgcata actttagctg tgatgctcca gataagtgtt   2460
tagaattcat tttatctttg actgatggga ctgataagaa gttaacgcac aatattttta   2520
catacaacat cgttttccag tgacctcctg agcggtggga agcattatgg gatagcaccg   2580
gctgtgactc gagttcattt gaaggcgatc tcttgcctgc aggttaaatg ggacggagtc   2640
agaatcactg tgagccgtct gtaatcagca aacagtctgt gggcttttct tactgtgttc   2700
tctctgtttg ccttagtttg gtgcaggaag agttccttgt gacagcgtcc tttgaggtgt   2760
gttgcaggag ctgaccattt gctccttgag ctgtgtgatg aactgttgtc cacttaatgg   2820
agttacagaa gcagcttctg ggagtcgcat ctggtcgcat acattcagtg ttttgggaag   2880
ctgtcagtgt ggtgtttgca ctgtgtttga atggtgttca tggtgggtct gttatgctcc   2940
tggatgattt ggggagatgt ggggctgctt ccgtggcaga caggatcagc tcagggcgct   3000
gctgcctatg gctgtgggaa acctcacagt tggtgtttga atagtggcca agtatgtcaa   3060
ttaaaaatac attttgaagg gaggtttgtc atagctctgt actttggcat gctctgctta   3120
ctgaaaacat actagctgta gctcaaaaaa agttgtgaat cctcagaata atacaggagc   3180
tggcaattgt ggctgctttc tctttgtgtt ccttttctct tgggttggat gaagctttaa   3240
aaaggaagga gccctggtga gggttggtca gtgtgcattt cattcttgga accagagagg   3300
aagttgcatc aactttcagg acgctgcaga gctcacttgc acaggtggtg ctccagtcta   3360
tgtgattttt ggggtcaaat cttgagatga tcttacaaaa tcagattttg tacccatcat   3420
gagcatgagg tgagtggttg tgctcggttt ctagctgcat gtatgtatac agacacgtgt   3480
atgcagacat gtctatgtgt gagtagttcg agtcagtcaa ggttactggc agcacctaaa   3540
gcgtatgcac cacataatgc atgcaggcaa aagtcctatc ttaggagcca tctcttcatg   3600
ggtttgggtt tatataggca gtatttttaa acagaatatc cgaagcactt tctggagttc   3660
tgtggtaatg cagtgacacc tatttggatg aaggaagatg tgtctgagga gcacgtaagc   3720
agatttgctg ccctaacaga gaggttttgg taaccgtgga aaaggttttc tcctggatct   3780
gtgtgtgctc ttggtgagct gcaatccatg acagggcaca accagatgag aaggaaaccc   3840
ggccatccca tgcttgagca cagctctgac tcagtagttc caccagatgt gccctttcag   3900
tcaaagtgtt ctgatctctt agagctttct gtagttcaag ttaccactca ctctccagct   3960
tgctcggtta atgtctgttg gcggcgttga gttggacttg ggaaaggtgt gtgtggtagg   4020
aacaagcaga gtgtgatgtg cttctgttat caggacttaa gctagagtgg ttggcagata   4080
ggaaatgcag ctattccttg aaagcaagca gatcatggat ggtcagccaa actgccctgg   4140
ctttggtggg agctgcactg cagaaggacc aaaccccaac aagatttggc acatttgttt   4200
```

-continued agaagataag cacagatggt tttgcacaag gcagctcctc ataatggtgg ctttgtagat 4260
ttagtccaaa tgttcttatt tagatctagc agcacatcac tgtgtccgtg cccatctaac 4320
ctcgctatcc taagtagagc agaccccaaa caaccttgtt caaaaactac cagtgcaaat 4380
aactgaacta aatatttgtt actgctgact gagaacagct gttcgagtgt agcattgtgg 4440
cttgttaatg tgagtgcccc aactctatgg tcttattaaa gaaacccaaa cattgctcag 4500
attttgttct tattgtcatc ataagacttg aatagtgatg gtaatgctta cgtagacgtg 4560
tcttgtgagt gcacttcagt gatttagaaa gaactggatt tcaagcaact ttggacctgt 4620
ggggggaggg agattaatga aggtttgaat cacattctaa ttctatgtac agtccttcat 4680
tactccacaa gcctaaatcc tatacagcct ccaggatagc tggaaactgt tgagatctgg 4740 acttttttt tttaatccaa gggctaactt gttgtaactt ggtataatta tctgctttcg 4800
gaaatgcatc tctgttggtt tgaaa 4825

<210> SEQ ID NO 49
<211> LENGTH: 189
<212> TYPE: PRT
<213> ORGANISM: Gallus gallus

<400> SEQUENCE: 49

Met Thr Glu Tyr Lys Leu Val Val Val Gly Ala Gly Gly Val Gly Lys
1 5 10 15

Ser Ala Leu Thr Ile Gln Leu Ile Gln Asn His Phe Val Asp Glu Tyr
20 25 30

Asp Pro Thr Ile Glu Asp Ser Tyr Arg Lys Gln Val Val Ile Asp Gly
35 40 45

Glu Thr Cys Leu Leu Asp Ile Leu Asp Thr Ala Gly Gln Glu Glu Tyr
50 55 60

Ser Ala Met Arg Asp Gln Tyr Met Arg Thr Gly Glu Gly Phe Leu Cys
65 70 75 80

Val Phe Ala Ile Asn Asn Ser Lys Ser Phe Ala Asp Ile Asn Leu Tyr
85 90 95

Arg Glu Gln Ile Lys Arg Val Lys Asp Ser Asp Asp Val Pro Met Val
100 105 110

Leu Val Gly Asn Lys Cys Asp Leu Pro Thr Arg Thr Val Asp Thr Lys
115 120 125

Gln Ala Gln Glu Leu Ala Lys Ser Tyr Gly Ile Pro Phe Ile Glu Thr
130 135 140

Ser Ala Lys Thr Arg Gln Gly Val Glu Asp Ala Phe Tyr Thr Leu Val
145 150 155 160

Arg Glu Ile Arg Gln Tyr Arg Met Lys Lys Leu Asn Ser Asn Glu Asp
165 170 175

Gly Asn Gln Gly Cys Met Gly Leu Ser Cys Ile Val Met
180 185

<210> SEQ ID NO 50
<211> LENGTH: 4283
<212> TYPE: DNA
<213> ORGANISM: Bos taurus

<400> SEQUENCE: 50
ggccgctccc tagtgggggc tgttcatggc ggttccgggg tctcccaaca attttcccgg 60
ttgtggtcgt aatctatccg aagtggaggc agtggagcta gaggttcttg ctggtgtgaa 120
atgactgagt acaaactggt ggtggttgga gcaggtggtg ttgggaaaag tgcactgaca 180

```
atccagctaa tccagaacca ctttgtagat gaatatgatc ccaccataga ggattcctac    240
cgaaaacagg tggttataga tggtgaaacc tgtctgttgg acatactgga tacagctgga    300
caagaggagt acagtgccat gagagaccaa tacatgagga caggcgaagg cttcctttgt    360
gtgtttgcca tcaataatag caaatcattt gcagatatta acctctacag ggaacagata    420
aagcgtgtaa aggactcgga tgatgtacct atggtgctag taggaaacaa gtgtgatttg    480
ccaacaagga cagttgacac aaaacaagcc catgaactgg ccaaaagtta tgggattcca    540
ttcattgaaa cctcagccaa gaccagacag ggtgttgaag atgcctttta cacactggta    600
agagaaatac gtcagtaccg aatgaaaaag ctcaacagca gtgatgatgg cactcaaggc    660
tgtatggggt tgccgtgtgt ggtgatgtaa caagatactt ttaaagttct cacatcagaa    720
aagagccact gtcaagctgc actgacaccc tggtcctgac ttccctggag gagaagtatt    780
cctgttgcta tcttcagttt caaaaagaag ctcctgctat ttccccaact ctcagtagat    840
caatataata ttctctattt gagaagttct caagaataac tacctcctca cttggttgtc    900
tgaccagaga attgaacctc ttgttactcc cagtattttt ccaccctggg ttctccccca    960
gcacacacaa acgcacctct gccacccagg tttttcatct gaaaagcaat taatactctg   1020
aaacagagaa ccaaactgta gaaacatgaa attctgtaga aaacaatgtc ttgagctcta   1080
aagtagcaac tgctggtgat tttttttttt ttttttcct ttttattgtt gaacttggaa   1140
ctatgttggt ttgtggagaa atgtcataaa ttactgtttt gctgagaata tagttaatgt   1200
tgctctctgg tttgtttgta atgttatcag ctatattcta taaactggca tctactctgt   1260
atttagaaat acaaaaatga atactgacct tttgagtcta ccctcatctt ctcgactttc   1320
ttgtaattaa atgtaacttt cacgatgaag tgccttttgc ctgggagtga ctcgtagact   1380
tcctttaaaa tacttcagtg gaatagatgt ctcagaaact gttatacata agaataaatg   1440
tctgagatat gtctatgacc catctagctt tgagggaaag atataccaat atgatagcag   1500
atgccatttc ttacatctat aacgttgatt ttctggagac ctattttggg gctctccgag   1560
agaaagatga gactataaat gattaggaat aatttcactt aatttttaca taacctccac   1620
tttttgtttt gtagtttact acctgcaaaa catataattt gattcctttt agcttacaga   1680
taatctaatg ttaaatgaac ttccattcat attttaattt ggatcatatc aggaagtcta   1740
catttgcagg tgttcaaaaa ttgtaaaagt gtgatgcagt tttatttaat agctgtgatc   1800
aatgattttc aagcctcaaa tatgttaata gacacatttt cactgtatat catggtatta   1860
ataattattg atgtatataa ttgtccttgg tccccttctc tgttcatcac ctcatggcaa   1920
tggcttgatt aattatttca gctgagtaaa gcatggtgct aatagaccag ggtcacagtg   1980
tcaaaacttc agtgagccag taagcatcac agagaaagaa attctttcac atttgctcac   2040
cattaactcc agctaatagt tttgccagat gtgtgtggtt agtcctgcaa ggaaaggaga   2100
agtcagttaa tacaaattct taaccaggac tggaaaaact tgttttcctg agaagggtca   2160
gcttagaagt ctttatctgg actctatttt tagccacatg gaaatcaaat taagctgatc   2220
tttttctca agtttttgag agtgaggatg cctcagatca acatttttaa aatattcttt   2280
attcttacgt tcttttaagg gtttaaaaca acgttgagta attagtctgg gcataccagg   2340
taacaagctg ataagtttgt gctgaacaag aagtagcctt tggattgaaa ttgctgtttt   2400
gagaagggat agaaaatata attaataatt atgagacttg acttttctat ttgcagataa   2460
tatcctgata attctgatga aaatagactt ggataatttt tgataaaaga atcgttccaa   2520
```

-continued

```
aatggccact tgctgttctt gtcttctaat gtgtaaatac ttactgaggt cctcttctaa   2580
tatgagttgt catttattaa gcaaattcca cattgccttg aaatgaattc ggaagagaag   2640
aaaaagtcat agtataccca gagaatgaaa aatccagaga attgtgctcc ttagtgttaa   2700
ttctgaagcc ttcgtagtcc acacccatag acagaaactc tctgccactt tgcttctgct   2760
cctcttggag cattgcgctg tcatttcctt gaggatagat tgaggcttgt caactcagtt   2820
gtattgtctt cctcctcttc ctcttgtctg tgtgactgac agtgtgactc ttactaatgt   2880
cagatgcggg gatgcgggga ggtggggggg agtagctcat tttaggctct tgcacccttt   2940
accgttgtat gtgtgtgtct tttagttttc tcaagaatgt tctaagcaca gaagtatcta   3000
aatggggcca aaattcagac ttgaaaatgt tcttttaata gcttcttaaa aagttacact   3060
ttggtgtgaa ttttggcagg atagagtgac aaactcttaa acgctgaata acttcagtta   3120
gtgtgttata gtttttagaa tatgtttgtg attgctgaaa acaattatag tttacctcaa   3180
aatctgaaag tctctttccc caagttaagt gcctggccag ctgtcaaaga ttacatatta   3240
ctttatgttt gtttgttttt taaaggttgc acattcaaga ttgtgaaaat aaggtgttct   3300
gtctgaaagc taccatgcct gtctgtaaat gaatccactg agtgctgtac ttgttccaac   3360
agcttactac agaatgctac ttggtaatat catactcgtt acagttttca cttcaggagt   3420
gtactaggta gaatgatcct gtgtgtattg tagtgggctc catgtttagt cttttcagca   3480
tcctttaaac tgctgtgaat ttttgtcttg acttgaaagc aaggatagag aaacacttta   3540
aagagatact ttgggttttt ttccattcca gaattggtga gcatagttag attttgcttt   3600
acatttacag tcatgaactc ttaagctggc agctacaacc aagaaccaaa agagggtgca   3660
ttctgcttct tgtaattcat ctttgctaat aaattatgag aagcaaagat aattaattag   3720
agaaactatt ttatttgggt ggtttctata aacaagggac tataattctt aaacattatt   3780
tttcattttt gctgtttctt taagaaacct aatgtgccac aacattattt taaggtgttt   3840
cttaaaagaa ttgtttttaa aagtgttctc attttcagag taattgtaga tatatttcaa   3900
aatataactg ataattttta aaggcctgag tactgaccta agaagcagtt gtatgaattc   3960
tctgggggga agggaggagc tcagtgaaag ttgtatgact tttatatttc tgtgccatca   4020
aataaaggta aaaatgtctt ttgtgcagtt ttgctgttca aacagaaact attggcctcc   4080
ttggccctaa atgaaagggc tggtatttta agttgactat tttattgtaa attaatccat   4140
cttaattttt ttaaatttgg ttgaatgttc tcttgttaaa tgtttaaaaa ataaaaactg   4200
gaagttcttt gcttagtcat aaaaaaaaaa aaaaaaaaaa aaaaaaaaaa aaaaaaaaaa   4260
aaaaaaataa aaaaaaaaaa aaa                                           4283
```

<210> SEQ ID NO 51
<211> LENGTH: 189
<212> TYPE: PRT
<213> ORGANISM: Bos taurus

<400> SEQUENCE: 51

```
Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60
```

```
Ser Ala Met Arg Asp Gln Tyr Met Arg Thr Gly Glu Gly Phe Leu Cys
65                  70                  75                  80

Val Phe Ala Ile Asn Asn Ser Lys Ser Phe Ala Asp Ile Asn Leu Tyr
                85                  90                  95

Arg Glu Gln Ile Lys Arg Val Lys Asp Ser Asp Asp Val Pro Met Val
            100                 105                 110

Leu Val Gly Asn Lys Cys Asp Leu Pro Thr Arg Thr Val Asp Thr Lys
        115                 120                 125

Gln Ala His Glu Leu Ala Lys Ser Tyr Gly Ile Pro Phe Ile Glu Thr
    130                 135                 140

Ser Ala Lys Thr Arg Gln Gly Val Glu Asp Ala Phe Tyr Thr Leu Val
145                 150                 155                 160

Arg Glu Ile Arg Gln Tyr Arg Met Lys Lys Leu Asn Ser Ser Asp Asp
                165                 170                 175

Gly Thr Gln Gly Cys Met Gly Leu Pro Cys Val Val Met
            180                 185


<210> SEQ ID NO 52
<211> LENGTH: 17
<212> TYPE: DNA
<213> ORGANISM: Artificial sequence
<220> FEATURE:
<223> OTHER INFORMATION: Synthetic sequence

<400> SEQUENCE: 52

gctggtgtga aatgact                                                    17


<210> SEQ ID NO 53
<211> LENGTH: 20
<212> TYPE: DNA
<213> ORGANISM: Artificial sequence
<220> FEATURE:
<223> OTHER INFORMATION: Synthetic sequence

<400> SEQUENCE: 53

gctaccactg ggcctcacct                                                 20


<210> SEQ ID NO 54
<211> LENGTH: 20
<212> TYPE: DNA
<213> ORGANISM: Artificial sequence
<220> FEATURE:
<223> OTHER INFORMATION: Synthetic sequence

<400> SEQUENCE: 54

ggatgtgccc tgaaggacaa                                                 20


<210> SEQ ID NO 55
<211> LENGTH: 20
<212> TYPE: DNA
<213> ORGANISM: Artificial sequence
<220> FEATURE:
<223> OTHER INFORMATION: Synthetic sequence

<400> SEQUENCE: 55

tgcggatcca gggtaagaag                                                 20


<210> SEQ ID NO 56
<211> LENGTH: 20
<212> TYPE: DNA
<213> ORGANISM: Artificial sequence
<220> FEATURE:
```

<223> OTHER INFORMATION: Synthetic sequence

<400> SEQUENCE: 56
gagtggcagg gggaagatgc 20

<210> SEQ ID NO 57
<211> LENGTH: 20
<212> TYPE: DNA
<213> ORGANISM: Artificial sequence
<220> FEATURE:
<223> OTHER INFORMATION: Synthetic sequence

<400> SEQUENCE: 57
cctcagggca ctgcaggatg 20

<210> SEQ ID NO 58
<211> LENGTH: 25
<212> TYPE: DNA
<213> ORGANISM: Artificial sequence
<220> FEATURE:
<223> OTHER INFORMATION: Synthetic sequence

<400> SEQUENCE: 58
gcccgacgtg cattcccgat tcctt 25

<210> SEQ ID NO 59
<211> LENGTH: 25
<212> TYPE: DNA
<213> ORGANISM: Artificial sequence
<220> FEATURE:
<223> OTHER INFORMATION: Synthetic sequence

<400> SEQUENCE: 59
gacggctttc tccctcttgc tgacg 25

<210> SEQ ID NO 60
<211> LENGTH: 20
<212> TYPE: DNA
<213> ORGANISM: Artificial sequence
<220> FEATURE:
<223> OTHER INFORMATION: Synthetic sequence

<400> SEQUENCE: 60
tcaagaggtg ccacgtctcc 20

<210> SEQ ID NO 61
<211> LENGTH: 22
<212> TYPE: DNA
<213> ORGANISM: Artificial sequence
<220> FEATURE:
<223> OTHER INFORMATION: Synthetic sequence

<400> SEQUENCE: 61
tcttggcagc aggatagtcc tt 22

<210> SEQ ID NO 62
<211> LENGTH: 41
<212> TYPE: DNA
<213> ORGANISM: Artificial sequence
<220> FEATURE:
<223> OTHER INFORMATION: Synthetic sequence

<400> SEQUENCE: 62
atatgatcca acaatagagg cttcctacag gaagcaagta g 41

<210> SEQ ID NO 63
<211> LENGTH: 41
<212> TYPE: DNA
<213> ORGANISM: Artificial sequence
<220> FEATURE:
<223> OTHER INFORMATION: Synthetic sequence

<400> SEQUENCE: 63
ctacttgctt cctgtaggaa gcctctattg ttggatcata t 41

<210> SEQ ID NO 64
<211> LENGTH: 45
<212> TYPE: DNA
<213> ORGANISM: Artificial sequence
<220> FEATURE:
<223> OTHER INFORMATION: Synthetic sequence

<400> SEQUENCE: 64
cattttgtgg acgaatatga tccaacaaat gaggattcct acagg 45

<210> SEQ ID NO 65
<211> LENGTH: 45
<212> TYPE: DNA
<213> ORGANISM: Artificial sequence
<220> FEATURE:
<223> OTHER INFORMATION: Synthetic sequence

<400> SEQUENCE: 65
cctgtaggaa tcctcatttg ttggatcata ttcgtccaca aaatg 45

<210> SEQ ID NO 66
<211> LENGTH: 41
<212> TYPE: DNA
<213> ORGANISM: Artificial Sequence
<220> FEATURE:
<223> OTHER INFORMATION: Synthetic sequence

<400> SEQUENCE: 66
atatgatcca acaatagagg cttcctacag gaagcaagta g 41

<210> SEQ ID NO 67
<211> LENGTH: 41
<212> TYPE: DNA
<213> ORGANISM: Artificial Sequence
<220> FEATURE:
<223> OTHER INFORMATION: Synthetic sequence

<400> SEQUENCE: 67
ctacttgctt cctgtaggaa gcctctattg ttggatcata t 41

<210> SEQ ID NO 68
<211> LENGTH: 45
<212> TYPE: DNA
<213> ORGANISM: Artificial Sequence
<220> FEATURE:
<223> OTHER INFORMATION: Synthetic sequence

<400> SEQUENCE: 68
cattttgtgg acgaatatga tccaacaaat gaggattcct acagg 45

<210> SEQ ID NO 69
<211> LENGTH: 45
<212> TYPE: DNA

-continued

<213> ORGANISM: Artificial Sequence
<220> FEATURE:
<223> OTHER INFORMATION: Synthetic sequence

<400> SEQUENCE: 69
cctgtaggaa tcctcatttg ttggatcata ttcgtccaca aaatg 45